US011746095B2

United States Patent
Kaldor et al.

(10) Patent No.: US 11,746,095 B2
(45) Date of Patent: *Sep. 5, 2023

(54) INHIBTORS OF RAF KINASES

(71) Applicant: Kinnate Biopharma Inc., San Diego, CA (US)

(72) Inventors: Stephen W. Kaldor, San Diego, CA (US); Toufike Kanouni, Rancho Santa Fe, CA (US); Eric Murphy, San Marcos, CA (US); Jason Cox, Rancho Santa Fe, CA (US); Robert Kania, Del Mar, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,327

(22) Filed: May 6, 2022

(65) Prior Publication Data

US 2022/0356160 A1  Nov. 10, 2022

Related U.S. Application Data

(63) Continuation of application No. 17/498,530, filed on Oct. 11, 2021, now Pat. No. 11,377,431.

(60) Provisional application No. 63/090,623, filed on Oct. 12, 2020.

(51) Int. Cl.
| | |
|---|---|
| C07D 295/155 | (2006.01) |
| C07D 405/12 | (2006.01) |
| C07D 401/12 | (2006.01) |

(52) U.S. Cl.
CPC ....... *C07D 295/155* (2013.01); *C07D 401/12* (2013.01); *C07D 405/12* (2013.01)

(58) Field of Classification Search
CPC . C07D 295/155; C07D 401/12; C07D 405/12
USPC ...................................................... 514/210.2
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 10,927,111 B2 | 2/2021 | Kaldaor et al. | |
| 11,098,031 B1 | 8/2021 | Kaldor et al. | |
| 11,377,431 B2* | 7/2022 | Kaldor | C07D 405/12 |
| 2004/0157827 A1 | 8/2004 | Pevarello et al. | |
| 2005/0256174 A1 | 11/2005 | Wood et al. | |
| 2007/0054916 A1 | 3/2007 | Patel et al. | |
| 2007/0244120 A1 | 10/2007 | Dumas et al. | |
| 2008/0114006 A1 | 5/2008 | Flynn et al. | |
| 2009/0036419 A1 | 2/2009 | Chen et al. | |
| 2009/0054436 A1 | 2/2009 | Borzilleri et al. | |
| 2011/0183997 A1 | 7/2011 | Chianelli et al. | |
| 2012/0040951 A1 | 2/2012 | Chuaqui et al. | |
| 2014/0275003 A1 | 9/2014 | Barsanti et al. | |
| 2015/0119392 A1 | 4/2015 | Flynn et al. | |
| 2016/0075727 A1 | 3/2016 | Burger et al. | |
| 2017/0260207 A1 | 9/2017 | Aversa et al. | |
| 2019/0175606 A1 | 6/2019 | Aversa et al. | |
| 2020/0347052 A1 | 11/2020 | Kaldor et al. | |
| 2021/0246135 A1 | 8/2021 | Kaldor et al. | |
| 2021/0300904 A1 | 9/2021 | Kaldor et al. | |
| 2022/0089569 A1 | 3/2022 | Kaldor et al. | |
| 2022/0340543 A1 | 10/2022 | Kaldor et al. | |
| 2023/0081390 A1 | 3/2023 | Kaldaor et al. | |

FOREIGN PATENT DOCUMENTS

| | | |
|---|---|---|
| EP | 2112150 B1 | 10/2013 |
| WO | WO-03068229 A1 | 8/2003 |
| WO | WO-2006071940 A2 | 7/2006 |
| WO | WO-2008034008 A2 | 3/2008 |
| WO | WO-201 3184119 A1 | 12/2013 |
| WO | WO-2014151616 A1 | 9/2014 |
| WO | WO-2016038581 A1 | 3/2016 |
| WO | WO-2016038582 A1 | 3/2016 |
| WO | WO-2020168172 A1 | 8/2020 |
| WO | WO-2020198058 A1 | 10/2020 |
| WO | WO-2020227020 A1 | 11/2020 |
| WO | WO-2021081375 A1 | 4/2021 |
| WO | WO-2022060996 A1 | 3/2022 |
| WO | WO-2022081469 A1 | 4/2022 |
| WO | WO-2022226221 A1 | 10/2022 |
| WO | WO-2022226261 A1 | 10/2022 |

OTHER PUBLICATIONS

Anastassiadis et al. Comprehensive assay of kinase catalytic activity reveals features of kinase inhibitor selectivity. Nat Biotechnol. 29(11):1039-45 (2011).
Berge et al. Pharmaceutical Salts. Journal of Pharmaceutical Sciences 66(1):1-19 (Jan. 1977).
CAS Chemical Structure Search #3191415 Updated (Apr. 2020).
CAS Chemical Structure Search dated Apr. 24, 2019 .
Chemical Structure Search report data dated Feb. 27, 2019.
Evans. Synthesis of radiolabeled compounds. J Radioanal Chem 64(1-2):9-32 (1981).
Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
Kabalka et al. The Synthesis of Radiolabeled Compounds via Organometallic Intermediates. Tetrahedron 45(21):6601-6621 (1989).
Lv et al. Design, synthesis and biological evaluation of novel 4-alkynylquinoline derivatives as PI3K/mTOR dual inhibitors. Eur J Med Chem 99:36-50 (2015).
Nishiguchi et al. Design and Discovery of N-(2-Methyl-5'-morpholino-6'-((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).

(Continued)

*Primary Examiner* — Kahsay Habte
(74) *Attorney, Agent, or Firm* — Wilson Sonsini Goodrich & Rosati

(57) ABSTRACT

Provided herein are inhibitors of receptor tyrosine kinase effector, RAF, pharmaceutical compositions comprising said compounds, and methods for using said compounds for the treatment of diseases.

10 Claims, No Drawings

(56) References Cited

OTHER PUBLICATIONS

PCT/US2020/024009 International Search Report and Written Opinion dated Jul. 28, 2020.
PCT/US2020/024009 Invitation to Pay Additional Fees dated Jun. 2, 2020.
PCT/US2020/030786 International Search Report and Written Opinion dated Sep. 14, 2020.
PCT/US2020/030786 Invitation to Pay Additional Fees dated Jul. 14, 2020.
PCT/US2020/057132 International Search Report and Written Opinion dated Feb. 9, 2021.
PCT/US2020/057132 Invitation to Pay Additional Fees dated Dec. 8, 2020.
PCT/US2021/050690 International Search Report and Written Opinion dated Dec. 27, 2021.
PCT/US2021/054403 International Search Report and Written Opinion dated Dec. 28, 2021.
Ramurthy et al. Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).
Reg/Caplus and Marpat. Science IP Report dated Sep. 17, 2020.
Rosse. Pyridyl Isonicotinamide Inhibitors of RAF Kinase. ACS Med. Chem. Lett. 7:1022-1023 (2016).
Science IP Report dated Jul. 13, 2020 (873 pgs).
Chapman et al. Improved survival with vemurafenib in melanoma with BRAF V600E mutation. New England Journal of Medicine 364(26):2507-2516 (2011).
Davies et al. Mutations of the BRAF Gene in Human Cancer. Nature 417:949-954 (2002).
Hauschild et al. Dabrafenib in BRAF-mutated Metastatic Melanoma: A Multicentre, Open-Label, Phase 3 Randomised Controlled Trial. Lancet 380(9839):358-65 (2012).
Owsley et al. Prevalence of class I-III BRAF mutations among 114,662 cancer patients in a large genomic database. Exp Biol Med (Maywood) 246(1):31-39 (2021).
PCT/US2022/025815 International Search Report and Written Opinion dated Jul. 28, 2022.
PCT/US2022/025875 International Search Report and Written Opinion dated Jul. 25, 2022.
Subbiah et al. Pan-Cancer Efficacy of Vemurafenib in BRAF V600-Mutant Non-Melanoma Cancers. Cancer Discov 10(5):657-663 (2020).
U.S. Appl. No. 17/167,599 Office Action dated Oct. 31, 2022.
Yaeger et al. Targeting Alterations in the RAF-MEK Pathway. Cancer Discov 9(3):329-341 (2019).

* cited by examiner

INHIBITORS OF RAF KINASES

CROSS-REFERENCE TO RELATED APPLICATION

This application is a continuation of prior U.S. patent application Ser. No. 17/498,530, filed on Oct. 11, 2021, and claims the benefit of U.S. Patent Application No. 63/090,623 filed on Oct. 12, 2020, all of which are incorporated by reference herein in their entireties.

BACKGROUND

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY OF THE INVENTION

Provided herein are inhibitors of the receptor tyrosine kinase effector Raf (RAF), pharmaceutical compositions comprising said compounds, and methods for using said compounds for the treatment of diseases.

One embodiment provides a compound, or pharmaceutically acceptable salt or solvate thereof, having the structure of Formula (I):

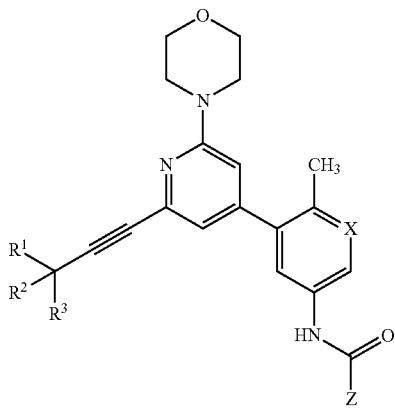

(I)

wherein,
X is N or C—H;
$R^1$ is selected from H, optionally substituted C1-C6 alkyl, or optionally substituted C3-C7 cycloalkyl;
$R^2$ is selected from H, optionally substituted C1-C6 alkyl, or optionally substituted C3-C7 cycloalkyl; or optionally, $R^1$ and $R^2$ join to form a ring;
$R^3$ is selected from H, —OH, —OR$^4$, —NH$_2$, —NHR$^4$, —N(R$^4$)$_2$, optionally substituted heterocyclyl, or optionally substituted heteroaryl;
each $R^4$ is independently selected from optionally substituted C1-C6 alkyl, optionally substituted C1-C6 acyl or optionally, $R^2$ and $R^4$ join to form a ring; and
Z is an optionally substituted aryl or heteroaryl.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

One embodiment provides a compound, or pharmaceutically acceptable salt or solvate thereof, having the structure of Formula (II):

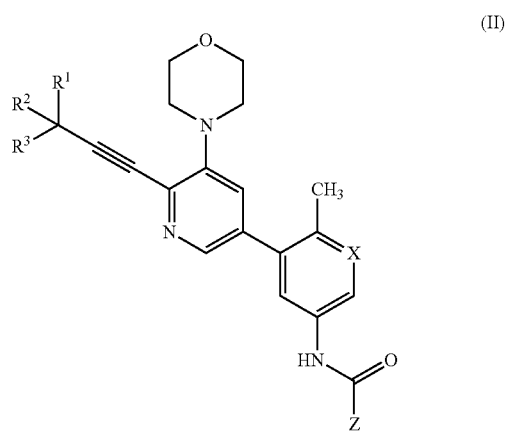

(II)

wherein,
X is N or C—H;
$R^1$ is selected from H, optionally substituted C1-C6 alkyl, or optionally substituted C3-C7 cycloalkyl;
$R^2$ is selected from H, optionally substituted C1-C6 alkyl, or optionally substituted C3-C7 cycloalkyl; or optionally, $R^1$ and $R^2$ join to form a ring;
$R^3$ is selected from H, —OH, —OR$^4$, —NH$_2$, —NHR$^4$, —N(R$^4$)$_2$, optionally substituted heterocyclyl, or optionally substituted heteroaryl;
each $R^4$ is independently selected from optionally substituted C1-C6 alkyl, optionally substituted C1-C6 acyl or optionally, $R^2$ and $R^4$ join to form a ring; and
Z is an optionally substituted aryl or heteroaryl.

One embodiment provides a pharmaceutical composition comprising a compound of Formula (II), or pharmaceutically acceptable salt or solvate thereof, and at least one pharmaceutically acceptable excipient.

One embodiment provides a method of treating a disease or disorder in a patient in need thereof comprising administering to the patient a compound of Formula (II), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N–$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —SR', —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R_a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR', —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR', —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —O$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^a$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$—R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

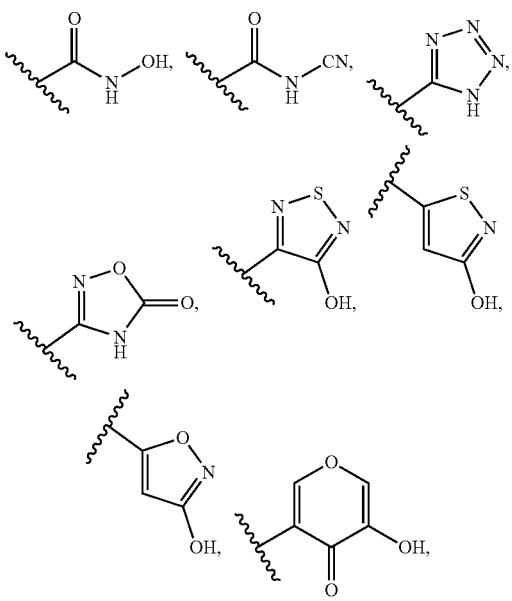

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above.

If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$) Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

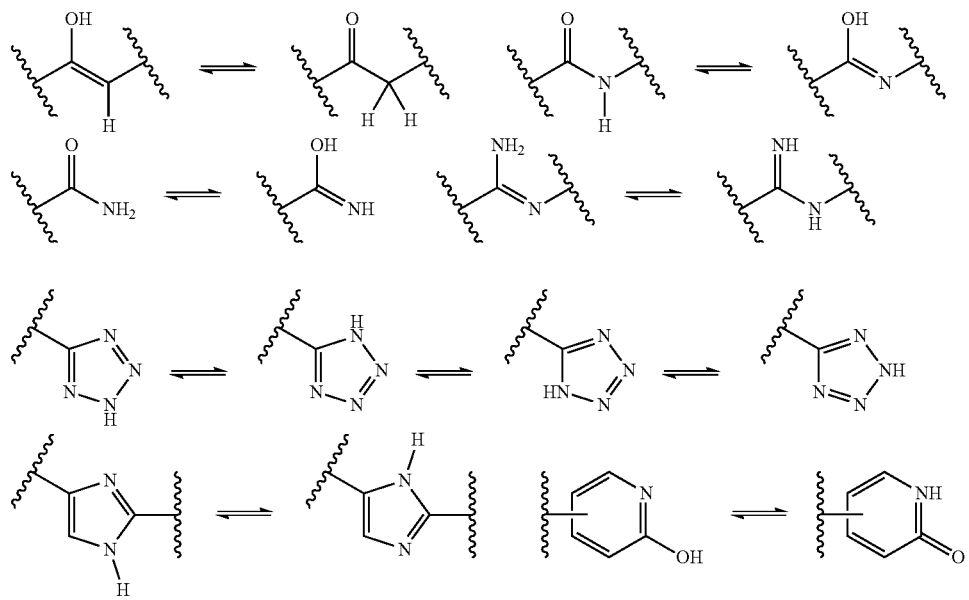

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

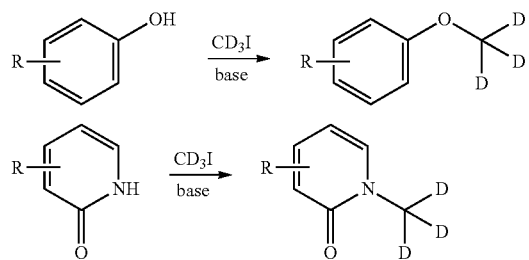

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

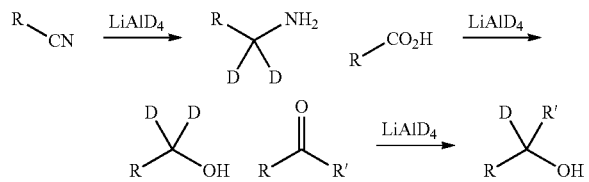

Deuterium gas and palladium catalyst are employed to reduce unsaturated carbon-carbon linkages and to perform a reductive substitution of aryl carbon-halogen bonds as illustrated, by way of example only, in the reaction schemes below.

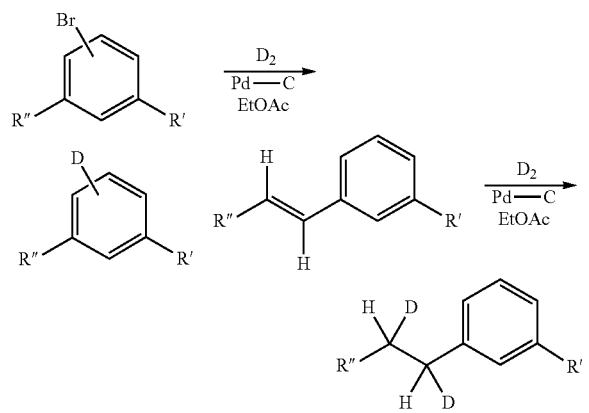

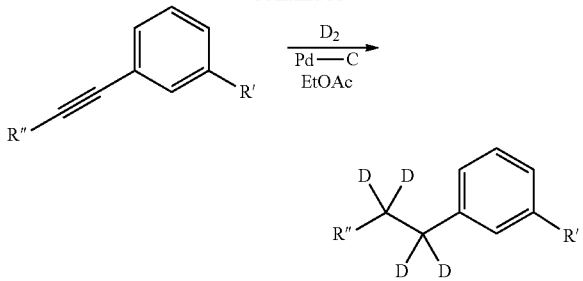

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heteroaromatic RAF inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms. The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The RAF Family of Kinases

The RAF kinases are a family of serine/threonine protein kinases constitute core components of the RAS-RAF-MEK-ERK mitogen activated protein kinase (MAPK) signalling cascade (also known as the MAPK/ERK pathway), a pathway that mediates signals from cell surface receptors to the nucleus to regulate cell growth, differentiation and survival. The RAF proteins are related to retroviral oncogenes and are structurally conserved from metazoans to mammals, as is the MAPK/ERK pathway. Their dysregulation leads to uncontrolled cellular proliferation, survival and dedifferentiation. Consequently, RAF kinases are altered or inappropriately activated in a majority of cancers.

The MAPK/ERK signalling pathway is a network of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, which communicate by adding phosphate groups to a neighboring protein, which acts as a molecular "on" or "off" switch, and overall the pathway can be divided into 3 steps: (i) Ras activation, (ii) a kinase signal transduction cascade, and (iii) regulation of translation and transcription. Briefly, an extracellular mitogen or a signaling molecule binds to the membrane receptor. This allows Ras (a small GTPase) to swap its GDP for a GTP and become active. Activated Ras activates the protein kinase activity of RAF kinase. RAF kinase phosphorylates and activates MEK (MEK1 and MEK2). MEK then phosphorylates and activates a MAPK (also known as ERK). MAPK activation regulates activities of several transcription factors and also alters the translation of mRNA to proteins. By altering the levels and activities of transcription factors, MAPK leads to altered transcription of genes that are important for the cell cycle.

There are three known mammalian RAF isoforms: C-RAF (also known as RAF-1, or c-RAF-1), B-RAF, and A-RAF. All RAF kinases share a common modular structure consisting of 3 conserved regions (CR1, CR2, and CR3) with distinct functions. CR1 contains (i) a Ras-binding domain (RBD), which is necessary for the interaction with Ras and with membrane phospholipids required for membrane recruitment, and (ii) a cysteine-rich domain (CRD), which is a secondary Ras-binding site and also necessary for the interaction of CR1 with the kinase domain for RAF autoinhibition. CR2 contains important inhibitory phosphorylation sites participating in the negative regulation of Ras binding and RAF activation. CR3 features the kinase domain, including the activation segment, whose phosphorylation is crucial for kinase activation.

Functionally, the RAF structure can be split into a regulatory N-terminal region, containing the RBD, which is critical for activation as well as inhibitory phosphorylation sites, and a catalytic C-terminal region, which includes phosphorylation sites necessary for the kinase activation. The regulatory domain restrains the activity of the kinase domain, and its removal results in constitutive oncogenic activation. However, the activity of the isolated C-RAF kinase domain is subjected to further regulation and can be stimulated by phorbol esters, v-Src, and phosphorylation.

The common and key step in the activation of all 3 RAF kinase isoforms is membrane recruitment by a Ras family protein. The RAF kinases are located in the cytosol in their inactive state when bound to 14-3-3 proteins. In the presence of active Ras, they translocate to the plasma membrane. Membrane translocation triggers further activation events, such as the binding of PP2A to dephosphorylate the inhibitory pS259 site in RAF-1 (and presumably the corresponding sites in A-RAF and B-RAF) and the co-localization with the kinases responsible for the multiple activating phosphorylations. The sequences forming the binding interface are well conserved in the RAF as well as Ras family indicating that several members of the Ras family have the ability to bind RAF kinases. H-Ras, N-Ras, and K-Ras stimulate all 3 RAF isoforms and are the only Ras proteins that activate B-RAF. In contrast, A-RAF is also activated by R-Ras3, while C-RAF responds weakly to R-Ras3, Rit, and TC21 as well. But, all RAF kinases share MEK1/2 kinases as substrates. MEK1/2 in turn activate ERK1/2, and this pathway regulates many cellular functions such as cell proliferation, differentiation, migration, or apoptosis.

C-RAF

C-RAF was first to be identified and is a ubiquitously expressed isoform. In humans, C-RAF is encoded by the RAFT gene. C-RAF also has a known splice variant preferentially expressed in the muscle and brain. C-RAF plays a critical role in mediating the cellular effects of growth factor signals. In the inactive state, C-RAF exists in a closed conformation in which the N-terminal regulatory region folds over and occludes the catalytic region. This conformation is stabilized by a 14-3-3 dimer binding to an N-terminal site, phospho-S259 (pS259), and a C-terminal site, pS621. Dephosphorylation of pS259 at the cell membrane by specific phosphatases (PP2A, PP1) releases 14-3-3 from its N-terminal binding site in C-RAF, thereby allowing conformational changes to occur that unmask the RBD and CRD domains in the CR1 region to enable Ras binding and membrane recruitment.

B-RAF

B-RAF is encoded in humans by the BRAF gene, also known as proto-oncogene B-RAF and v-RAF murine sarcoma viral oncogene homolog B. Alternative splicing gives rise to multiple B-RAF isoforms which are differentially expressed in various tissues. Whereas activation of A-RAF and C-RAF requires both phosphorylation and dephosphorylation of certain residues, as well as binding to other proteins, B-RAF becomes activated immediately upon translocation to the plasma membrane. B-RAF exhibits higher basal kinase activity than A-RAF and C-RAF. B-RAF requires Ras and 14-3-3 binding for its activation and is inhibited or activated by PKA depending on the levels of 14-3-3 expression, which need to be high for permitting activation. B-RAF activity is also regulated by splicing. B-RAF isoforms containing exon 8b are more phosphorylated on the inhibitory S365 site, leading to an increased interaction with 14-3-3 and strengthening the inhibitory interaction between N-terminal regulatory domain and kinase domain, altogether resulting in lower kinase activity.

A-RAF

Serine/threonine-protein kinase A-RAF or A-RAF is an enzyme encoded by the ARAF gene in humans. There are 2 known splice isoforms of A-RAF-DA-RAF1 and D-RAF2. They lack the kinase domain and act as dominant inhibitory mutants of Ras and ARF GTPases. DA-RAF1 is a positive regulator of myogenic differentiation by mediating the inhibition of the ERK pathway required for differentiation. There are several ways A-RAF is different from the other RAF kinases. A-RAF is the only steroid hormone-regulated Raf isoform. In addition, the A-RAFprotein has amino acid substitutions in a negatively charged region upstream of the kinase domain (N-region), which contributes to its low basal activity. A-RAF is also only weakly activated by oncogenic H-Ras and Src and also displays low kinase activity towards MEK (the lowest kinase activity towards MEK proteins in the Raf kinase family). In addition to phosphorylating MEK, A-RAF also inhibits MST2, a tumor suppressor and pro-apoptotic kinase not found in the MAPK pathway. By inhibiting MST2, A-RAF prevents apoptosis from occurring. However, this inhibition is only occurs when the splice factor heterogenous nuclear ribonucleoprotein H (hnRNP H) maintains the expression of a full-length A-RAF protein. Tumorous cells often overexpress hnRNP H which leads to full-length expression of A-Raf which then inhibits apoptosis, allowing cancerous cells that should be destroyed to stay alive. A-RAF also binds to pyruvate kinase M2 (PKM2), again outside the MAPK pathway. PKM2 is an isozyme of pyruvate kinase that is responsible for the Warburg effect in cancer cells. A-RAF upregulates the activity of PKM2 by promoting a conformational change in PKM2. This causes PKM2 to transition from its low-activity dimeric form to a highly active tetrameric form. This causes more glucose carbons to be converted to pyruvate and lactate, producing energy for the cell, linking A-Raf to energy metabolism regulation and cell transformation, both of which are very important in tumorigenesis.

RAF Kinase Inhibitors

Aberrant activation of the MAPK/ERK pathway is frequently found in various cancers and is a target for cancer therapeutics. In particular, B-RAF has emerged as one of the most attractive molecular targets for cancer therapeutics because somatic mutations of B-RAF have frequently been found in human tumors. Approximately 20% of all cancer samples tested to date harbor mutations in B-RAF. B-RAF-V600E, a missense mutation in the kinase domain generated by the substitution of glutamic acid with valine at position 600 is the most common B-RAF mutation. C-RAF is mutated in ~1% of the various tumor types tested and the rate of mutations in A-RAF is even lower. B-RAF and C-RAF form both homo- and heterodimers as part of their activation mechanism and A-RAF stabilizes the B-RAF:C-RAF complexes to sustain signaling efficiency. Also, it is C-RAF, not B-RAF, that transmits signals from oncogenic RAS to MEK. Therefore, in different contexts, each of the RAF isoforms act as a potential therapeutic target.

Sorafenib was the first RAF inhibitor to enter clinical trials. Sorafenib is a broad specificity drug that inhibits additional kinases, including vascular endothelial growth factor receptor family (VEGFR-2 and VEGFR-3), platelet-derived growth factor receptor family (PDGFR-b and KIT) and FLT3. Clinical trials showed no correlation between the clinical responses with B-RAF mutation status, indicating it is a poor inhibitor of B-RAF. This led to the development of a new generation of B-RAF inhibitors, including, but not limited to vemurafenib, SB-590885, and dabrafenib (GSK2118436). Although the initial results of the clinical studies in B-RAF-mutant melanoma were encouraging, as clinical testing began in other B-RAF-mutated cancers (such as thyroid and colorectal cancers) it became apparent that tumors of different cell types harboring B-RAF mutations responded differently to selective B-RAF inhibition. Moreover, the existence of both primary and secondary resistance to RAF inhibition poses as one of the greatest challenge to the progress of RAF kinase inhibitor therapy. The mechanisms of resistance fall into two broad categories. Intrinsic/primary resistance is displayed by approximately 50% of patients. The other 50% of the patients initially respond (>30% tumor shrinkage) to RAF inhibitor but subsequently develop progressive disease associated with acquired/secondary resistance to RAF inhibitor. These two categories are not mutually exclusive because nearly all responders have remaining disease and, thus, may display intrinsic resistance. The determinants of primary RAF inhibitor resistance seem to vary with tumor type, with alteration in RTK signaling also being involved. Potential mechanisms of secondary B-RAF inhibitor resistance include, but are not limited to, reactivation of ERK1/2 pathways, upregulation of RTK signaling, the upregulation of receptor tyrosine kinases, mutations in RAS, and upregulation of COT. B-Raf alternative splicing and amplification of B-RAF-V600E have also been implicated in ~30 and 20% of patients, respectively. Moreover, RAF kinase inhibitors cause paradoxical activation of the MAPK pathway, which, in some instances, leads to the development of secondary RAS mutation-driven malignancies. As such, there is a need in the field for new RAF kinase inhibitors that overcome the existing pitfalls and challenges posed by the current inhibitors.

Heteroaromatic RAF Inhibitory Compounds

In one aspect, provided herein is a heteroaromatic RAF inhibitory compound.

One embodiment provides a compound, or pharmaceutically acceptable salt or solvate thereof, having the structure of Formula (I):

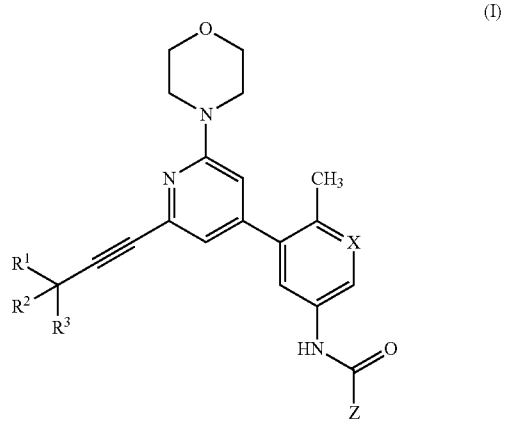

(I)

wherein,

X is N or C—H;

$R^1$ is selected from H, optionally substituted $C_1$-C6 alkyl, or optionally substituted C3-C7 cycloalkyl;

$R^2$ is selected from H, optionally substituted C1-C6 alkyl, or optionally substituted C3-C7 cycloalkyl; or optionally, $R^1$ and $R^2$ join to form a ring;

$R^3$ is selected from H, —OH, —$OR^4$, —$NH_2$, —$NHR^4$, —$N(R^4)_2$, optionally substituted heterocyclyl, or optionally substituted heteroaryl;

each $R^4$ is independently selected from optionally substituted C1-C6 alkyl, optionally substituted C1-C6 acyl or optionally, $R^2$ and $R^4$ join to form a ring; and Z is an optionally substituted aryl or heteroaryl.

One embodiment provides the compound of Formula (I), or pharmaceutically acceptable salt or solvate thereof, wherein X is N.

One embodiment provides the compound of Formula (I), or pharmaceutically acceptable salt or solvate thereof, wherein X is C—H.

One embodiment provides the compound of Formula (I), or pharmaceutically acceptable salt or solvate thereof, wherein $R^1$ is H. Another embodiment provides the compound, or pharmaceutically acceptable salt or solvate thereof, wherein $R^1$ is optionally substituted C1-C6 alkyl. Another embodiment provides the compound, or pharmaceutically acceptable salt or solvate thereof, wherein the optionally substituted alkyl is substituted with at least one halogen. Another embodiment provides the compound, or pharmaceutically acceptable salt or solvate thereof, wherein $R^1$ is $CH_3$. Another embodiment provides the compound, or pharmaceutically acceptable salt or solvate thereof, wherein $R^1$ is $CF_3$. Another embodiment provides the compound, or pharmaceutically acceptable salt or solvate thereof, wherein $R^1$ is optionally substituted C3-C7 cycloalkyl.

One embodiment provides the compound of Formula (I), or pharmaceutically acceptable salt or solvate thereof, wherein $R^2$ is H. Another embodiment provides the compound, or pharmaceutically acceptable salt or solvate thereof, wherein $R^2$ is optionally substituted C1-C6 alkyl. Another embodiment provides the compound, or pharmaceutically acceptable salt or solvate thereof, wherein $R^2$ is optionally substituted C3-C7 cycloalkyl.

One embodiment provides the compound of Formula (I), or pharmaceutically acceptable salt or solvate thereof, wherein $R^1$ and $R^2$ join to form a ring. Another embodiment provides the compound, or pharmaceutically acceptable salt or solvate thereof, wherein $R^1$ and $R^2$ join to form an optionally substituted cycloalkyl ring. Another embodiment provides the compound, or pharmaceutically acceptable salt or solvate thereof, wherein $R^1$ and $R^2$ join to form an optionally substituted heterocyclyl ring. Another embodiment provides the compound, or pharmaceutically acceptable salt or solvate thereof, wherein the optionally substituted heterocyclyl ring is selected from an optionally substituted pyrrolidine, optionally substituted piperidine, optionally substituted azetidine, optionally substituted tetrahydropyran, optionally substituted tetrahydrofuran or optionally substituted oxetane.

One embodiment provides the compound of Formula (I), or pharmaceutically acceptable salt or solvate thereof, wherein $R^1$ and $R^2$ are both optionally substituted C1-C6 alkyl. Another embodiment provides the compound, or pharmaceutically acceptable salt or solvate thereof, wherein $R^1$ and $R^2$ are $CH_3$.

One embodiment provides the compound of Formula (I), or pharmaceutically acceptable salt or solvate thereof, wherein $R^3$ is —OH. Another embodiment provides the compound, or pharmaceutically acceptable salt or solvate thereof, wherein $R^3$ is —$NH_2$. Another embodiment provides the compound, or pharmaceutically acceptable salt or solvate thereof, wherein $R^3$ is —$NHR^4$. Another embodiment provides the compound, or pharmaceutically acceptable salt or solvate thereof, wherein $R^3$ is —$N(R^4)_2$. Another embodiment provides the compound, or pharmaceutically acceptable salt or solvate thereof, wherein $R^3$ is —$OR^4$. Another embodiment provides the compound, or pharmaceutically acceptable salt or solvate thereof, wherein $R^3$ is optionally substituted heterocyclyl. Another embodiment provides the compound, or pharmaceutically acceptable salt or solvate thereof, wherein $R^3$ is optionally substituted heteroaryl.

One embodiment provides the compound of Formula (I), or pharmaceutically acceptable salt or solvate thereof, wherein $R^4$ is optionally substituted C1-C6 alkyl. Another embodiment provides the compound, or pharmaceutically acceptable salt or solvate thereof, wherein $R^4$ is optionally substituted C1-C6 acyl.

One embodiment provides the compound of Formula (I), or pharmaceutically acceptable salt or solvate thereof, wherein $R^2$ and $R^4$ join to form a ring. Another embodiment provides the compound, or pharmaceutically acceptable salt or solvate thereof, wherein $R^2$ and $R^4$ join to form an optionally substituted heterocyclyl ring. Another embodiment provides the compound, or pharmaceutically acceptable salt or solvate thereof, wherein optionally substituted heterocyclyl ring is an oxopyrrolidine ring, or an optionally substituted oxomorpholine ring.

One embodiment provides the compound of Formula (I), or pharmaceutically acceptable salt or solvate thereof, wherein Z is an optionally substituted aryl. Another embodiment provides the compound, or pharmaceutically acceptable salt or solvate thereof, wherein the optionally substituted aryl is an optionally substituted phenyl. Another embodiment provides the compound, or pharmaceutically acceptable salt or solvate thereof, wherein the optionally substituted phenyl is an optionally substituted 3-(trifluoromethyl)phenyl. Another embodiment provides the compound, or pharmaceutically acceptable salt or solvate thereof, wherein Z is a 3-(trifluoromethyl)phenyl.

One embodiment provides the compound of Formula (I), or pharmaceutically acceptable salt or solvate thereof, wherein Z is an optionally substituted heteroaryl. Another embodiment provides the compound, or pharmaceutically acceptable salt or solvate thereof, wherein the optionally substituted heteroaryl is an optionally substituted six-membered heteroaryl. Another embodiment provides the compound, or pharmaceutically acceptable salt or solvate thereof, wherein the optionally substituted six-membered heteroaryl is an optionally substituted pyridyl. Another embodiment provides the compound, or pharmaceutically acceptable salt or solvate thereof, wherein the optionally substituted six-membered heteroaryl is an optionally substituted pyrimidine. Another embodiment provides the compound, or pharmaceutically acceptable salt or solvate thereof, wherein the optionally substituted pyridyl is an optionally substituted 2-(trifluoromethyl)pyrid-4-yl. Another embodiment provides the compound, or pharmaceutically acceptable salt or solvate thereof, wherein Z is a 2-(trifluoromethyl)pyrid-4-yl.

One embodiment provides a compound, or pharmaceutically acceptable salt or solvate thereof, having the structure of Formula (II):

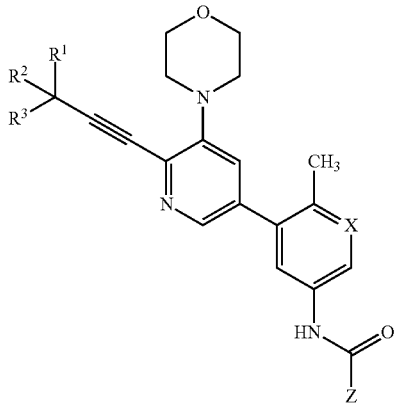

(II)

wherein,
X is N or C—H;
$R^1$ is selected from H, optionally substituted C1-C6 alkyl, or optionally substituted C3-C7 cycloalkyl;
$R^2$ is selected from H, optionally substituted C1-C6 alkyl, or optionally substituted C3-C7 cycloalkyl; or optionally, $R^1$ and $R^2$ join to form a ring;
$R^3$ is selected from H, —OH, —OR$^4$, —NH$_2$, —NHR$^4$, —N(R$^4$)$_2$, optionally substituted heterocyclyl, or optionally substituted heteroaryl;
each $R^4$ is independently selected from optionally substituted C1-C6 alkyl, optionally substituted C1-C6 acyl or optionally, $R^2$ and $R^4$ join to form a ring; and
Z is an optionally substituted aryl or heteroaryl.

One embodiment provides the compound of Formula (II), or pharmaceutically acceptable salt or solvate thereof, wherein X is N.

One embodiment provides the compound of Formula (II), or pharmaceutically acceptable salt or solvate thereof, wherein X is C—H.

One embodiment provides the compound of Formula (II), or pharmaceutically acceptable salt or solvate thereof, wherein $R^1$ is H. Another embodiment provides the compound, or pharmaceutically acceptable salt or solvate thereof, wherein $R^1$ is optionally substituted C1-C6 alkyl. Another embodiment provides the compound, or pharmaceutically acceptable salt or solvate thereof, wherein the optionally substituted alkyl is substituted with at least one halogen. Another embodiment provides the compound, or pharmaceutically acceptable salt or solvate thereof, wherein $R^1$ is CH$_3$. Another embodiment provides the compound, or pharmaceutically acceptable salt or solvate thereof, wherein $R^1$ is CF$_3$. Another embodiment provides the compound, or pharmaceutically acceptable salt or solvate thereof, wherein $R^1$ is optionally substituted C3-C7 cycloalkyl.

One embodiment provides the compound of Formula (II), or pharmaceutically acceptable salt or solvate thereof, wherein $R^2$ is H. Another embodiment provides the compound, or pharmaceutically acceptable salt or solvate thereof, wherein $R^2$ is optionally substituted C1-C6 alkyl. Another embodiment provides the compound, or pharmaceutically acceptable salt or solvate thereof, wherein $R^2$ is optionally substituted C3-C7 cycloalkyl.

One embodiment provides the compound of Formula (II), or pharmaceutically acceptable salt or solvate thereof, wherein $R^1$ and $R^2$ join to form a ring. Another embodiment provides the compound, or pharmaceutically acceptable salt or solvate thereof, wherein $R^1$ and $R^2$ join to form an optionally substituted cycloalkyl ring. Another embodiment provides the compound, or pharmaceutically acceptable salt or solvate thereof, wherein $R^1$ and $R^2$ join to form an optionally substituted heterocyclyl ring. Another embodiment provides the compound, or pharmaceutically acceptable salt or solvate thereof, wherein the optionally substituted heterocyclyl ring is selected from an optionally substituted pyrrolidine, optionally substituted piperidine, optionally substituted azetidine, optionally substituted tetrahydropyran, optionally substituted tetrahydrofuran or optionally substituted oxetane.

One embodiment provides the compound of Formula (II), or pharmaceutically acceptable salt or solvate thereof, wherein $R^1$ and $R^2$ are both optionally substituted C1-C6 alkyl. Another embodiment provides the compound, or pharmaceutically acceptable salt or solvate thereof, wherein $R^1$ and $R^2$ are CH$_3$.

One embodiment provides the compound of Formula (II), or pharmaceutically acceptable salt or solvate thereof, wherein $R^3$ is —OH. Another embodiment provides the compound, or pharmaceutically acceptable salt or solvate thereof, wherein $R^3$ is —NH$_2$. Another embodiment provides the compound, or pharmaceutically acceptable salt or solvate thereof, wherein $R^3$ is —$NHR^4$. Another embodiment provides the compound, or pharmaceutically acceptable salt or solvate thereof, wherein $R^3$ is —$N(R^4)_2$. Another embodiment provides the compound, or pharmaceutically acceptable salt or solvate thereof, wherein $R^3$ is —$OR^4$. Another embodiment provides the compound, or pharmaceutically acceptable salt or solvate thereof, wherein $R^3$ is optionally substituted heterocyclyl. Another embodiment provides the compound, or pharmaceutically acceptable salt or solvate thereof, wherein $R^3$ is optionally substituted heteroaryl.

One embodiment provides the compound of Formula (II), or pharmaceutically acceptable salt or solvate thereof, wherein $R^4$ is optionally substituted C1-C6 alkyl. Another embodiment provides the compound, or pharmaceutically acceptable salt or solvate thereof, wherein $R^4$ is optionally substituted C1-C6 acyl.

One embodiment provides the compound of Formula (II), or pharmaceutically acceptable salt or solvate thereof, wherein $R^1$ and $R^4$ join to form a ring. Another embodiment provides the compound, or pharmaceutically acceptable salt or solvate thereof, wherein $R^1$ and $R^4$ join to form an optionally substituted heterocyclyl ring. Another embodiment provides the compound, or pharmaceutically acceptable salt or solvate thereof, wherein optionally substituted heterocyclyl ring is an oxopyrrolidine ring, or an optionally substituted oxomorpholine ring.

One embodiment provides the compound of Formula (II), or pharmaceutically acceptable salt or solvate thereof, wherein Z is an optionally substituted aryl. Another embodiment provides the compound, or pharmaceutically acceptable salt or solvate thereof, wherein the optionally substituted aryl is an optionally substituted phenyl. Another embodiment provides the compound, or pharmaceutically acceptable salt or solvate thereof, wherein the optionally substituted phenyl is an optionally substituted 3-(trifluoromethyl)phenyl. Another embodiment provides the compound, or pharmaceutically acceptable salt or solvate thereof, wherein Z is a 3-(trifluoromethyl)phenyl.

One embodiment provides the compound of Formula (II), or pharmaceutically acceptable salt or solvate thereof, wherein Z is an optionally substituted heteroaryl. Another embodiment provides the compound, or pharmaceutically acceptable salt or solvate thereof, wherein the optionally substituted heteroaryl is an optionally substituted six-membered heteroaryl. Another embodiment provides the compound, or pharmaceutically acceptable salt or solvate thereof, wherein the optionally substituted six-membered heteroaryl is an optionally substituted pyridyl. Another embodiment provides the compound, or pharmaceutically acceptable salt or solvate thereof, wherein the optionally substituted six-membered heteroaryl is an optionally substituted pyrimidine. Another embodiment provides the compound, or pharmaceutically acceptable salt or solvate thereof, wherein the optionally substituted pyridyl is an optionally substituted 2-(trifluoromethyl)pyrid-4-yl. Another embodiment provides the compound, or pharmaceutically acceptable salt or solvate thereof, wherein Z is a 2-(trifluoromethyl)pyrid-4-yl.

One embodiment provides the compound of Formula (II), or pharmaceutically acceptable salt or solvate thereof, wherein Z is an optionally substituted heteroaryl and $R^1$ and $R^2$ are both optionally substituted C1-C6 alkyl. Another embodiment provides the compound, or pharmaceutically acceptable salt or solvate thereof, wherein Z is an optionally substituted pyridyl and $R^1$ and $R^2$ are both optionally substituted C1-C6 alkyl. Another embodiment provides the compound, or pharmaceutically acceptable salt or solvate thereof, wherein Z is an optionally substituted 2-(trifluoromethyl)pyrid-4-yl, and $R^1$ and $R^2$ are both optionally substituted C1-C6 alkyl. Another embodiment provides the compound, or pharmaceutically acceptable salt or solvate thereof, wherein Z is a 2-(trifluoromethyl)pyrid-4-yl and $R^1$ and $R^2$ are both optionally substituted C1-C6 alkyl. Another embodiment provides the compound, or pharmaceutically acceptable salt or solvate thereof, wherein Z is a 2-(trifluoromethyl)pyrid-4-yl and $R^1$ and $R^2$ are both $CH_3$.

One embodiment provides a compound, or pharmaceutically acceptable salt or solvate thereof, having the structure of Formula (III):

wherein,

X is N or C—H; and

Z is an optionally substituted aryl or heteroaryl.

One embodiment provides the compound of Formula (III), or pharmaceutically acceptable salt or solvate thereof, wherein X is N.

One embodiment provides the compound of Formula (III), or pharmaceutically acceptable salt or solvate thereof, wherein X is C—H.

One embodiment provides the compound of Formula (III), or pharmaceutically acceptable salt or solvate thereof, wherein Z is an optionally substituted aryl. Another embodiment provides the compound, or pharmaceutically acceptable salt or solvate thereof, wherein the optionally substituted aryl is an optionally substituted phenyl. Another embodiment provides the compound, or pharmaceutically acceptable salt or solvate thereof, wherein the optionally substituted phenyl is an optionally substituted 3-(trifluoromethyl)phenyl. Another embodiment provides the compound, or pharmaceutically acceptable salt or solvate thereof, wherein Z is a 3-(trifluoromethyl)phenyl.

One embodiment provides the compound of Formula (III), or pharmaceutically acceptable salt or solvate thereof, wherein Z is an optionally substituted heteroaryl. Another embodiment provides the compound, or pharmaceutically acceptable salt or solvate thereof, wherein the optionally substituted heteroaryl is an optionally substituted six-membered heteroaryl. Another embodiment provides the compound, or pharmaceutically acceptable salt or solvate thereof, wherein the optionally substituted six-membered heteroaryl is an optionally substituted pyridyl. Another embodiment provides the compound, or pharmaceutically acceptable salt or solvate thereof, wherein the optionally substituted six-membered heteroaryl is an optionally substituted pyrimidine. Another embodiment provides the compound, or pharmaceutically acceptable salt or solvate thereof, wherein the optionally substituted pyridyl is an optionally substituted 2-(trifluoromethyl)pyrid-4-yl. Another embodiment provides the compound, or pharmaceutically acceptable salt or solvate thereof, wherein Z is a 2-(trifluoromethyl)pyrid-4-yl.

One embodiment provides a compound, or pharmaceutically acceptable salt or solvate thereof, having the structure of Formula (R$^a$):

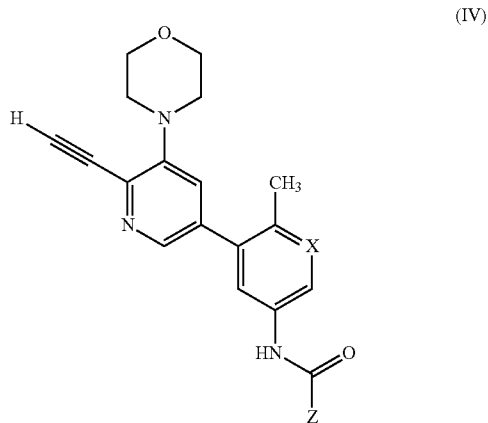

(IV)

wherein,

X is N or C—H; and

Z is an optionally substituted aryl or heteroaryl.

One embodiment provides the compound of Formula (R$^a$), or pharmaceutically acceptable salt or solvate thereof, wherein X is N.

One embodiment provides the compound of Formula (R$^a$), or pharmaceutically acceptable salt or solvate thereof, wherein X is C—H.

One embodiment provides the compound of Formula (R$^a$), or pharmaceutically acceptable salt or solvate thereof, wherein Z is an optionally substituted aryl. Another embodiment provides the compound, or pharmaceutically acceptable salt or solvate thereof, wherein the optionally substituted aryl is an optionally substituted phenyl. Another embodiment provides the compound, or pharmaceutically acceptable salt or solvate thereof, wherein the optionally substituted phenyl is an optionally substituted 3-(trifluoromethyl)phenyl. Another embodiment provides the compound, or pharmaceutically acceptable salt or solvate thereof, wherein Z is a 3-(trifluoromethyl)phenyl.

One embodiment provides the compound of Formula (R$^a$), or pharmaceutically acceptable salt or solvate thereof, wherein Z is an optionally substituted heteroaryl. Another embodiment provides the compound, or pharmaceutically acceptable salt or solvate thereof, wherein the optionally substituted heteroaryl is an optionally substituted six-membered heteroaryl. Another embodiment provides the compound, or pharmaceutically acceptable salt or solvate thereof, wherein the optionally substituted six-membered heteroaryl is an optionally substituted pyridyl. Another embodiment provides the compound, or pharmaceutically acceptable salt or solvate thereof, wherein the optionally substituted six-membered heteroaryl is an optionally substituted pyrimidine. Another embodiment provides the compound, or pharmaceutically acceptable salt or solvate thereof, wherein the optionally substituted pyridyl is an optionally substituted 2-(trifluoromethyl)pyrid-4-yl. Another embodiment provides the compound, or pharmaceutically acceptable salt or solvate thereof, wherein Z is a 2-(trifluoromethyl)pyrid-4-yl.

In some embodiments, the heteroaromatic RAF kinase inhibitory compound as described herein has a structure provided in Table 1.

TABLE 1

| Synthetic Chemistry Example | Compound Structure | Compound Name |
|---|---|---|
| 1 | 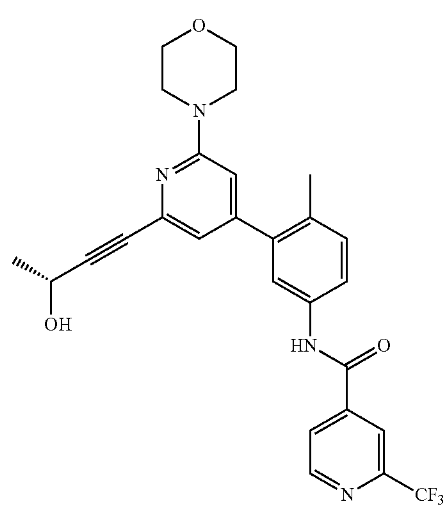 [SMILES: Cc1ccc(NC(=O)c2ccnc(C(F)(F)F)c2)cc1-c1cc(C#C[C@@H](C)O)nc(N2CCOCC2)c1] | N-(3-[2-[(3R)-3-hydroxybut-1-yn-1-yl]-6-(morpholin-4-yl)pyridin-4-yl]-4-methylphenyl)-2-(trifluoromethyl)pyridine-4-carboxamide |

TABLE 1-continued

| Synthetic Chemistry Example | Compound Structure | Compound Name |
|---|---|---|
| 2 | 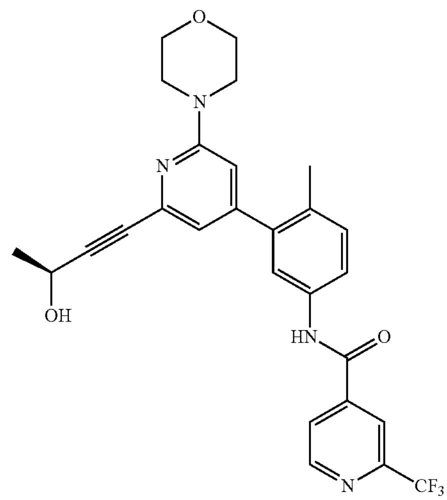 [SMILES: Cc1ccc(NC(=O)c2ccnc(C(F)(F)F)c2)cc1-c1cc(C#C[C@H](C)O)nc(N2CCOCC2)c1] | N-(3-[2-[(3S)-3-hydroxybut-1-yn-1-yl]-6-(morpholin-4-yl)pyridin-4-yl]-4-methylphenyl)-2-(trifluoromethyl)pyridine-4-carboxamide |
| 3 | 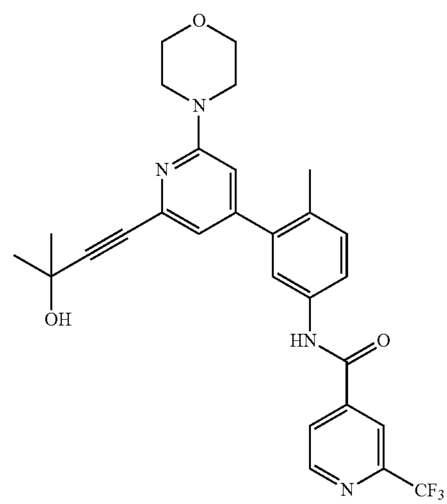 [SMILES: Cc1ccc(NC(=O)c2ccnc(C(F)(F)F)c2)cc1-c1cc(C#CC(C)(C)O)nc(N2CCOCC2)c1] | N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide |
| 4 | 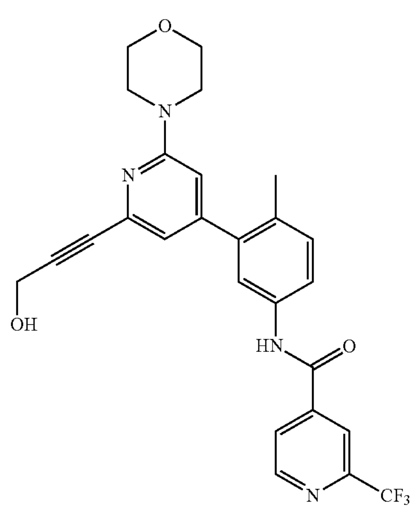 [SMILES: Cc1ccc(NC(=O)c2ccnc(C(F)(F)F)c2)cc1-c1cc(C#CCO)nc(N2CCOCC2)c1] | N-[3-[2-(3-hydroxyprop-1-yn-1-yl)-6-(morpholin-4-yl)pyridin-4-yl]-4-methylphenyl]-2-(trifluoromethyl)pyridine-4-carboxamide |

TABLE 1-continued

| Synthetic Chemistry Example | Compound Structure | Compound Name |
|---|---|---|
| 5 | 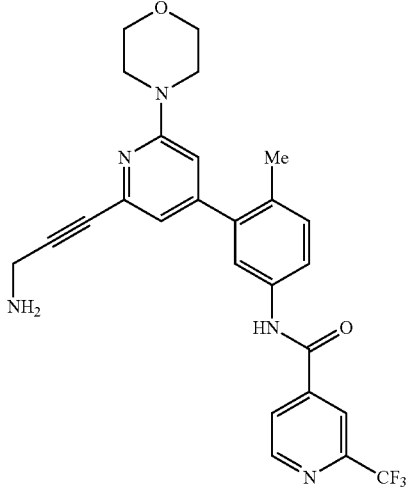 [SMILES: Cc1ccc(NC(=O)c2ccnc(C(F)(F)F)c2)cc1-c1cc(C#CCN)nc(N2CCOCC2)c1] | (3S)-N-[3-[2-(2-ammopyrimidin-4-yl)-6-(morpholin-4-yl)pyridin-4-yl]-4-methylphenyl]-3-(2,2,2-trifluoroethyl)pyrrolidine-1-carboxamide |
| 6 | 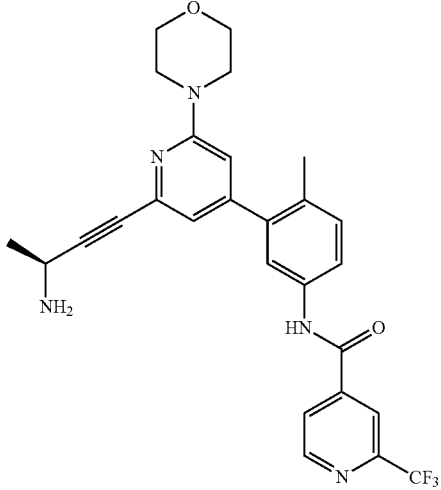 [SMILES: Cc1ccc(NC(=O)c2ccnc(C(F)(F)F)c2)cc1-c1cc(C#C[C@H](C)N)nc(N2CCOCC2)c1] | N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide |
| 7 | 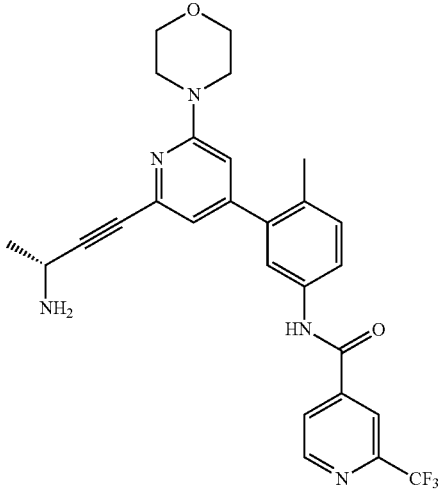 [SMILES: Cc1ccc(NC(=O)c2ccnc(C(F)(F)F)c2)cc1-c1cc(C#C[C@@H](C)N)nc(N2CCOCC2)c1] | N-(3-{2-[(3R)-3-aminobut-1-yn-1-yl]-6-(morpholin-4-yl)pyridin-4-yl}-4-methylphenyl)-2-(trifluoromethyl)pyridine-4-carboxamide |

TABLE 1-continued

| Synthetic Chemistry Example | Compound Structure | Compound Name |
|---|---|---|
| 8 | 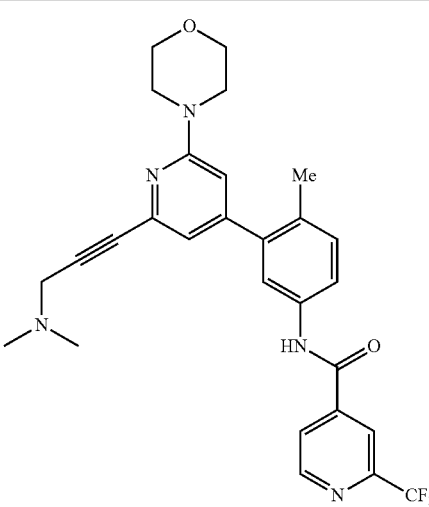 | N-(3-{2-[3-(dimethylamino)prop-1-yn-1-yl]-6-(morpholin-4-yl)pyridin-4-yl}-4-methylphenyl)-2-(trifluoromethyl)pyridine-4-carboxamide |
| 9 | 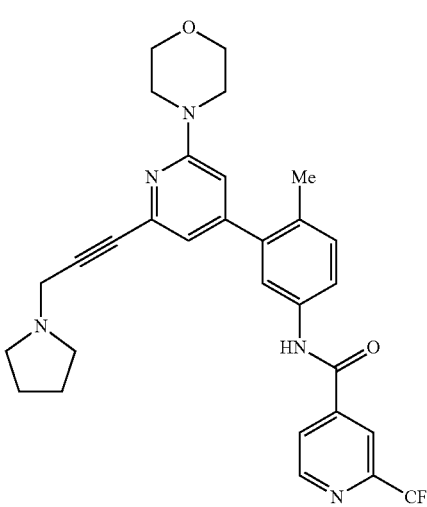 | N-(4-methyl-3-{2-(morpholin-4-yl)-6-[3-(pyrrolidin-1-yl)prop-1-yn-1-yl]pyridin-4-yl]phenyl}-2-(trifluoromethyl)pyridine-4-carboxamide |
| 10 | 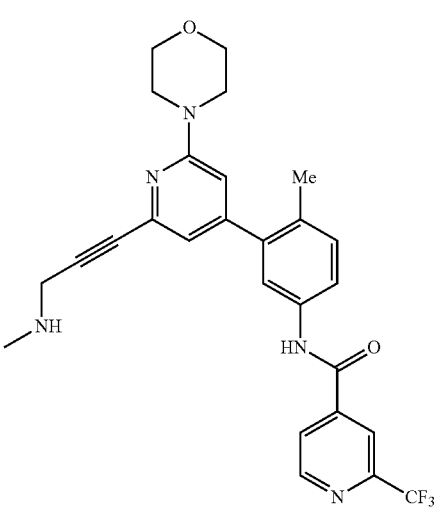 [SMILES: CNCC#Cc1cc(-c2cc(NC(=O)c3ccnc(C(F)(F)F)c3)ccc2C)cc(N2CCOCC2)n1] | N-(4-methyl-3-{2-[3-(methylamino)prop-1-yn-1-yl]-6-(morpholin-4-yl)pyridin-4-yl}phenyl)-2-(trifluoromethyl)pyridine-4-carboxamide |

TABLE 1-continued

| Synthetic Chemistry Example | Compound Structure | Compound Name |
|---|---|---|
| 11 | 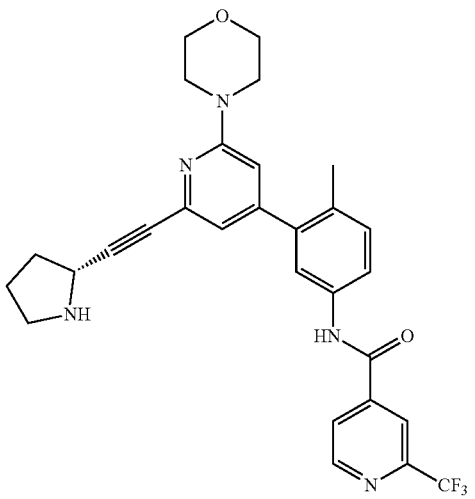 [SMILES: Cc1ccc(NC(=O)c2ccnc(C(F)(F)F)c2)cc1-c1cc(C#C[C@H]2CCCN2)nc(N2CCOCC2)c1] | N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide |
| 12 and 13 | 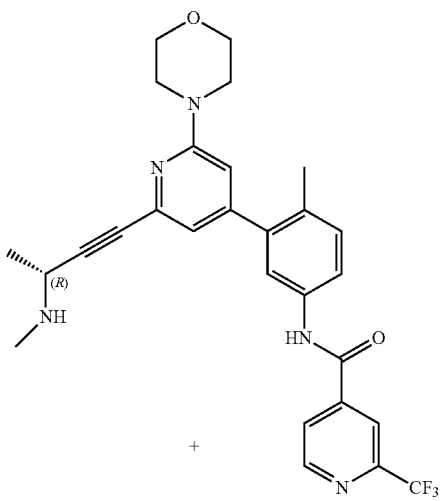<br>+<br>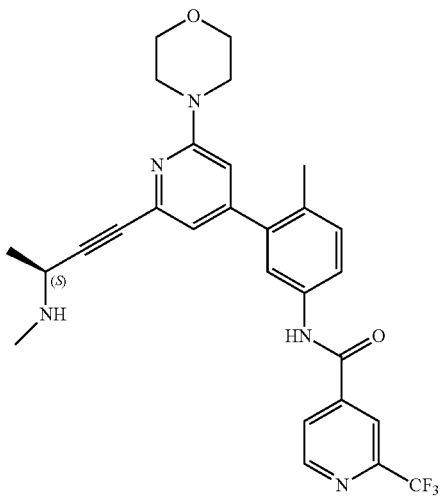 | N-(4-methyl-3-{2-[(3R)-3-(methylamino)but-1-yn-1-yl]-6-(morpholin-4-yl)pyridin-4-yl}phenyl)-2-(trifluoromethyl)pyridine-4-carboxamide and N-[3-[2-(3-hydroxyprop-1-yn-1-yl)-6-(morpholin-4-yl)pyridin-4-yl]-4-methylphenyl]-2-(trifluoromethyl)pyridine-4-carboxamide |

TABLE 1-continued

| Synthetic Chemistry Example | Compound Structure | Compound Name |
|---|---|---|
| 14 | 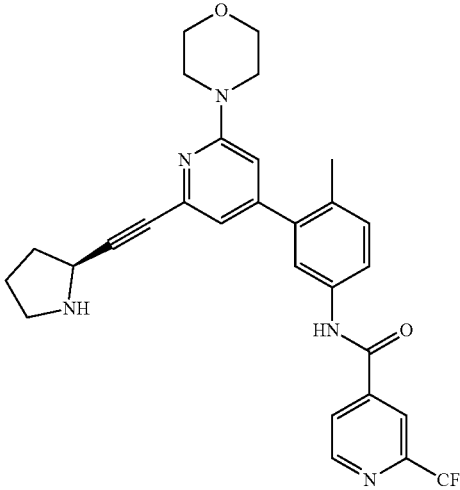 | N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide |
| 15 and 16 | 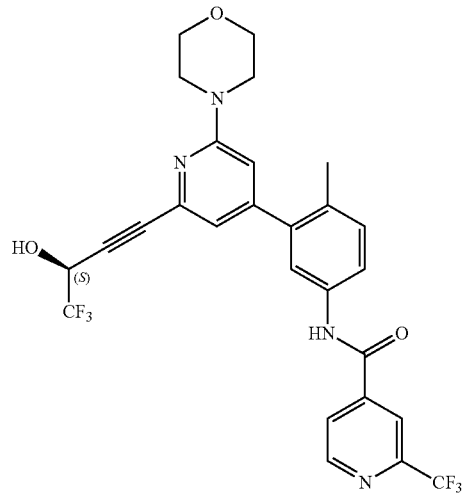<br />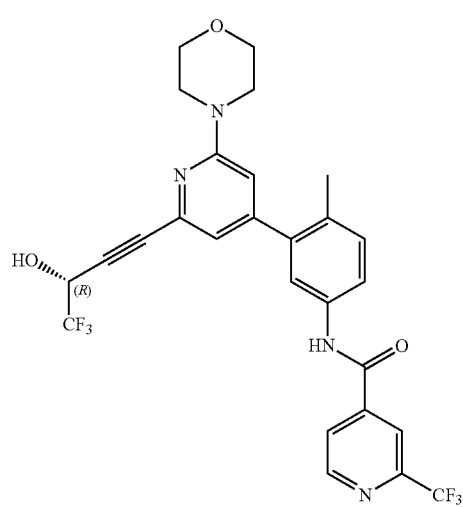 | N-{4-methyl-3-[2-(morpholin-4-yl)-6-[(3,S)-4,4,4-trifluoro-3-hydroxybut-1-yn-1-yl]pyridin-4-yl]phenyl}-2-(trifluoromethyl)pyridine-4-carboxamide and N-{4-methyl-3-[2-(morpholin-4-yl)-6-[(3N)-4,4,4-trifluoro-3-hydroxybut-1-yn-1-yl]pyridin-4-yl]phenyl}-2-(trifluoromethyl)pyridine-4-carboxamide |

TABLE 1-continued

| Synthetic Chemistry Example | Compound Structure | Compound Name |
|---|---|---|
| 17 | 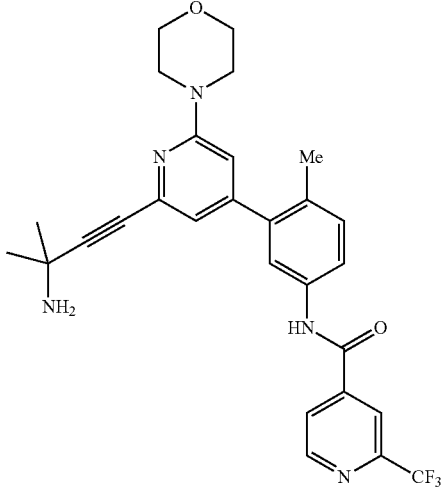 [SMILES: Cc1ccc(NC(=O)c2ccnc(C(F)(F)F)c2)cc1-c1cc(C#CC(C)(C)N)nc(N2CCOCC2)c1] | N-{3-[2-(3-amino-3-methylbut-1-yn-1-yl)-6-(morpholin-4-yl)pyridin-4-yl]-4-methylphenyl)-2-(trifluoromethyl)pyridine-4-carboxamide |
| 18 | 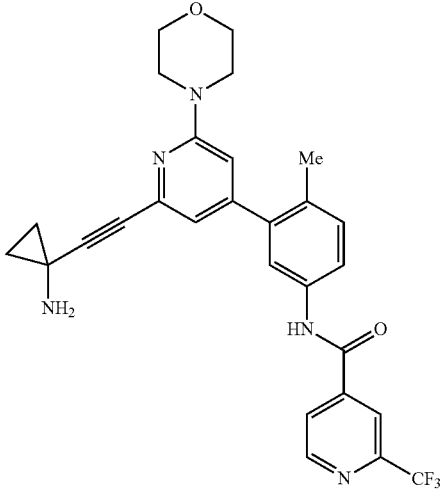 [SMILES: Cc1ccc(NC(=O)c2ccnc(C(F)(F)F)c2)cc1-c1cc(C#CC2(N)CC2)nc(N2CCOCC2)c1] | N-(3-{2-[(3S)-3-atninobut-1-yn-1-yl]-6-(morpholin-4-yl)pyridin-4-yl}-4-methylphenyl}-2-(trifluoromethyl)pyridine-4-carboxamide |
| 19 | 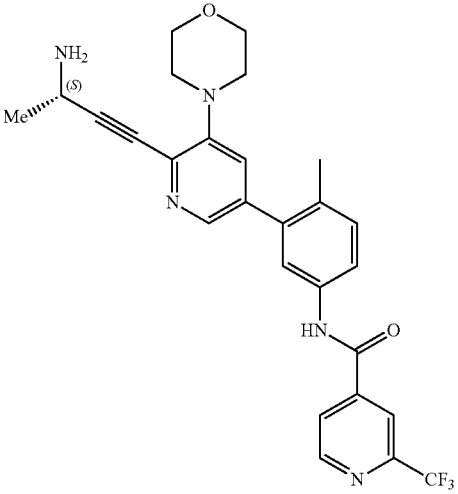 | N-(3-{6-[(3S)-3-aminobut-1-yn-1-yl]-5-(morpholin-4-yl)pyridin-3-yl}-4-methylphenyl)-2-(trifluoromethyl)pyridine-4-carboxamide |

TABLE 1-continued

| Synthetic Chemistry Example | Compound Structure | Compound Name |
|---|---|---|
| 20 | 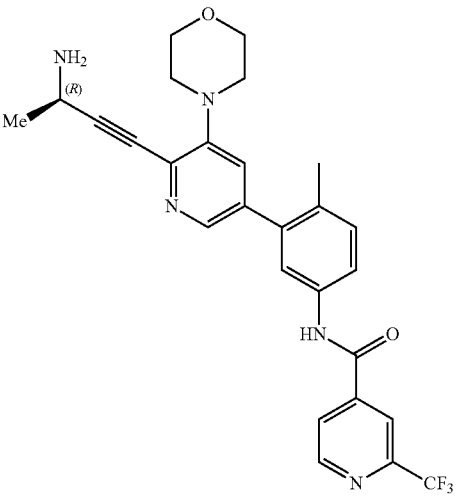 | N-(3-{6-[(3R)-3-aminobut-1-yn-1-yl]-5-(morpholin-4-yl)pyridin-3-yl}-4-methylphenyl)-2-(trifluoromethyl)pyridine-4-carboxamide |
| 21 | 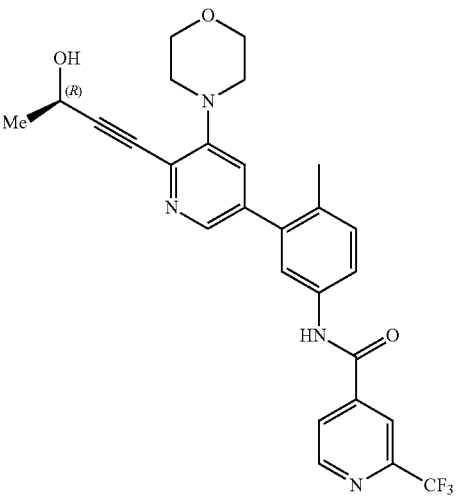 | N-(3-{6-[(3S)-3-Hydroxybut-1-yn-1-yl]-5-(morpholin-4-yl)pyridin-3-yl}-4-methylphenyl)-2-(trifluoromethyl)pyridine-4-carboxamide |
| 22 | 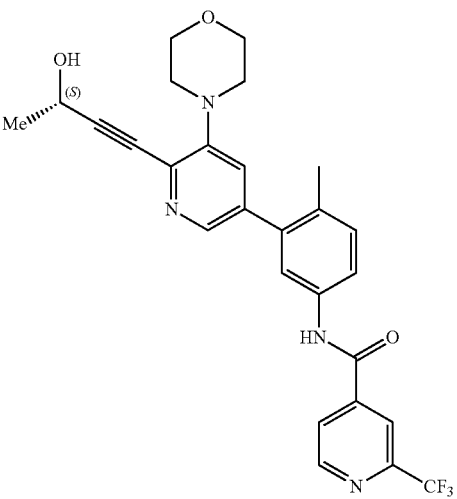 | N-(3-{6-[(3S)-3-Hydroxybut-1-yn-1-yl]-5-(morpholin-4-yl)pyridin-3-yl}-4-methylphenyl)-2-(trifluoromethyl)pyridine-4-carboxamide |

TABLE 1-continued

| Synthetic Chemistry Example | Compound Structure | Compound Name |
|---|---|---|
| 23 | 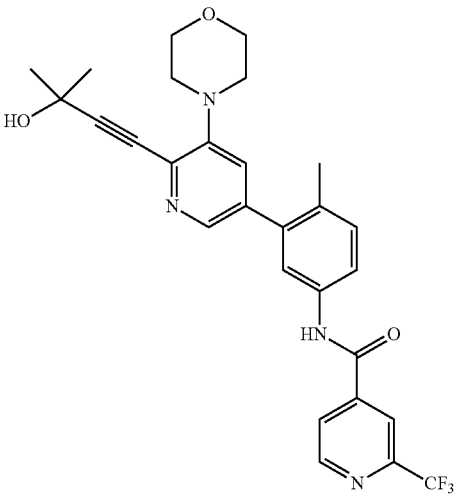 [SMILES: Cc1ccc(NC(=O)c2ccnc(C(F)(F)F)c2)cc1-c1cnc(C#CC(C)(C)O)c(N2CCOCC2)c1] | N-{3-[6-(3-Hydroxy-3-methylbut-1-yn-1-yl)-5-(morpholin-4-yl)pyridin-3-yl]-4-methylphenyl}-2-(trifluoromethyl)pyridine-4-carboxamide |
| 24 | 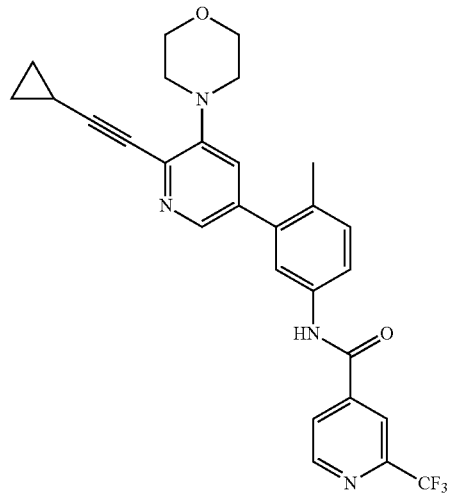 [SMILES: Cc1ccc(NC(=O)c2ccnc(C(F)(F)F)c2)cc1-c1cnc(C#CC2CC2)c(N2CCOCC2)c1] | N-{3-[6-(2-Cyclopropylethynyl)-5-(morpholin-4-yl)pyridin-3-yl]-4-methylphenyl}-2-(trifluoromethyl)pyridine-4-carboxamide |
| 25 | 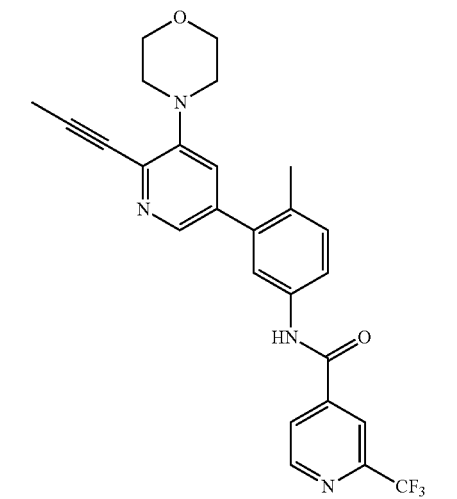 [SMILES: CC#Cc1ncc(-c2cc(NC(=O)c3ccnc(C(F)(F)F)c3)ccc2C)cc1N1CCOCC1] | N-{4-Methyl-3-[5-(morpholin-4-yl)-6-(prop-1-yn-1-yl)pyridin-3-yl]phenyl}-2-(trifluoromethyl)pyridine-4-carboxamide |

TABLE 1-continued

| Synthetic Chemistry Example | Compound Structure | Compound Name |
|---|---|---|
| 26 | 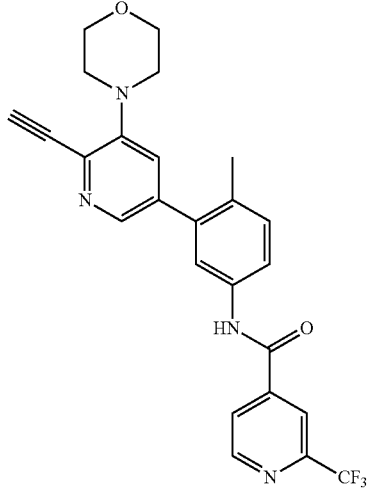 [SMILES: C#Cc1ncc(-c2cc(NC(=O)c3ccnc(C(F)(F)F)c3)ccc2C)cc1N1CCOCC1] | N-{3-[6-Ethynyl-5-(morpholin-4-yl)pyridin-3-yl]-4-methylphenyl}-2-(trifluoromethyl)pyridine-4-carboxamide |
| 27 | 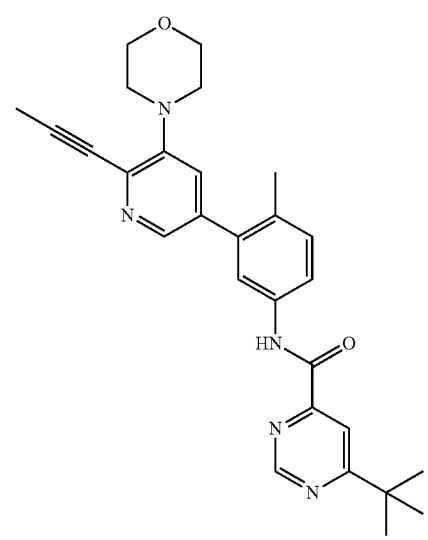 [SMILES: CC#Cc1ncc(-c2cc(NC(=O)c3cc(C(C)(C)C)ncn3)ccc2C)cc1N1CCOCC1] | 6-Tert-butyl-N-{4-methyl-3-[5-(morpholin-4-yl)-6-(prop-1-yn-1-yl)pyridin-3-yl]phenyl}pyrimidine-4-carboxamide |
| 28 | 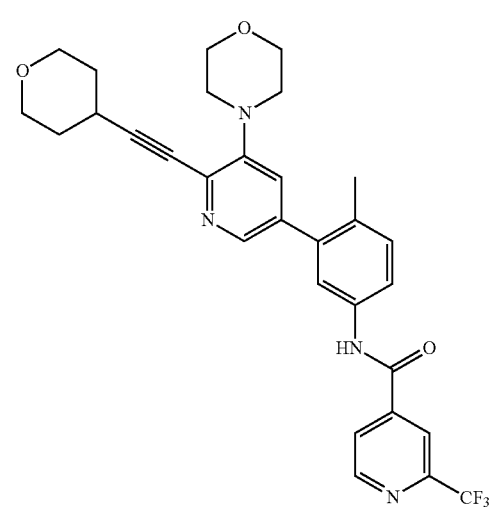 [SMILES: Cc1ccc(NC(=O)c2ccnc(C(F)(F)F)c2)cc1-c1cnc(C#CC2CCOCC2)c(N2CCOCC2)c1] | N-(4-methyl-3-(5-morpholino-6-((tetrahydro-2H-pyran-4-yl)ethynyl)pyridin-3-yl)phenyl)-2-(trifluoromethyl)isonicotinamide |

TABLE 1-continued

| Synthetic Chemistry Example | Compound Structure | Compound Name |
|---|---|---|
| 29 | 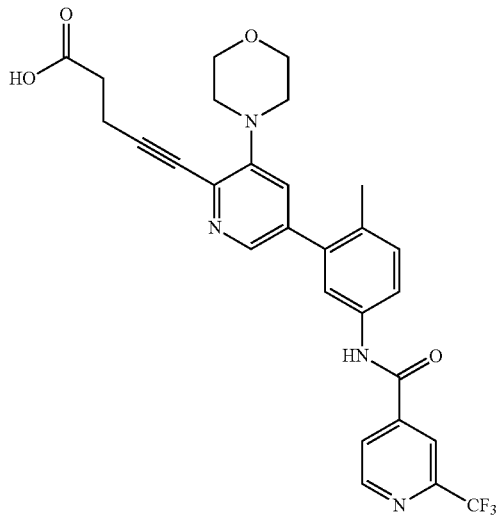 [SMILES: Cc1ccc(NC(=O)c2ccnc(C(F)(F)F)c2)cc1-c1cnc(C#CCCC(=O)O)c(N2CCOCC2)c1] | 5-(5-(2-methyl-5-(2-(trifluoromethyl)isonicotinamido)phenyl)-3-morpholinopyridin-2-yl)pent-4-ynoic acid |
| 30 | 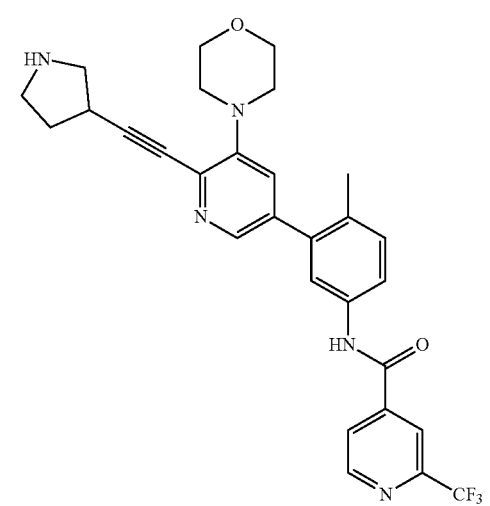 [SMILES: Cc1ccc(NC(=O)c2ccnc(C(F)(F)F)c2)cc1-c1cnc(C#CC2CCNC2)c(N2CCOCC2)c1] | N-(4-methyl-3-(5-morpholino-6-(pyrrolidin-3-ylethynyl)pyridin-3-yl)phenyl)-2-(trifluoromethyl)isonicotinamide |
| 31 | 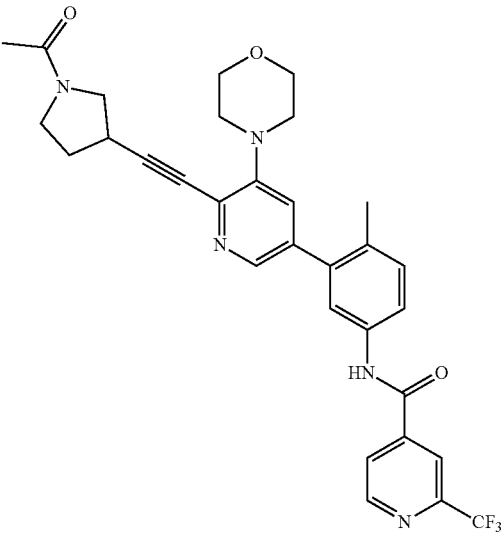 [SMILES: CC(=O)N1CCC(C#Cc2ncc(-c3cc(NC(=O)c4ccnc(C(F)(F)F)c4)ccc3C)cc2N2CCOCC2)C1] | N-(3-(6-((1-acetylpyrrolidin-3-yl)ethynyl)-5-morpholinopyridin-3-yl)-4-methylphenyl)-2-(trifluoromethyl)isonicotinamide |

TABLE 1-continued

| Synthetic Chemistry Example | Compound Structure | Compound Name |
|---|---|---|
| 32 | 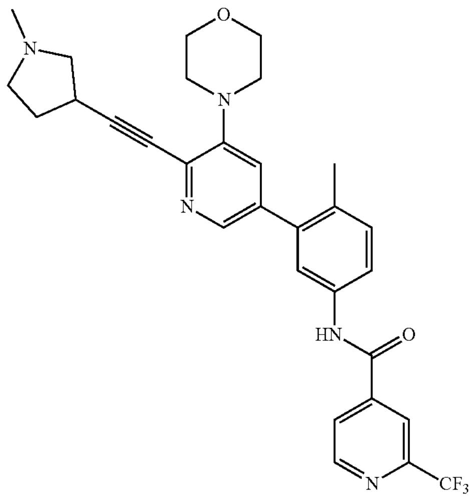 [SMILES: Cc1ccc(NC(=O)c2ccnc(C(F)(F)F)c2)cc1-c1cnc(C#CC2CCN(C)C2)c(N2CCOCC2)c1] | N-(4-methyl-3-(6-((1-methylpyrrolidin-3-yl)ethynyl)-5-morpholinopyridin-3-yl)phenyl)-2-(trifluoromethyl)isonicotinamide |
| 33 | 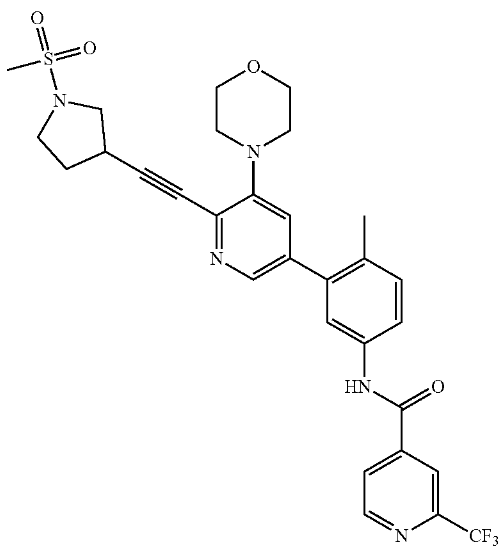 [SMILES: Cc1ccc(NC(=O)c2ccnc(C(F)(F)F)c2)cc1-c1cnc(C#CC2CCN(S(C)(=O)=O)C2)c(N2CCOCC2)c1] | N-(4-methyl-3-(6-((1-(methylsulfonyl(pyrrolidin-3-yl)ethynyl)-5-morpholinopyridin-3-yl)phenyl)-2-(trifluoromethyl)isonicotinamide |
| 34 | 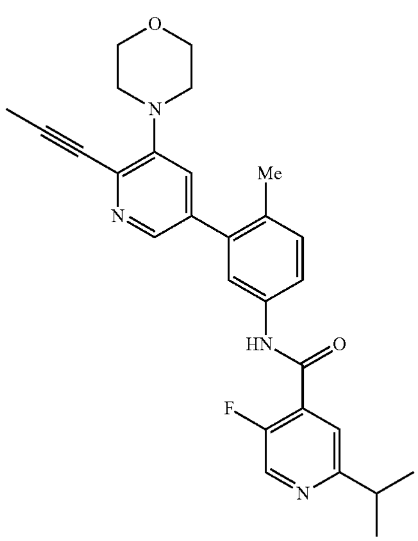 [SMILES: CC#Cc1ncc(-c2cc(NC(=O)c3cc(C(C)C)ncc3F)ccc2C)cc1N1CCOCC1] | 5-fluoro-2-isopropyl-N-(4-methyl-3-(5-morpholino-6-(prop-1-yn-1-yl)pyridin-3-yl)phenyl)isonicotinamide |

TABLE 1-continued

| Synthetic Chemistry Example | Compound Structure | Compound Name |
|---|---|---|
| 35 | 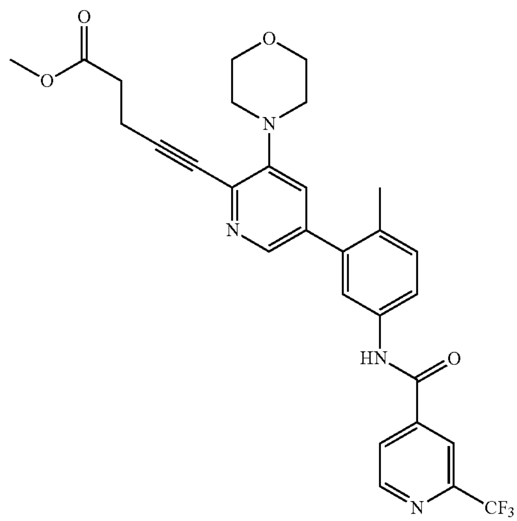 [SMILES: COC(=O)CCC#Cc1ncc(-c2cc(NC(=O)c3ccnc(C(F)(F)F)c3)ccc2C)cc1N1CCOCC1] | methyl-5-(5-(2-methyl-5-(2-(trifluoromethyl)isonicotinamido)phenyl)-3-morpholinopyridin-2-yl)pent-4-ynoate |
| 36 | 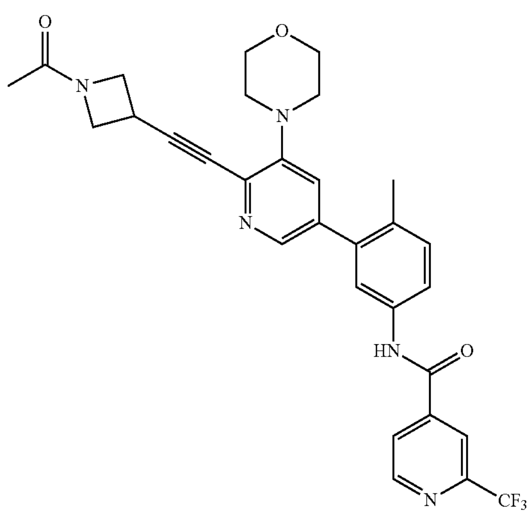 [SMILES: CC(=O)N1CC(C#Cc2ncc(-c3cc(NC(=O)c4ccnc(C(F)(F)F)c4)ccc3C)cc2N2CCOCC2)C1] | N-(3-(6-((1-acetylazetidin-3-yl)ethynyl)-5-morpholinopyridin-3-yl)-4-niethylphenyl)-2-(trifluoromethyl)isonicotinamide |
| 37 | 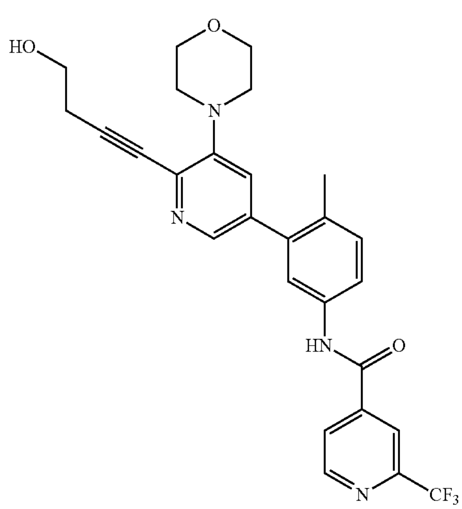 [SMILES: Cc1ccc(NC(=O)c2ccnc(C(F)(F)F)c2)cc1-c1cnc(C#CCCO)c(N2CCOCC2)c1] | N-(3-(6-(4-hydroxybut-1-yn-1-yl)-5-morpholinopyridin-3-yl)-4-methylphenyl)-2-(trifluoromethyl)isonicotinamide |

TABLE 1-continued

| Synthetic Chemistry Example | Compound Structure | Compound Name |
|---|---|---|
| 38 | 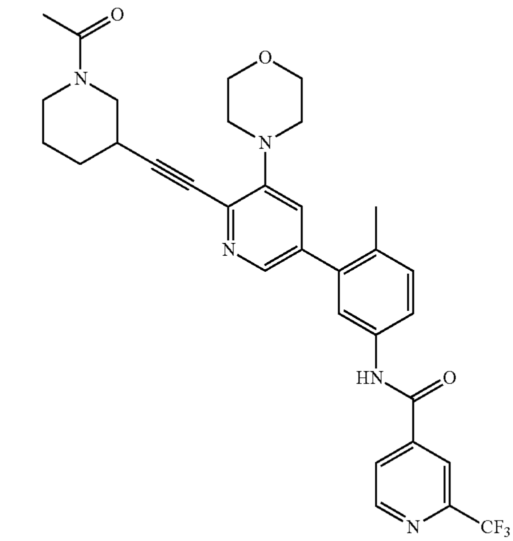 [SMILES: CC(=O)N1CCCC(C#Cc2ncc(-c3cc(NC(=O)c4ccnc(C(F)(F)F)c4)ccc3C)cc2N2CCOCC2)C1] | N-(3-(6-((1-acetylpiperidin-3-yl)ethynyl)-5-morpholinopyridin-3-yl)-4-methylphenyl)-2-(trifluoromethyl)isonicotinainide |
| 39 | 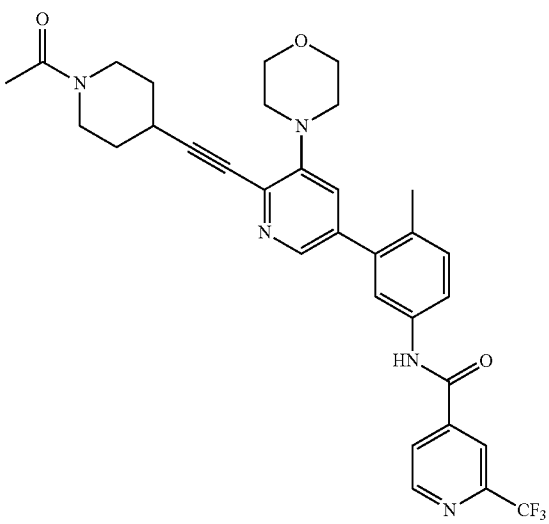 [SMILES: CC(=O)N1CCC(C#Cc2ncc(-c3cc(NC(=O)c4ccnc(C(F)(F)F)c4)ccc3C)cc2N2CCOCC2)CC1] | N-(3-(6-((1-acetylpiperidin-4-yl)ethynyl)-5-morpholinopyridin-3-yl)-4-methylphenyl)-2-(trifluoromethyl)isonicotinamide |
| 40 | 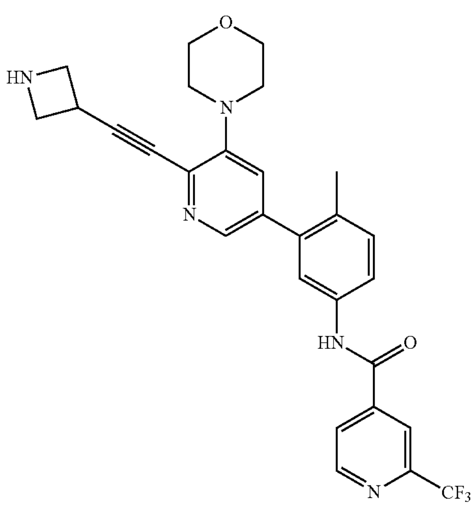 [SMILES: Cc1ccc(NC(=O)c2ccnc(C(F)(F)F)c2)cc1-c1cnc(C#CC2CNC2)c(N2CCOCC2)c1] | N-(3-(6-(azetidin-3-ylethynyl)-5-morpholinopyridin-3-yl)-4-methylphenyl)-2-(trifluoromethyl)isonicotinamide |

TABLE 1-continued

| Synthetic Chemistry Example | Compound Structure | Compound Name |
|---|---|---|
| 41 | 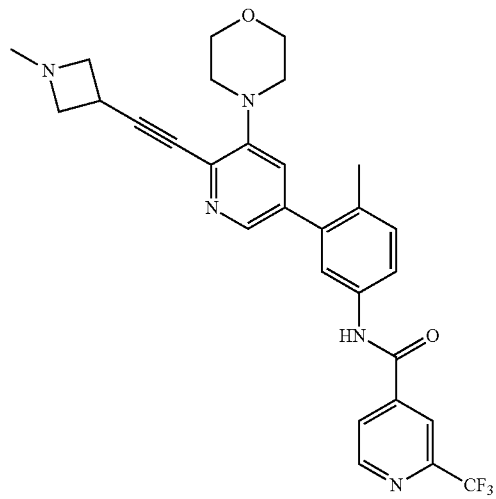 [SMILES: Cc1ccc(NC(=O)c2ccnc(C(F)(F)F)c2)cc1-c1cnc(C#CC2CN(C)C2)c(N2CCOCC2)c1] | N-(4-methyl-3-(6-((1-methylazetidin-3-yl)ethynyl)-5-morpholinopyridin-3-yl)phenyl)-2-(trifluoromethyl)isonicotinamide |
| 42 | 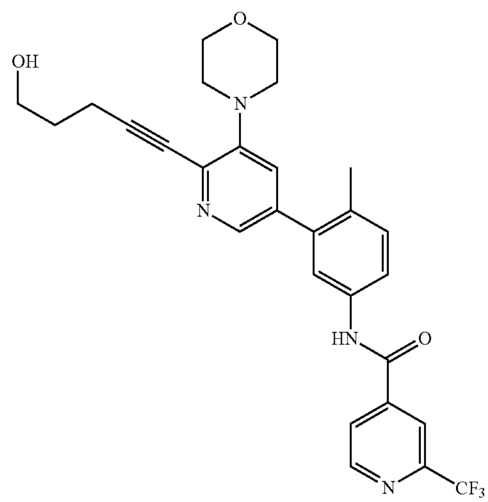 [SMILES: Cc1ccc(NC(=O)c2ccnc(C(F)(F)F)c2)cc1-c1cnc(C#CCCCO)c(N2CCOCC2)c1] | N-(3-(6-(5-hydroxypent-1-yn-1-yl)-5-morpholinopyridin-3-yl)-4-methylphenyl)-2-(trifluoromethyl)isonicotinamide |
| 43 | 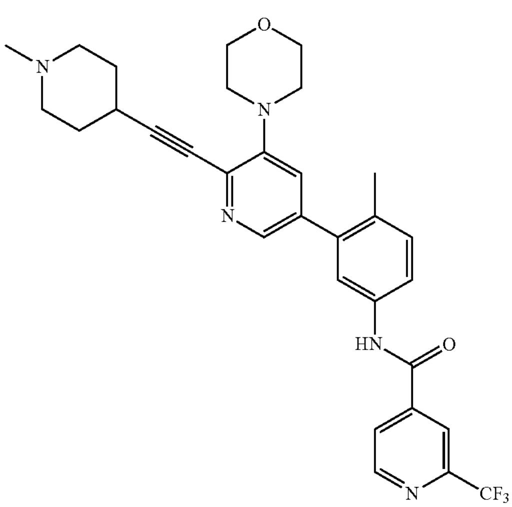 [SMILES: Cc1ccc(NC(=O)c2ccnc(C(F)(F)F)c2)cc1-c1cnc(C#CC2CCN(C)CC2)c(N2CCOCC2)c1] | N-(4-methyl-3-(6-((1-methylpiperidin-4-yl)ethynyl)-5-morpholinopyridin-3-yl)phenyl)-2-(trifluoromethyl)isonicotinamide |

TABLE 1-continued

| Synthetic Chemistry Example | Compound Structure | Compound Name |
|---|---|---|
| 44 | 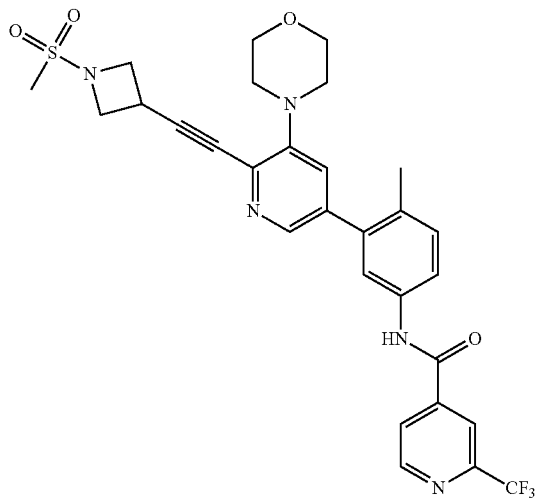 [SMILES: Cc1ccc(NC(=O)c2ccnc(C(F)(F)F)c2)cc1-c1cnc(C#CC2CN(S(C)(=O)=O)C2)c(N2CCOCC2)c1] | N-(4-methyl-3-(6-((1-(methylsulfonyl)azetidin-3-yl)ethynyl)-5-morpholinopyridin-3-yl)phenyl)-2-(trifluoromethyl)isonicotinamide |
| 45 | 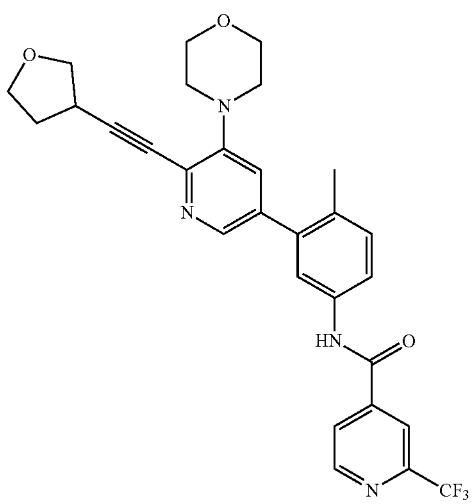 [SMILES: Cc1ccc(NC(=O)c2ccnc(C(F)(F)F)c2)cc1-c1cnc(C#CC2CCOC2)c(N2CCOCC2)c1] | N-(4-methyl-3-(5-morpholino-6-((tetrahydrofuran-3-yl)ethynyl)pyridin-3-yl)phenyl)-2-(trifluoromethyl)isonicotinamide |
| 46 | 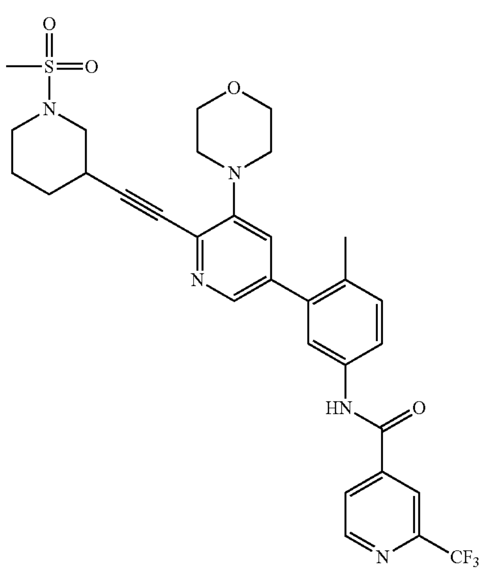 [SMILES: Cc1ccc(NC(=O)c2ccnc(C(F)(F)F)c2)cc1-c1cnc(C#CC2CCCN(S(C)(=O)=O)C2)c(N2CCOCC2)c1] | N-(4-methyl-3-(6-((1-(methylsulfonyl)piperidin-3-yl)ethynyl)-5-morpholinopyridin-3-yl)phenyl)-2-(trifluoromethyl)isonicotinamide |

TABLE 1-continued

| Synthetic Chemistry Example | Compound Structure | Compound Name |
|---|---|---|
| 47 | 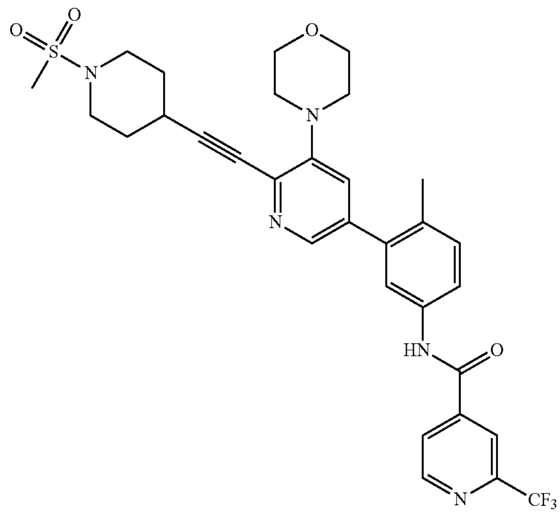 [SMILES: Cc1ccc(NC(=O)c2ccnc(C(F)(F)F)c2)cc1-c1cnc(C#CC2CCN(S(C)(=O)=O)CC2)c(N2CCOCC2)c1] | N-(4-methyl-3-(6-((1-(methylsulfonyl)piperidin-4-yl)ethynyl)-5-morpholinopyridin-3-yl)phenyl)-2-(trifluoromethyl)isonicotinamide |
| 48 | 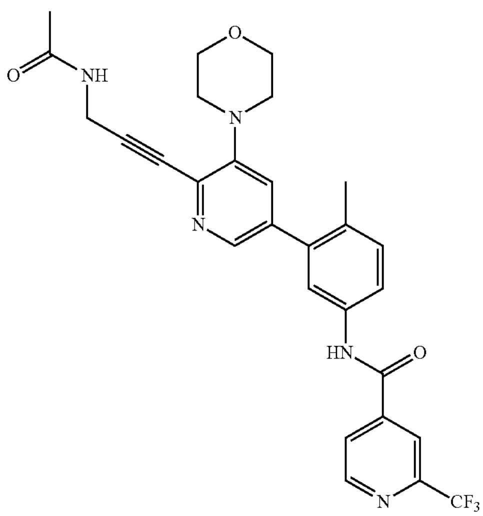 [SMILES: CC(=O)NCC#Cc1ncc(-c2cc(NC(=O)c3ccnc(C(F)(F)F)c3)ccc2C)cc1N1CCOCC1] | N-(3-(6-(3-acetamidoprop-1-yn-1-yl)-5-morpholinopyridin-3-yl)-4-methylphenyl)-2-(trifluoromethyl)isonicotinamide |
| 49 | 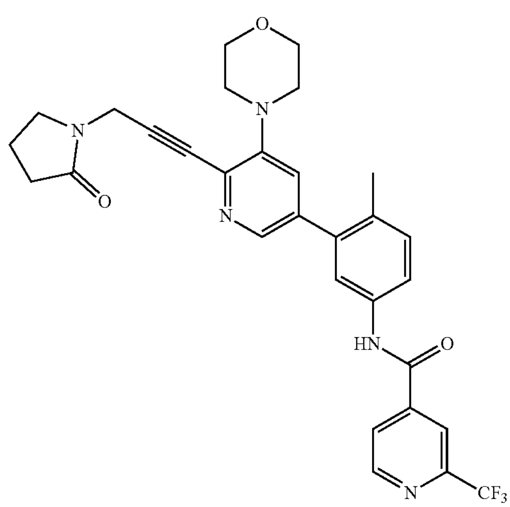 [SMILES: Cc1ccc(NC(=O)c2ccnc(C(F)(F)F)c2)cc1-c1cnc(C#CCN2CCCC2=O)c(N2CCOCC2)c1] | N-(4-methyl-3-(5-morpholino-6-(3-(2-oxopyrrolidin-1-yl)prop-1-yn-1-yl)pyridin-3-yl)phenyl)-2-(trifluoromethyl)isonicotinamide |

TABLE 1-continued

| Synthetic Chemistry Example | Compound Structure | Compound Name |
|---|---|---|
| 50 | 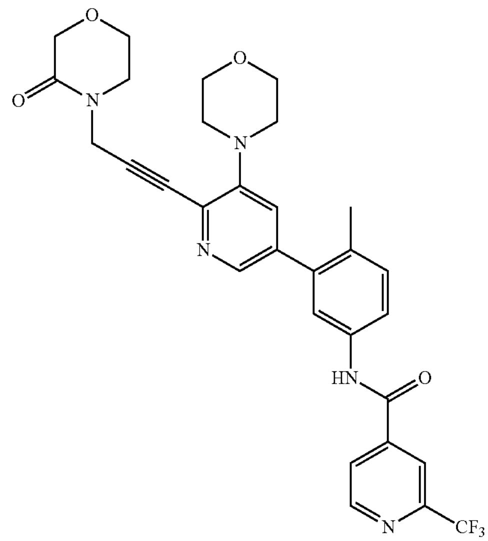 [SMILES: Cc1ccc(NC(=O)c2ccnc(C(F)(F)F)c2)cc1-c1cnc(C#CCN2CCOCC2=O)c(N2CCOCC2)c1] | N-(4-methyl-3-(5-morpholino-6-(3-(3-oxomorpholino)prop-1-yn-1-yl)pyridin-3-yl)phenyl)-2-(trifluoromethyl)isonicotinamide |
| 51 | 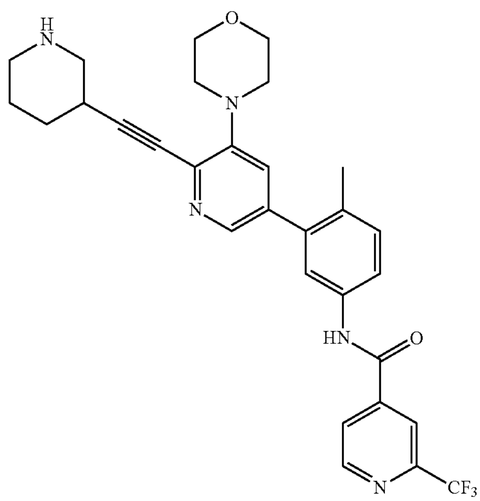 [SMILES: Cc1ccc(NC(=O)c2ccnc(C(F)(F)F)c2)cc1-c1cnc(C#CC2CCCNC2)c(N2CCOCC2)c1] | N-(4-methyl-3-(5-morpholino-6-(piperidin-3-ylethynyl)pyridin-3-yl)phenyl)-2-(trifluoromethyl)isonicotinamide |
| 52 | 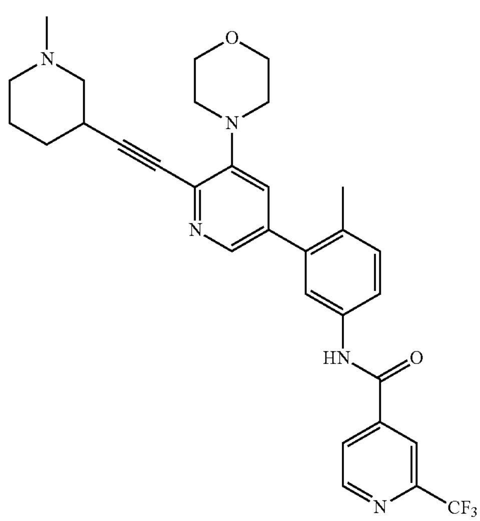 [SMILES: Cc1ccc(NC(=O)c2ccnc(C(F)(F)F)c2)cc1-c1cnc(C#CC2CCCN(C)C2)c(N2CCOCC2)c1] | N-(4-methyl-3-(6-((1-methylpiperidin-3-yl)ethynyl)-5-morpholinopyridin-3-yl)phenyl)-2-(trifluoromethyl)isonicotinamide |

TABLE 1-continued

| Synthetic Chemistry Example | Compound Structure | Compound Name |
|---|---|---|
| 53 | 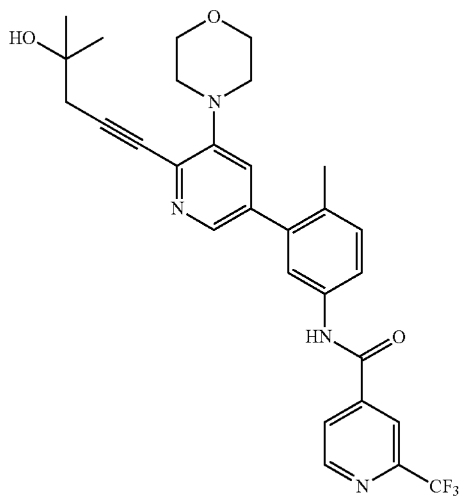 [SMILES: Cc1ccc(NC(=O)c2ccnc(C(F)(F)F)c2)cc1-c1cnc(C#CCC(C)(C)O)c(N2CCOCC2)c1] | N-(3-(6-(4-hydroxy-4-methylpent-1-yn-1-yl)-5-morpliolinopyridin-3-yl)-4-methylphenyl)-2-(trifluoromethyl)isonicotinamide |
| 54 | 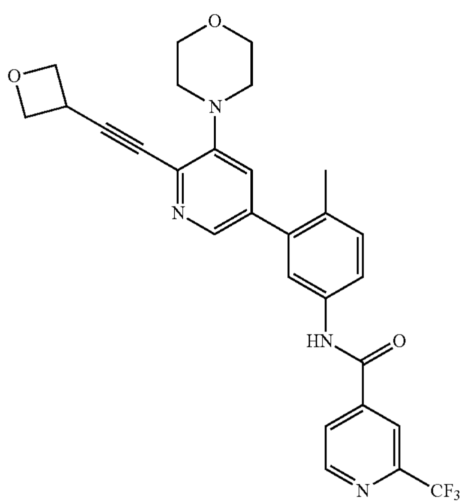 [SMILES: Cc1ccc(NC(=O)c2ccnc(C(F)(F)F)c2)cc1-c1cnc(C#CC2COC2)c(N2CCOCC2)c1] | N-(4-methyl-3-(5-morpholino-6-(oxetan-3-ylethynyl)pyridin-3-yl)phenyl)-2-(trifluoromethyl)isonicotinamide |
| 55 | 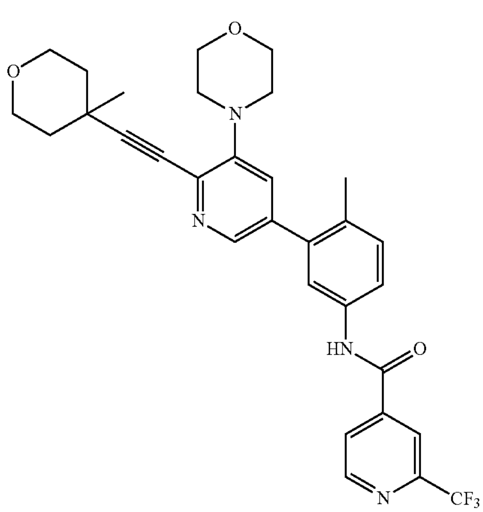 [SMILES: Cc1ccc(NC(=O)c2ccnc(C(F)(F)F)c2)cc1-c1cnc(C#CC2(C)CCOCC2)c(N2CCOCC2)c1] | N-(4-methyl-3-(6-((4-methyltetrahydro-2H-pyran-4-yl)ethynyl)-5-morpholinopyridin-3-yl)phenyl)-2-(trifluoromethyl)isonicotinamide |

TABLE 1-continued

| Synthetic Chemistry Example | Compound Structure | Compound Name |
|---|---|---|
| 56 | 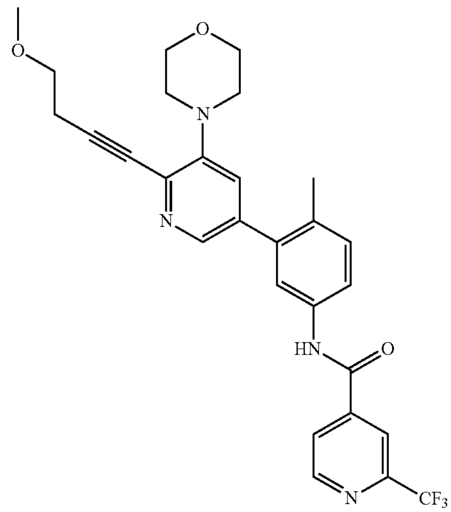 [SMILES: COCCC#Cc1ncc(-c2cc(NC(=O)c3ccnc(C(F)(F)F)c3)ccc2C)cc1N1CCOCC1] | N-(3-(6-(4-methoxybut-1-yn-1-yl)-5-morpholinopyridin-3-yl)-4-methylphenyl)-2-(trifluoromethyl)isonicotinamide |
| 57 | 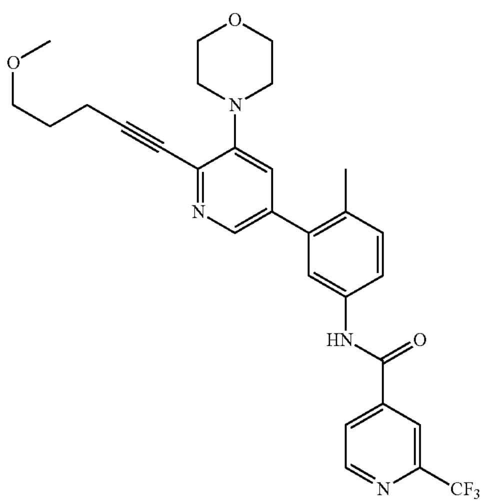 [SMILES: COCCCC#Cc1ncc(-c2cc(NC(=O)c3ccnc(C(F)(F)F)c3)ccc2C)cc1N1CCOCC1] | N-(3-(6-(5-methoxypent-1-yn-1-yl)-5-morpholinopyridin-3-yl)-4-methylphenyl)-2-(trifluoromethyl)isonicotinamide |
| 58 | 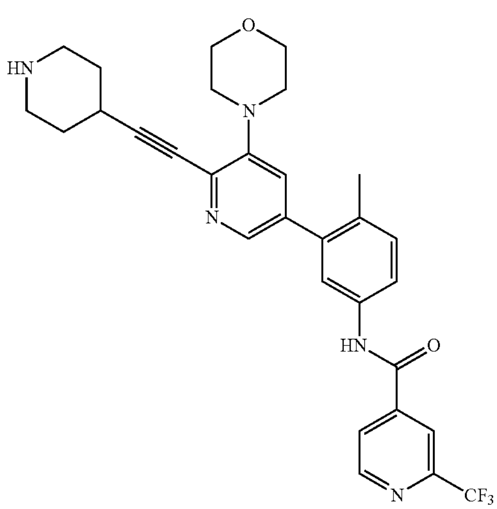 [SMILES: Cc1ccc(NC(=O)c2ccnc(C(F)(F)F)c2)cc1-c1cnc(C#CC2CCNCC2)c(N2CCOCC2)c1] | N-(4-methyl-3-(5-morpholino-6-(piperidin-4-ylethynyl)pyridin-3-yl)phenyl)-2-(tiifluoromethyl)isonicotinamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heteroaromatic RAF kinase inhibitory compound described herein is administered as a pure chemical. In other embodiments, the heteroaromatic RAF kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one heteroaromatic RAF kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), (II), (III), or ($R^a$), or a pharmaceutically acceptable salt or solvate thereof.

One embodiment provides a method of preparing a pharmaceutical composition comprising mixing a compound of Formula (I), (II), (III), or ($R^a$), or a pharmaceutically acceptable salt or solvate thereof, and a pharmaceutically acceptable carrier.

In certain embodiments, the heteroaromatic RAF kinase inhibitory compound as described by Formula (I), (II), (III), or ($R^a$), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

In some embodiments, the heteroaromatic RAF kinase inhibitory compound as described by Formula (I), (II), (III), or ($R^a$), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic RAF kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of cancer or neoplastic disease.

One embodiment provides a use of a compound of Formula (I), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient.

One embodiment provides a compound of Formula (II), or a pharmaceutically acceptable salt or solvate thereof, for use in a method of treatment of the human or animal body.

One embodiment provides a compound of Formula (II), or a pharmaceutically acceptable salt or solvate thereof, for use in a method of treatment of cancer or neoplastic disease.

One embodiment provides a use of a compound of Formula (II), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (II), or a pharmaceutically acceptable salt or solvate thereof. In some embodiments, described herein is a method of treating cancer in a patient in need thereof comprising administering to the patient a pharmaceutical composition comprising a compound of Formula (II), or a pharmaceutically acceptable salt or solvate thereof, and a pharmaceutically acceptable excipient.

One embodiment provides a compound of Formula (III), or a pharmaceutically acceptable salt or solvate thereof, for use in a method of treatment of the human or animal body.

One embodiment provides a compound of Formula (III), or a pharmaceutically acceptable salt or solvate thereof, for use in a method of treatment of cancer or neoplastic disease.

One embodiment provides a use of a compound of Formula (III), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (III), or a pharmaceutically acceptable salt or solvate thereof. In some embodiments, described herein is a method of treating cancer in a patient in need thereof comprising administering to the patient a pharmaceutical composition comprising a compound of Formula (III), or a pharmaceutically acceptable salt or solvate thereof, and a pharmaceutically acceptable excipient.

One embodiment provides a compound of Formula ($R^a$), or a pharmaceutically acceptable salt or solvate thereof, for use in a method of treatment of the human or animal body.

One embodiment provides a compound of Formula ($R^a$), or a pharmaceutically acceptable salt or solvate thereof, for use in a method of treatment of cancer or neoplastic disease.

One embodiment provides a use of a compound of Formula ($R^a$), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula ($R^a$), or a pharmaceutically acceptable salt or solvate thereof. In some embodiments, described herein is a method of treating cancer in a patient in need thereof comprising administering to the patient a pharmaceutical composition comprising a compound of Formula ($R^a$), or a pharmaceutically acceptable salt or solvate thereof, and a pharmaceutically acceptable excipient.

Provided herein is the method wherein the pharmaceutical composition is administered orally.

Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic RAF kinase inhibitory compounds disclosed herein are synthesized according to the following examples. As used below, and throughout the description of the invention, the following abbreviations, unless otherwise indicated, shall be understood to have the following meanings:

° C. degrees Celsius $\delta_H$ chemical shift in parts per million downfield from tetramethylsilane DCM dichloromethane ($CH_2Cl_2$)

DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
M+ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Intermediate 1: Tert-butyl N-(1-{2-[4-chloro-6-(morpholin-4-yl)pyridin-2-yl]ethynyl}cyclopropyl) carbamate

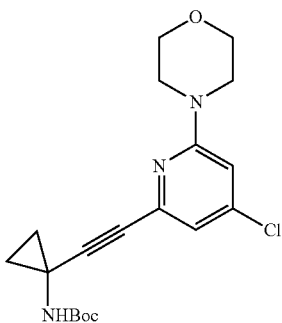

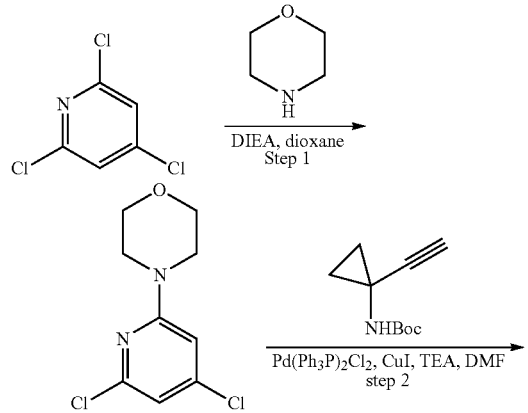

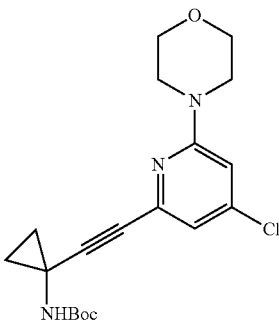

Step 1: 4-(4,6-Dichloropyridin-2-yl)morpholine

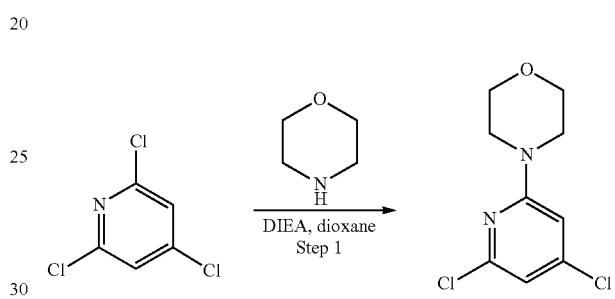

To a stirred mixture of 2,4,6-trichloropyridine (29.2 g, 160.061 mmol), morpholine (14 mL, 160.061 mmol) in 1,4-dioxane (160 mL) was added DIEA (28 mL, 160.061 mmol). The reaction mixture was stirred for 16 h at 85° C. under nitrogen atmosphere. The resulting mixture was allowed to cool down to room temperature. The reaction was quenched with water (700 mL). The resulting mixture was extracted with EtOAc (3×600 mL). The combined organic layers was washed with brine (3×400 mL), dried over anhydrous $Na_2SO_4$. After filtration, the filtrate was concentrated under reduced pressure. The residue was purified by silica gel column chromatography, eluted with PE/EA (3/1). The fractions contained desired product were combined and concentrated to afford 4-(4,6-dichloropyridin-2-yl)morpholine (24.77 g, 66%) as a white solid. MS ESI calculated for $C_9H_{10}Cl_2N_2O$ [M+H]+, 233.02; found 233.00. $^1$H NMR (400 MHz, Chloroform-d) δ 6.68 (d, J=1.6 Hz, 1H), 6.49 (d, J=1.2 Hz, 1H), 3.82-3.80 (m, 4H), 3.55-3.52 (m, 4H).

Step 2: Tert-butyl N-(1-{2-[4-chloro-6-(morpholin-4-yl)pyridin-2-yl]ethynyl}cyclopropyl)carbamate

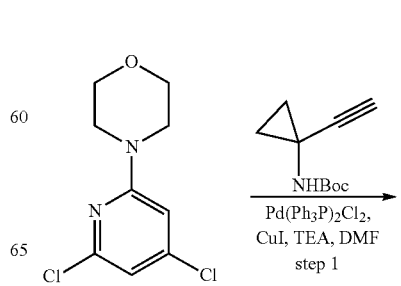

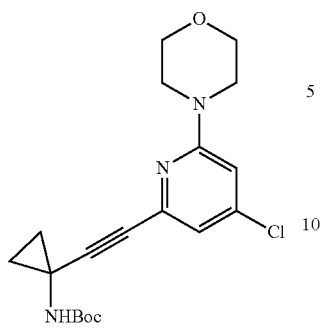

To a stirred mixture of 4-(4,6-dichloropyridin-2-yl)morpholine (350 mg, 1.502 mmol), tert-butyl N-(1-ethynylcyclopropyl)carbamate (353 mg, 1.953 mmol), Pd(PPh₃)₂Cl₂ (105 mg, 0.150 mmol) and CuI (57 mg, 0.300 mmol) in DMF (5 mL) was added TEA (1 mL). The reaction mixture was stirred for 4 h at 80° C. under nitrogen atmosphere. The resulting mixture was quenched with water (30 mL). The resulting mixture was extracted with EtOAc (3×25 mL). The combined organic layers was washed with brine (20 mL), dried over anhydrous Na₂SO₄. After filtration, the filtrate was concentrated under reduced pressure. The residue was purified by silica gel column chromatography, eluted with PE/EtOAc (2/1). The fractions contained desired product were combined and concentrated to afford tert-butyl N-(1-{2-[4-chloro-6-(morpholin-4-yl)pyridin-2-yl]ethynyl}cyclopropyl)carbamate (350 mg, 62%) as a light yellow solid. MS ESI calculated for $C_{19}H_{24}ClN_3O_3$ [M+H]⁺, 378.15, 380.15, found 378.05, 380.05. ¹H NMR (400 MHz, Chloroform-d) δ 6.78 (s, 1H), 6.54 (d, J=1.6 Hz, 1H), 5.10 (s, 1H), 3.83-3.77 (m, 4H), 3.54-3.49 (m, 4H), 1.49 (s, 9H), 1.37-1.34 (m, 2H), 1.24-1.20 (m, 2H).

Intermediate 2: (2R)-4-[5-Chloro-3-(morpholin-4-yl)pyridin-2-yl]but-3-yn-2-ol

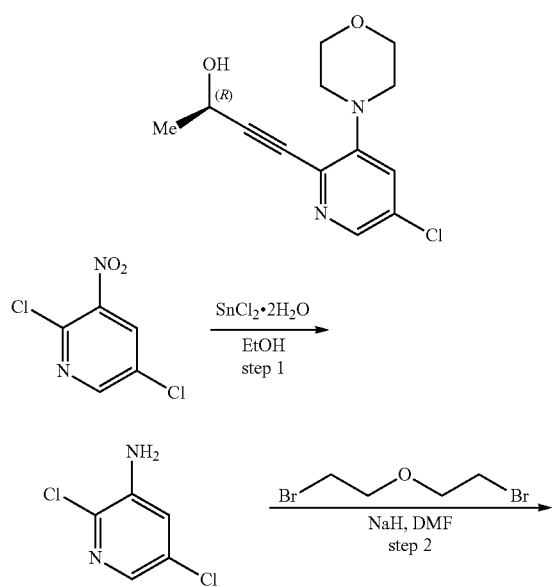

Step 1: 2,5-Dichloropyridin-3-amine

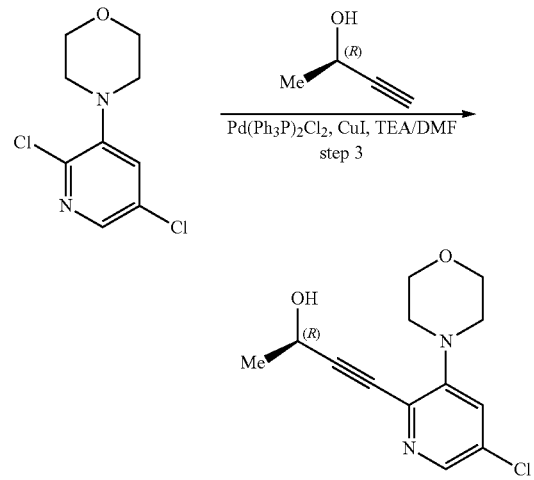

To a stirred mixture of 2,5-dichloro-3-nitropyridine (5.00 g, 25.909 mmol) in EtOH (50 mL) was added SnCl₂·2H₂O (29.00 g, 129.545 mmol) in portions at room temperature. The resulting mixture was stirred for 16 h at 70° C. under nitrogen atmosphere. The resulting mixture was concentrated under reduced pressure. The residue was basified to pH 8 with saturated Na₂CO₃ (aq.) (200 mL). The resulting mixture was filtered, the filter cake was washed with EtOAc (3×50 mL). The combined filtrates were extracted with EtOAc (3×100 mL). The combined organic layers were washed with brine (100 mL), dried over anhydrous Na₂SO₄. After filtration, the filtrate was concentrated under reduced pressure. The residue was purified by silica gel column chromatography, eluted with PE/EtOAc (4/1). The fractions contained desired product were combined and concentrated to afford 2,5-dichloropyridin-3-amine (3.00 g, 82%) as a light yellow solid. MS ESI calculated for $C_5H_4Cl_2N_2$ [M−H]⁻, 160.98, 162.98, 164.98; found 161.20, 163.20, 165.20. ¹H NMR (300 MHz, Chloroform-d) δ 7.76-7.75 (m, 1H), 7.06-7.05 (m, 1H), 4.14 (brs, 2H).

Step 2: 4-(2,5-Dichloropyridin-3-yl)morpholine

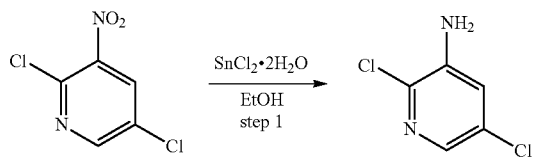 [SMILES: O=[N+]([O-])c1cc(Cl)cnc1Cl ; Nc1cc(Cl)cnc1Cl]

-continued

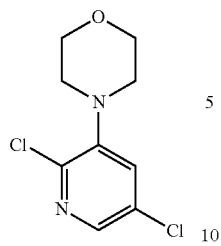

To a stirred mixture of 2,5-dichloropyridin-3-amine (3.00 g, 18.405 mmol) and NaH (2.00 g, 46.013 mmol, 60%) in DMF (30 mL) was added 1-bromo-2-(2-bromoethoxy)ethane (6.00 g, 27.608 mmol). The reaction mixture was stirred for 5 h at room temperature. The reaction was quenched by the addition of water (100 mL) at room temperature. The resulting mixture was extracted with EtOAc (3×100 mL). The combined organic layers was washed with brine (100 mL), dried over anhydrous Na$_2$SO$_4$. After filtration, the filtrate was concentrated under reduced pressure. The residue was purified by silica gel column chromatography, eluted with PE/EtOAc (5/1). The fractions contained desired product were combined and concentrated to afford 4-(2,5-dichloropyridin-3-yl)morpholine (3.00 g, 70%) as an orange solid. MS ESI calculated for C$_9$H$_{10}$Cl$_2$N$_2$O [M+H]$^+$, 233.02, 235.02, 237.02; found 232.95, 234.95, 236.95. $^1$H NMR (400 MHz, Chloroform-d) δ 8.06-8.05 (m, 1H), 7.30-7.29 (m, 1H), 3.91-3.80 (m, 4H), 3.12-3.09 (m, 4H).

Step 3: (2R)-4-[5-Chloro-3-(morpholin-4-yl)pyridin-2-yl]but-3-yn-2-ol

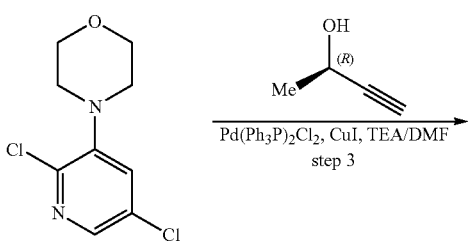

-continued

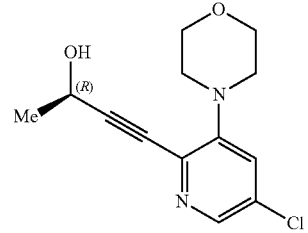

To a stirred mixture of 4-(2,5-dichloropyridin-3-yl)morpholine (600 mg, 2.574 mmol), (2R)-but-3-yn-2-ol (360 mg, 5.148 mmol), Pd(PPh$_3$)$_2$Cl$_2$ (181 mg, 0.257 mmol) and CuI (98 mg, 0.515 mmol) in DMF (6 mL) was added TEA (1 mL). The reaction mixture was degassed with nitrogen for three times and stirred for 3 h at 80° C. under argon atmosphere. The reaction mixture was allowed to cool down to room temperature. The reaction was quenched by the addition of water (2 mL) at room temperature. The residue was purified by reverse flash chromatography with the following conditions: column, C18 silica gel; mobile phase, CH$_3$CN in water (10 mmol/L NH$_4$HCO$_3$), 15% to 50% gradient in 20 min; detector, UV 254 nm. The fractions contained desired product were combined and concentrated to afford (2R)-4-[5-chloro-3-(morpholin-4-yl)pyridin-2-yl]but-3-yn-2-ol (500 mg, 73%) as yellow oil. MS ESI calculated for C$_{13}$H$_{15}$ClN$_2$O$_2$ [M+H]$^+$, 267.08, 269.08; found 267.05, 269.05. $^1$H NMR (400 MHz, DMSO-d$_6$) δ 8.17-8.16 (m, 1H), 7.45-7.49 (m, 1H), 5.57-5.56 (m, 1H), 4.68-4.61 (m, 1H), 3.77-3.74 (m, 4H), 3.19-3.17 (m, 4H), 1.39 (d, J=6.6 Hz, 3H).

The following compounds in Table 2 were prepared using procedures similar to those described in Intermediate 2 using appropriate starting materials.

TABLE 2

| Entry | Structure | IUPACName | Exact Mass [M + H]$^+$ |
|---|---|---|---|
| 3 | 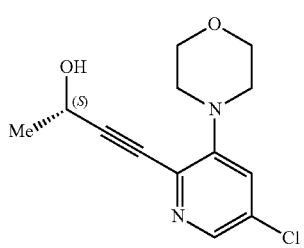 | (2S)-4-[5-Chloro-3-(morpholin-4-yl)pyridin-2-yl]but-3-yn-2-ol | Calc'd 267.08, 269.08, found 267.00, 269.00 |

TABLE 2-continued

| Entry | Structure | IUPACName | Exact Mass [M + H]+ |
|---|---|---|---|
| 4 | 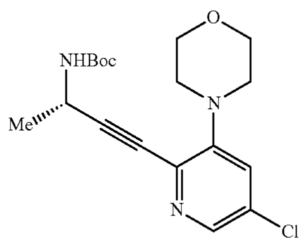 [SMILES: C[C@@H](C#Cc1ncc(Cl)cc1N1CCOCC1)NC(=O)OC(C)(C)C] | Tert-butyl N-[(2R)-4-[5-chloro-3-(morpholin-4-yl)pyridin-2-yl]but-3-yn-2-yl]carbamate | Calc'd 366.20, 368.20, found 366.10, 368.10 |
| 5 | 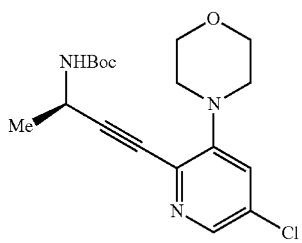 [SMILES: C[C@H](C#Cc1ncc(Cl)cc1N1CCOCC1)NC(=O)OC(C)(C)C] | Tert-butyl N-[(2R)-4-[5-chloro-3-(morpholin-4-yl)pyridin-2-yl]but-3-yn-2-yl]carbamate | Calc'd 366.20, 368.20, found 366.10, 368.10 |
| 6 | 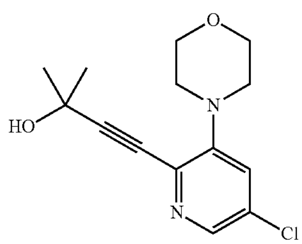 [SMILES: CC(C)(O)C#Cc1ncc(Cl)cc1N1CCOCC1] | 4-[5-Chloro-3-(morpholin-4-yl)pyridin-2-yl]-2-methylbut-3-yn-2-ol | Calc'd 281.10, 283.10; found 281.15, 283.15 |
| 7 | 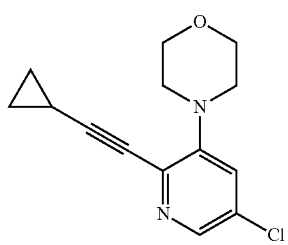 [SMILES: Clc1cnc(C#CC2CC2)c(N2CCOCC2)c1] | 4-[5-Chloro-2-(2-cyclopropylethynyl)pyridin-3-yl]morpholine | Calc'd 263.09, 265.09; found 263.10, 265.10 |
| 8 | 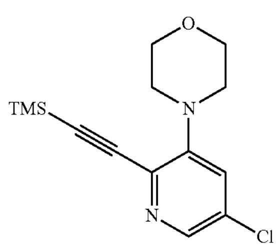 [SMILES: C[Si](C)(C)C#Cc1ncc(Cl)cc1N1CCOCC1] | 4-{5-Chloro-2-[2-(trimethylsilyl)ethynyl]pyridin-3-yl}morpholine | Calc'd 295.10, 297.10; found 295.15, 297.15 |
| 9 | 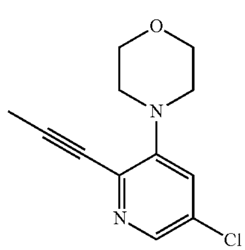 [SMILES: CC#Cc1ncc(Cl)cc1N1CCOCC1] | 4-[5-Chloro-2-(prop-1-yn-1-yl)pyridin-3-yl]morpholine | Calc'd 237.07, 239.07; found 237.10, 239.10 |

Intermediate 10: N-(4-Methyl-3-(4,4,5,5-tetramethyl-1,3,2-dioxaborolan-2-yl)phenyl)-2-(trifluoromethyl)isonicotinamide

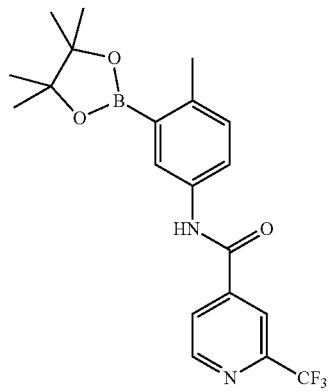 [SMILES: Cc1ccc(NC(=O)c2ccnc(C(F)(F)F)c2)cc1B1OC(C)(C)C(C)(C)O1]

Step 1: N-(4-Methyl-3-(4,4,5,5-tetramethyl-1,3,2-dioxaborolan-2-yl)phenyl)-2-(trifluoromethyl)isonicotinamide

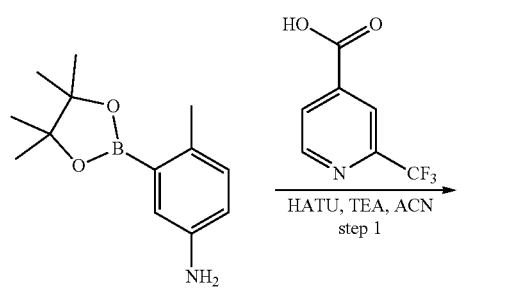

To a stirred solution of 4-methyl-3-(4,4,5,5-tetramethyl-1,3,2-dioxaborolan-2-yl)aniline (2.00 g, 7.965 mmol) and 2-(trifluoromethyl)pyridine-4-carboxylic acid (1.67 g, 8.761 mmol) in CH$_3$CN (15 mL) were added HATU (4.54 g, 11.947 mmol) and TEA (1.61 g, 15.930 mmol). The resulting mixture was stirred for 16 h at room temperature. The resulting mixture was diluted with water (50 mL) and extracted with EtOAc (3×50 mL). The combined organic layers was washed with brine (50 mL), dried over anhydrous Na$_2$SO$_4$. After filtration, the filtrate was concentrated under reduced pressure. The residue was purified by silica gel column chromatography, eluted with PE/EtOAc (1/1). The fractions contained desired product were combined and concentrated to afford N-(4-methyl-3-(4,4,5,5-tetramethyl-1,3,2-dioxaborolan-2-yl)phenyl)-2-(trifluoromethyl)isonicotinamide (1.50 g, 44%) as a yellow solid. MS ESI calculated for C$_{20}$H$_{22}$BF$_3$N$_2$O$_3$ [M+H]$^+$, 407.17, found 407.15. $^1$H NMR (400 MHz, Chloroform-d) δ 8.95-8.94 (m, 1H), 8.58-8.55 (d, J=8.9 Hz, 1H), 8.16 (s, 1H), 7.98-7.93 (m, 3H), 7.02-6.97 (m, 1H), 2.55 (s, 3H), 1.36 (s, 12H).

Example 1: N-(3-[2-[(3R)-3-hydroxybut-1-yn-1-yl]-6-(morpholin-4-yl)pyridin-4-yl]-4-methylphenyl)-2-(trifluoromethyl)pyridine-4-carboxamide

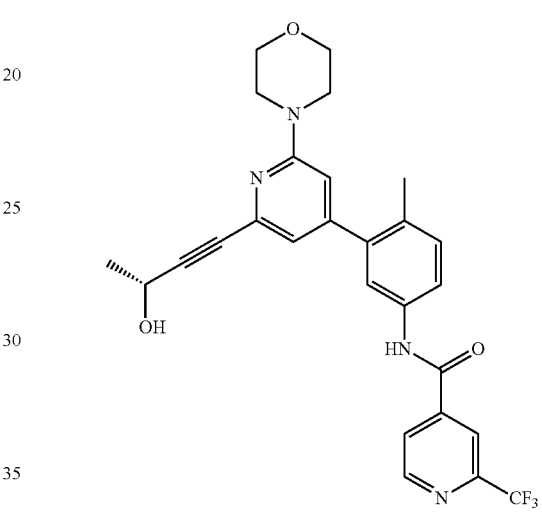

Synthetic Scheme

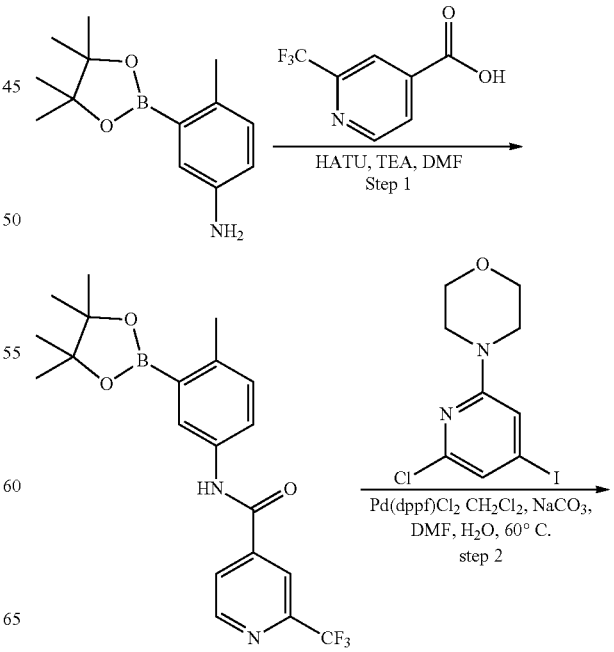

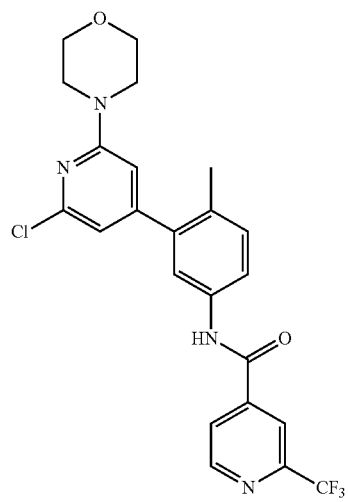
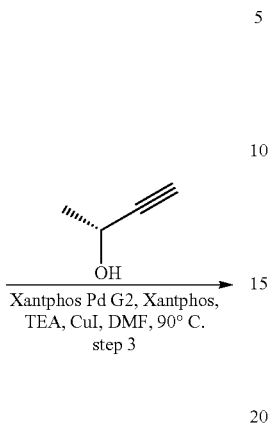
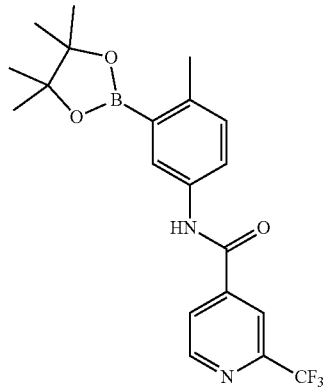

To a stirred solution of 2-(trifluoromethyl)pyridine-4-carboxylic acid (1.23 g, 6.43 mmol) and HATU (3.26 g, 8.58 mmol) in DMF (10 mL) were added TEA (2.38 mL, 23.57 mmol) and 4-methyl-3-(4,4,5,5-tetramethyl-1,3,2-dioxaborolan-2-yl)aniline (1 g, 4.29 mmol). The reaction mixture was stirred for 1.5 h at room temperature. The resulting mixture was diluted with water (30 mL) and extracted with EtOAc (3×80 mL). The combined organic layers were washed with brine (5×40 mL), dried over anhydrous $Na_2SO_4$ and filtered. The filtrate was concentrated under reduced pressure. The residue was purified by silica gel column chromatography, eluted with 25% EtOAc in PE to afford N-(4-methyl-3-(4,4,5,5-tetramethyl-1,3,2-dioxaborolan-2-yl)phenyl)-2-(trifluoromethyl)isonicotinamide (1.45 g, 83%) as an off-white solid. MS ESI calculated for $C_{20}H_{22}BF_3N_2O_3$ [M+H]$^+$, 407.17, found 407.10. $^1$H NMR (300 MHz, DMSO-$d_6$) δ 10.64 (s, 1H), 9.00 (d, J=5.0 Hz, 1H), 8.42 (d, J=1.4 Hz, 1H), 8.27-8.19 (m, 1H), 8.00-7.88 (m, 2H), 7.23 (d, J=8.2 Hz, 1H), 2.47 (s, 3H), 1.33 (s, 12H). $^{19}$F NMR (282 MHz, DMSO-$d_6$) δ −66.48.

Preparation 1B: N-(3-(2-chloro-6-morpholinopyridin-4-yl)-4-methylphenyl)-2-(trifluoromethyl)isonicotinamide

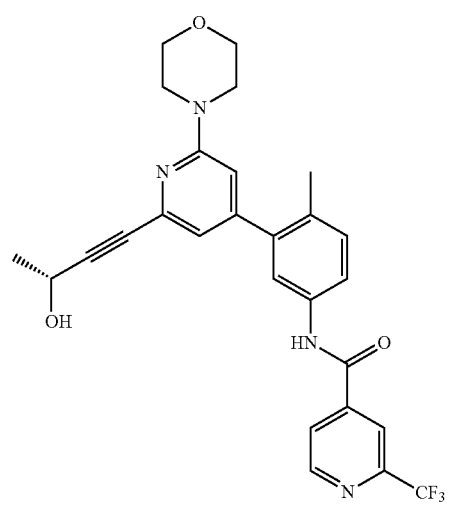 [SMILES: Cc1ccc(NC(=O)c2ccnc(C(F)(F)F)c2)cc1-c1cc(C#C[C@@H](C)O)nc(N2CCOCC2)c1]

Preparation 1A: N-(4-methyl-3-(4,4,5,5-tetramethyl-1,3,2-dioxaborolan-2-yl)phenyl)-2-(trifluoromethyl)isonicotinamide

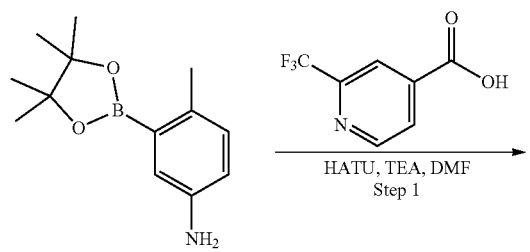

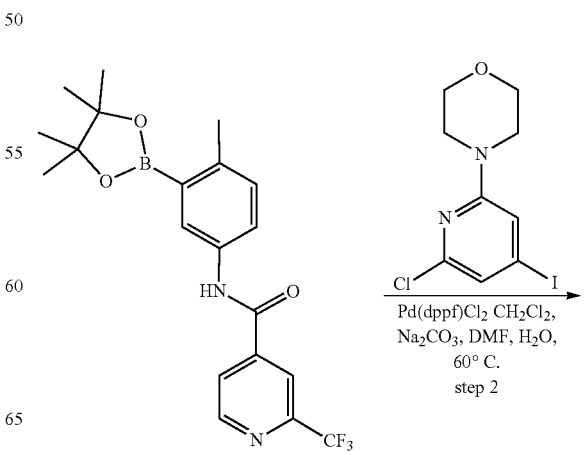

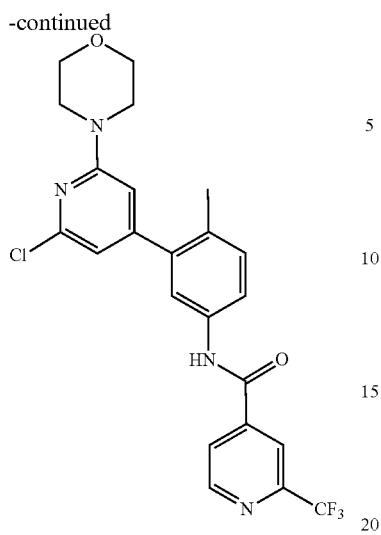

A mixture of 4-(6-chloro-4-iodopyridin-2-yl)morpholine (2.00 g, 6.162 mmol), N-[4-methyl-3-(4,4,5,5-tetramethyl-1,3,2-dioxaborolan-2-yl)phenyl]-2-(trifluoromethyl)pyridine-4-carboxamide (2.50 g, 6.162 mmol), Na$_2$CO$_3$ (1.96 g, 18.486 mmol) and Pd(dppf)Cl$_2$·CH$_2$Cl$_2$ (502 mg, 0.616 mmol) in DMF (40 mL) and H$_2$O (10 mL) was stirred at 60 degrees C. for 2 h under N$_2$ atmosphere. The reaction was quenched with water (50 mL) at room temperature. The resulting mixture was extracted with EtOAc (100 mL). The combined organic layers were washed with brine (3×50 mL), dried over anhydrous Na$_2$SO$_4$. After filtration, the filtrate was concentrated under reduced pressure. The residue was purified by silica gel column chromatography, eluted with PE/EtOAc (1/1) to afford N-(3-(2-chloro-6-morpholinopyridin-4-yl)-4-methylphenyl)-2-(trifluoromethyl)isonicotinamide (2 g, 68%) as a brown solid. MS ESI calculated for C$_{23}$H$_{20}$ClF$_3$N$_4$O$_2$ [M+H]$^+$, 477.12; found 477.20. $^1$H NMR (400 MHz, chloroform-d) δ 8.94-8.87 (m, 1H), 8.23 (s, 1H), 8.12 (s, 1H), 7.94 (s, 1H), 7.60-7.47 (m, 2H), 7.30 (s, 1H), 6.62 (s, 1H), 6.43 (s, 1H), 3.83 (t, J=4.4 Hz, 4H), 3.55 (t, J=4.7 Hz, 4H), 2.28 (s, 3H).

Preparation 1: N-(3-[2-[(3R)-3-hydroxybut-1-yn-1-yl]-6-(morpholin-4-yl)pyridin-4-yl]-4-methylphenyl)-2-(trifluoromethyl)pyridine-4-carboxamide

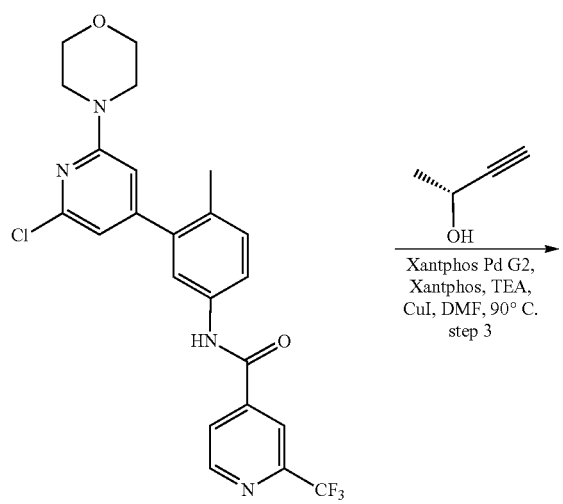

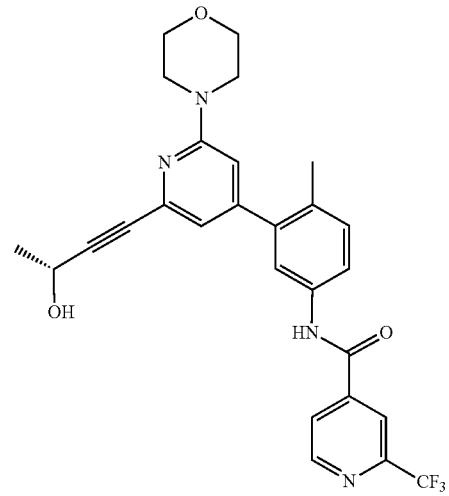

A mixture of (2R)-but-3-yn-2-ol (88 mg, 1.258 mmol), N—[3-[2-chloro-6-(morpholin-4-yl)pyridin-4-yl]-4-methylphenyl]-2-(trifluoromethyl)pyridine-4-carboxamide (300 mg, 0.629 mmol), XantPhos (36 mg, 0.063 mmol), 2nd Generation XantPhos precatalyst (56 mg, 0.063 mmol), CuI (6 mg, 0.031 mmol) and TEA (191 mg, 1.887 mmol) in DMF (5 mL) was stirred at 90 degrees C. for 16 h under N$_2$ atmosphere. The mixture was allowed to cool down to room temperature. The reaction was quenched with water (20 mL). The resulting mixture was extracted with EtOAc (50 mL). The combined organic layers were washed with brine (3×50 mL), dried over anhydrous Na$_2$SO$_4$. After filtration, the filtrate was concentrated under reduced pressure. The residue was purified by Prep-TLC with PE/EtOAc (1/1). The crude was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 60% B in 30 min; 254/220 nm to afford N-(3-[2-[(3R)-3-hydroxybut-1-yn-1-yl]-6-(morpholin-4-yl)pyridin-4-yl]-4-methylphenyl)-2-(trifluoromethyl)pyridine-4-carboxamide (193 mg, 60%) as a light yellow solid. MS ESI calculated for C$_{27}$H$_{25}$F$_3$N$_4$O$_3$ [M+H]$^+$, 511.19 found 511.05. $^1$H NMR (400 MHz, chloroform-d) δ 8.94 (d, J=5.0 Hz, 1H), 8.13 (s, 1H), 8.07 (s, 1H), 7.97-7.92 (m, 1H), 7.60 (d, J=8.6 Hz, 1H), 7.50 (d, J=2.4 Hz, 1H), 7.32 (d, J=8.3 Hz, 1H), 6.82 (d, J=1.2 Hz, 1H), 6.54 (d, J=1.2 Hz, 1H), 4.78-4.75 (m, 1H), 3.86-3.79 (m, 4H), 3.59-3.51 (m, 4H), 2.29 (s, 3H), 1.57 (d, J=6.7 Hz, 3H). $^{19}$F NMR (376 MHz, chloroform-d) δ −67.99 (3F).

Example 2: N-(3-[2-[(3S)-3-hydroxybut-1-yn-1-yl]-6-(morpholin-4-yl)pyridin-4-yl]-4-methylphenyl)-2-(trifluoromethyl)pyridine-4-carboxamide

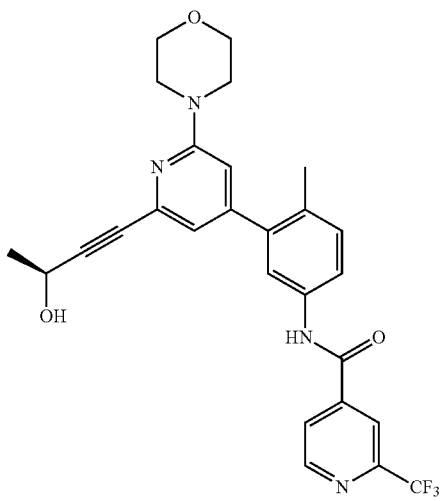 [SMILES: Cc1ccc(NC(=O)c2ccnc(C(F)(F)F)c2)cc1-c1cc(C#C[C@H](C)O)nc(N2CCOCC2)c1]

Preparation 2: N-(3-[2-[(3S)-3-hydroxybut-1-yn-1-yl]-6-(morpholin-4-yl)pyridin-4-yl]-4-methylphenyl)-2-(trifluoromethyl)pyridine-4-carboxamide

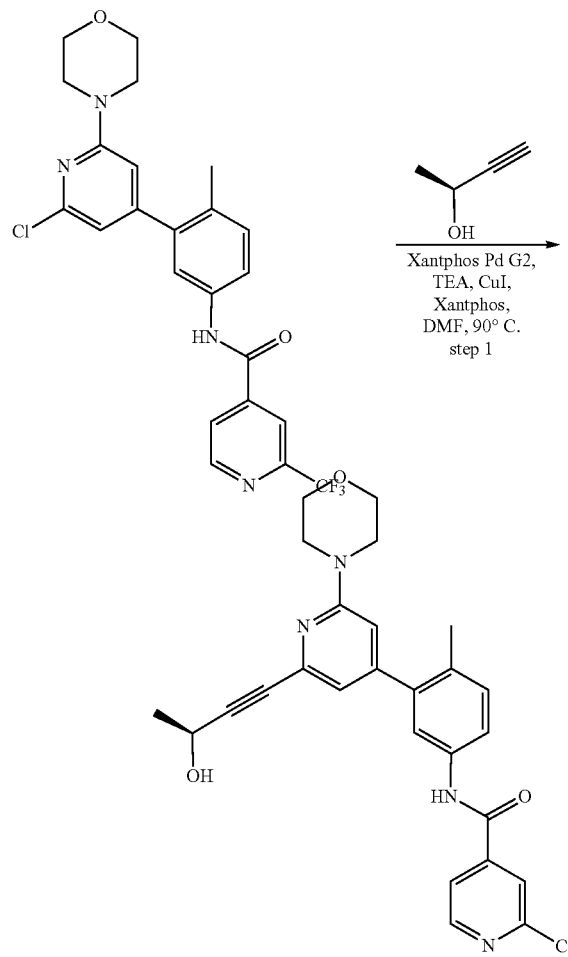

A mixture of N-[3-[2-chloro-6-(morpholin-4-yl)pyridin-4-yl]-4-methylphenyl]-2-(trifluoromethyl)pyridine-4-carboxamide (300 mg, 0.629 mmol), (2S)-but-3-yn-2-ol (88 mg, 1.258 mmol), XantPhos (36 mg, 0.063 mmol), DMF (6 mL), 2nd Generation XantPhos precatalyst (56 mg, 0.063 mmol), CuI (6 mg, 0.031 mmol) and TEA (191 mg, 1.887 mmol) was stirred for 16 h at 90 degrees C. under a nitrogen atmosphere. The resulting mixture was concentrated under reduced pressure. The residue was purified by reverse phase flash chromatography with the following conditions: Column: Spherical C18, 20-40 um, 120 g; Mobile Phase A: water (plus 5 mM $NH_4HCO_3$); Mobile Phase B: $CH_3CN$; Flow rate: 50 mL/min; Gradient: 5%-5% B, 10 min, 40% B-65% B gradient in 25 min; Detector: 220 nm. The fractions containing the desired product were collected at 61% B and concentrated under reduced pressure to afford N-(3-[2-[(3S)-3-hydroxybut-1-yn-1-yl]-6-(morpholin-4-yl)pyridin-4-yl]-4-methylphenyl)-2-(trifluoromethyl)pyridine-4-carboxamide (193 mg, 60%) as a white solid. MS ESI calculated for $C_{27}H_{25}F_3N_4O^3$ [M+H]$^+$, 511.19, found 511.10. $^1$H NMR (400 MHz, chloroform-d) δ 8.91 (d, J=5.0 Hz, 1H), 8.12 (t, J=3.8 Hz, 2H), 7.94-7.92 (m, 1H), 7.59-7.57 (m, 1H), 7.49 (d, J=2.4 Hz, 1H), 7.29 (d, J=8.3 Hz, 1H), 6.79 (d, J=1.1 Hz, 1H), 6.53 (d, J=1.2 Hz, 1H), 4.75-4.71 (m, 1H), 3.84-3.78 (m, 4H), 3.55 (t, J=4.9 Hz, 4H), 2.26 (s, 3H), 1.55 (d, J=6.7 Hz, 3H). $^{19}$F NMR (376 MHz, DMSO-d$_6$) δ −67.98 (3F).

Example 3: N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide

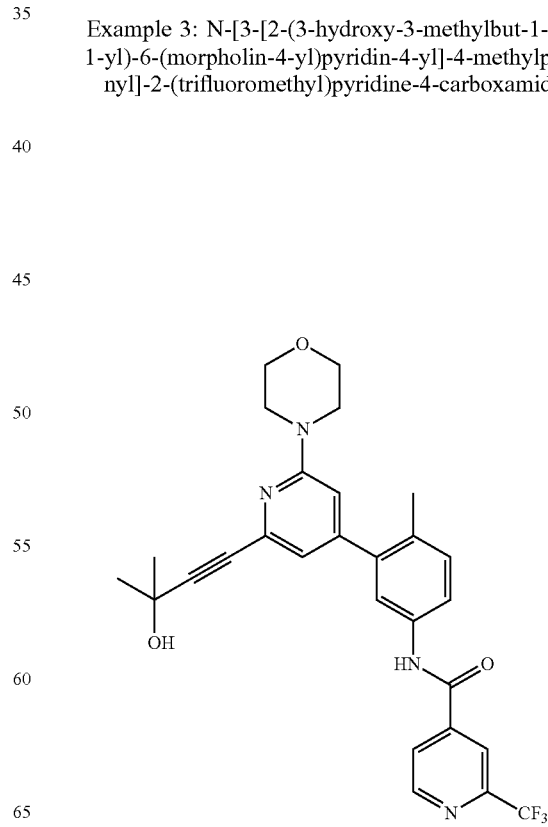

Preparation 3: N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide

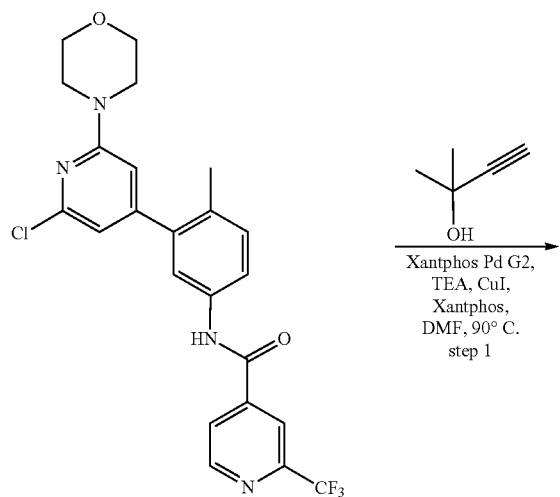

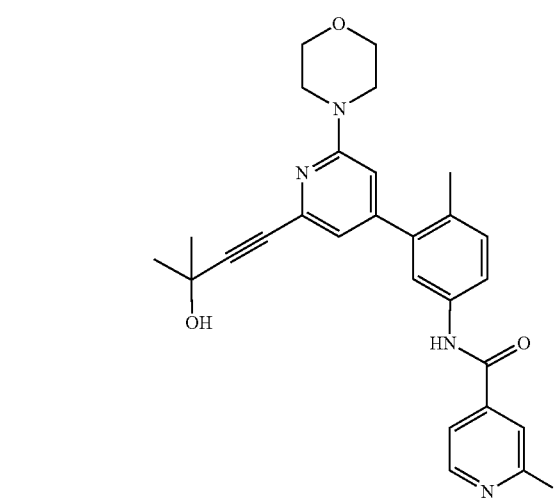

A mixture of N-[3-[2-chloro-6-(morpholin-4-yl)pyridin-4-yl]-4-methylphenyl]-2-(trifluoromethyl)pyridine-4-carboxamide (300 mg, 0.629 mmol), 2-methyl-3-butyn-2-ol (106 mg, 1.258 mmol), DMF (3 mL), 2nd Generation XantPhos precatalyst (50 mg, 0.063 mmol), XantPhos (36 mg, 0.063 mmol), CuI (6 mg, 0.031 mmol) and TEA (191 mg, 1.887 mmol) was stirred for 16 h at 60 degrees C. under nitrogen atmosphere. The mixture was allowed to cool down to room temperature. The residue was purified by reverse phase flash chromatography with the following conditions: Column: Spherical C18, 20-40 um, 120 g; Mobile Phase A: water (plus 5 mM NH₄HCO₃); Mobile Phase B: CH₃CN; Flow rate: 50 mL/min; Gradient: 5%-5% B, 10 min, 30% B-70% B gradient in 30 min; Detector: 220 nm to afford N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide (80 mg, 24%) as a white solid. MS ESI calculated for $C_{28}H_{27}F_3N_4O_3$ [M+H]⁺, 525.20, found 525.10. ¹H NMR (400 MHz, chloroform-d) δ 8.94 (d, J=5.0 Hz, 1H), 8.13 (d, J=5.4 Hz, 2H), 8.00-7.94 (m, 1H), 7.62-7.60 (m, 1H), 7.52 (d, J=2.3 Hz, 1H), 7.32 (d, J=8.3 Hz, 1H), 6.81 (d, J=1.2 Hz, 1H), 6.56-6.52 (m, 1H), 3.87-3.80 (m, 4H), 3.58 (t, J=4.9 Hz, 4H), 2.29 (s, 3H), 1.64 (s, 6H). ¹⁹F NMR (376 MHz, chloroform-d) δ −67.74 (3F).

Example 4: N-[3-[2-(3-hydroxyprop-1-yn-1-yl)-6-(morpholin-4-yl)pyridin-4-yl]-4-methylphenyl]-2-(trifluoromethyl)pyridine-4-carboxamide Synthetic Scheme

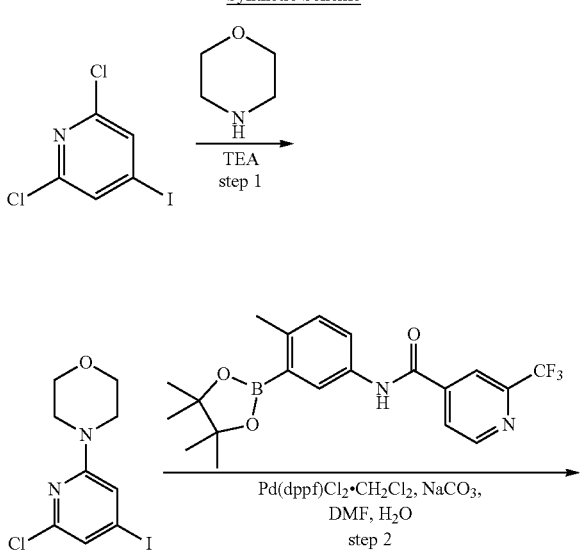

89
-continued

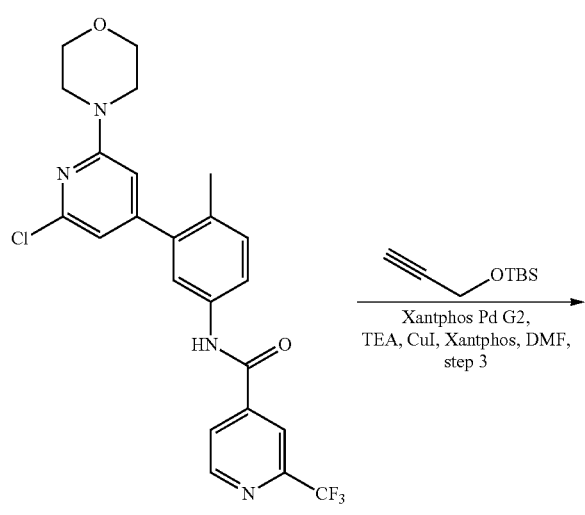

90

Preparation 4A:
4-(6-chloro-4-iodopyridin-2-yl)morpholine

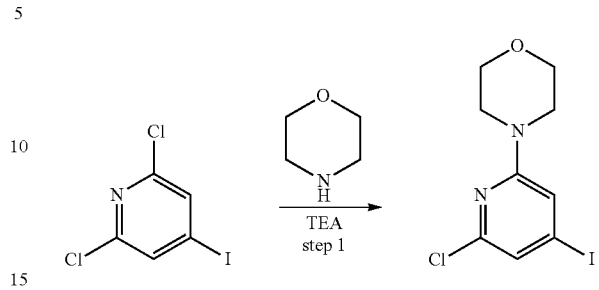

A mixture of 2,6-dichloro-4-iodopyridine (8.50 g, 31.03 mmol), TEA (3.14 g, 31.03 mmol) and morpholine (2.70 g, 30.99 mmol) was stirred for 2 h at 100° C. under nitrogen atmosphere. The resulting mixture was diluted with EtOAc (200 mL), washed with sat. NaHCO$_3$ (sat., 3×100 mL) and concentrated under reduced pressure. The residue was purified by silica gel column chromatography, eluted with hexane/EtOAc (5/1) to afford 4-(6-chloro-4-iodopyridin-2-yl)morpholine (4.28 g, 42%) as a white solid. MS ESI calculated for $C_9H_{10}ClIN_2O$ [M+]$^+$, 324.95, found 324.95. $^1$H NMR (400 MHz, DMSO-d$_6$) δ 7.18 (d, J=0.8 Hz, 1H), 7.08 (d, J=0.8 Hz, 1H), 3.67-3.65 (m, 4H), 3.47-3.45 (m, 4H).

Preparation 4B: N-(3-(2-chloro-6-morpholinopyridin-4-yl)-4-methylphenyl)-2-(trifluoromethyl)isonicotinamide

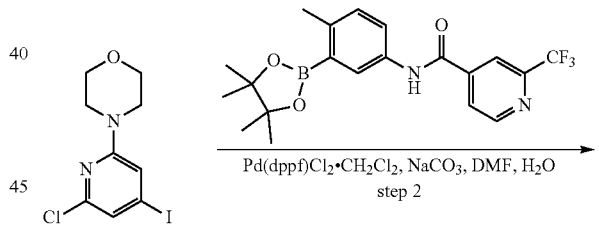

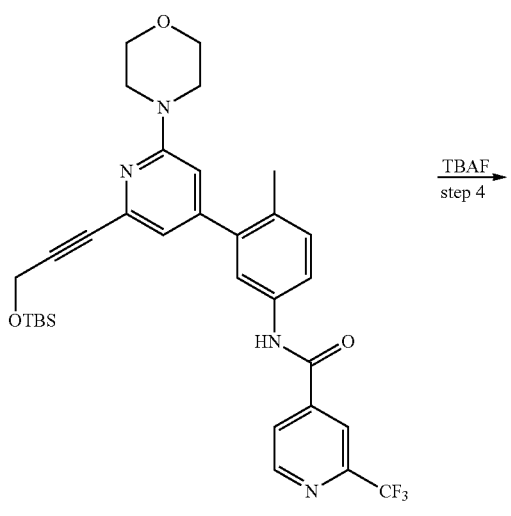

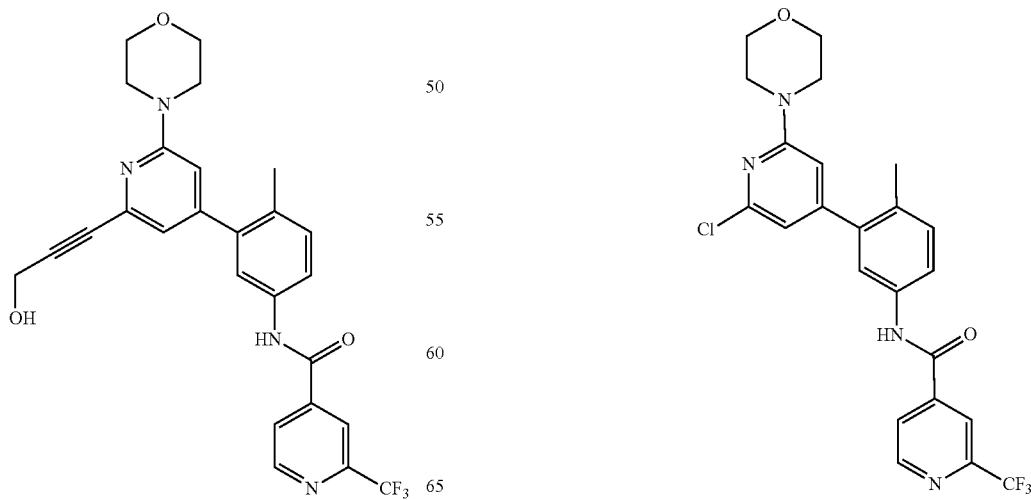

A mixture of 4-(6-chloro-4-iodopyridin-2-yl)morpholine (2.00 g, 6.16 mmol), N-[4-methyl-3-(4,4,5,5-tetramethyl-1,3,2-dioxaborolan-2-yl)phenyl]-2-(trifluoromethyl)pyridine-4-carboxamide (2.50 g, 6.16 mmol), $Na_2CO_3$ (1.96 g, 18.486 mmol) and $Pd(dppf)Cl_2 \cdot CH_2Cl_2$ (0.50 g, 0.62 mmol) in DMF (40 mL) and $H_2O$ (10 mL) was stirred at 60° C. for 2 h under $N_2$ atmosphere. The reaction was quenched with water (50 mL) and extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EtOAc (1/1) to afford N-(3-(2-chloro-6-morpholinopyridin-4-yl)-4-methylphenyl)-2-(trifluoromethyl)isonicotinamide (2.00 g, 68%) as a brown solid. MS ESI calculated for $C_{23}H_{20}ClF_3N_4O_2$ $[M+H]^+$, 477.12; found 477.20. $^1H$ NMR (400 MHz, Chloroform-d) δ 8.94-8.87 (m, 1H), 8.23 (s, 1H), 8.12 (s, 1H), 7.94 (s, 1H), 7.60-7.47 (m, 2H), 7.30 (s, 1H), 6.62 (s, 1H), 6.43 (s, 1H), 3.84-3.81 (m, 4H), 3.55-3.51 (m, 4H), 2.28 (s, 3H).

Preparation 4C: N-[3-(2-[3-[(tert-butyldimethylsilyl)oxy]prop-1-yn-1-yl]-6-(morpholin-4-yl)pyridin-4-yl)-4-methylphenyl]-2-(trifluoromethyl)pyridine-4-carboxamide

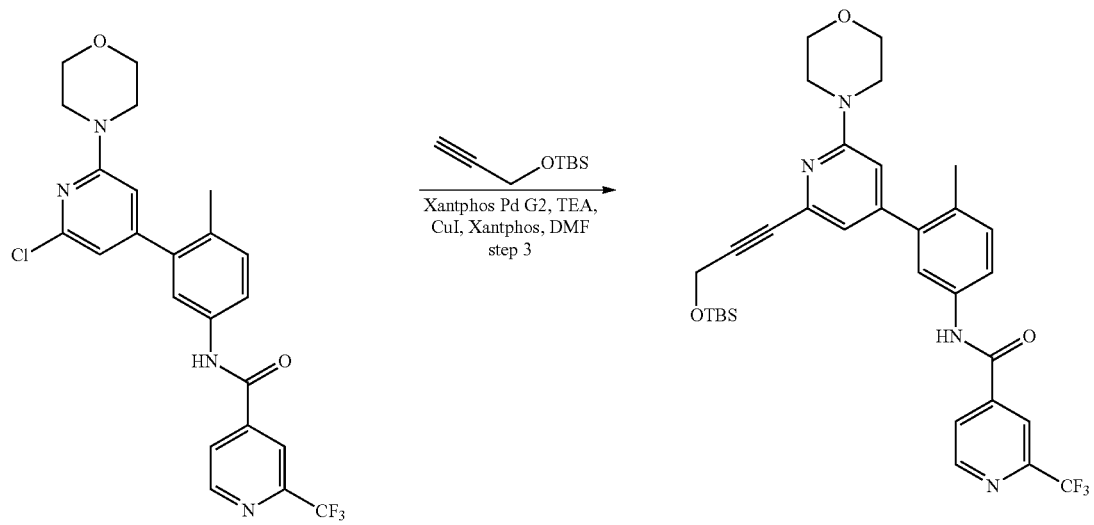 [SMILES: Cc1ccc(NC(=O)c2ccnc(C(F)(F)F)c2)cc1-c1cc(Cl)nc(N2CCOCC2)c1 ; C#CCO[Si](C)(C)C(C)(C)C ; Cc1ccc(NC(=O)c2ccnc(C(F)(F)F)c2)cc1-c1cc(C#CCO[Si](C)(C)C(C)(C)C)nc(N2CCOCC2)c1]

A mixture of N-[3-[2-chloro-6-(morpholin-4-yl)pyridin-4-yl]-4-methylphenyl]-2-(trifluoromethyl)pyridine-4-carboxamide (300 mg, 0.629 mmol), tert-butyldimethyl(prop-2-yn-1-yloxy)silane (214 mg, 1.258 mmol), 2nd Generation XantPhos precatalyst (56 mg, 0.063 mmol), XantPhos (36 mg, 0.063 mmol), TEA (191 mg, 1.887 mmol) and CuI (6 mg, 0.031 mmol) in DMF (5 mL) was stirred at 90° C. for 16 h under $N_2$ atmosphere. The reaction was quenched with water (50 mL) and extracted with EtOAc (3×50 mL). The combined organic layers were washed with brine (3×20 mL), dried over anhydrous $Na_2SO_4$. After filtration, the filtrate was concentrated under reduced pressure. The residue was purified by Prep-TLC with PE/EtOAc (1/1) to afford N-[3-(2-[3-[(tert-butyldimethylsilyl)oxy]prop-1-yn-1-yl]-6-(morpholin-4-yl)pyridin-4-yl)-4-methylphenyl]-2-(trifluoromethyl)pyridine-4-carboxamide (350 mg, 91%) as brown oil. MS ESI calculated for $C_{32}H_{37}F_3N_4O_3Si$ $[M+H]^+$, 611.26, found 611.15. $^1H$ NMR (400 MHz, Chloroform-d) δ 8.75 (d, J=5.0 Hz, 1H), 7.95-7.93 (m, 2H), 7.81-7.76 (m, 1H), 7.46 (dd, J=8.4, 2.4 Hz, 1H), 7.30 (d, J=2.4 Hz, 1H), 7.14 (d, J=8.4 Hz, 1H), 6.64 (d, J=1.2 Hz, 1H), 6.35 (d, J=1.2 Hz, 1H), 4.38 (s, 2H), 3.65-3.61 (m, 4H), 3.42-3.35 (m, 4H), 2.11 (s, 3H), 0.77 (s, 9H), 0.01 (s, 6H).

Example 4: N-[3-[2-(3-hydroxyprop-1-yn-1-yl)-6-(morpholin-4-yl)pyridin-4-yl]-4-methylphenyl]-2-(trifluoromethyl)pyridine-4-carboxamide

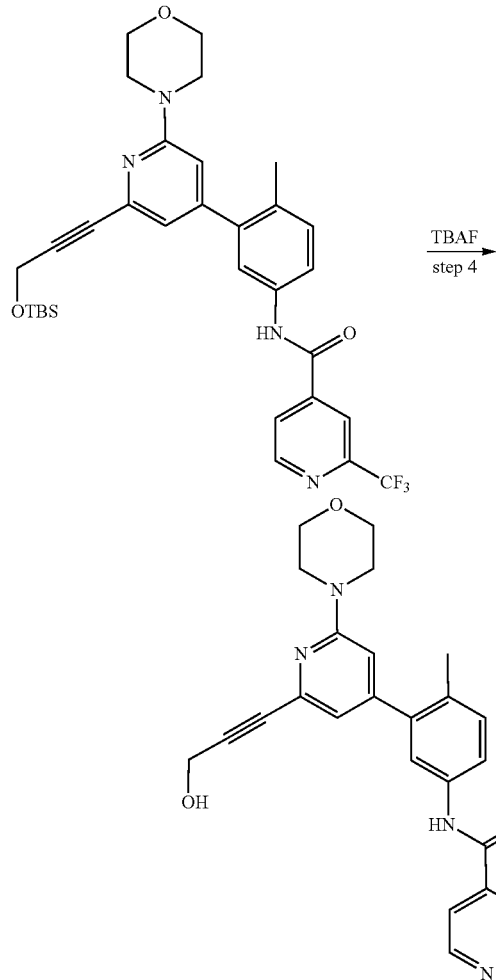

A mixture of N-[3-(2-[3-[(tert-butyldimethylsilyl)oxy]prop-1-yn-1-yl]-6-(morpholin-4-yl)pyridin-4-yl)-4-methylphenyl]-2-(trifluoromethyl)pyridine-4-carboxamide (400 mg, 0.66 mmol) in TBAF (5 mL, 1 M in THF) was stirred for 1 h at room temperature. The reaction was quenched with water (20 mL). The resulting mixture was extracted with EtOAc (3×50 mL). The combined organic layers were washed with brine (3×20 mL), dried over anhydrous Na$_2$SO$_4$. After filtration, the filtrate was concentrated under reduced pressure. The residue was purified by Prep-TLC with PE/EtOAc (1/2). The crude product was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 60% B in 30 min; 254/220 nm to afford N-[3-[2-(3-hydroxyprop-1-yn-1-yl)-6-(morpholin-4-yl)pyridin-4-yl]-4-methylphenyl]-2-(trifluoromethyl)pyridine-4-carboxamide (142 mg, 44%) as a light yellow solid. MS ESI calculated for C$_{26}$H$_{23}$F$_3$N$_4$O$_3$ [M+H]$^+$, 497.17, found 497.10. $^1$H NMR (400 MHz, Chloroform-d) δ 8.92 (d, J=4.8 Hz, 1H), 8.29 (s, 1H), 8.14 (s, 1H), 7.98 (d, J=4.4 Hz, 1H), 7.61 (dd, J=8.4, 2.0 Hz, 1H), 7.51 (d, J=1.6 Hz, 1H), 7.29 (d, J=9.2 Hz, 1H), 6.80 (s, 1H), 6.56 (s, 1H), 4.51 (s, 2H), 3.84-3.81 (m, 4H), 3.57-3.55 (m, 4H), 2.27 (s, 3H). $^{19}$F NMR (376 MHz, Chloroform-d) δ −67.96 (3F).

Example 5: (3S)—N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide

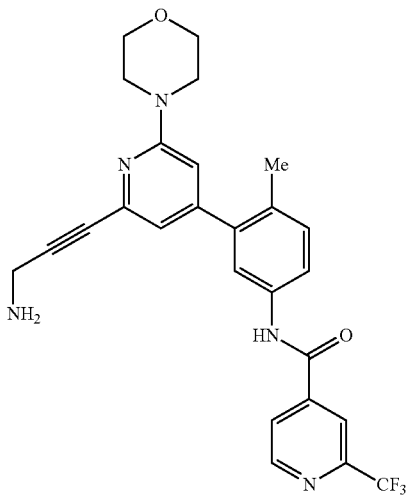 [SMILES: Cc1ccc(NC(=O)c2ccnc(C(F)(F)F)c2)cc1-c1cc(C#CCN)nc(N2CCOCC2)c1]

Synthetic Scheme

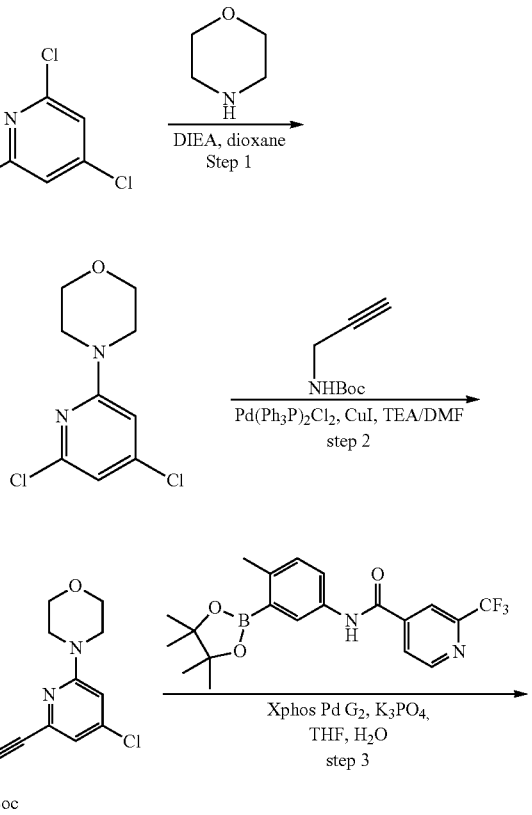

-continued

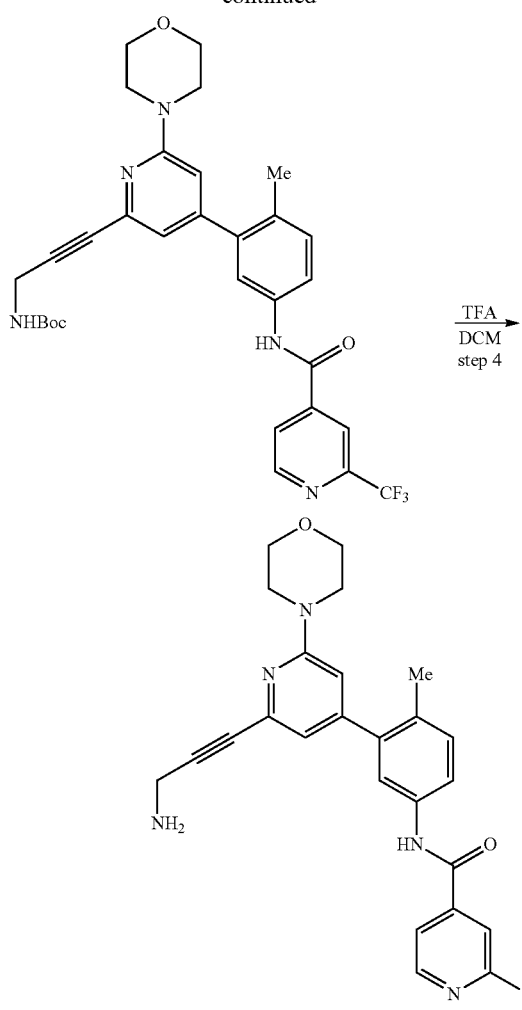

Preparation 5A:
4-(4,6-dichloropyridin-2-yl)morpholine

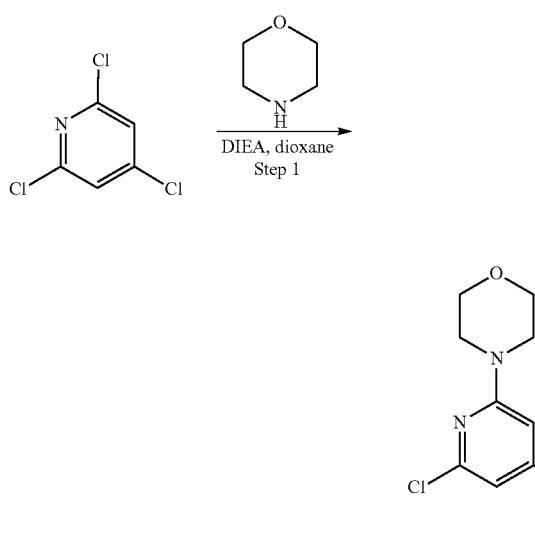

A mixture of 2,4,6-trichloropyridine (29.20 g, 160.06 mmol), morpholine (14 mL, 160.06 mmol) and DIEA (28 mL, 215.72 mmol) in 1,4-dioxane (160 mL) was stirred for 16 h at 85° C. The mixture was allowed to cool down to room temperature. The reaction was quenched with water (300 mL). The resulting mixture was extracted with EtOAc (3×200 mL). The combined organic layers were washed with brine (300 mL), dried over anhydrous $Na_2SO_4$. After filtration, the filtrate was concentrated under reduced pressure. The residue was purified by silica gel column chromatography, eluted with EtOAc/PE (15/85) to afford 4-(4,6-dichloropyridin-2-yl)morpholine (19.10 g, 51%) as an off-white solid. MS ESI calculated for $C_9H_{10}Cl_2N_2O$ $[M+H]^+$, 233.02, found 232.90. $^1$H NMR (400 MHz, Chloroform-d) δ 6.67 (d, J=1.2 Hz, 1H), 6.48 (d, J=1.2 Hz, 1H), 3.83-3.76 (m, 4H), 3.56-3.49 (m, 4H).

Preparation 5B: tert-butyl N-{3-[4-chloro-6-(morpholin-4-yl)pyridin-2-yl]prop-2-yn-1-yl}carbamate

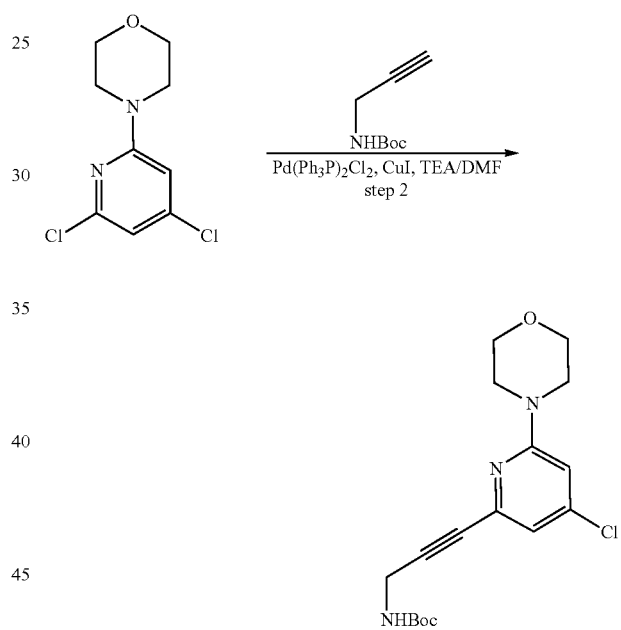

A mixture of 4-(4,6-dichloropyridin-2-yl)morpholine (500 mg, 2.145 mmol), tert-butyl N-(prop-2-yn-1-yl)carbamate (666 mg, 4.290 mmol), TEA (1 mL), DMF (5 mL), CuI (82 mg, 0.429 mmol) and Pd(PPh$_3$)$_2$Cl$_2$ (150 mg, 0.215 mmol) was stirred for 16 h at 80° C. under nitrogen atmosphere. The resulting mixture was diluted with water (30 mL) and extracted with EtOAc (3×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EtOAc (5/4) to afford tert-butyl N-{3-[4-chloro-6-(morpholin-4-yl)pyridin-2-yl]prop-2-yn-1-yl}carbamate (210 mg, 23%) as a yellow solid. MS ESI calculated for $C_{17}H_{22}ClN_3O_3$ $[M+H]^+$, 352.13, found 352.20. $^1$H NMR (300 MHz, Chloroform-d) δ 6.81 (d, J=1.5 Hz, 1H), 6.59 (d, J=1.5 Hz, 1H), 4.18 (d, J=5.6 Hz, 2H), 3.86-3.76 (m, 4H), 3.58-3.49 (m, 4H), 1.49 (s, 9H).

Preparation 5C: tert-butyl N-[3-(4-{2-methyl-5-[2-(trifluoromethyl)pyridine-4-amido]phenyl}-6-(morpholin-4-yl)pyridin-2-yl)prop-2-yn-1-yl]carbamate

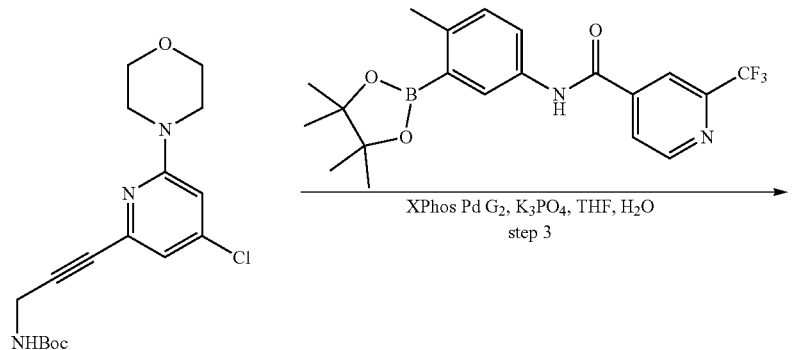

A mixture of tert-butyl N-{3-[4-chloro-6-(morpholin-4-yl)pyridin-2-yl]prop-2-yn-1-yl}carbamate (220 mg, 0.625 mmol), $K_3PO_4$ (265.46 mg, 1.250 mmol), N-[4-methyl-3-(4,4,5,5-tetramethyl-1,3,2-dioxaborolan-2-yl)phenyl]-2-(trifluoromethyl)pyridine-4-carboxamide (279 mg, 0.688 mmol), THF (2 mL), $H_2O$ (0.2 mL) and 2nd Generation XantPhos precatalyst (49 mg, 0.063 mmol) was stirred for 2 h at 80° C. under nitrogen atmosphere. The resulting mixture was concentrated under reduced pressure. The residue was purified by silica gel column chromatography, eluted with PE/EtOAc/EtOH (4/3/1) to afford tert-butyl N-[3-(4-{2-methyl-5-[2-(trifluoromethyl)pyridine-4-amido]phenyl}-6-(morpholin-4-yl)pyridin-2-yl)prop-2-yn-1-yl]carbamate (170 mg, 45%) as a white solid. MS ESI calculated for $C_{31}H_{32}F_3N_5O_4$ $[M+H]^+$, 596.24; found 596.15; $^1H$ NMR (300 MHz, Chloroform-d) δ 8.95 (d, J=5.2 Hz, 1H), 8.14 (s, 1H), 8.06 (s, 1H), 7.97 (d, J=4.8 Hz, 1H), 7.61 (s, 1H), 7.52 (s, 1H), 7.33 (d, J=8.4 Hz, 1H), 6.82 (d, J=1.2 Hz, 1H), 6.56 (s, 1H), 4.26-4.15 (m, 2H), 3.85-3.81 (m, 4H), 3.62-3.58 (m, 4H), 2.29 (s, 3H), 1.48 (s, 9H).

Example 5: N-{3-[2-(3-aminoprop-1-yn-1-yl)-6-(morpholin-4-yl)pyridin-4-yl]-4-methylphenyl}-2-(trifluoromethyl)pyridine-4-carboxamide

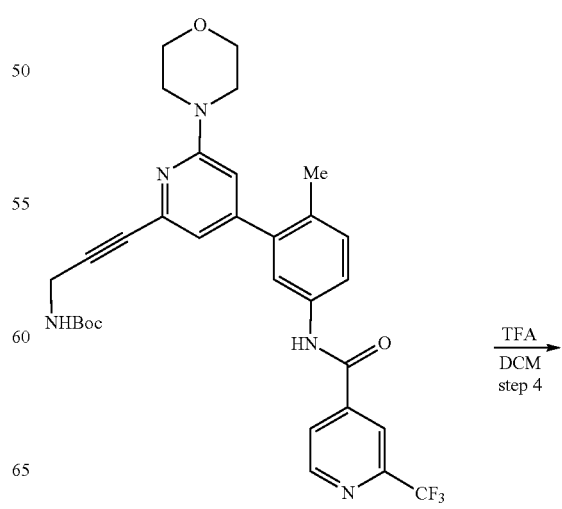

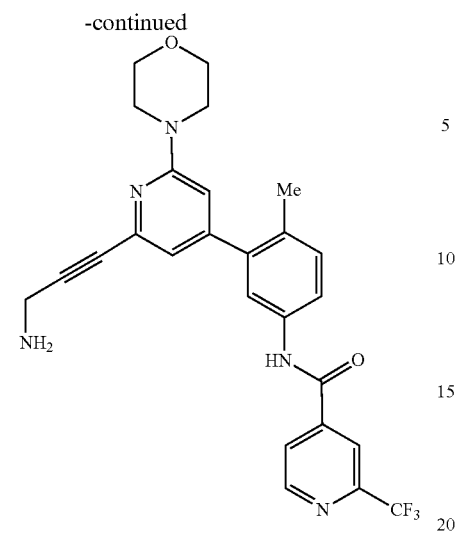

To a stirred mixture of tert-butyl N-[3-(4-{2-methyl-5-[2-(trifluoromethyl)pyridine-4-amido]phenyl}-6-(morpholin-4-yl)pyridin-2-yl)prop-2-yn-1-yl]carbamate (170 mg, 0.285 mmol) in DCM (4 mL) was added TFA (1 mL) dropwise at 0° C. The reaction mixture was stirred for 30 min at room temperature. The resulting mixture was concentrated under reduced pressure. The residue was purified by reverse phase chromatography, eluted with CH$_3$CN/water (with 0.05% NH$_4$HCO$_3$) (10% to 50%) to afford N-{3-[2-(3-aminoprop-1-yn-1-yl)-6-(morpholin-4-yl)pyridin-4-yl]-4-methylphenyl}-2-(trifluoromethyl)pyridine-4-carboxamide (100.7 mg, 70%) as a white solid. MS ESI calculated for C$_{26}$H$_{24}$F$_3$N$_5$O$_2$ [M+H]$^+$, 496.19, found 496.25. $^1$H NMR (300 MHz, Chloroform-d) δ 8.96 (d, J=5.1 Hz, 1H), 8.12 (s, 1H), 7.95-7.92 (m, 2H), 7.63-7.52 (m, 2H), 7.33 (d, J=8.4 Hz, 1H), 6.82 (s, 1H), 6.54 (s, 1H), 3.86-3.83 (m, 4H), 3.69 (s, 2H), 3.62-3.53 (m, 4H), 2.30 (s, 3H). $^{19}$F NMR (282 MHz, Chloroform-d) δ −67.93 (3F).

Example 6: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide Synthetic Scheme

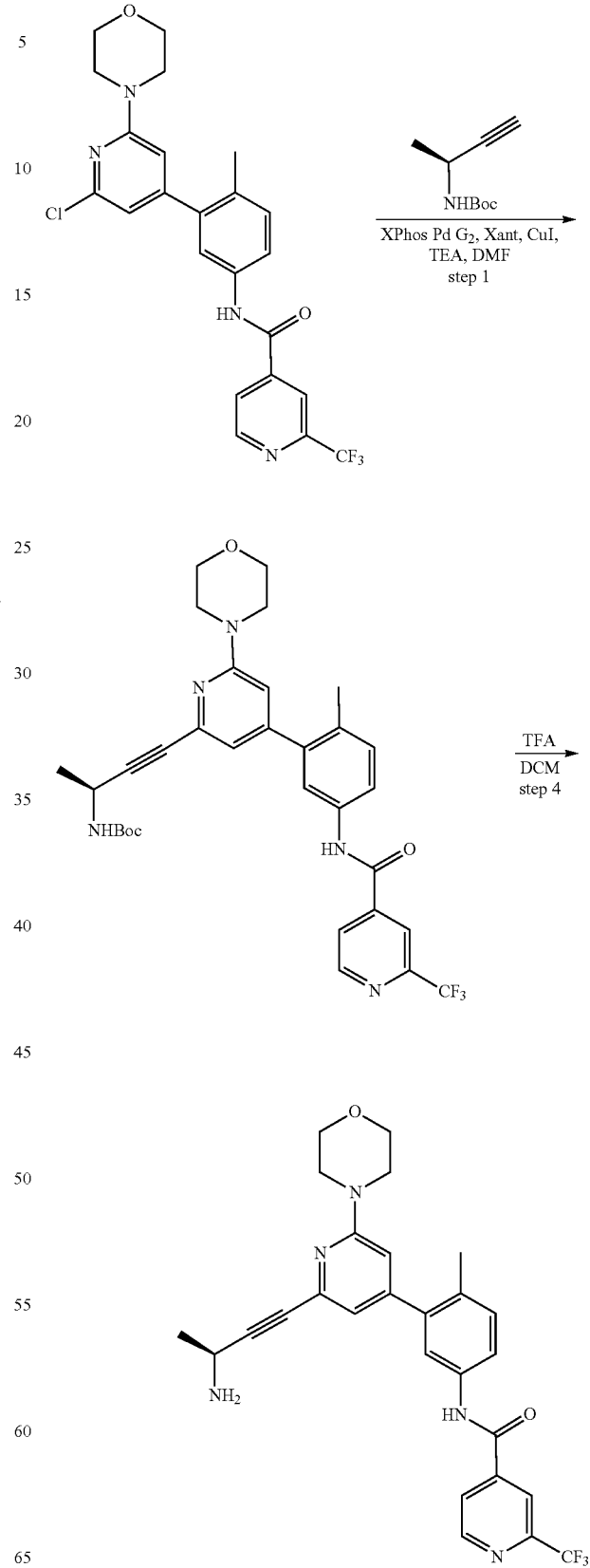

Preparation 6A: tert-butyl N-[(2S)-4-(4-{2-methyl-5-[2-(trifluoromethyl)pyridine-4-amido]phenyl}-6-(morpholin-4-yl)pyridin-2-yl]but-3-yn-2-yl]carbamate

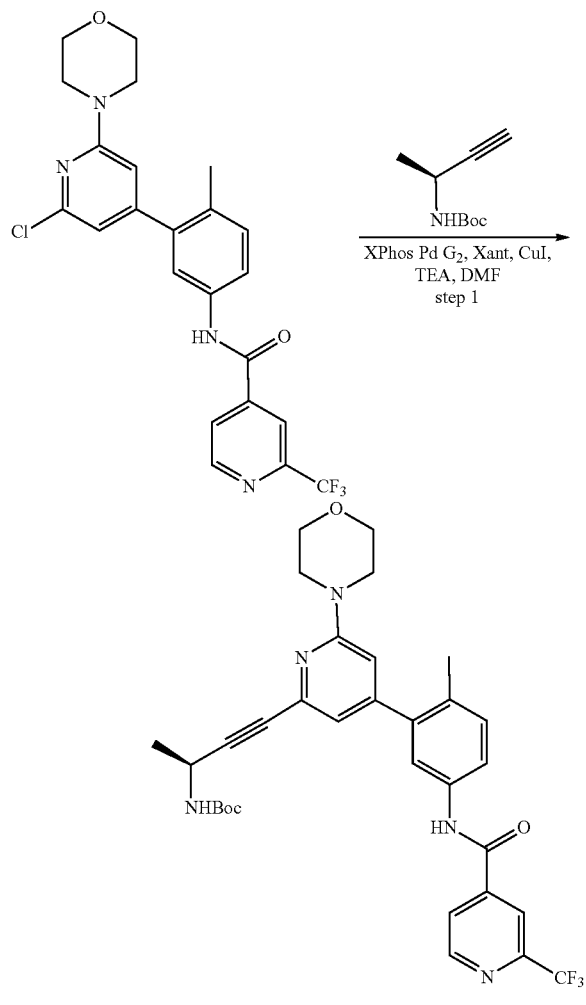

A mixture of N-{3-[2-chloro-6-(morpholin-4-yl)pyridin-4-yl]-4-methylphenyl}-2-(trifluoromethyl)pyridine-4-carboxamide (500 mg, 1.048 mmol) and tert-butyl N-[(2S)-but-3-yn-2-yl]carbamate (355 mg, 2.096 mmol) in DMF (10 mL), TEA (318 mg, 3.144 mmo), 2nd Generation XantPhos precatalyst (93 mg, 0.105 mmol), XantPhos (61 mg, 0.105 mmol) and CuI (10 mg, 0.052 mmol) was stirred for 16 h at 80° C. under nitrogen atmosphere. The reaction was quenched by the addition of water (30 mL). The resulting mixture was extracted with EtOAc (3×50 mL). The combined organic layers were washed with brine (2×40 mL), dried over anhydrous $Na_2SO_4$. After filtration, the filtrate was concentrated under reduced pressure. The residue was purified by silica gel column chromatography, eluted with PE/EtOH/EtOAc (4/1/1) to afford tert-butyl N-[(2S)-4-(4-{2-methyl-5-[2-(trifluoromethyl)pyridine-4-amido]phenyl}-6-(morpholin-4-yl)pyridin-2-yl]but-3-yn-2-yl]carbamate (489 mg, 76%) as an off-white solid. MS ESI calculated for $C_{32}H_{34}F_3N_5O_4$ [M+H]$^+$ 610.26; found 610.40. $^1$H NMR (300 MHz, Chloroform-d) δ 8.91 (d, J=4.8 Hz, 1H), 8.35 (s, 1H), 8.16 (s, 1H), 8.00-7.94 (m, 1H), 7.64 (d, J=8.1 Hz, 1H), 7.47 (s, 1H), 7.28 (d, J=8.1 Hz, 1H), 6.76 (d, J=1.2 Hz, 1H), 6.51 (s, 1H), 4.93 (s, 1H), 4.70 (s, 1H), 3.82-3.79 (m, 4H), 3.56-3.53 (m, 4H), 2.25 (s, 3H), 1.48 (d, J=6.9 Hz, 3H), 1.43 (s, 9H).

Example 6: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide To a solution of tert-butyl N-[(2S)-4-(4-{2-methyl-5-[2-(trifluoromethyl)pyridine-4-amido]phenyl}-6-(morpholin-4-yl)pyridin-2-yl]but-3-yn-2-yl]carbamate (489 mg, 0.802 mmol) and DCM (5 mL) was added TFA (1 mL). The resulting mixture was stirred for 1 h at room temperature. The resulting mixture was concentration under reduced pressure. The residue was neutralized to pH 8 with saturated $NaHCO_3$. The resulting mixture was extracted with EtOAc (3×30 mL). The combined organic layers were washed with brine (2×10 mL), dried over anhydrous $Na_2SO_4$. After filtration, the filtrate was concentrated under reduced pressure. The residue was purified by reverse flash chromatography with the following conditions: C18 column; mobile phase, $CH_3CN$ in water (10 mmol/L $NH_4HCO_3$), 10% to 50%; detector, UV 254 nm to afford N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide (230 mg, 56%) as an off-white solid. MS ESI calculated for $C_{27}H_{26}F_3N_5O_2$ [M+H]$^+$ 510.20; found 510.20. $^1$H NMR (400 MHz, Chloroform-d) δ 8.94 (d, J=4.8 Hz, 1H), 8.13 (s, 1H), 8.07 (s, 1H), 7.96 (d, J=4.8 Hz, 1H), 7.60 (d, J=8.4 Hz, 1H), 7.50 (s, 1H), 7.31 (d, J=8.4 Hz, 1H), 6.80 (s, 1H), 6.52 (s, 1H), 3.98 (s, 1H), 3.85-3.81 (m, 4H), 3.58-3.54 (m, 4H), 2.29 (s, 3H), 1.48 (d, J=6.0 Hz, 3H). $^{19}$F NMR (376 MHz, Chloroform-d) δ −67.94 (3F).

Example 7: N-(3-{2-[(3R)-3-aminobut-1-yn-1-yl]-6-(morpholin-4-yl)pyridin-4-yl}-4-methylphenyl)-2-(trifluoromethyl)pyridine-4-carboxamide

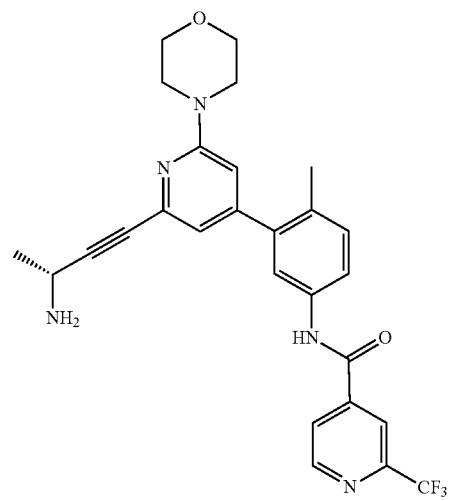 [SMILES: Cc1ccc(NC(=O)c2ccnc(C(F)(F)F)c2)cc1-c1cc(C#C[C@@H](C)N)nc(N2CCOCC2)c1]

Preparation 7A: tert-butyl N-[(2R)-4-(4-{2-methyl-5-[2-(trifluoromethyl)pyridine-4-amido]phenyl}-6-(morpholin-4-yl)pyridin-2-yl)but-3-yn-2-yl]carbamate

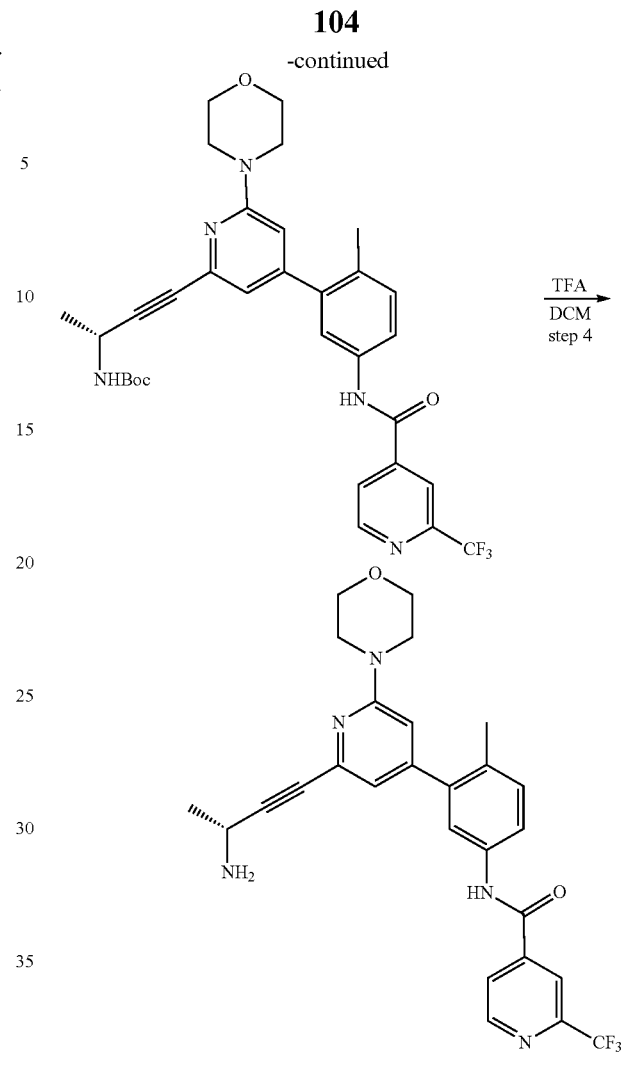

Synthetic Scheme

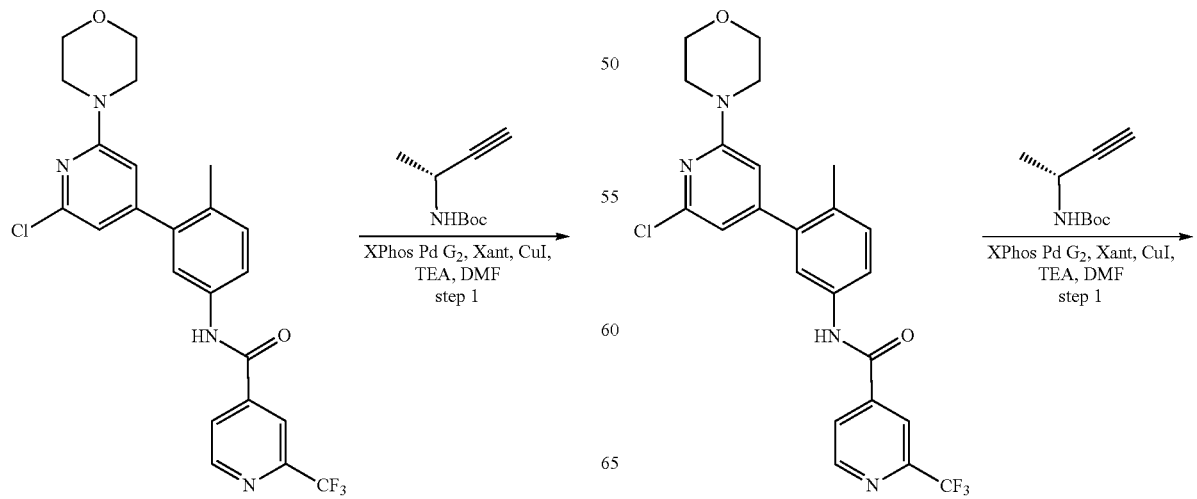

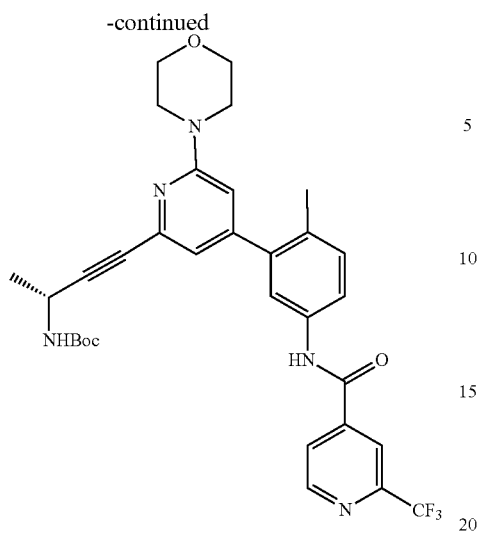

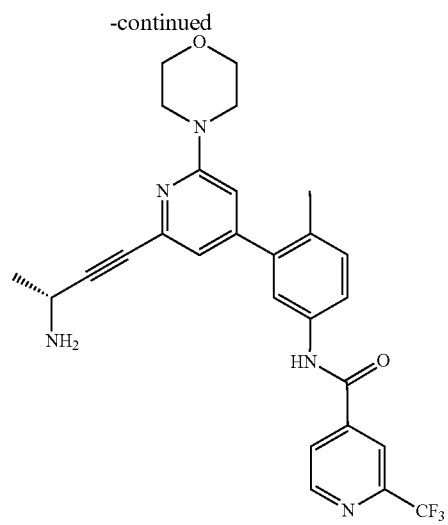

A mixture of N-{3-[2-chloro-6-(morpholin-4-yl)pyridin-4-yl]-4-methylphenyl}-2-(trifluoromethyl)pyridine-4-carboxamide (500 mg, 1.048 mmol) and tert-butyl N-[(2R)-but-3-yn-2-yl]carbamate (355 mg, 2.096 mmol) in DMF (10 mL), TEA (318 mg, 3.144 mmo), 2nd Generation XantPhos precatalyst (93 mg, 0.105 mmol), XantPhos (61 mg, 0.105 mmol) and CuI (10 mg, 0.052 mmol) was stirred for 16 h at 80° C. under nitrogen atmosphere. The reaction was quenched by the addition of water (30 mL). The resulting mixture was extracted with EtOAc (3×50 mL). The combined organic layers were washed with brine (2×40 mL), dried over anhydrous Na$_2$SO$_4$. After filtration, the filtrate was concentrated under reduced pressure. The residue was purified by silica gel column chromatography, eluted with PE/EtOH/EtOAc (4/1/1) to afford tert-butyl N-[(2R)-4-(4-{2-methyl-5-[2-(trifluoromethyl)pyridine-4-amido]phenyl}-6-(morpholin-4-yl)pyridin-2-yl)but-3-yn-2-yl]carbamate (450 mg, 70%) as an off-white solid. MS ESI calculated for C$_{32}$H$_{34}$F$_3$N$_5$O$_4$ [M+H]$^+$ 610.26; found 610.30. $^1$H NMR (300 MHz, Chloroform-d) δ 8.94 (d, J=4.8 Hz, 1H), 8.35 (s, 1H), 8.16 (s, 1H), 8.00-7.94 (m, 1H), 7.64 (d, J=8.4 Hz, 1H), 7.47 (s, 1H), 7.28 (d, J=8.1 Hz, 1H), 6.76 (d, J=1.1 Hz, 1H), 6.51 (s, 1H), 4.93 (s, 1H), 4.74 (s, 1H), 3.86-3.82 (m, 4H), 3.60-3.56 (m, 4H), 2.25 (s, 3H), 1.48 (d, J=6.9 Hz, 3H), 1.43 (s, 9H).

To a solution of tert-butyl N-[(2R)-4-(4-{2-methyl-5-[2-(trifluoromethyl)pyridine-4-amido]phenyl}-6-(morpholin-4-yl)pyridin-2-yl)but-3-yn-2-yl]carbamate (450 mg, 0.738 mmol) and DCM (5 mL) was added TFA (1 mL). The resulting mixture was stirred for 1 h at room temperature. The resulting mixture was concentration under reduced pressure. The residue was neutralized to pH 8 with saturated NaHCO$_3$. The resulting mixture was extracted with EtOAc (3×30 mL). The combined organic layers were washed with brine (2×10 mL), dried over anhydrous Na$_2$SO$_4$. After filtration, the filtrate was concentrated under reduced pressure. The residue was purified by reverse flash chromatography with the following conditions: C18 column; mobile phase, CH$_3$CN in water (10 mmol/L NH$_4$HCO$_3$), 10% to 50%; detector, UV 254 nm to afford N-(3-{2-[(3R)-3-aminobut-1-yn-1-yl]-6-(morpholin-4-yl)pyridin-4-yl}-4-methylphenyl)-2-(trifluoromethyl)pyridine-4-carboxamide (210 mg, 56%) as an off-white solid. MS ESI calculated for C$_{27}$H$_{26}$F$_3$N$_5$O$_2$ [M+H]$^+$ 510.20; found 510.20. $^1$H NMR (400 MHz, Chloroform-d) δ 8.94 (d, J=4.8 Hz, 1H), 8.13 (s, 1H), 8.05 (s, 1H), 7.99-7.93 (m, 1H), 7.60 (d, J=7.6 Hz, 1H), 7.50 (s, 1H), 7.31 (d, J=8.4 Hz, 1H), 6.81 (s, 1H), 6.52 (s, 1H), 3.99 (s, 1H), 3.85-3.81 (m, 4H), 3.58-3.54 (m, 4H), 2.29 (s, 3H), 1.48 (d, J=6.4 Hz, 3H). $^{19}$F NMR (376 MHz, Chloroform-d) δ −67.95 (3F).

Example 7: N-(3-{2-[(3R)-3-aminobut-1-yn-1-yl]-6-(morpholin-4-yl)pyridin-4-yl}-4-methylphenyl)-2-(trifluoromethyl)pyridine-4-carboxamide Example 8: N-(3-{2-[3-(dimethylamino)prop-1-yn-1-yl]-6-(morpholin-4-yl)pyridin-4-yl}-4-methylphenyl)-2-(trifluoromethyl)pyridine-4-carboxamide

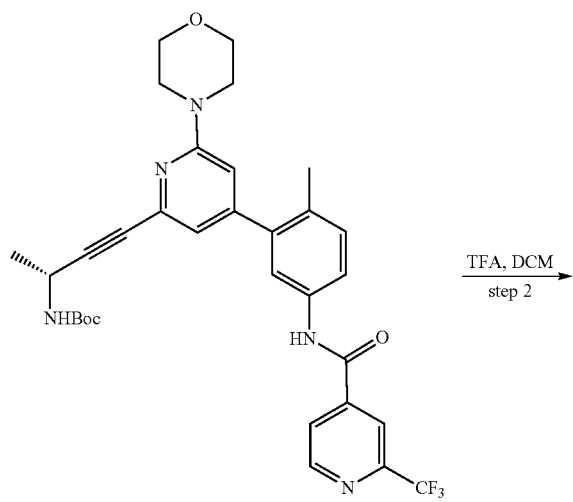

TFA, DCM
step 2

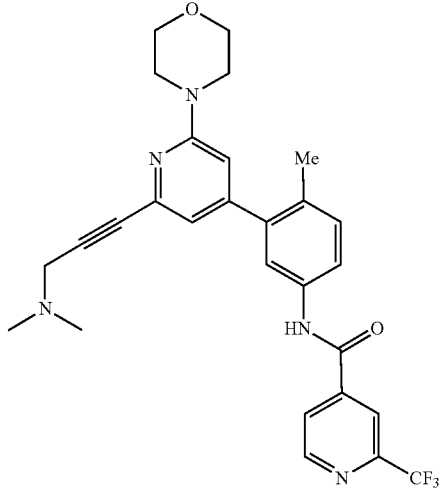 [SMILES: Cc1ccc(NC(=O)c2ccnc(C(F)(F)F)c2)cc1-c1cc(C#CCN(C)C)nc(N2CCOCC2)c1]

Synthetic Scheme

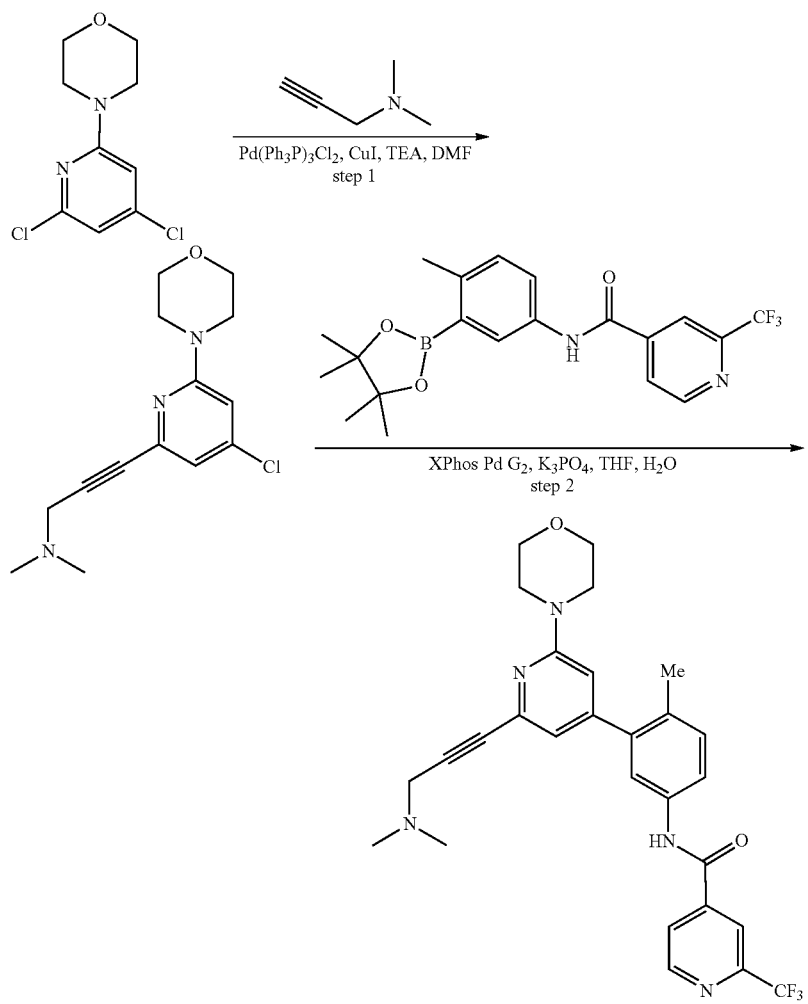

Preparation 8A: {3-[4-chloro-6-(morpholin-4-yl)pyridin-2-yl]prop-2-yn-1-yl}dimethylamine

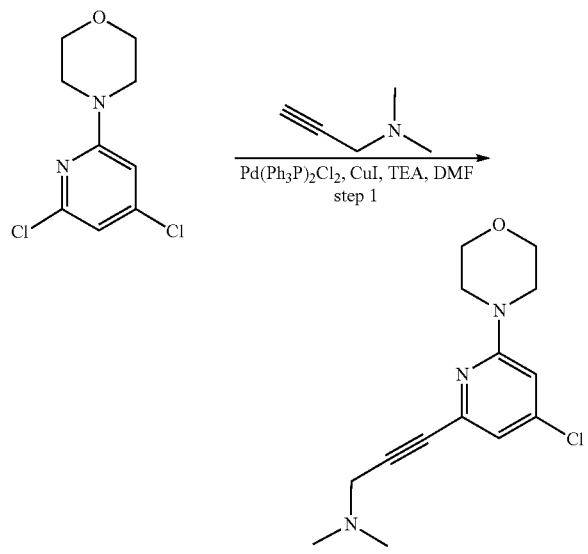

A mixture of 4-(4,6-dichloropyridin-2-yl)morpholine (300 mg, 1.287 mmol), dimethyl(prop-2-yn-1-yl)amine (214 mg, 2.574 mmol), Pd(PPh$_3$)$_2$Cl$_2$ (90 mg, 0.129 mmol) and CuI (49 mg, 0.257 mmol) in TEA (2 mL) and DMF (10 mL) was stirred for 2 h 80° C. under nitrogen atmosphere. The reaction was quenched by the addition of water (30 mL). The resulting mixture was extracted with EtOAc (3×30 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EtOAc (1/1) to afford {3-[4-chloro-6-(morpholin-4-yl)pyridin-2-yl]prop-2-yn-1-yl}dimethylamine (261 mg, 73%) as a brown solid. MS ESI calculated for C$_{14}$H$_{19}$ClN$_3$O [M+H]$^+$, 280.11, found 280.20. $^1$H NMR (400 MHz, Chloroform-d) δ 6.81 (d, J=1.5 Hz, 1H), 6.55 (d, J=1.5 Hz, 1H), 3.81-3.77 (m, 4H), 3.53-3.49 (m, 6H), 2.38 (s, 6H).

Example 8: N-(3-{2-[3-(dimethylamino)prop-1-yn-1-yl]-6-(morpholin-4-yl)pyridin-4-yl}-4-methylphenyl)-2-(trifluoromethyl)pyridine-4-carboxamide

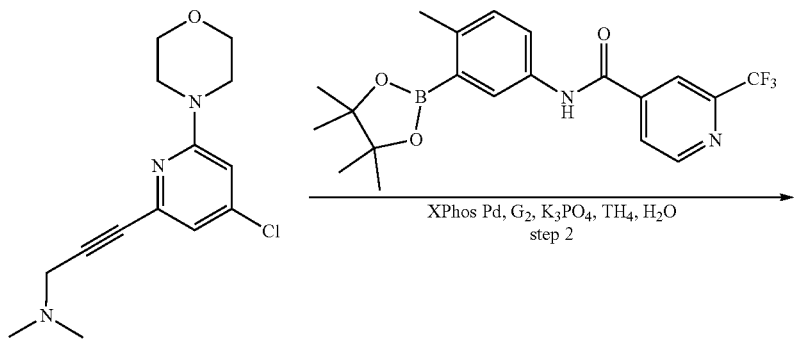

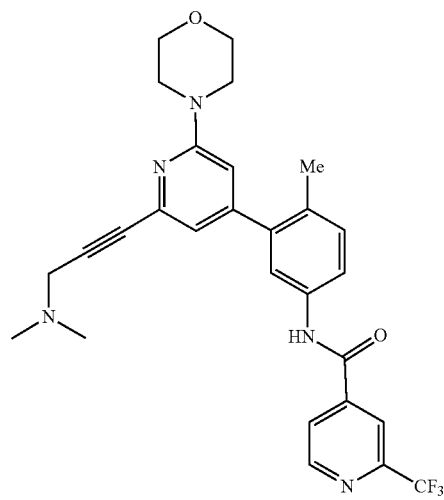

A mixture of {3-[4-chloro-6-(morpholin-4-yl)pyridin-2-yl]prop-2-yn-1-yl}dimethylamine (160 mg, 0.572 mmol), N-[4-methyl-3-(4,4,5,5-tetramethyl-1,3,2-dioxaborolan-2-yl)phenyl]-2-(trifluoromethyl)pyridine-4-carboxamide (232 mg, 0.572 mmol), 2nd Generation XPhos Precatalyst (50 mg, 0.057 mmol) and K$_3$PO$_4$ (243 mg, 1.144 mmol) in THF (2 mL) and H$_2$O (0.2 mL) was stirred for 2 h at 80° C. under nitrogen atmosphere. The resulting mixture was concentrated under reduced pressure. The residue was purified by reverse flash chromatography with the following conditions: C18 column; mobile phase, MeOH in water, 30% to 70%; detector, UV 254 nm to afford N-(3-{2-[3-(dimethylamino)prop-1-yn-1-yl]-6-(morpholin-4-yl)pyridin-4-yl}-4-methylphenyl)-2-(trifluoromethyl)pyridine-4-carboxamide (117.2 mg, 39%) as a white solid. MS ESI calculated for C$_{28}$H$_{29}$F$_3$N$_5$O$_2$ [M+H]$^+$, 524.22; found 524.25. $^1$H NMR (300 MHz, DMSO-d$_6$) δ 10.70 (s, 1H), 9.01 (d, J=5.1 Hz, 1H), 8.39 (s, 1H), 8.21 (d, J=4.8 Hz, 1H), 7.79 (dd, J=8.1, 2.1 Hz, 1H), 7.66 (d, J=2.1 Hz, 1H), 7.36 (d, J=8.4 Hz, 1H), 6.81-6.79 (m, 2H), 3.73-3.69 (m, 4H), 3.53-3.47 (m, 6H), 2.26 (s, 9H). $^{19}$F NMR (282 MHz, DMSO-d$_6$) δ −66.45 (3F).

Example 9: N-{4-methyl-3-[2-(morpholin-4-yl)-6-[3-(pyrrolidin-1-yl)prop-1-yn-1-yl]pyridin-4-yl]phenyl}-2-(trifluoromethyl)pyridine-4-carboxamide

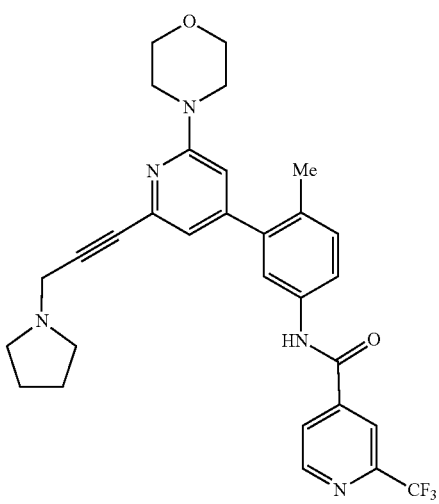 [SMILES: Cc1ccc(NC(=O)c2ccnc(C(F)(F)F)c2)cc1-c1cc(C#CCN2CCCC2)nc(N2CCOCC2)c1]

Synthetic Scheme
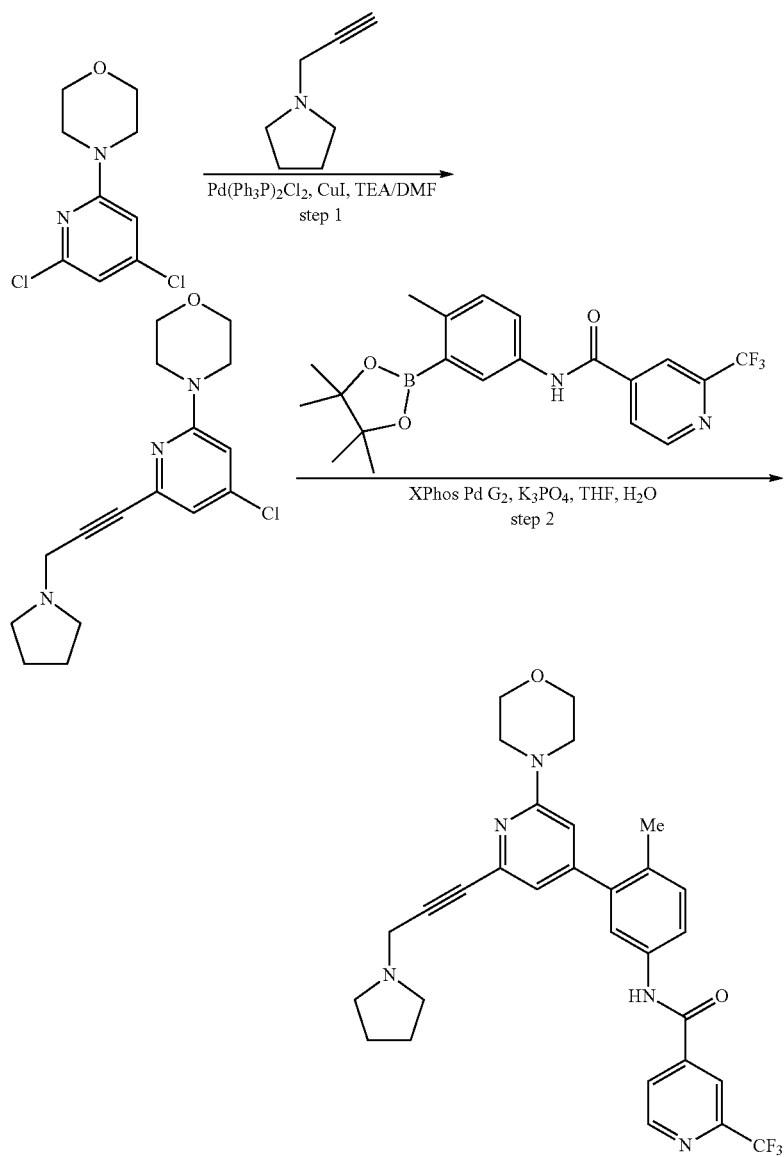
Preparation 9A: 4-{4-chloro-6-[3-(pyrrolidin-1-yl)prop-1-yn-1-yl]pyridin-2-yl}morpholine
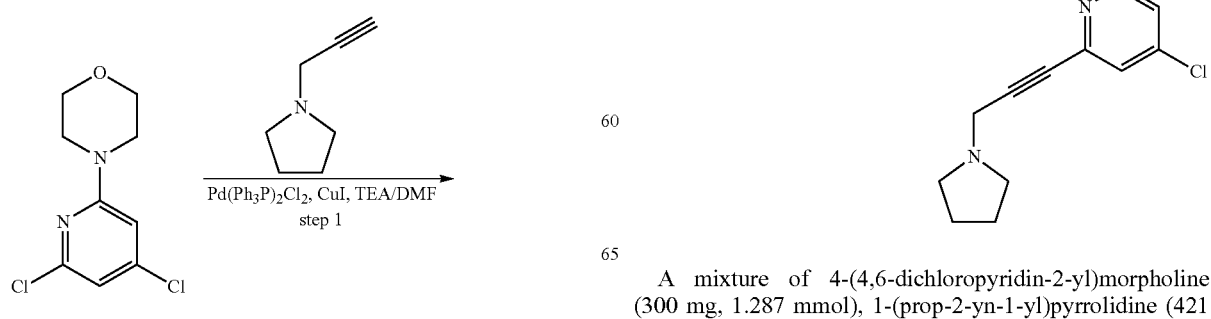
A mixture of 4-(4,6-dichloropyridin-2-yl)morpholine (300 mg, 1.287 mmol), 1-(prop-2-yn-1-yl)pyrrolidine (421 mg, 3.861 mmol), Pd(PPh$_3$)$_2$Cl$_2$ (90 mg, 0.129 mmol) and CuI (49 mg, 0.257 mmol) in TEA (2 mL) and DMF (10 mL) was stirred for overnight at 80° C. under argon atmosphere. The reaction was quenched by the addition of water (30 mL). The resulting mixture was extracted with EtOAc (3×30 mL). The combined organic layers were washed with brine (15 mL), dried over anhydrous Na$_2$SO$_4$. After filtration, the filtrate was concentrated under reduced pressure. The residue was purified by silica gel column chromatography, eluted with CH$_2$Cl$_2$/MeOH (10/1) to afford 4-{4-chloro-6-[3-(pyrrolidin-1-yl)prop-1-yn-1-yl]pyridin-2-yl}morpholine (85 mg, 21%) as a light yellow oil. MS ESI calculated for C$_{16}$H$_{20}$ClN$_3$O [M+H]$^+$, 306.13, found 306.05. $^1$H NMR (400 MHz, Chloroform-d) δ 6.83 (d, J=1.5 Hz, 1H), 6.57 (d, J=1.5 Hz, 1H), 3.83-3.79 (m, 4H), 3.69 (s, 2H), 3.55-3.52 (m, 4H), 2.77-2.71 (s, 4H), 1.90-1.84 (m, 4H).

Example 9: N-{4-methyl-3-[2-(morpholin-4-yl)-6-[3-(pyrrolidin-1-yl)prop-1-yn-1-yl]pyridin-4-yl]phenyl}-2-(trifluoromethyl)pyridine-4-carboxamide yl)phenyl]-2-(trifluoromethyl)pyridine-4-carboxamide (117 mg, 0.288 mmol), 2nd Generation Xphos Precatalyst (21 mg, 0.026 mmol) and K$_3$PO$_4$ (111 mg, 0.524 mmol) in THF (2 mL) and H$_2$O (0.2 mL) was stirred for 2 h at 80° C. under nitrogen atmosphere. The resulting mixture was concentrated under reduced pressure. The residue was purified by silica gel column chromatography, eluted with CH$_2$Cl$_2$/MeOH (10/1). The crude product was purified by reverse flash chromatography with the following conditions: C18 column; mobile phase, CH$_3$CN in water (10 mmol/L NH$_4$HCO$_3$), 60% to 80%; detector, UV 254 nm to afford N-{4-methyl-3-[2-(morpholin-4-yl)-6-[3-(pyrrolidin-1-yl)prop-1-yn-1-yl]pyridin-4-yl]phenyl}-2-(trifluoromethyl)pyridine-4-carboxamide (47 mg, 33%) as a white solid. MS ESI calculated for C$_{30}$H$_{30}$F$_3$N$_5$O$_2$ [M+H]$^+$, 550.24, found 550.30. $^1$H NMR (400 MHz, DMSO-d$_6$) δ 10.70 (s, 1H), 9.00 (d, J=4.8 Hz, 1H), 8.37 (s, 1H), 8.20 (d, J=4.8 Hz, 1H), 7.76 (dd, J=8.4, 1.6 Hz, 1H), 7.64 (s, 1H), 7.34 (d, J=8.4 Hz, 1H), 6.79 (s, 1H), 6.77 (s, 1H), 3.71-3.67 (m, 4H), 3.61 (s,

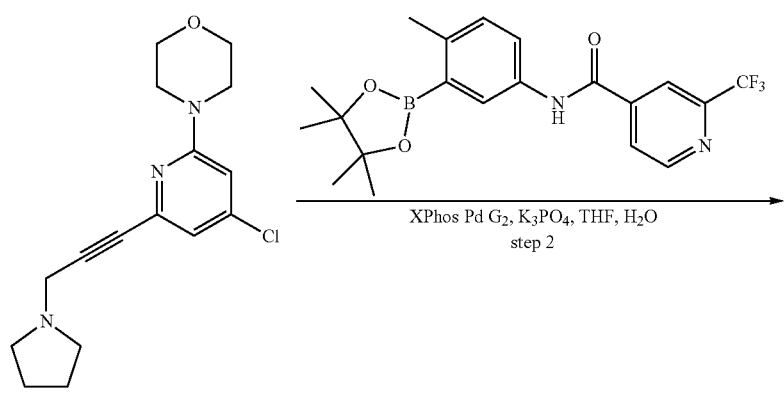

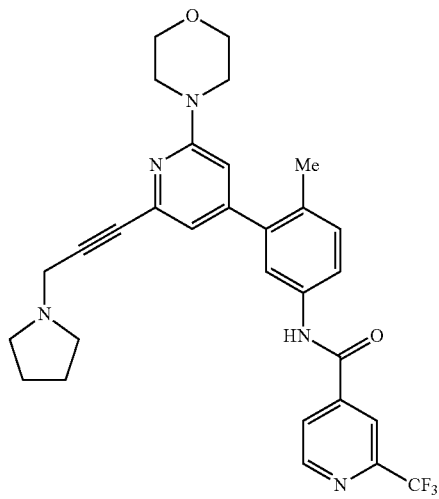

A mixture of 4-{4-chloro-6-[3-(pyrrolidin-1-yl)prop-1-yn-1-yl]pyridin-2-yl}morpholine (80 mg, 0.262 mmol), N-[4-methyl-3-(4,4,5,5-tetramethyl-1,3,2-dioxaborolan-2-

2H), 3.51-3.47 (m, 4H), 2.59-2.55 (m, 4H), 2.24 (s, 3H), 1.73-1.69 (m, 4H). $^{19}$F NMR (376 MHz, DMSO-d$_6$) δ −66.46 (3F).

Example 10: N-(4-methyl-3-{2-[3-(methylamino)prop-1-yn-1-yl]-6-(morpholin-4-yl)pyridin-4-yl}phenyl)-2-(trifluoromethyl)pyridine-4-carboxamide
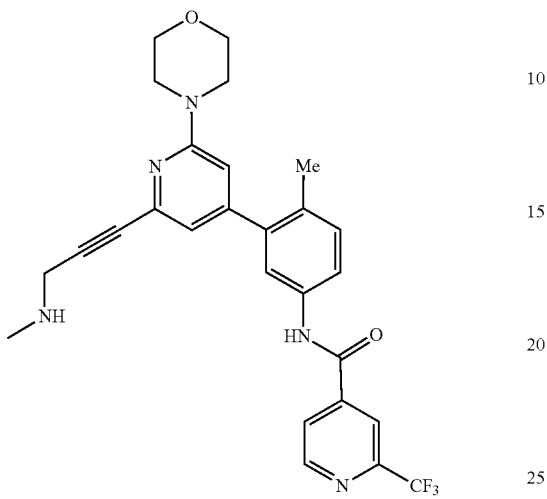
Synthetic Scheme
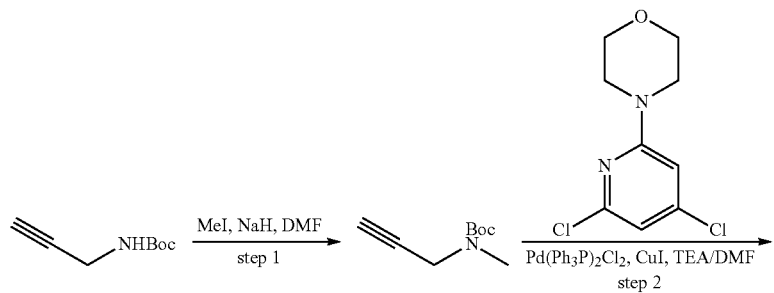
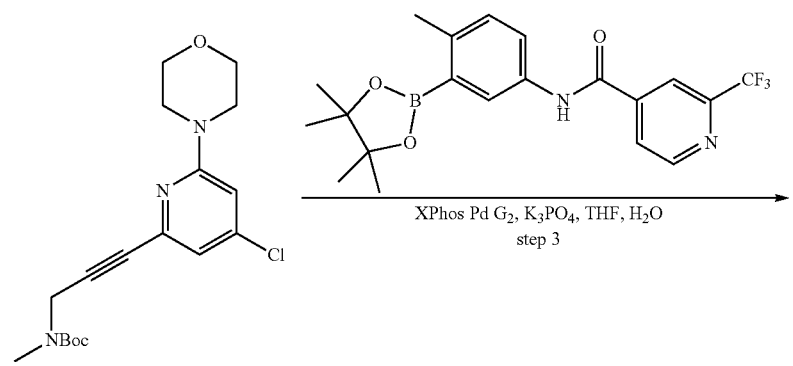

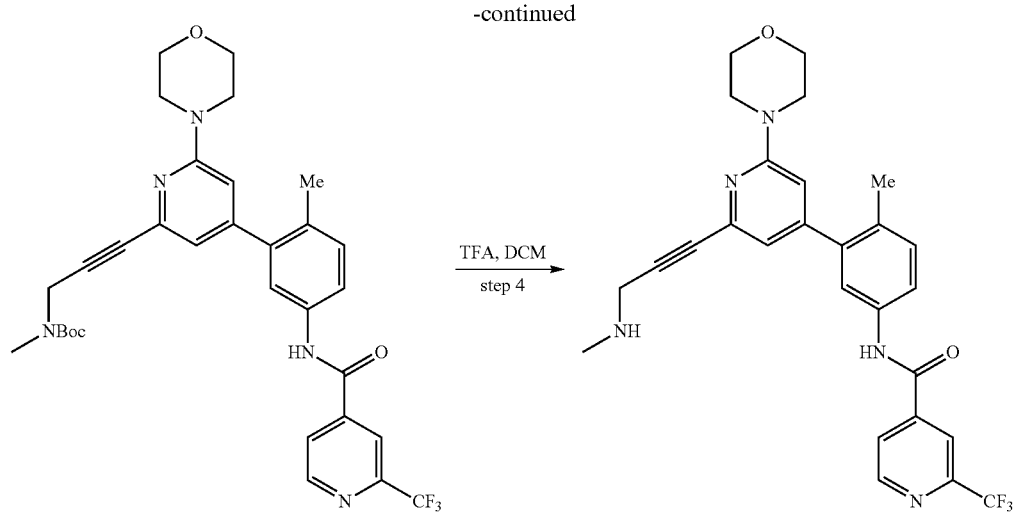

Preparation 10A: tert-butyl N-methyl-N-(prop-2-yn-1-yl)carbamate

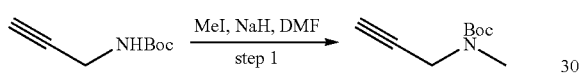

A mixture of tert-butyl N-(prop-2-yn-1-yl)carbamate (2.00 g, 12.89 mmol) in DMF (20 mL) and sodium hydride (0.46 g, 19.331 mmol) was stirred for 1 h at 0° C. To this was added methyl iodide (3.66 g, 25.77 mmol) dropwise at 0° C. The resulting mixture was stirred for 2 h at room temperature. The reaction was quenched by the addition of water (100 mL). The resulting mixture was extracted with EtOAc (3×150 mL). The combined organic layers were washed with brine (150 mL), dried over anhydrous $Na_2SO_4$. After filtration, the filtrate was concentrated under reduced pressure. The residue was purified by silica gel column chromatography, eluted with PE/EtOAc (10/1) to afford tert-butyl N-methyl-N-(prop-2-yn-1-yl)carbamate (1.86 g, 85%) as a light yellow oil. $^1$H NMR (400 MHz, Chloroform-d) δ 4.04 (s, 2H), 2.92 (s, 3H), 2.22 (s, 1H), 1.47 (s, 9H).

Preparation 10B: tert-butyl N-{3-[4-chloro-6-(morpholin-4-yl)pyridin-2-yl]prop-2-yn-1-yl}-N-methylcarbamate

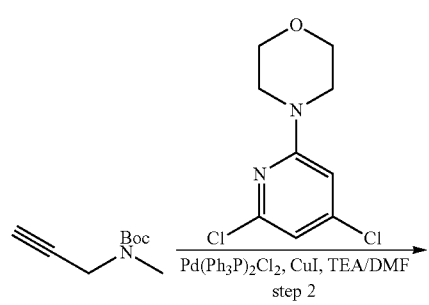

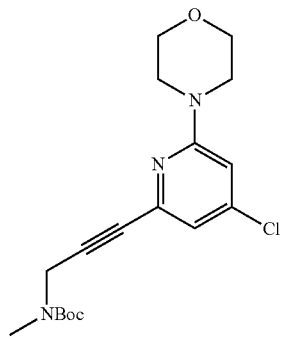

A mixture of 4-(4,6-dichloropyridin-2-yl)morpholine (500 mg, 2.145 mmol), tert-butyl N-methyl-N-(prop-2-yn-1-yl)carbamate (267 mg, 3.218 mmol), Pd(PPh$_3$)$_2$Cl$_2$ (150 mg, 0.215 mmol) and CuI (82 mg, 0.429 mmol) in TEA (2 mL) and DMF (10 mL) was stirred for 2 h 80° C. under nitrogen atmosphere. The reaction was quenched by the addition of water (30 mL). The resulting mixture was extracted with EtOAc (3×30 mL). The combined organic layers were washed with brine (15 mL), dried over anhydrous $Na_2SO_4$. After filtration, the filtrate was concentrated under reduced pressure. The residue was purified by silica gel column chromatography, eluted with PE/EtOAc (1/1) to afford tert-butyl N-{3-[4-chloro-6-(morpholin-4-yl)pyridin-2-yl]prop-2-yn-1-yl}-N-methylcarbamate (369 mg, 61%) as a yellow oil. MS ESI calculated for $C_{18}H_{25}ClN_3O_3$ [M+H]$^+$, 366.15, found 366.20. $^1$H NMR (400 MHz, Chloroform-d) δ 6.80 (s, 1H), 6.56 (s, 1H), 4.32-4.23 (m, 2H), 3.82-3.75 (m, 4H), 3.55-3.48 (m, 4H), 2.97 (s, 3H), 1.48 (s, 9H).

Preparation 10C: tert-butyl N-methyl-N-[3-(4-{2-methyl-5-[2-(trifluoromethyl)pyridine-4-amido]phenyl}-6-(morpholin-4-yl)pyridin-2-yl)prop-2-yn-1-yl]carbamate

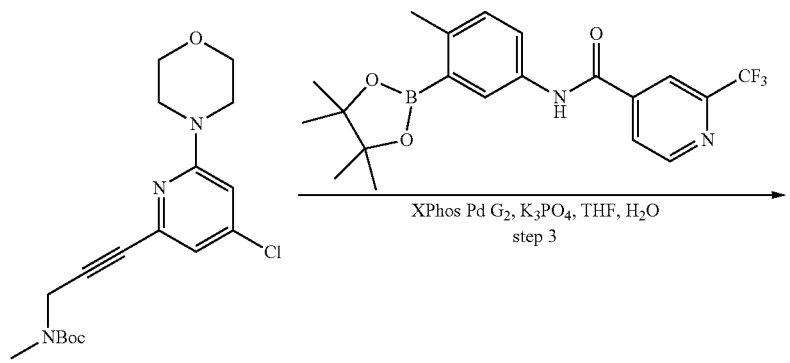

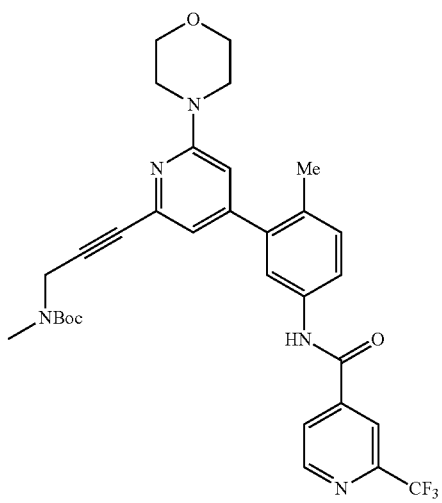 [SMILES: CNCC#Cc1cc(-c2cc(NC(=O)c3ccnc(C(F)(F)F)c3)ccc2C)cc(N2CCOCC2)n1]

A mixture of tert-butyl N-{3-[4-chloro-6-(morpholin-4-yl)pyridin-2-yl]prop-2-yn-1-yl}-N-methylcarbamate (200 mg, 0.547 mmol), N-[4-methyl-3-(4,4,5,5-tetramethyl-1,3,2-dioxaborolan-2-yl)phenyl]-2-(trifluoromethyl)pyridine-4-carboxamide (222 mg, 0.547 mmol), 2nd Generation XPhos Precatalyst (43 mg, 0.055 mmol) and K$_3$PO$_4$ (232 mg, 1.094 mmol) in THF (2 mL) and H$_2$O (0.2 mL) was stirred for 2 h at 80° C. under nitrogen atmosphere. The resulting mixture was concentrated under reduced pressure. The residue was purified by silica gel column chromatography, eluted with PE/EtOAc (1/1) to afford tert-butyl N-methyl-N-[3-(4-{2-methyl-5-[2-(trifluoromethyl)pyridine-4-amido]phenyl}-6-(morpholin-4-yl)pyridin-2-yl)prop-2-yn-1-yl]carbamate (208 mg, crude) as a brown solid. MS ESI calculated for C$_{32}$H$_{34}$F$_3$N$_5$O$_4$ [M+H]$^+$, 610.26, found 610.30.

Example 10: N-(4-methyl-3-{2-[3-(methylamino)prop-1-yn-1-yl]-6-(morpholin-4-yl)pyridin-4-yl}phenyl)-2-(trifluoromethyl)pyridine-4-carboxamide

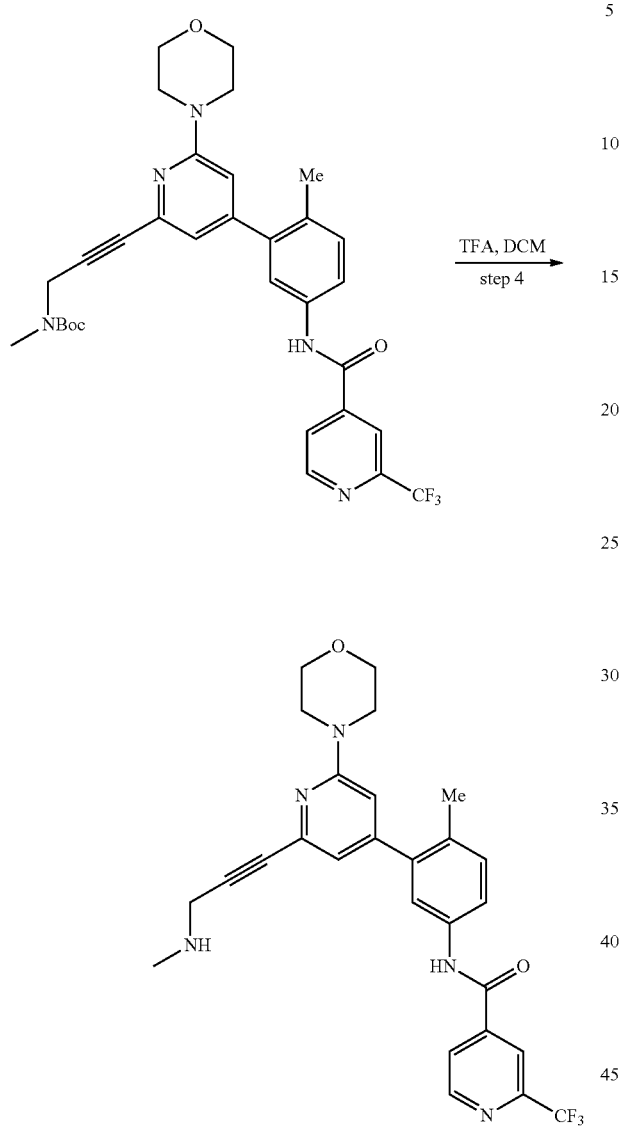

To a solution of tert-butyl N-methyl-N-[3-(4-{2-methyl-5-[2-(trifluoromethyl)pyridine-4-amido]phenyl}-6-(morpholin-4-yl)pyridin-2-yl)prop-2-yn-1-yl]carbamate (200 mg, 0.328 mmol) and DCM (5 mL) was added TFA (1 mL). The resulting mixture was stirred for 1 h at room temperature. The mixture was concentrated under reduced pressure and then neutralized to pH 8 with saturated NaHCO$_3$. The resulting mixture was extracted with EtOAc (3×30 mL). The combined organic layers were washed with brine (2×10 mL), dried over anhydrous Na$_2$SO$_4$. After filtration, the filtrate was concentrated under reduced pressure. The residue was purified by reverse flash chromatography with the following conditions: C18 column; mobile phase, CH$_3$CN in water (10 mmol/L NH$_4$HCO$_3$), 30% to 65%; detector, UV 254 nm to afford N-(4-methyl-3-{2-[3-(methylamino)prop-1-yn-1-yl]-6-(morpholin-4-yl)pyridin-4-yl}phenyl)-2-(trifluoromethyl)pyridine-4-carboxamide (83.5 mg, 50%) as a yellow solid. MS ESI calculated for C$_{27}$H$_{26}$F$_3$N$_5$O$_2$ [M+H]$^+$, 510.20, found 510.30. $^1$H NMR (300 MHz, DMSO-d$_6$) δ 10.69 (s, 1H), 9.00 (d, J=5.1 Hz, 1H), 8.38 (s, 1H), 8.19 (d, J=5.1 Hz, 1H), 7.76 (dd, J=8.4, 2.1 Hz, 1H), 7.65 (d, J=2.1 Hz, 1H), 7.34 (d, J=8.4 Hz, 1H), 6.78 (s, 1H), 6.76 (s, 1H), 3.72-3.66 (m, 4H), 3.52-3.48 (m, 6H), 2.34 (s, 3H), 2.24 (s, 3H). $^{19}$F NMR (282 MHz, DMSO-d$_6$) δ −66.50 (3F).

Example 11: N-{4-methyl-3-[2-(morpholin-4-yl)-6-{2-[(2R)-pyrrolidin-2-yl]ethynyl}pyridin-4-yl]phenyl}-2-(trifluoromethyl)pyridine-4-carboxamide

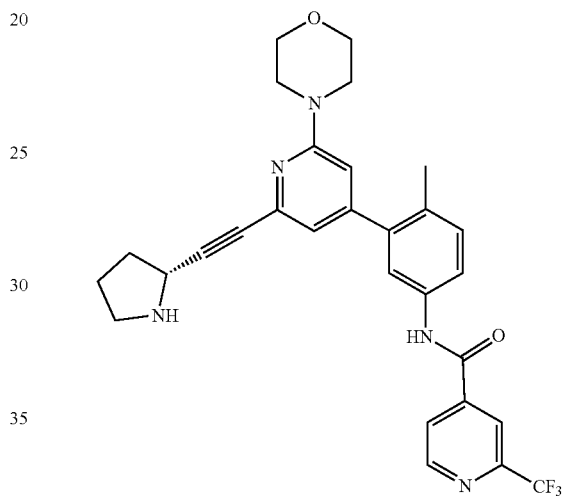

Synthetic Scheme

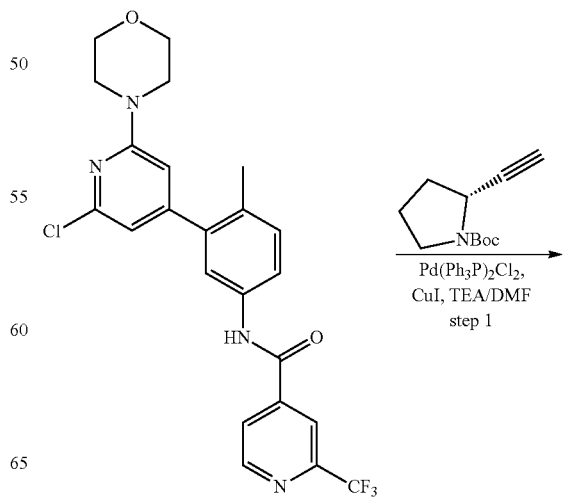

123

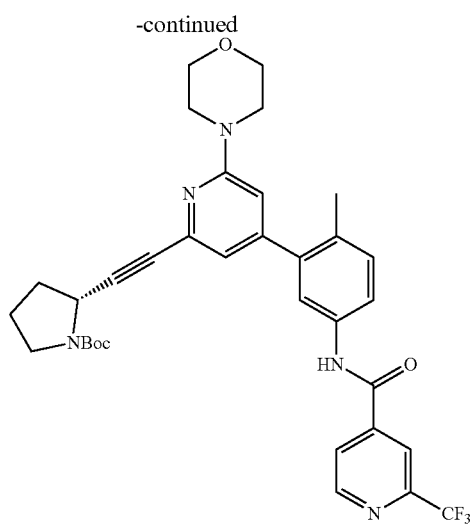

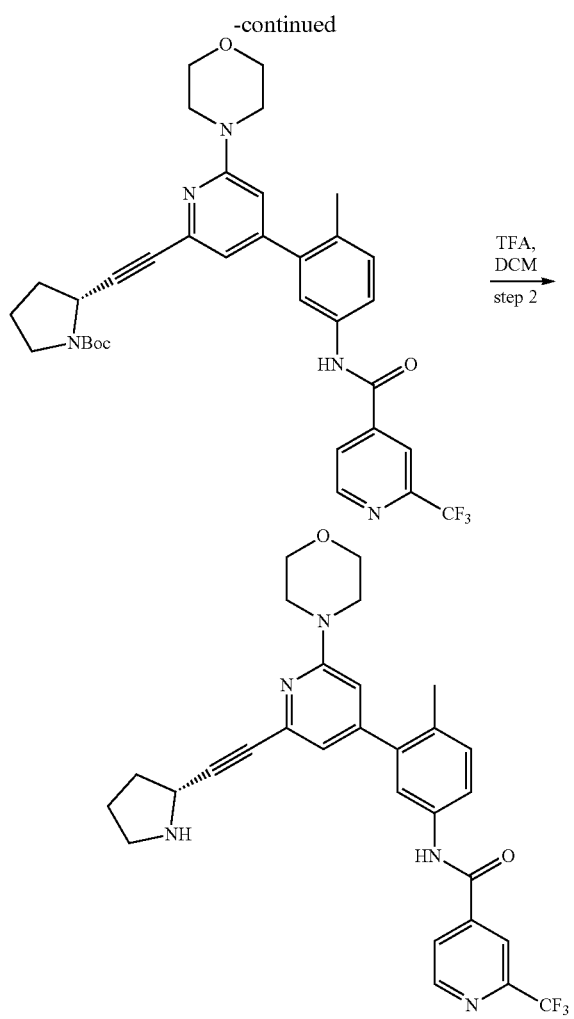

Preparation 11A: tert-butyl (2R)-2-[2-(4-{2-methyl-5-[2-(trifluoromethyl)pyridine-4-amido]phenyl}-6-(morpholin-4-yl)pyridin-2-yl)ethynyl]pyrrolidine-1-carboxylate

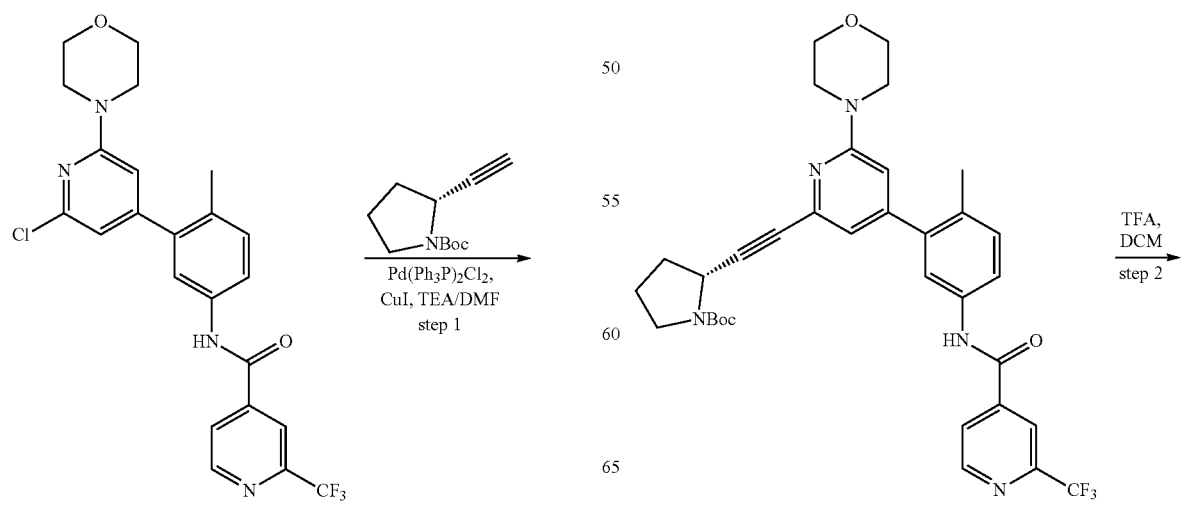

A mixture of N-{3-[2-chloro-6-(morpholin-4-yl)pyridin-4-yl]-4-methylphenyl}-2-(trifluoromethyl)pyridine-4-carboxamide (300 mg, 0.629 mmol), TEA (191 mg, 1.887 mmol), tert-butyl (2R)-2-ethynylpyrrolidine-1-carboxylate (246 mg, 1.258 mmol), CuI (24 mg, 0.126 mmol) and Pd(PPh$_3$)$_2$Cl$_2$ (44 mg, 0.063 mmol) in DMF (4 mL) was stirred for 16 h at 80° C. under nitrogen atmosphere. The resulting mixture was diluted with water (50 mL). The resulting mixture was extracted with EtOAc (3×30 mL). The combined organic layers were washed with brine (3×30 mL), dried over anhydrous Na$_2$SO$_4$. After filtration, the filtrate was concentrated under reduced pressure. The residue was purified by silica gel column chromatography, eluted with PE/EtOAc (1/1) to afford tert-butyl (2R)-2-[2-(4-{2-methyl-5-[2-(trifluoromethyl)pyridine-4-amido]phenyl}-6-(morpholin-4-yl)pyridin-2-yl)ethynyl]pyrrolidine-1-carboxylate (200 mg, crude) as a light yellow solid; MS ESI calculated for C$_{34}$H$_{36}$F$_3$N$_5$O$_4$ [M+H]$^+$, 636.27; found 636.35.

Example 11: N-{4-methyl-3-[2-(morpholin-4-yl)-6-{2-[(2R)-pyrrolidin-2-yl]ethynyl}pyridin-4-yl]phenyl}-2-(trifluoromethyl)pyridine-4-carboxamide

125

-continued

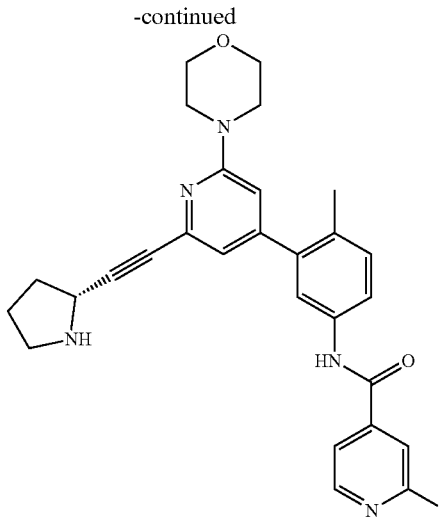

A mixture of tert-butyl (2R)-2-[2-[4-{2-methyl-5-[2-(trifluoromethyl)pyridine-4-amido]phenyl}-6-(morpholin-4-

126 yl)pyridin-2-yl)ethynyl]pyrrolidine-1-carboxylate (230 mg, 0.334 mmol) in DCM (4 mL) was added TFA (1 mg) at 0° C. The reaction mixture was stirred for 30 min at room temperature. The resulting mixture was concentrated under reduced pressure. The residue was purified by reverse phase chromatography, eluted with 65% $CH_3CN$ in water (with 0.05% $NH_4HCO_3$) to afford N-{4-methyl-3-[2-(morpholin-4-yl)-6-{2-[(2R)-pyrrolidin-2-yl]ethynyl}pyridin-4-yl]phenyl}-2-(trifluoromethyl)pyridine-4-carboxamide (95.1 mg, 49%) as a white solid. MS ESI calculated for $C_{29}H_{28}F_3N_5O_2$ $[M+H]^+$, 536.22; found 536.30. $^1$H NMR (400 MHz, Chloroform-d) δ 8.94 (d, J=4.8 Hz, 1H), 8.19 (s, 1H), 8.15 (s, 1H), 8.00-7.94 (m, 1H), 7.66-7.59 (m, 1H), 7.47 (s, 1H), 7.30 (d, J=8.4 Hz, 1H), 6.80 (s, 1H), 6.51 (s, 1H), 4.13-4.09 (m, 1H), 3.84-3.81 (m, 4H), 3.59-3.52 (m, 4H), 3.21-3.14 (m, 1H), 3.01-2.95 (m, 1H), 2.28 (s, 3H), 2.20-2.13 (m, 1H), 2.04-1.98 (m, 2H), 1.87-1.78 (m, 1H). $^{19}$F NMR (376 MHz, Chloroform-d) δ −67.83 (3F).

Examples 12 and 13: N-(4-methyl-3-{2-[(3R)-3-(methylamino)but-1-yn-1-yl]-6-(morpholin-4-yl)pyridin-4-yl}phenyl)-2-(trifluoromethyl)pyridine-4-carboxamide

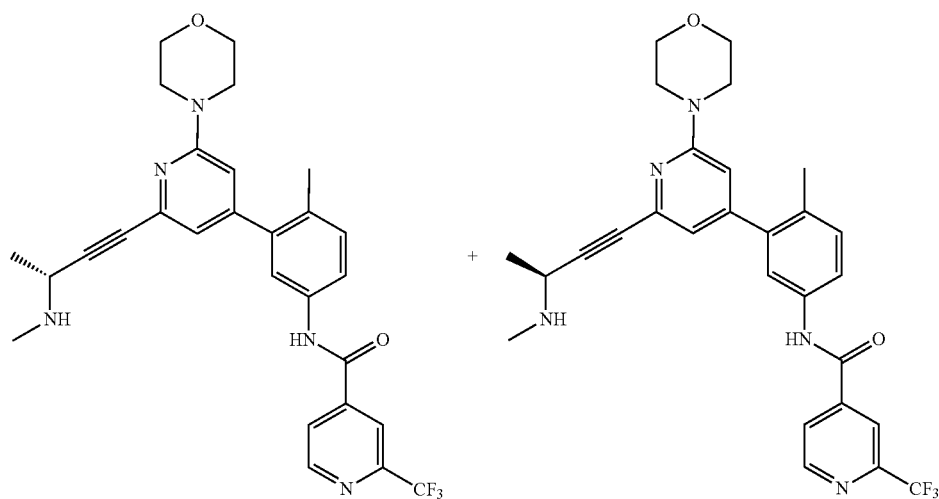 [SMILES: CN[C@H](C)C#Cc1cc(-c2cc(NC(=O)c3ccnc(C(F)(F)F)c3)ccc2C)cc(N2CCOCC2)n1 ; CN[C@@H](C)C#Cc1cc(-c2cc(NC(=O)c3ccnc(C(F)(F)F)c3)ccc2C)cc(N2CCOCC2)n1]

Synthetic Scheme

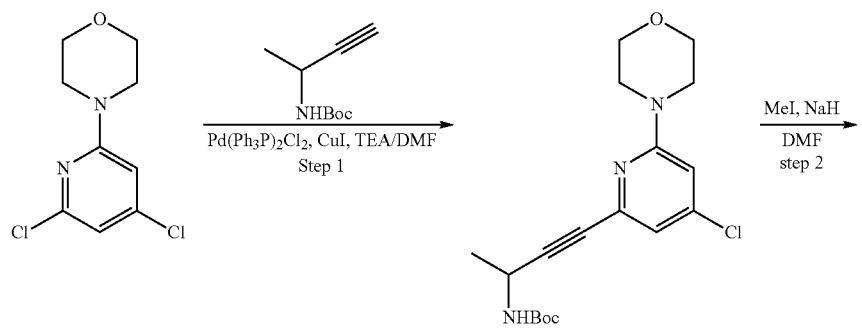

-continued
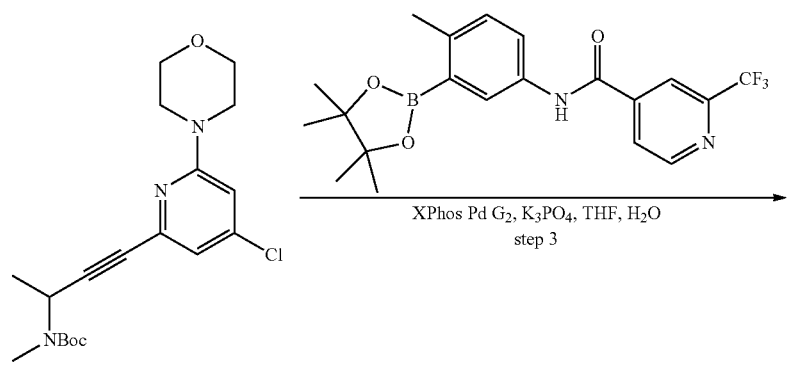
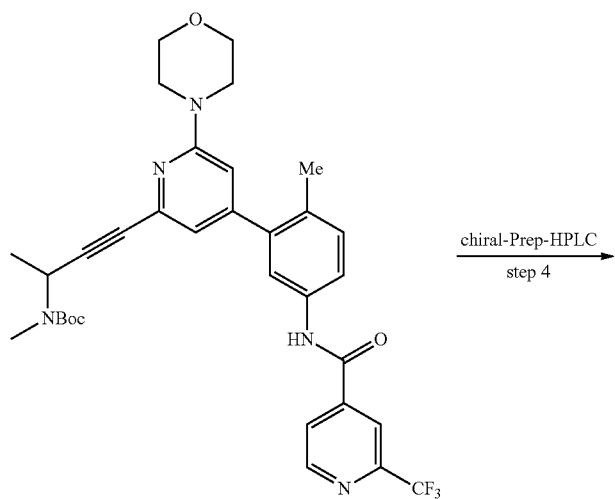
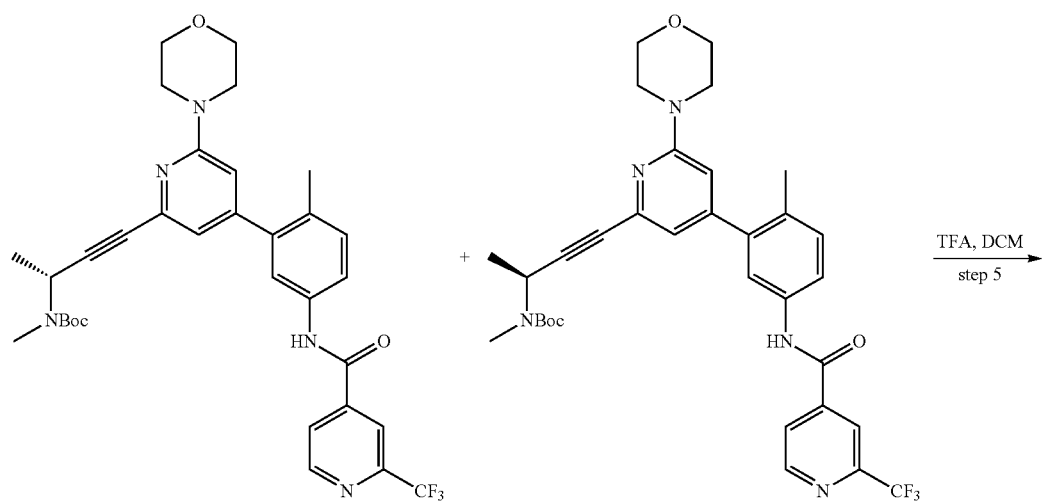

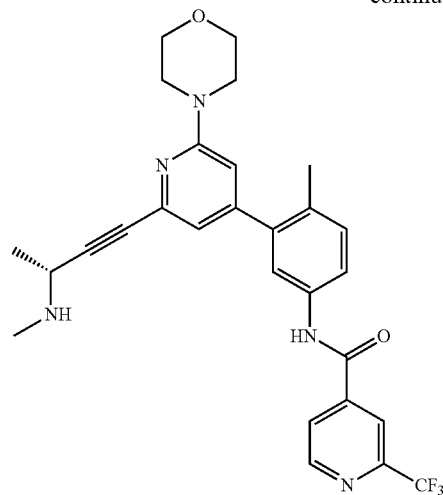

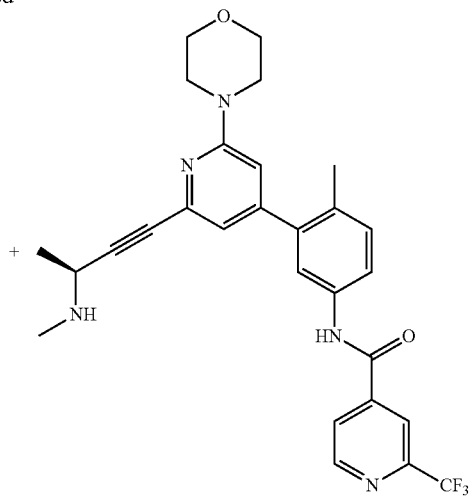

Preparation 12A: tert-butyl N-[4-[4-chloro-6-(morpholin-4-yl)pyridin-2-yl]but-3-yn-2-yl]carbamate Preparation 12B: tert-butyl N-{4-[4-chloro-6-(morpholin-4-yl)pyridin-2-yl]but-3-yn-2-yl}-N-methylcarbamate

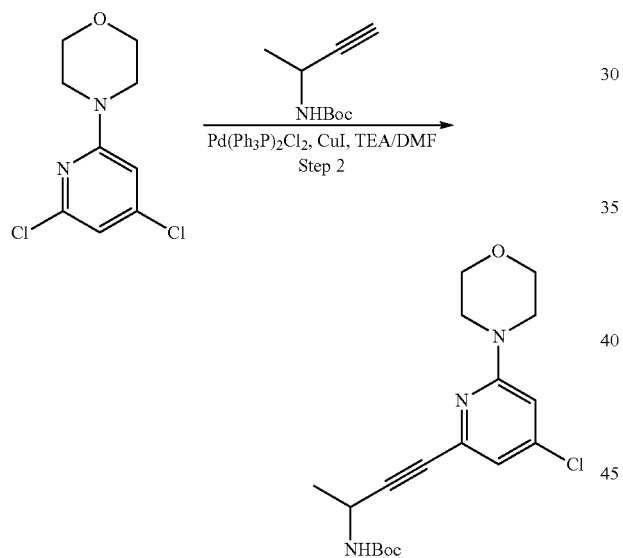

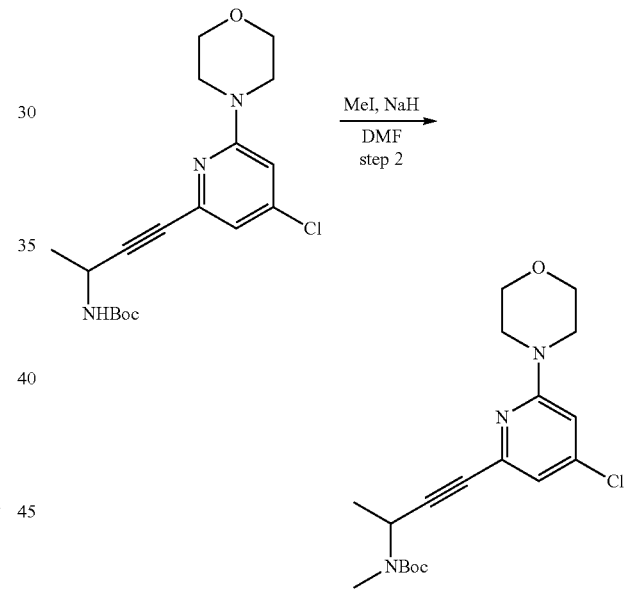

A mixture of 4-(4,6-dichloropyridin-2-yl)morpholine (570 mg, 2.445 mmol) and tert-butyl N-(but-3-yn-2-yl)carbamate (828 mg, 4.891 mmol), TEA (1.5 mL), DMF (6 mL), Pd(PPh$_3$)$_2$Cl$_2$ (172 mg, 0.245 mmol) and CuI (93 mg, 0.489 mmol) was stirred for 16 h at 80° C. under argon atmosphere. The resulting mixture was quenched with water (100 mL) and extracted with EtOAc (3×100 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with PE/EtOAc (5/1) to afford tert-butyl N-[4-[4-chloro-6-(morpholin-4-yl)pyridin-2-yl]but-3-yn-2-yl]carbamate (850 mg, 95%) as a yellow solid. MS ESI calculated for C$_{18}$H$_{24}$ClN$_3$O$_3$ [M+H]$^+$, 366.15, found 366.20. $^1$H NMR (400 MHz, Chloroform-d) δ 6.81 (s, 1H), 6.58 (s, 1H), 3.82-3.80 (m, 4H), 3.56-3.53 (m, 4H), 1.51-1.44 (m, 12H).

To a stirred mixture of tert-butyl N-{4-[4-chloro-6-(morpholin-4-yl)pyridin-2-yl]but-3-yn-2-yl}carbamate (500 mg, 1.367 mmol) and NaH (82 mg, 2.050 mmol) in DMF (5 mL) was added MeI (388 mg, 2.734 mmol) at 0° C. The resulting mixture was stirred for 3 h at room temperature. The mixture was quenched by the addition of water (20 mL). The resulting mixture was extracted with EtOAc (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc (4/1) to afford tert-butyl N-{4-[4-chloro-6-(morpholin-4-yl)pyridin-2-yl]but-3-yn-2-yl}-N-methylcarbamate (500 mg, 96%) as an orange oil. MS ESI calculated for C$_{19}$H$_{26}$ClN$_3$O$_3$ [M+H]$^+$, 380.17, found 380.10. $^1$H NMR (400 MHz, Chloroform-d) δ 6.79 (d, J=1.6 Hz, 1H), 6.55 (d, J=1.6 Hz, 1H), 3.82-3.77 (m, 5H), 3.53-3.50 (m, 4H), 2.91 (s, 3H), 1.47 (s, 9H), 1.45-1.42 (m, 3H).

Preparation 12C: tert-butyl N-methyl-N-[4-(4-{2-methyl-5-[2-(trifluoromethyl)pyridine-4-amido]phenyl}-6-(morpholin-4-yl)pyridin-2-yl)but-3-yn-2-yl]carbamate

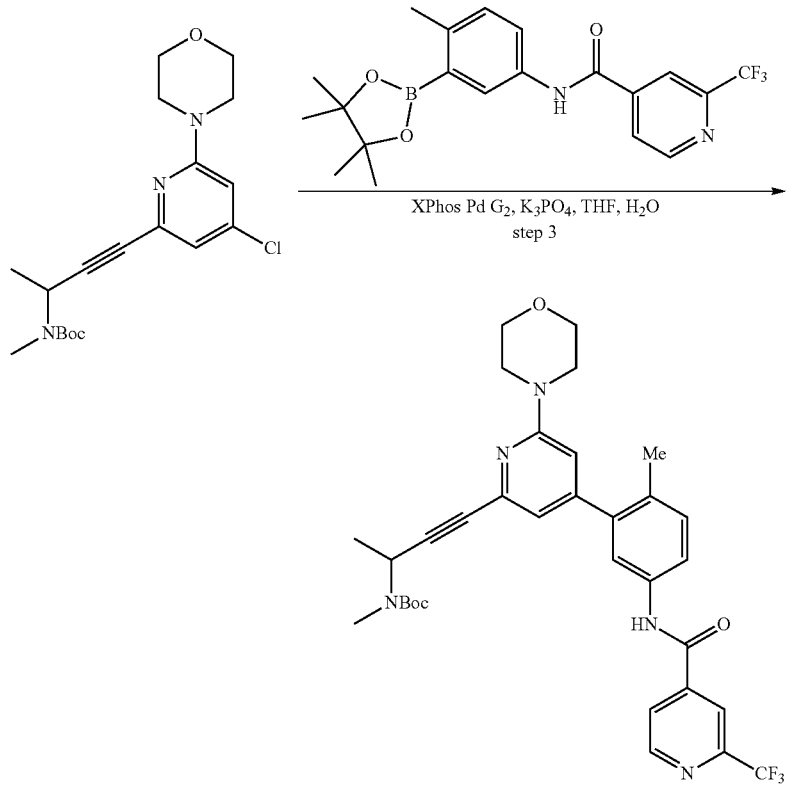

A mixture of tert-butyl N-{4-[4-chloro-6-(morpholin-4-yl)pyridin-2-yl]but-3-yn-2-yl}-N-methylcarbamate (460 mg, 1.211 mmol), N-[4-methyl-3-(4,4,5,5-tetramethyl-1,3,2-dioxaborolan-2-yl)phenyl]-2-(trifluoromethyl)pyridine-4-carboxamide (492 mg, 1.211 mmol), 2$^{nd}$ Generation Xphos precatalyst (95 mg, 0.121 mmol) and K$_3$PO$_4$ (514 mg, 2.422 mmol) in THF (5 mL) and H$_2$O (0.5 mL) was stirred for 16 h at 80° C. under nitrogen atmosphere. The reaction was quenched by the addition of water (30 mL). The resulting mixture was extracted with EtOAc (3×30 mL). The combined organic layers were washed with brine (30 mL), dried over anhydrous Na$_2$SO$_4$. After filtration, the filtrate was concentrated under reduced pressure. The residue was purified by silica gel column chromatography, eluted with CH$_2$Cl$_2$/EtOAc (4/1) to afford tert-butyl N-methyl-N-[4-(4-{2-methyl-5-[2-(trifluoromethyl)pyridine-4-amido]phenyl}-6-(morpholin-4-yl)pyridin-2-yl)but-3-yn-2-yl]carbamate (268 mg, 35%) as a light yellow oil. MS ESI calculated for C$_{33}$H$_{36}$F$_3$N$_5$O$_4$ [M+H]$^+$, 624.27, found 624.40. $^1$H NMR (300 MHz, Chloroform-d) δ 8.92 (d, J=5.1 Hz, 1H), 8.37 (s, 1H), 8.16 (s, 1H), 7.97 (d, J=5.1 Hz, 1H), 7.63 (d, J=8.1 Hz, 1H), 7.48 (s, 1H), 7.31 (d, J=7.8 Hz, 1H), 6.79 (s, 1H), 6.52 (s, 1H), 5.40-5.26 (m, 1H), 3.84-3.80 (m, 4H), 3.56-3.52 (m, 4H), 2.92 (s, 3H), 2.27 (s, 3H), 1.43 (d, J=6.9 Hz, 3H), 1.26 (s, 9H).

Preparations 12D and 13D: tert-butyl N-methyl-N-[(2R)-4-(4-{2-methyl-5-[2-(trifluoromethyl)pyridine-4-amido]phenyl}-6-(morpholin-4-yl)pyridin-2-yl)but-3-yn-2-yl]carbamate and tert-butyl N-methyl-N-[(2S)-4-(4-{2-methyl-5-[2-(trifluoromethyl)pyridine-4-amido]phenyl}-6-(morpholin-4-yl)pyridin-2-yl)but-3-yn-2-yl]carbamate

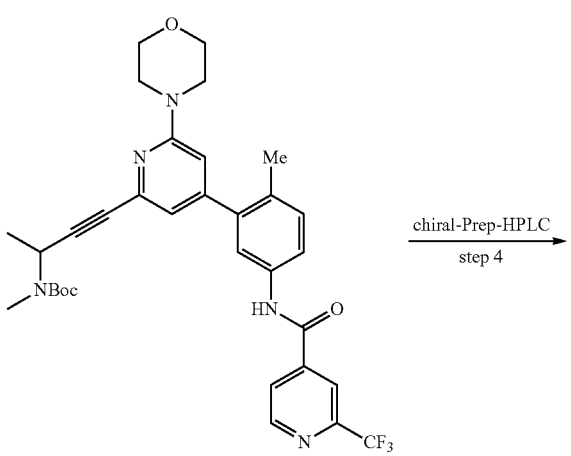

133
-continued

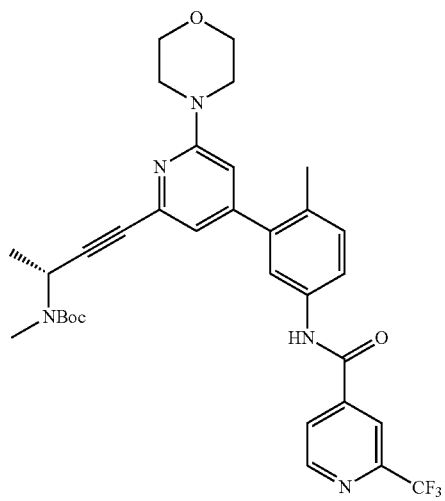

Tert-butyl N-methyl-N-[4-(4-{2-methyl-5-[2-(trifluoromethyl)pyridine-4-amido]phenyl}-6-(morpholin-4-yl)pyridin-2-yl)but-3-yn-2-yl]carbamate (280 mg, 0.449 mmol) was resolved by Prep-HPLC with the following conditions Column: CHIRALPAK IE, 2×25 cm, 5 μm; Mobile Phase A: Hexane (0.5% 2 M NH$_3$-MeOH), Mobile Phase B: EtOH; Flow rate: 20 mL/min; A:B=85:15; 220/254 nm, to give:

Preparation 12D as an off-white oil (90 mg, 32%), RT$_1$: 14.34 min. MS ESI calculated for C$_{33}$H$_{36}$F$_3$N$_5$O$_4$ [M+H]$^+$, 624.27, found 624.15.

Preparation 13D as an off-white oil (100 mg, 36%), RT$_2$: 19.93 min. MS ESI calculated for C$_{33}$H$_{36}$F$_3$N$_5$O$_4$ [M+H]$^+$, 624.27, found 624.15.

134
Examples 12 and 13: N-(4-methyl-3-{2-[(3R)-3-(methylamino)but-1-yn-1-yl]-6-(morpholin-4-yl)pyridin-4-yl}phenyl)-2-(trifluoromethyl)pyridine-4-carboxamide 135
-continued

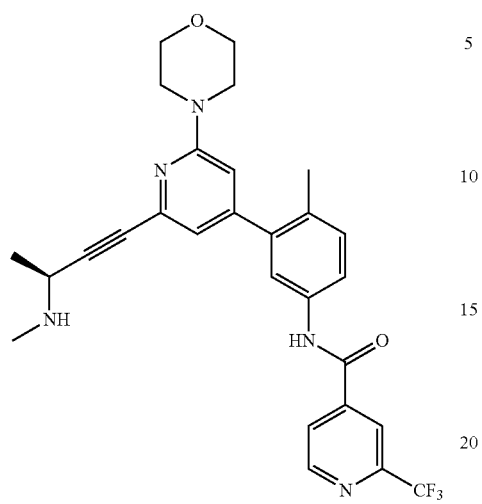

A mixture of Preparation 12D (90 mg, 0.144 mmol) in DCM (3 mL) and TFA (1 mL) was stirred for 2 h at room temperature. The resulting mixture was concentrated under reduced pressure. The residue was basified to pH 7 with saturated Na₂CO₃. The resulting mixture was extracted with EtOAc (3×50 mL). The combined organic layers were washed with brine (20 mL), dried over anhydrous Na₂SO₄. After filtration, the filtrate was concentrated under reduced pressure. The residue was purified by reverse flash chromatography with the following conditions: C18 column; mobile phase, CH₃CN in water (10 mmol/L NH₄HCO₃), 45% to 85% to Example 12 (24 mg, 24%) as a white solid. MS ESI calculated for C₂₈H₂₈F₃N₅O₂ [M+H]⁺, 524.22, found 524.15. ¹H NMR (400 MHz, DMSO-d₆) δ 10.69 (s, 1H), 9.00 (d, J=4.8 Hz, 1H), 8.37 (s, 1H), 8.20 (d, J=4.4 Hz, 1H), 7.77 (d, J=6.4 Hz, 1H), 7.65 (s, 1H), 7.34 (d, J=8.4 Hz, 1H), 6.78 (s, 1H), 6.74 (s, 1H), 3.74-3.68 (m, 4H), 3.58-3.55 (m, 1H), 3.53-3.48 (m, 4H), 2.36 (s, 3H), 2.25 (s, 3H), 1.31 (d, J=6.8 Hz, 3H). ¹⁹F NMR (376 MHz, DMSO-d₆) δ −66.46 (3F).

A stirred mixture of Preparation 13D (100 mg, 0.160 mmol) in DCM (3 mL) and TFA (1 mL) was stirred for 2 h at room temperature. The resulting mixture was concentrated under reduced pressure. The residue was basified to pH 7 with saturated Na₂CO₃. The resulting mixture was extracted with EtOAc (3×50 mL). The combined organic layers were washed with brine (20 mL), dried over anhydrous Na₂SO₄. After filtration, the filtrate was concentrated under reduced pressure. The residue was purified by reverse flash chromatography with the following conditions: C18 column; mobile phase, CH₃CN in water (10 mmol/L NH₄HCO₃), 45% to 85% to give Example 13 (35 mg, 41%) as a white solid. MS ESI calculated for C₂₈H₂₈F₃N₅O₂ [M+H]⁺, 524.22, found 524.15. ¹H NMR (400 MHz, DMSO-d₆) δ 10.69 (s, 1H), 9.00 (d, J=4.8 Hz, 1H), 8.37 (s, 1H), 8.20 (d, J=5.2 Hz, 1H), 7.76 (dd, J=8.0, 2.0 Hz, 1H), 7.66 (s, 1H), 7.34 (d, J=8.4 Hz, 1H), 6.77 (s, 1H), 6.74 (s, 1H), 3.74-3.66 (m, 4H), 3.63-3.56 (m, 1H), 3.51-3.47 (m, 4H), 2.36 (s, 3H), 2.25 (s, 3H), 1.31 (d, J=6.8 Hz, 3H). ¹⁹F NMR (376 MHz, DMSO-d₆)-66.46 (3F).

Example 14: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide

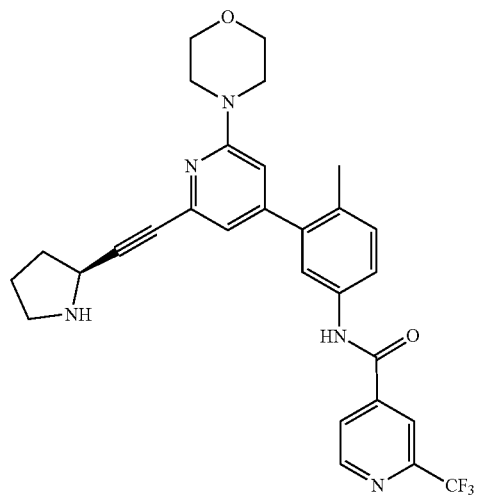 [SMILES: Cc1ccc(NC(=O)c2ccnc(C(F)(F)F)c2)cc1-c1cc(C#C[C@@H]2CCCN2)nc(N2CCOCC2)c1]

Synthetic Scheme

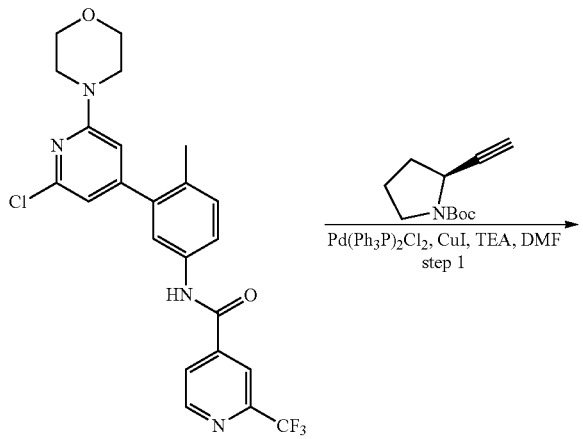

Pd(Ph₃P)₂Cl₂, CuI, TEA, DMF
step 1

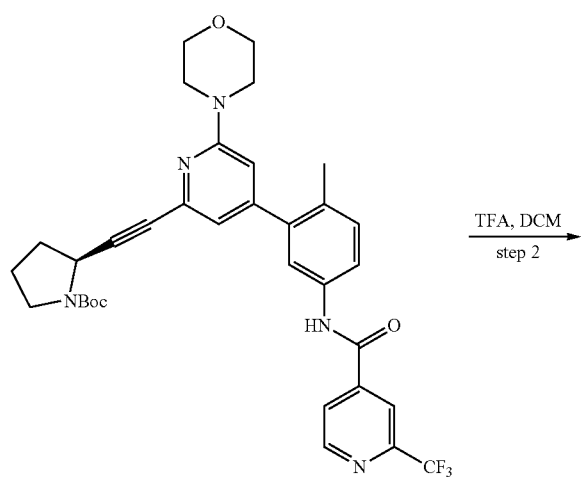

TFA, DCM
step 2

-continued

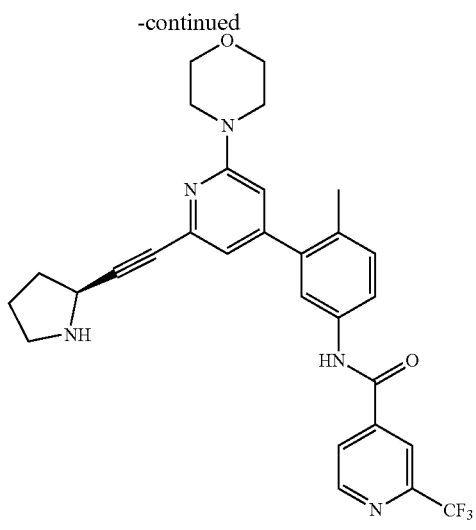

Preparation 14A: tert-butyl (2S)-2-[2-(4-{2-methyl-5-[2-(trifluoromethyl)pyridine-4-amido]phenyl}-6-(morpholin-4-yl)pyridin-2-yl)ethynyl]pyrrolidine-1-carboxylate

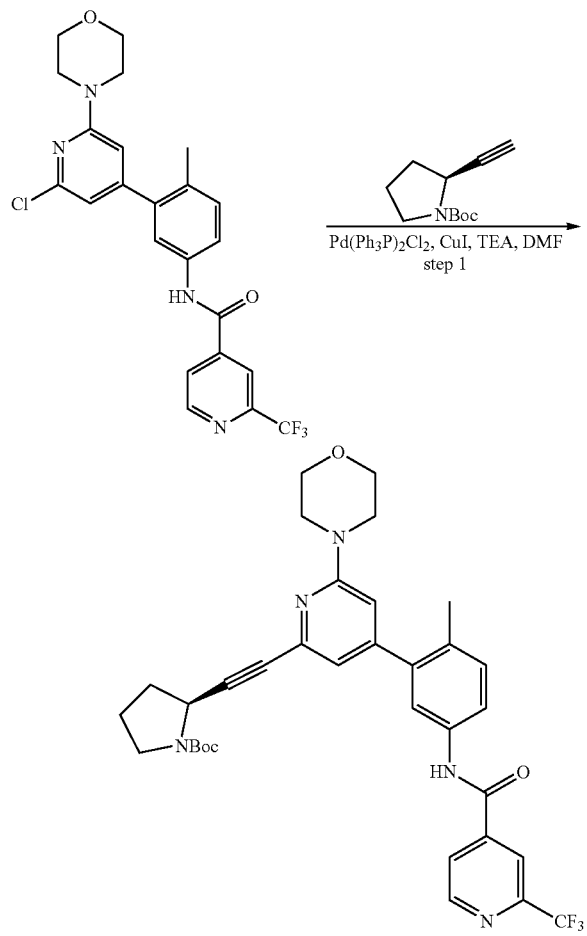

A mixture of N-{3-[2-chloro-6-(morpholin-4-yl)pyridin-4-yl]-4-methylphenyl}-2-(trifluoromethyl)pyridine-4-carboxamide (300 mg, 0.629 mmol), TEA (191 mg, 1.887 mmol), tert-butyl (2R)-2-ethynylpyrrolidine-1-carboxylate (246 mg, 1.258 mmol), CuI (24 mg, 0.126 mmol) and Pd(PPh$_3$)$_2$Cl$_2$ (44 mg, 0.063 mmol) in DMF (4 mL) was stirred for 16 h at 80° C. under nitrogen atmosphere. The resulting mixture was diluted with water (50 mL). The resulting mixture was extracted with EtOAc (3×30 mL). The combined organic layers were washed with brine (3×30 mL), dried over anhydrous Na$_2$SO$_4$. After filtration, the filtrate was concentrated under reduced pressure. The residue was purified by silica gel column chromatography, eluted with PE/EtOAc (6/4) to afford tert-butyl (2S)-2-[2-(4-{2-methyl-5-[2-(trifluoromethyl)pyridine-4-amido]phenyl}-6-(morpholin-4-yl)pyridin-2-yl)ethynyl]pyrrolidine-1-carboxylate (200 mg, crude) as a light yellow solid; MS ESI calculated for C$_{34}$H$_{36}$F$_3$N$_5$O$_4$ [M+H]$^+$, 636.27; found 636.75.

Example 14: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide

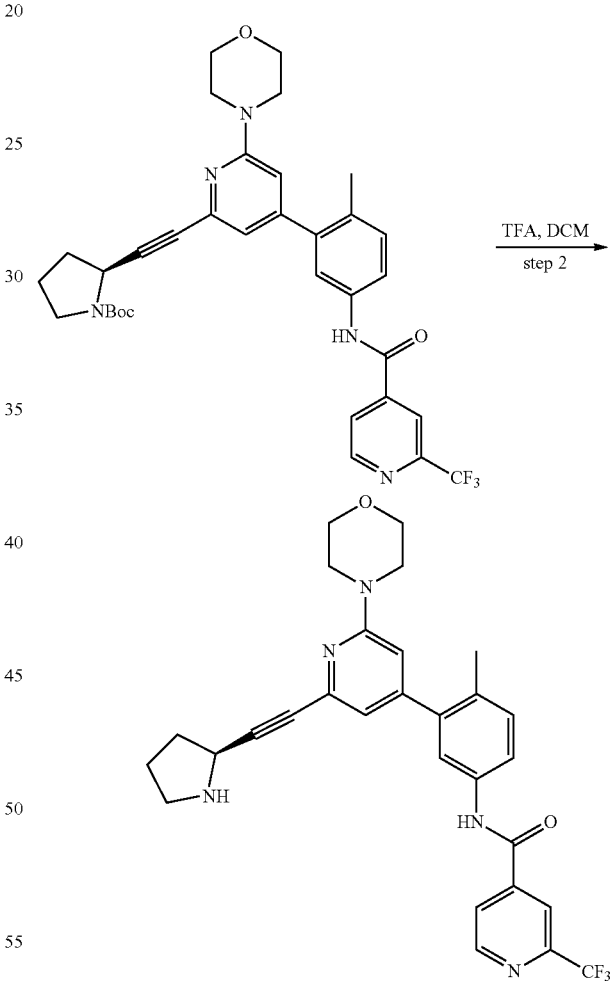

A mixture of tert-butyl (2S)-2-[2-(4-{2-methyl-5-[2-(trifluoromethyl)pyridine-4-amido]phenyl}-6-(morpholin-4-yl)pyridin-2-yl)ethynyl]pyrrolidine-1-carboxylate (230 mg, 0.334 mmol) in DCM (4 mL) was added TFA (1 mg). The reaction mixture was stirred for 30 min at room temperature. The resulting mixture was concentrated under reduced pressure. The residue was purified by reverse phase chromatography, eluted with 60% CH$_3$CN in water (with 0.05% NH$_4$HCO$_3$) to afford N-{4-methyl-3-[2-(morpholin-4-yl)-6-{2-[(2S)-pyrrolidin-2-yl]ethynyl}pyridin-4-yl]phenyl}-2-

(trifluoromethyl)pyridine-4-carboxamide (71.1 mg, 38%) as a white solid. MS ESI calculated for $C_{29}H_{28}F_3N_5O_2$ [M+H]$^+$, 536.22; found 536.20. $^1$H NMR (400 MHz, Chloroform-d) δ 8.94 (d, J=4.8 Hz, 1H), 8.15 (s, 2H), 7.97 (d, J=4.8 Hz, 1H), 7.64-7.62 (m, 1H), 7.48 (s, 1H), 7.31 (d, J=8.4 Hz, 1H), 6.80 (s, 1H), 6.51 (s, 1H), 4.14-4.10 (m, 1H), 3.85-3.81 (m, 4H), 3.59-3.52 (m, 4H), 3.20-3.15 (m, 1H), 3.02-2.96 (m, 1H), 2.28 (s, 3H), 2.20-2.13 (m, 1H), 2.04-1.80 (m, 3H). $^{19}$F NMR (376 MHz, Chloroform-d) −67.98 (3F).

Examples 15 and 16: N-{4-methyl-3-[2-(morpholin-4-yl)-6-[(3S)-4,4,4-trifluoro-3-hydroxybut-1-yn-1-yl]pyridin-4-yl]phenyl}-2-(trifluoromethyl)pyridine-4-carboxamide and N-{4-methyl-3-[2-(morpholin-4-yl)-6-[(3R)-4,4,4-trifluoro-3-hydroxybut-1-yn-1-yl]pyridin-4-yl]phenyl}-2-(trifluoromethyl)pyridine-4-carboxamide

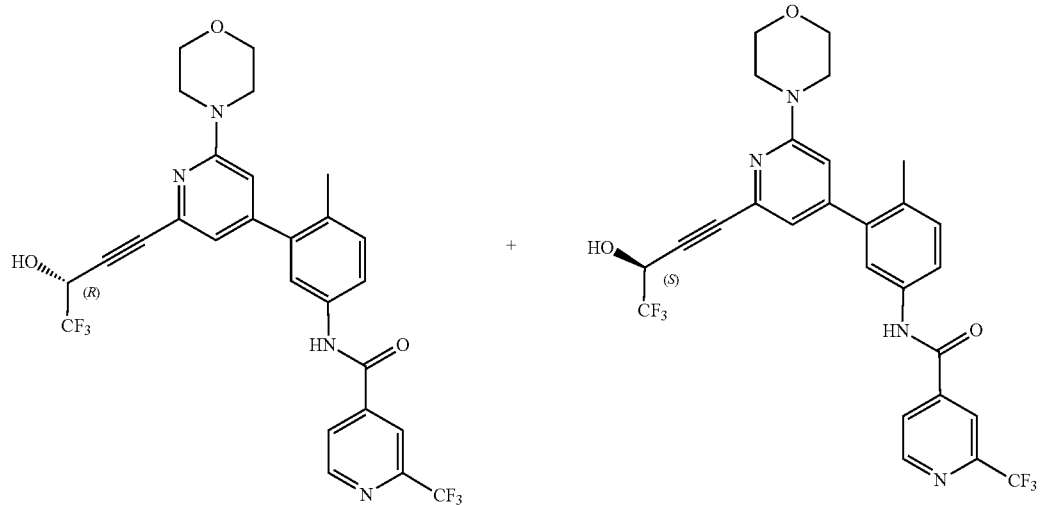

Synthetic Scheme

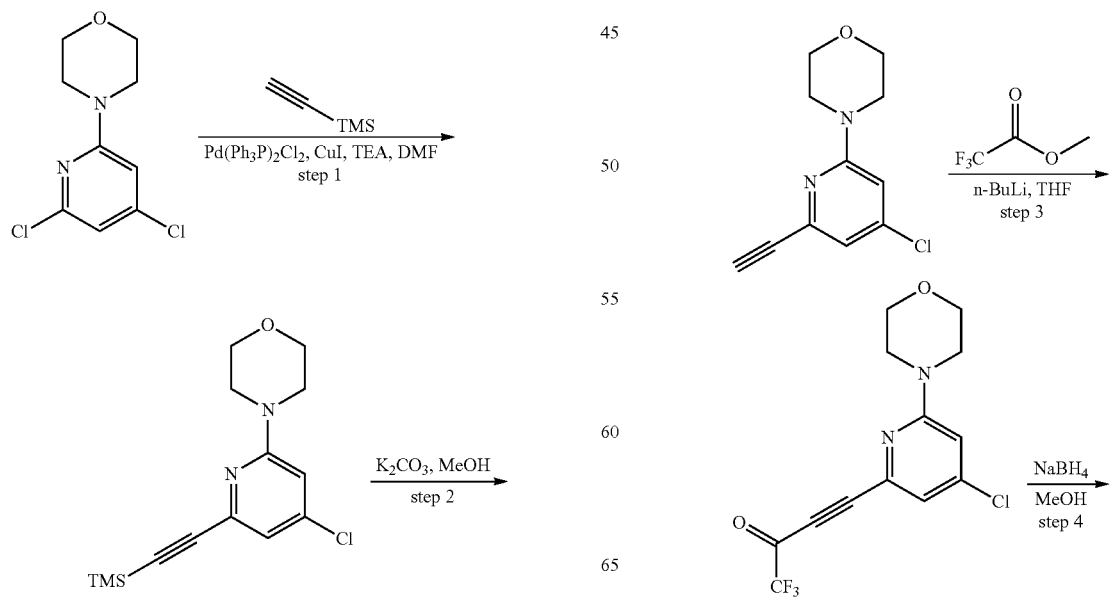

-continued

-continued

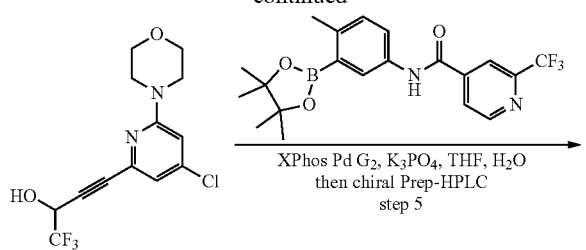

XPhos Pd G₂, K₃PO₄, THF, H₂O
then chiral Prep-HPLC
step 5

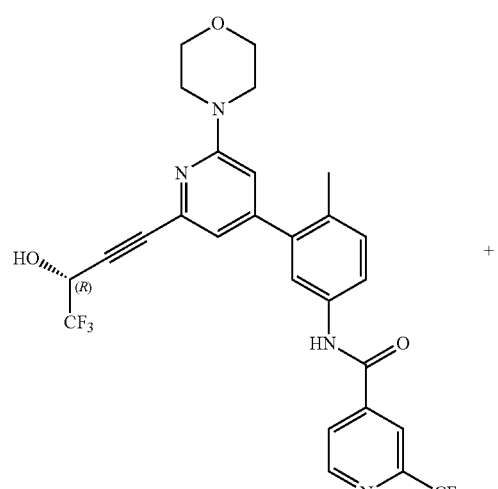

+

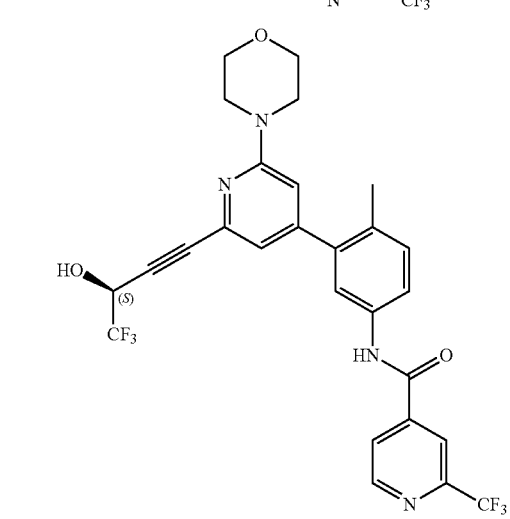

Preparation 15A: 4-{4-chloro-6-[2-(trimethylsilyl)ethynyl]pyridin-2-yl}morpholine

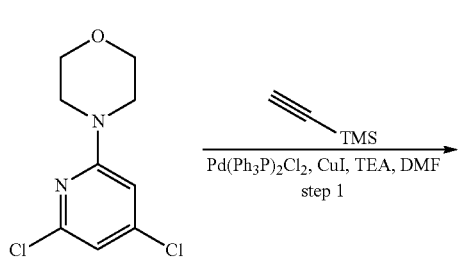

-continued

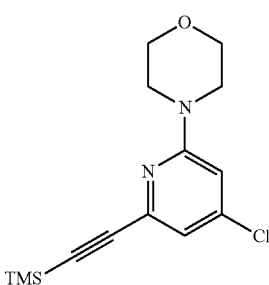

A mixture of 4-(4,6-dichloropyridin-2-yl)morpholine (2.00 g, 8.58 mmol), trimethylsilylacetylene (1.69 g, 17.16 mmol), Pd(PPh₃)₂Cl₂ (0.60 g, 0.86 mmol), CuI (0.33 g, 1.72 mmol) in TEA (4 mL) and DMF (20 mL) was stirred for 16 h at 80° C. under nitrogen atmosphere. The resulting mixture was quenched with H₂O (30 mL) and extracted with EtOAc (3×30 mL). The combined organic layers were washed with brine (20 mL), dried over anhydrous Na₂SO₄. After filtration, the filtrate was concentrated under reduced pressure. The residue was purified by silica gel column chromatography, eluted with PE/EtOAc (5/1) to afford 4-{4-chloro-6-[2-(trimethylsilyl)ethynyl]pyridin-2-yl}morpholine (1.71 g, 68%) as light yellow oil. MS ESI calculated for $C_{14}H_{19}ClN_2OSi$ [M+H]⁺, 295.10, found 295.05. ¹H NMR (400 MHz, Chloroform-d) δ 6.87 (d, J=1.6 Hz, 1H), 6.58 (d, J=1.6 Hz, 1H), 3.83-3.79 (m, 4H), 3.56-3.53 (m, 4H), 0.28 (s, 9H).

Preparation 15B:
4-(4-chloro-6-ethynylpyridin-2-yl)morpholine

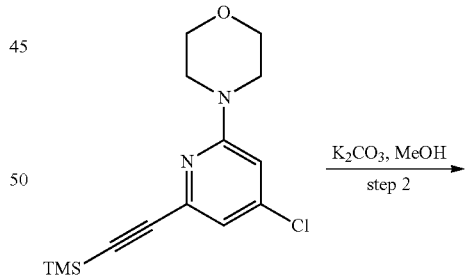

K₂CO₃, MeOH
step 2

A solution of 4-{4-chloro-6-[2-(trimethylsilyl)ethynyl]pyridin-2-yl}morpholine (1.71 g, 5.80 mmol) and K$_2$CO$_3$ (1.60 g, 11.58 mmol) in MeOH (15 mL) was stirred for 1 h at room temperature. The resulting mixture was concentrated under reduced pressure. The residue was purified by silica gel column chromatography, eluted with PE/EtOAc (5/1) to afford 4-(4-chloro-6-ethynylpyridin-2-yl)morpholine (1.23 g, 95%) as light yellow oil. MS ESI calculated for C$_{11}$H$_{11}$ClN$_2$O [M+H]$^+$, 223.06, found 223.15. $^1$H NMR (400 MHz, Chloroform-d) δ 6.88 (d, J=1.6 Hz, 1H), 6.62 (d, J=1.6 Hz, 1H), 3.84-3.79 (m, 4H), 3.58-3.53 (m, 4H), 3.11 (s, 1H).

Preparation 15C: 4-[4-chloro-6-(morpholin-4-yl)pyridin-2-yl]-1,1,1-trifluorobut-3-yn-2-one

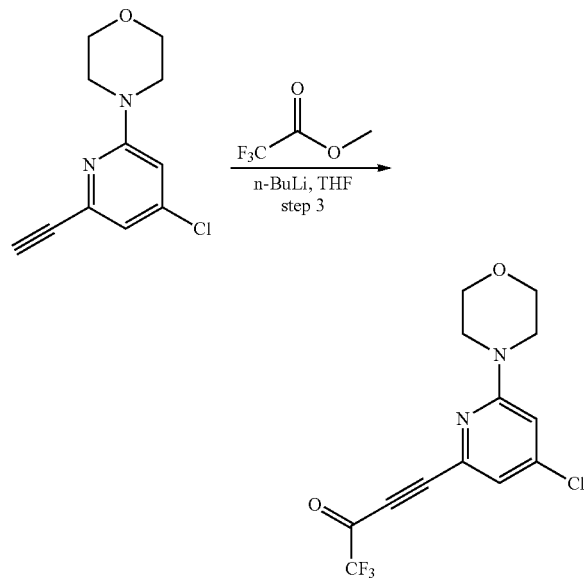

To a solution of 4-(4-chloro-6-ethynylpyridin-2-yl)morpholine (1.00 g, 4.49 mmol) in THF (40 mL) was added n-BuLi (2.2 mL, 34.34 mmol) dropwise at −78° C. under nitrogen atmosphere. The resulting mixture was stirred for 30 min at −78° C. under nitrogen atmosphere. A stirred solution of methyltrifluoroacetate (1.44 g, 11.23 mmol) and BF$_3$·Et$_2$O (1.52 g, 22.45 mmol) in THF was added to above mixture dropwise at −78° C. under nitrogen atmosphere. The resulting mixture was stirred for 2 h at −78° C. under nitrogen atmosphere. The reaction was quenched with sat. NH$_4$Cl (20 mL). The resulting mixture was extracted with EtOAc (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc (2/1) to afford 4-[4-chloro-6-(morpholin-4-yl)pyridin-2-yl]-1,1,1-trifluorobut-3-yn-2-one (1.19 g, 83%) as a light yellow solid. MS ESI calculated for C$_{13}$H$_{10}$ClF$_3$N$_2$O$_2$ [M+H]$^+$, 319.04, found 319.20. $^1$H NMR (400 MHz, Chloroform-d) δ 7.04 (d, J=1.2 Hz, 1H), 6.74 (d, J=1.6 Hz, 1H), 3.82-3.79 (m, 4H), 3.58-3.55 (m, 4H). $^{19}$F NMR (376 MHz, Chloroform-d) δ −77.79 (3F).

Preparation 15D: 4-[4-chloro-6-(morpholin-4-yl)pyridin-2-yl]-1,1,1-trifluorobut-3-yn-2-ol

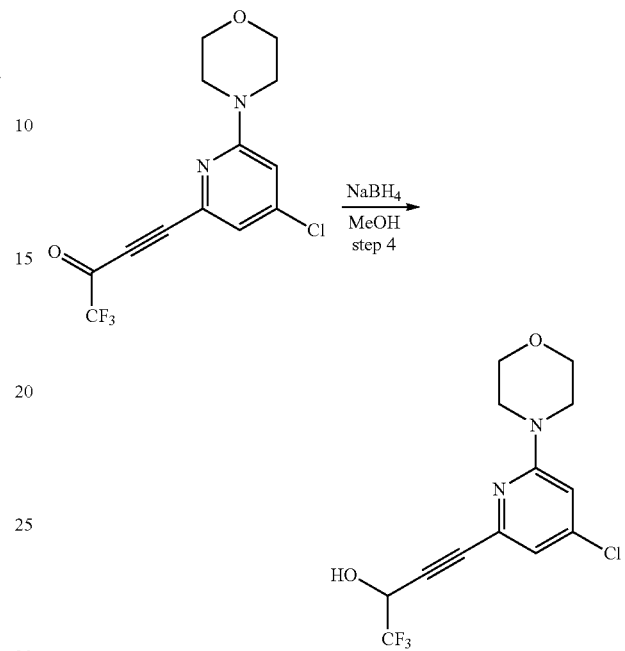

A mixture of 4-[4-chloro-6-(morpholin-4-yl)pyridin-2-yl]-1,1,1-trifluorobut-3-yn-2-one (1.12 g, 3.51 mmol) and NaBH$_4$ (0.27 g, 7.03 mmol) in MeOH (10 mL) was stirred for 1 h at room temperature. The resulting mixture was concentrated under reduced pressure. The residue was purified by silica gel column chromatography, eluted with PE/EtOAc (2/1) to afford 4-[4-chloro-6-(morpholin-4-yl)pyridin-2-yl]-1,1,1-trifluorobut-3-yn-2-ol (600 mg, 53%) as a light yellow solid. MS ESI calculated for C$_{13}$H$_{12}$ClF$_3$N$_2$O$_2$ [M+H]$^+$, 321.05, found 321.05. $^1$H NMR (400 MHz, Chloroform-d) δ 6.88 (d, J=1.2 Hz, 1H), 6.63 (d, J=1.2 Hz, 1H), 4.95-4.90 (m, 1H), 3.88-3.82 (m, 4H), 3.58-3.54 (m, 4H). $^{19}$F NMR (376 MHz, Chloroform-d) δ −78.94 (3F).

Examples 15 and 16: N-{4-methyl-3-[2-(morpholin-4-yl)-6-[(3S)-4,4,4-trifluoro-3-hydroxybut-1-yn-1-yl)pyridin-4-yl]phenyl}-2-(trifluoromethyl)pyridine-4-carboxamide and N-{4-methyl-3-[2-(morpholin-4-yl)-6-[(3R)-4,4,4-trifluoro-3-hydroxybut-1-yn-1-yl]pyridin-4-yl]phenyl}-2-(trifluoromethyl)pyridine-4-carboxamide

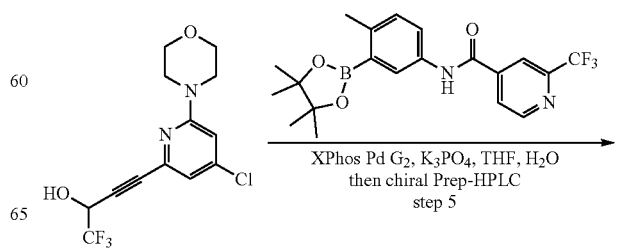

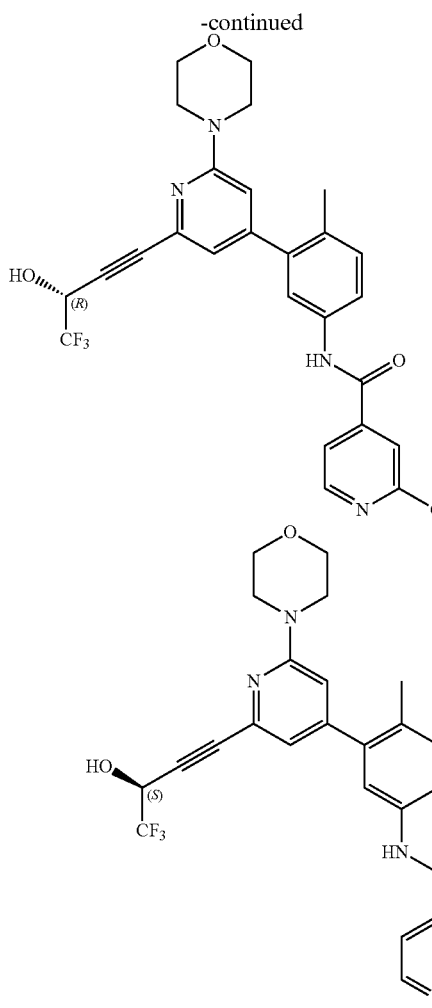

A mixture of 4-[4-chloro-6-(morpholin-4-yl)pyridin-2-yl]-1,1,1-trifluorobut-3-yn-2-ol (400 mg, 1.247 mmol), N-[4-methyl-3-(4,4,5,5-tetramethyl-1,3,2-dioxaborolan-2-yl)phenyl]-2-(trifluoromethyl)pyridine-4-carboxamide (456 mg, 1.122 mmol), $K_3PO_4$ (529 mg, 2.494 mmol) and $2^{nd}$ Generation Xphos Precatalyst (986 mg, 0.125 mmol) in THF (10 mL) and $H_2O$ (1 mL) was stirred for 2 h at 80° C. under nitrogen atmosphere. The resulting mixture was concentrated under reduced pressure. The residue was purified by silica gel column chromatography, eluted with PE/EtOAc (1/1). The crude product was purified by Prep-CHIRAL-HPLC with the following conditions: Column: CHIRALPAK AD-H, 2×25 cm, 5 μm; Mobile Phase A: Hexane (0.5% 2M $NH_3$-MeOH), Mobile Phase B: IPA; Flow rate: 20 mL/min; A:B+85:15; 220/254 nm, to give:

Example 15

191 mg (27%) as a white solid, $RT_1$:13.54 min. MS ESI calculated for $C_{27}H_{22}F_6N_4O_3[M+H]^+$, 565.16, found 565.20. $^1H$ NMR (400 MHz, DMSO-$d_6$) δ 10.70 (s, 1H), 9.00 (d, J=5.2 Hz, 1H), 8.37 (s, 1H), 8.21 (d, J=5.2 Hz, 1H), 7.78-7.75 (m, 1H), 7.67 (d, J=2.0 Hz, 1H), 7.36 (d, J=8.4 Hz, 1H), 7.22 (d, J=7.2 Hz, 1H), 6.89 (s, 1H), 6.84 (s, 1H), 5.34-5.27 (m, 1H), 3.72-3.68 (m, 4H), 3.54-3.50 (m, 4H), 2.25 (s, 3H). $^{19}F$ NMR (376 MHz, DMSO-$d_6$) δ −66.46 (3F), −77.41 (3F).

Example 16

131 mg (19%) as a white solid, $RT_2$: 19.37 min. MS ESI calculated for $C_{27}H_{22}F_6N_4O_3$ [M+H]$^+$, 565.16, found 565.20. $^1H$ NMR (400 MHz, DMSO-$d_6$) δ 10.69 (s, 1H), 9.00 (d, J=4.8 Hz, 1H), 8.37 (s, 1H), 8.20 (d, J=5.2 Hz, 1H), 7.78-7.75 (m, 1H), 7.66 (d, J=1.6 Hz, 1H), 7.36 (d, J=8.4 Hz, 1H), 7.22 (d, J=7.2 Hz, 1H), 6.88 (s, 1H), 6.83 (s, 1H), 5.32-5.28 (m, 1H), 3.72-3.68 (m, 4H), 3.53-3.49 (m, 4H), 2.25 (s, 3H). $^{19}F$ NMR (376 MHz, DMSO-$d_6$) δ −61.71 (3F), −72.66 (3F).

Example 17: N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide

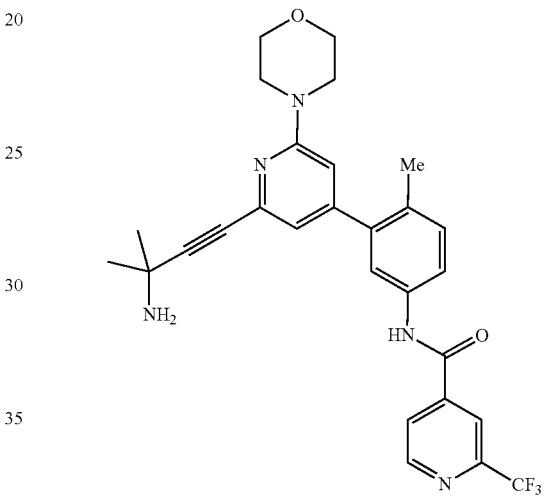

Synthetic Scheme

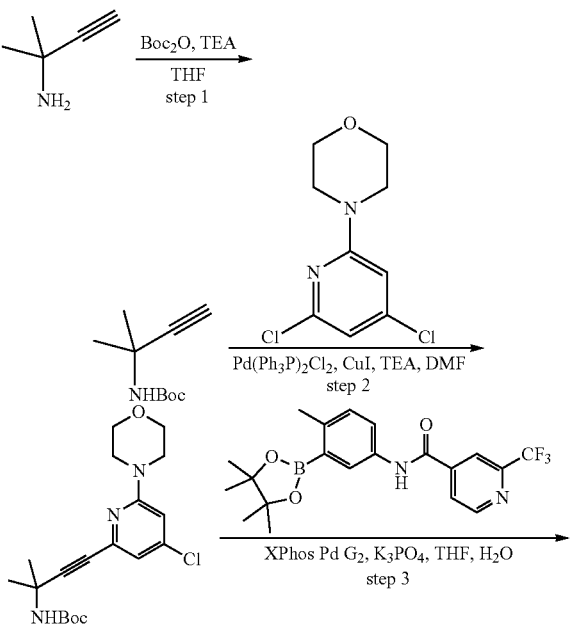

147

-continued

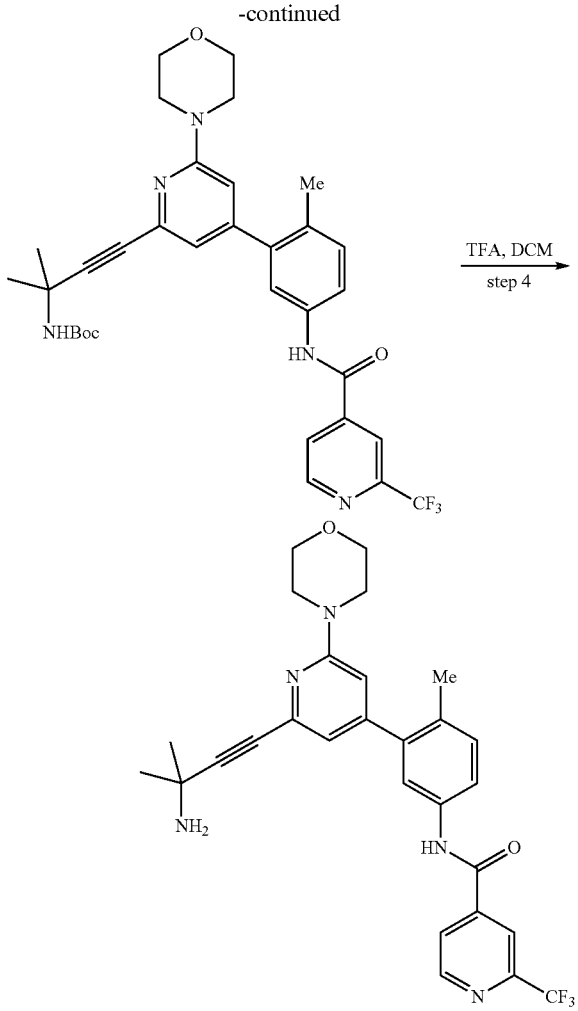

Preparation 17A: tert-butyl
N-(2-methylbut-3-yn-2-yl) carbamate

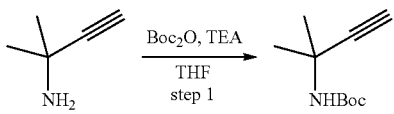

A mixture of 2-amine-2-methyl-3-butyn (2.00 g, 24.06 mmol), Boc$_2$O (6.30 g, 28.87 mmol) and TEA (7.30 g, 72.17 mmol) in DCM (50 mL) was stirred for 16 h at room temperature. The reaction was quenched by the addition of water (50 mL). The resulting mixture was extracted with DCM (3×30 mL). The organic layers were washed with brine (30 mL), dried over anhydrous Na$_2$SO$_4$. After filtration, the filtrate was concentrated under reduced pressure. The residue was purified by silica gel column chromatography, eluted with PE/EtOAc (5/1) to afford tert-butyl N-(2-methylbut-3-yn-2-yl) carbamate (3.20 g, 72%) as a white solid. C$_{10}$H$_{17}$NO$_2$, $^1$H NMR (400 MHz, Chloroform-d) δ 4.70 (s, 1H), 1.60 (s, 6H), 1.47 (s, 9H).

148

Preparation 17B: tert-butyl N-{4-[4-chloro-6-(morpholin-4-yl)pyridin-2-yl]-2-methylbut-3-yn-2-yl}carbamate

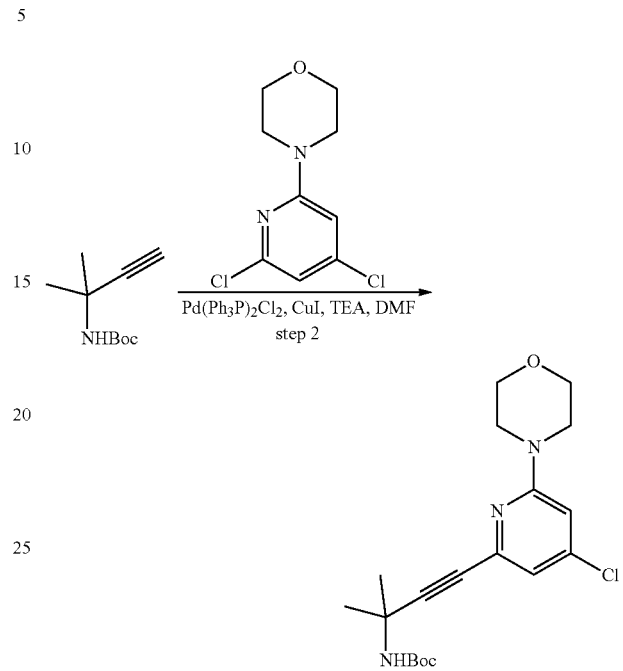

A mixture of 4-(4,6-dichloropyridin-2-yl)morpholine (500 mg, 2.145 mmol), tert-butyl N-(2-methylbut-3-yn-2-yl)carbamate (511 mg, 2.788 mmol), Pd(PPh$_3$)$_2$Cl$_2$ (150 mg, 0.215 mmol) and CuI (82 mg, 0.429 mmol) in TEA (2 mL) and DMF (10 mL) was stirred for 16 h at 80° C. under nitrogen atmosphere. The resulting mixture was diluted with water (40 mL). The resulting mixture was extracted with EtOAc (3×50 mL). The combined organic layers were washed with brine (40 mL), dried over anhydrous Na$_2$SO$_4$. After filtration, the filtrate was concentrated under reduced pressure. The residue was purified by silica gel column chromatography, eluted with PE/EtOAc (2/1) to afford tert-butyl N-{4-[4-chloro-6-(morpholin-4-yl)pyridin-2-yl]-2-methylbut-3-yn-2-yl}carbamate (612 mg, 75%) as a white solid. MS ESI calculated for C$_{19}$H$_{26}$ClN$_3$O$_3$ [M+H]$^+$, 380.17; found 380.30. $^1$H NMR (400 MHz, Chloroform-d) δ 6.81 (d, J=1.6 Hz, 1H), 6.55 (d, J=1.6 Hz, 1H), 4.81 (s, 1H), 3.84-3.77 (m, 4H), 3.56-3.51 (m, 4H), 1.68 (s, 6H), 1.47 (s, 9H).

Preparation 17C: tert-butyl N-[3-(4-{2-methyl-5-[2-(trifluoromethyl)pyridine-4-amido]phenyl}-6-(morpholin-4-yl)pyridin-2-yl)prop-2-yn-1-yl]carbamate

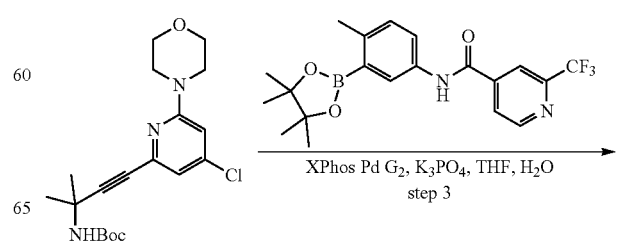

-continued

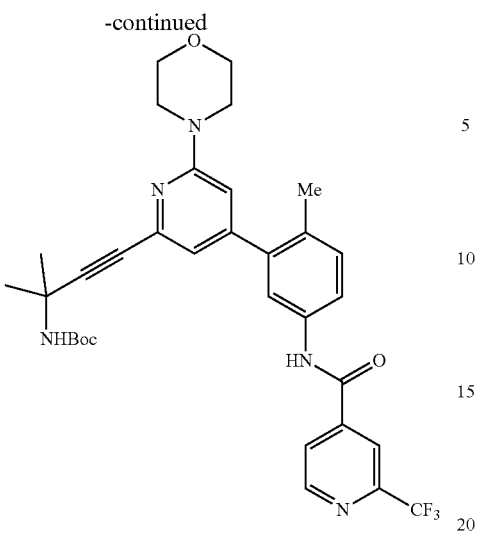

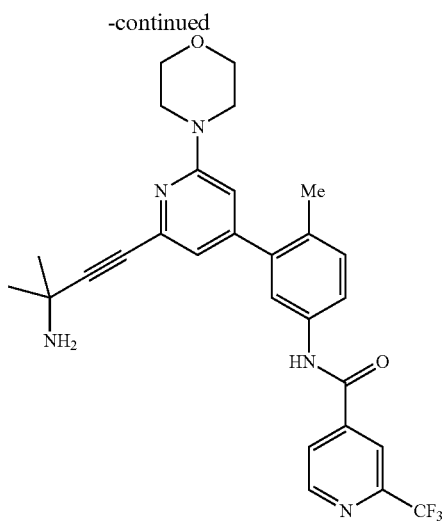

A mixture of tert-butyl N-{4-[4-chloro-6-(morpholin-4-yl)pyridin-2-yl]-2-methylbut-3-yn-2-yl}carbamate (100 mg, 0.263 mmol), N-[4-methyl-3-(4,4,5,5-tetramethyl-1,3,2-dioxaborolan-2-yl)phenyl]-2-(trifluoromethyl)pyridine-4-carboxamide (107 mg, 0.263 mmol), 2$^{nd}$ Generation XPhos Precatalyst (21 mg, 0.026 mmol) and K$_3$PO$_4$ (112 mg, 0.526 mmol) in THF (2 mL) and H$_2$O (0.4 mL) was stirred for 2 h at 80° C. under nitrogen atmosphere. The resulting mixture was diluted with water (20 mL). The resulting mixture was extracted with EtOAc (3×20 mL). The combined organic layers were washed with brine (10 mL), dried over anhydrous Na$_2$SO$_4$. After filtration, the filtrate was concentrated under reduced pressure. The residue was purified by Prep-TLC with DCM/MeOH (10/1) to afford tert-butyl N-[2-methyl-4-(4-{2-methyl-5-[2-(trifluoromethyl)pyridine-4-amido]phenyl}-6-(morpholin-4-yl)pyridin-2-yl)but-3-yn-2-yl]carbamate (130 mg, 79%) as a white solid. MS ESI calculated for C$_{33}$H$_{36}$F$_3$N$_5$O$_4$ [M+H]$^+$, 624.27; found 624.35. $^1$H NMR (400 MHz, Chloroform-d) δ 8.94 (d, J=4.8 Hz, 1H), 8.36 (s, 1H), 8.20 (s, 1H), 8.02 (d, J=4.8 Hz, 1H), 7.71 (d, J=8.4 Hz, 1H), 7.45 (s, 1H), 7.31 (s, 1H), 6.78 (s, 1H), 6.52 (s, 1H), 4.86 (s, 1H), 3.84-3.80 (m, 4H), 3.58-3.54 (m, 4H), 2.27 (s, 3H), 1.45 (s, 6H), 1.26 (s, 9H).

Example 17: N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide

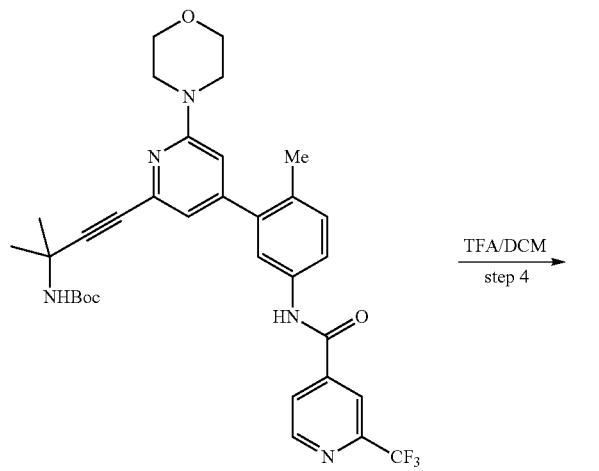

A mixture of tert-butyl N-[2-methyl-4-(4-{2-methyl-5-[2-(trifluoromethyl)pyridine-4-amido]phenyl}-6-(morpholin-4-yl)pyridin-2-yl)but-3-yn-2-yl]carbamate (150 mg, 0.241 mmol) and TFA (3 mL) in DCM (3 mL) was stirred for 1 h at room temperature. The resulting mixture was concentrated under reduced pressure. The residue was purified by reverse phase Flash chromatography with the following conditions: Column: WelFlash™ C18-I, 20-40 μm, 120 g; Eluent A: water (10 mmol/L NH$_4$HCO$_3$); Eluent B: CH$_3$CN; Gradient: 50% to 70% B; Flow rate: 60 mL/min; Detector: 220/254 nm to afford N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide (100 mg, 79%) as a light-yellow solid. MS ESI calculated for C$_{28}$H$_{28}$F$_3$N$_5$O$_2$ [M+H]$^+$, 524.22; found 524.20. $^1$H NMR (300 MHz, DMSO-d$_6$) δ 10.69 (s, 1H), 8.99 (d, J=5.1 Hz, 1H), 8.37 (s, 1H), 8.20 (d, J=5.1 Hz, 1H), 7.78-7.74 (m, 1H), 7.65 (d, J=2.1 Hz, 1H), 7.34 (d, J=8.7 Hz, 1H), 6.75 (s, 1H), 6.69 (d, J=0.9 Hz, 1H), 3.71-3.68 (m, 4H), 3.50-3.47 (m, 4H), 2.24 (s, 3H), 1.37 (s, 6H). $^{19}$F NMR (282 MHz, DMSO-d$_6$) δ −66.46 (3F).

Example 18: N-(3-{2-[2-(1-aminocyclopropyl)ethynyl]-6-(morpholin-4-yl)pyridin-4-yl}-4-methylphenyl)-2-(trifluoromethyl)pyridine-4-carboxamide

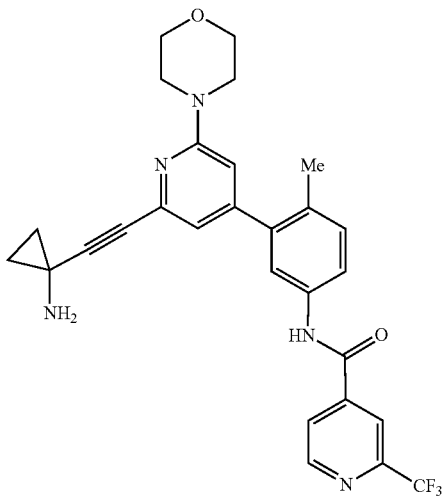 [SMILES: Cc1ccc(NC(=O)c2ccnc(C(F)(F)F)c2)cc1-c1cc(C#CC2(N)CC2)nc(N2CCOCC2)c1]

151

Synthetic Scheme

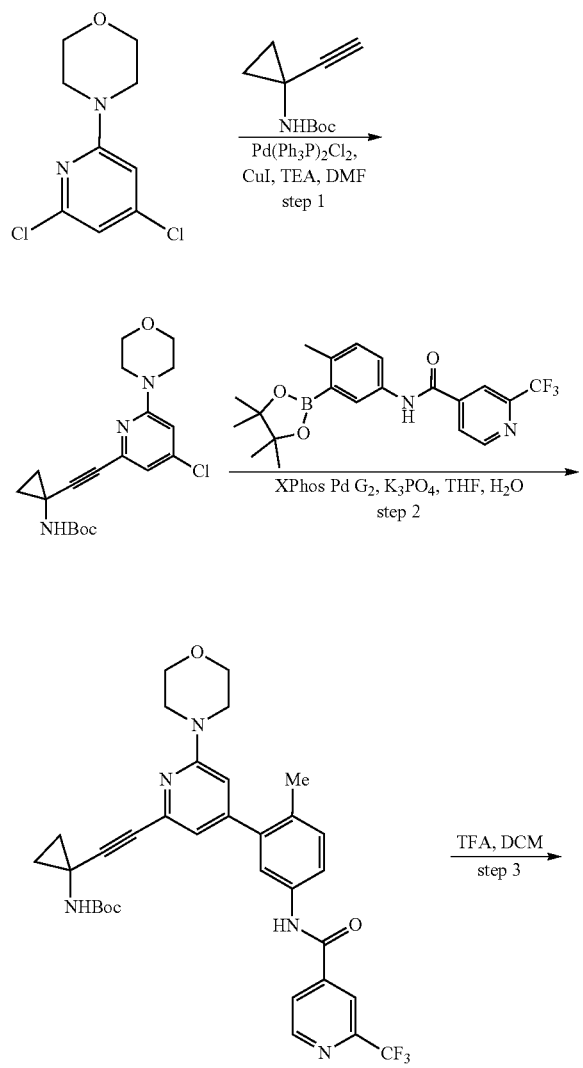

TFA, DCM
step 3

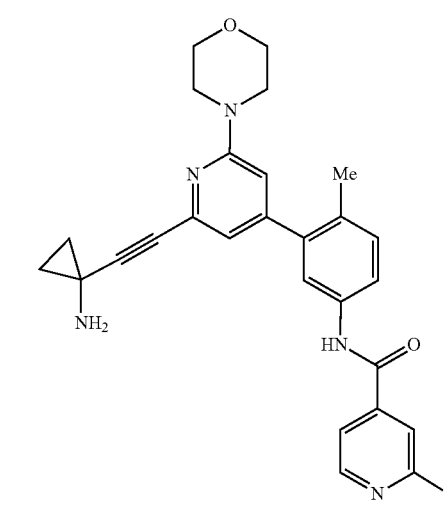

152

Preparation 18A: tert-butyl N-(1-{2-[4-chloro-6-(morpholin-4-yl)pyridin-2-yl]ethynyl}cyclopropyl)carbamate A mixture of 4-(4,6-dichloropyridin-2-yl)morpholine (350 mg, 1.502 mmol), tert-butyl N-(1-ethynylcyclopropyl)carbamate (353 mg, 1.953 mmol), Pd(PPh$_3$)$_2$Cl$_2$ (105 mg, 0.150 mmol) and CuI (57 mg, 0.300 mmol) in TEA (1 mL) and DMF (5 mL) was stirred for 4 h at 80° C. under nitrogen atmosphere. The reaction was quenched with water (30 ml). The resulting mixture was extracted with EtOAc (3×25 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EtOAc (2/1) to afford tert-butyl N-(1-{2-[4-chloro-6-(morpholin-4-yl)pyridin-2-yl]ethynyl}cyclopropyl)carbamate (350 mg, 62%) as a light yellow solid. MS ESI calculated for C$_{19}$H$_{24}$ClN$_3$O$_3$ [M+H]$^+$, 378.15, found 378.05. $^1$H NMR (400 MHz, Chloroform-d) δ 6.78 (s, 1H), 6.54 (d, J=1.6 Hz, 1H), 5.10 (s, 1H), 3.83-3.77 (m, 4H), 3.54-3.49 (m, 4H), 1.49 (s, 9H), 1.37-1.34 (m, 2H), 1.24-1.20 (m, 2H).

Preparation 18B: tert-butyl N-{1-[2-(4-{2-methyl-5-[2-(trifluoromethyl)pyridine-4-amido]phenyl}-6-(morpholin-4-yl)pyridin-2-yl)ethynyl]cyclopropyl}carbamate

Example 18: N-(3-{2-[2-(1-aminocyclopropyl)ethynyl]-6-(morpholin-4-yl)pyridin-4-yl}-4-methylphenyl)-2-(trifluoromethyl)pyridine-4-carboxamide

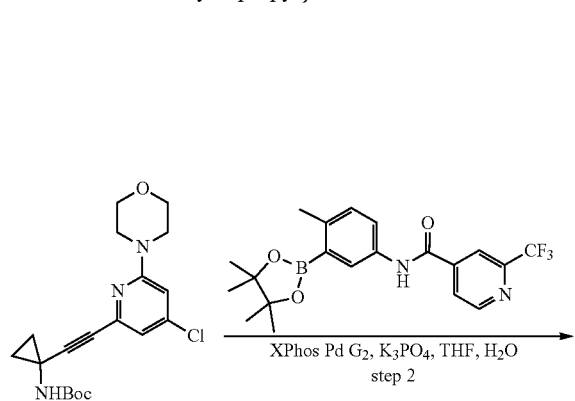

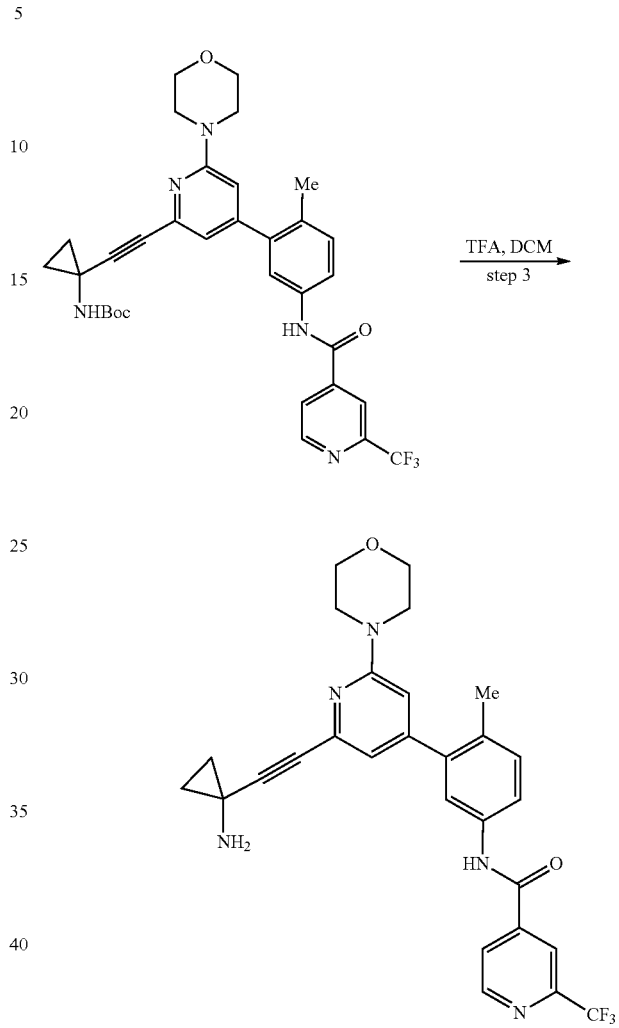

A mixture of tert-butyl N-(1-{2-[4-chloro-6-(morpholin-4-yl)pyridin-2-yl]ethynyl}cyclopropyl)carbamate (200 mg, 0.529 mmol), N-[4-methyl-3-(4,4,5,5-tetramethyl-1,3,2-dioxaborolan-2-yl)phenyl]-2-(trifluoromethyl)pyridine-4-carboxamide (193 mg, 0.476 mmol), 2$^{nd}$ Generation Xphos Precatalyst (42 mg, 0.053 mmol) and K$_3$PO$_4$ (225 mg, 1.058 mmol) in THF (5 mL) and H$_2$O (0.5 mL) was stirred for 2 h at 80° C. under nitrogen atmosphere. The resulting mixture was concentrated under reduced pressure. The residue was purified by Prep-TLC with PE/EtOAc (1/1) to afford tert-butyl N-{1-[2-(4-{2-methyl-5-[2-(trifluoromethyl)pyridine-4-amido]phenyl}-6-(morpholin-4-yl)pyridin-2-yl)ethynyl]cyclopropyl}carbamate (160 mg, 49%) as a light yellow solid. MS ESI calculated for C$_{33}$H$_{34}$F$_3$N$_5$O$_4$ [M+H]$^+$, 622.26, found 622.35. $^1$H NMR (400 MHz, Chloroform-d) δ 8.91 (d, J=4.8 Hz, 1H), 8.25 (s, 1H), 8.12-8.00 (m, 1H), 7.76 (s, 1H), 7.38 (s, 1H), 7.25 (d, J=8.4 Hz, 1H), 6.69 (s, 1H), 6.46 (s, 1H), 5.27 (s, 1H), 3.82-3.78 (4H), 3.52-3.48 (m, 4H), 2.24 (s, 3H), 1.43 (s, 9H), 1.19-1.18 (m, 2H), 0.93-0.81 (m, 2H). $^{19}$F NMR (376 MHz, Chloroform-d) δ −67.93 (3F).

A solution of tert-butyl N-{1-[2-(4-{2-methyl-5-[2-(trifluoromethyl)pyridine-4-amido]phenyl}-6-(morpholin-4-yl)pyridin-2-yl)ethynyl]cyclopropyl}carbamate (150 mg, 0.241 mmol), DCM (2 mL) and TFA (0.5 mL) was stirred for 1 h at room temperature. The resulting mixture was concentrated under reduced pressure. The residue product was purified by reverse phase flash with the following conditions: Column: Spherical C18, 20~40 μm, 120 g; Mobile Phase A: water (10 mM NH$_4$HCO$_3$); Mobile Phase B: CH$_3$CN; Flow rate: 60 mL/min; Gradient: 40% to 60% B, Detector: 220 nm to afford N-(3-{2-[2-(1-aminocyclopropyl)ethynyl]-6-(morpholin-4-yl)pyridin-4-yl}-4-methylphenyl)-2-(trifluoromethyl)pyridine-4-carboxamide (45 mg, 36%) as a white solid. MS ESI calculated for C$_{28}$H$_{26}$F$_3$N$_5$O$_2$ [M+H]$^+$, 522.20, found 522.20. $^1$H NMR (400 MHz, DMSO-d$_6$) δ 10.68 (s, 1H), 9.00 (d, J=4.8 Hz, 1H), 8.37 (s, 1H), 8.20 (d, J=4.8 Hz, 1H), 7.75 (d, J=8.4 Hz, 1H), 7.65 (d, J=2.0 Hz, 1H), 7.34 (d, J=8.4 Hz, 1H), 6.74 (s, 1H), 6.69 (s, 1H), 3.70-3.67 (m, 4H), 3.49-3.46 (m, 4H), 2.23 (s, 3H), 0.96-0.94 (m, 2H), 0.88-0.85 (m, 2H). $^{19}$F NMR (376 MHz, DMSO-d$_6$) δ −66.46 (3F).

The following compounds in Table 3 were prepared using procedures similar to those described in Example 18 using appropriate starting materials.

TABLE 3

| Entry | Structure | IUPAC Name | Exact Mass [M + H]+ |
|---|---|---|---|
| 19 | 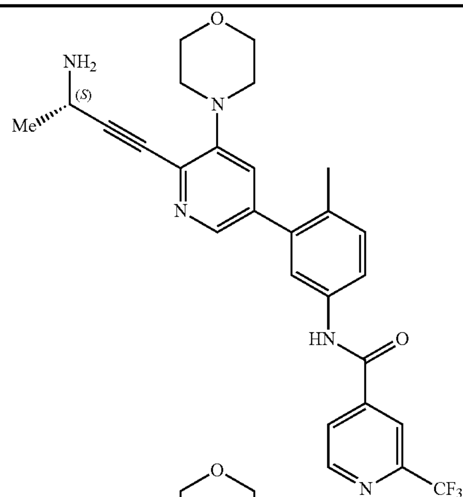 | N-(3-{6-[(3S)-3-aminobut-1-yn-1-yl]-5-(morpholin-4-yl)pyridin-3-yl}-4-methylphenyl)-2-(trifluoromethyl)pyridine-4-carboxamide | Calc'd 510.20, found 510.25 |
| 20 | 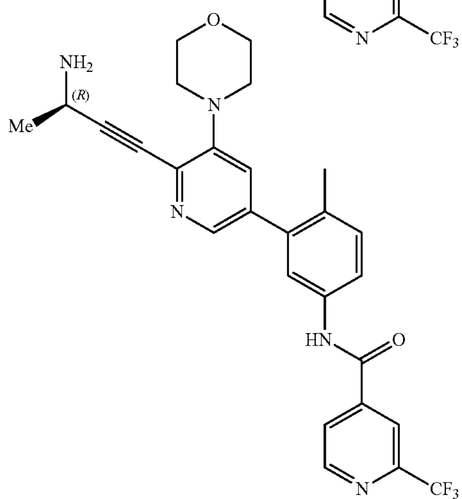 | N-(3-{6-[(3R)-3-aminobut-1-yn-1-yl]-5-(morpholin-4-yl)pyridin-3-yl}-4-methylphenyl)-2-(trifluoromethyl)pyridine-4-carboxamide | Calc'd 508.20, found 508.20 |

Example 21: N-(3-{6-[(3R)-3-Hydroxybut-1-yn-1-yl]-5-(morpholin-4-yl)pyridin-3-yl}-4-methylphenyl)-2-(trifluoromethyl)pyridine-4-carboxamide Step 1: N-(3-{6-[(3R)-3-Hydroxybut-1-yn-1-yl]-5-(morpholin-4-yl)pyridin-3-yl}-4-methylphenyl)-2-(trifluoromethyl)pyridine-4-carboxamide

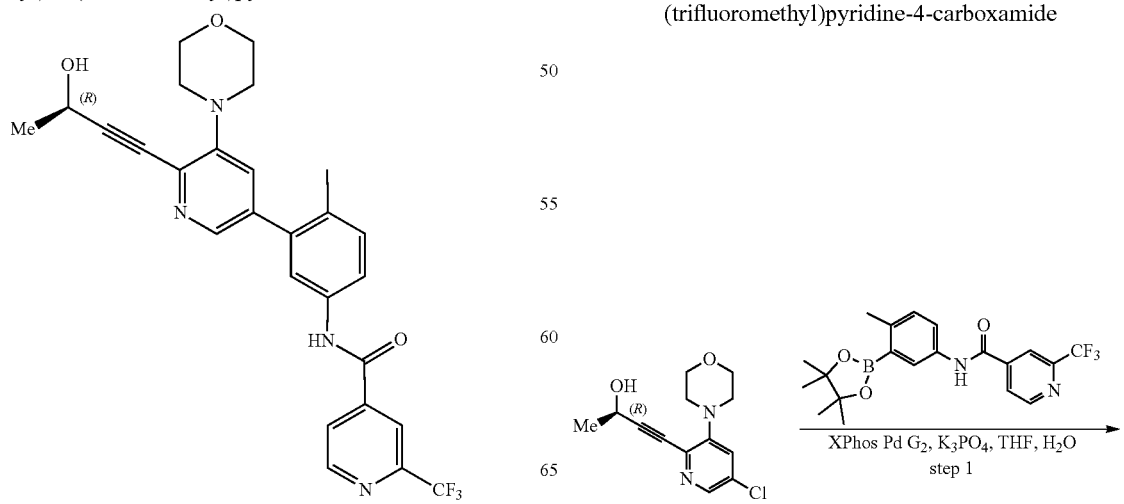

XPhos Pd G$_2$, K$_3$PO$_4$, THF, H$_2$O
step 1

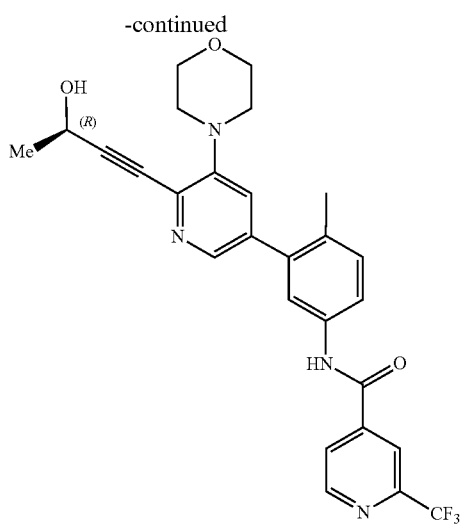

To a stirred mixture of (2R)-4-[5-chloro-3-(morpholin-4-yl)pyridin-2-yl]but-3-yn-2-ol (150 mg, 0.562 mmol), N-[4-methyl-3-(4,4,5,5-tetramethyl-1,3,2-dioxaborolan-2-yl)phenyl]-2-(trifluoromethyl)pyridine-4-carboxamide (206 mg, 0.506 mmol) in THF (1 mL) and H$_2$O (0.1 mL) were added K$_3$PO$_4$ (239 mg, 1.124 mmol) and 2$^{nd}$ Generation X-Phos precatalyst (44 mg, 0.056 mmol). The reaction mixture was stirred for 16 h at 80° C. under nitrogen atmosphere. The resulting mixture was quenched with water (50 mL). The resulting mixture was extracted with EtOAc (3×50 mL). The combined organic layers was washed with brine (30 mL), dried over anhydrous Na$_2$SO$_4$. After filtration, the filtrate was concentrated under reduced pressure. The residue was purified by reverse flash chromatography with the following conditions: column, C18 silica gel; mobile phase, CH$_3$CN in water (10 mmol/L NH$_4$HCO$_3$), 35% to 65% gradient in 25 min. The fractions contained desired product were combined and concentrated to afford N-(3-{6-[(3R)-3-hydroxybut-1-yn-1-yl]-5-(morpholin-4-yl)pyridin-3-yl}-4-methylphenyl)-2-(trifluoromethyl)pyridine-4-carboxamide (88 mg, 31%) as an off-white solid. MS ESI calculated for C$_{27}$H$_{25}$F$_3$N$_4$O$_3$ [M+H]$^+$, 511.19; found 511.30. $^1$H NMR (400 MHz, DMSO-d$_6$) δ 10.72 (s, 1H), 9.00-8.99 (m, 1H), 8.37 (s, 1H), 8.21-8.15 (m, 2H), 7.79-7.76 (m, 1H), 7.67-7.66 (m, 1H), 7.38-7.35 (m, 2H), 5.57-5.55 (m, 1H), 4.69-4.66 (m, 1H), 3.79-3.77 (m, 4H), 3.21-3.19 (m, 4H), 2.25 (s, 3H), 1.42 (d, J=6.4 Hz, 3H). $^{19}$F NMR (376 MHz, DMSO-d$_6$) δ −66.45 (3F).

The following compounds in Table 4 were prepared using procedures similar to those described in Example 21 using appropriate starting materials.

TABLE 4

| Entry | Structure | IUPAC Name | Exact Mass [M + H]$^+$ |
|---|---|---|---|
| 22 | 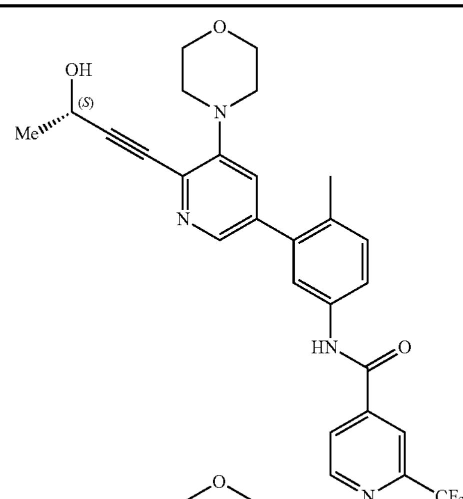 | N-(3-{6-[(3R)-Hydroxybut-1-yn-1-yl]-5-(morpholin-4-yl)pyridin-3-yl}-4-methylphenyl)-2-(trifluoromethyl)pyridine-4-carboxamide | Calc'd 511.19, found 511.20 |
| 23 | 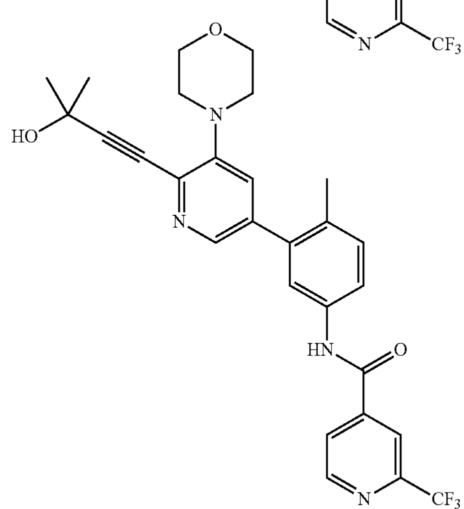 | N-{3-[6-(3-Hydroxy-3-methylbut-1-yn-1-yl)-5-(morpholin-4-yl)pyridin-3-yl]-4-methylphenyl}-2-(trifluoromethyl)pyridine-4-carboxamide | Calc'd 525.20, found 525.35 |

TABLE 4-continued

| Entry | Structure | IUPAC Name | Exact Mass [M + H]+ |
|---|---|---|---|
| 24 | 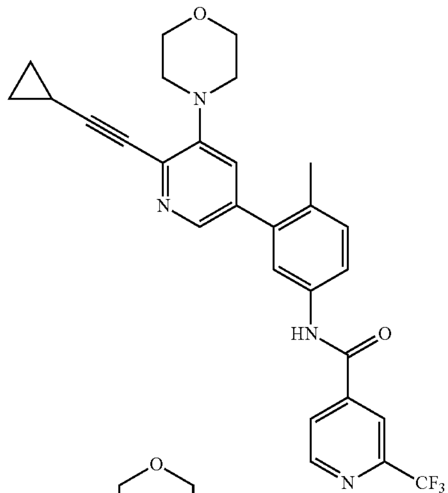 [SMILES: Cc1ccc(NC(=O)c2ccnc(C(F)(F)F)c2)cc1-c1cnc(C#CC2CC2)c(N2CCOCC2)c1] | N-{3-[6-(2-Cyclopropylethynyl)-5-(morpholin-4-yl)pyridin-3-yl]-4-methylphenyl}-2-(trifluoromethyl)pyridine-4-carboxamide | Calc'd 507.19, found 507.15 |
| 25 | 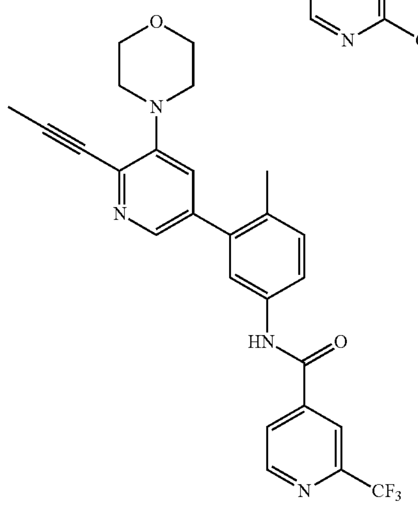 | N-{4-Methyl-3-[5-(morpholin-4-yl)-6-(prop-1-yn-1-yl)pyridin-3-yl]phenyl}-2-(trifluoromethyl)pyridine-4-carboxamide | Calc'd 481.18, found 481.35 |

Example 26: N-{3-[6-Ethynyl-5-(morpholin-4-yl)pyridin-3-yl]-4-methylphenyl}-2-(trifluoromethyl)pyridine-4-carboxamide

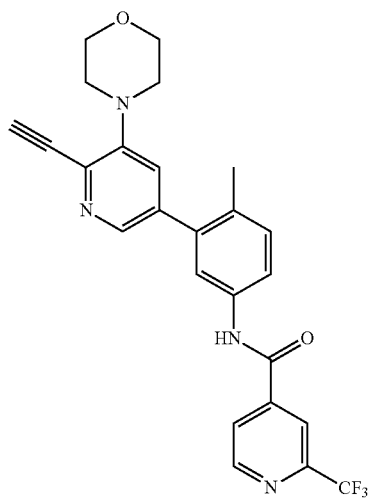

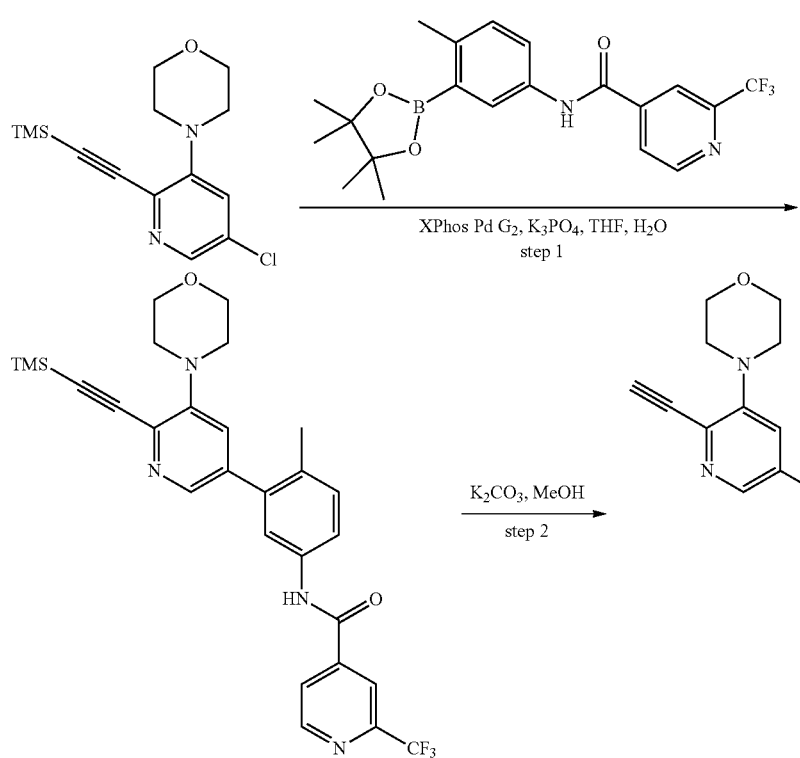

Step 1: N-{4-Methyl-3-[5-(morpholin-4-yl)-6-[2-(trimethylsilyl)ethynyl]pyridin-3-yl]phenyl}-2-(trifluoromethyl)pyridine-4-carboxamide

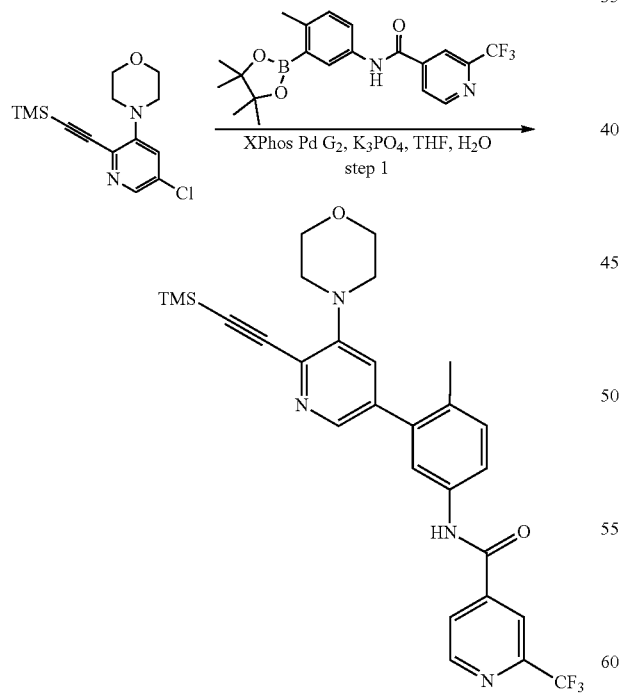

To a stirred mixture of 4-{5-chloro-2-[2-(trimethylsilyl)ethynyl]pyridin-3-yl}morpholine (200 mg, 0.678 mmol), N-[4-methyl-3-(4,4,5,5-tetramethyl-1,3,2-dioxaborolan-2-yl)phenyl]-2-(trifluoromethyl)pyridine-4-carboxamide (248 mg, 0.610 mmol) and 2nd Generation XPhos precatalyst (53 mg, 0.068 mmol) in THF (2 mL) and $H_2O$ (0.2 mL) was added $K_3PO_4$ (432 mg, 2.034 mmol). The reaction mixture was stirred for 2 h at 80° C. under nitrogen atmosphere. The reaction was quenched with water (50 mL). The resulting mixture was extracted with EA (2×50 mL). The combined organic layers was washed with brine (50 mL), dried over anhydrous $Na_2SO_4$. After filtration, the filtrate was concentrated under reduced pressure. The residue was purified by silica gel column chromatography, eluted with PE/EA (1/1). The fractions contained desired product were combined and concentrated to afford N-{4-methyl-3-[5-(morpholin-4-yl)-6-[2-(trimethylsilyl)ethynyl]pyridin-3-yl]phenyl}-2-(trifluoromethyl)pyridine-4-carboxamide (143 mg, 39%) as an off-white solid. MS ESI calculated for $C_{28}H_{29}F_3N_4O_2Si$ $[M+H]^+$, 539.20, found 539.20.

Step 2: N-{3-[6-Ethynyl-5-(morpholin-4-yl)pyridin-3-yl]-4-methylphenyl}-2-(trifluoromethyl)pyridine-4-carboxamide

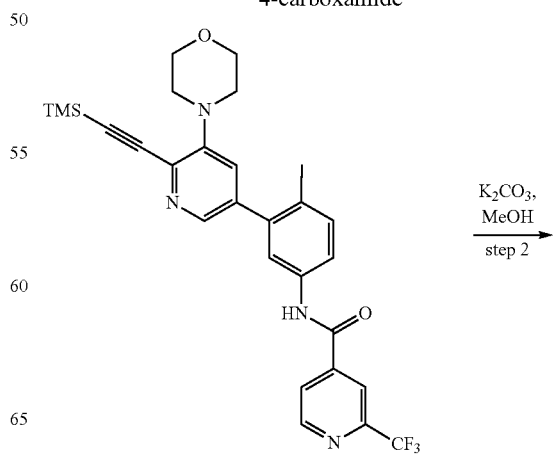

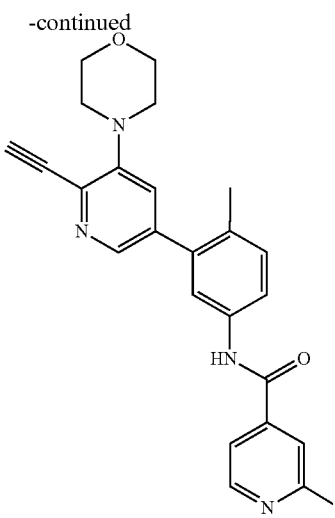

To a stirred mixture of N-{4-methyl-3-[5-(morpholin-4-yl)-6-[2-(trimethylsilyl)ethynyl]pyridin-3-yl]phenyl}-2-(trifluoromethyl)pyridine-4-carboxamide (93 mg, 0.173 mmol) in MeOH (1.3 mL) was added K$_2$CO$_3$ (48 mg, 0.346 mmol). The reaction mixture was stirred for 2 h at room temperature. The resulting mixture was quenched with water (10 mL) and extracted with EA (2×10 mL). The combined organic layers was washed with brine (5 mL), dried over anhydrous Na$_2$SO$_4$. After filtration, the filtrate was concentrated under reduced pressure. The residue was purified by silica gel column chromatography, eluted with PE/EA/EtOH (4/3/1). The fractions contained desired product were combined and concentrated to afford N-{3-[6-ethynyl-5-(morpholin-4-yl)pyridin-3-yl]-4-methylphenyl}-2-(trifluoromethyl)pyridine-4-carboxamide (20 mg, 24%) as an off-white solid. MS ESI calculated for C$_{25}$H$_{21}$F$_3$N$_4$O$_2$ [M+H]$^+$, 467.17; found 467.30. $^1$H NMR (400 MHz, Chloroform-d) δ 8.94 (d, J=5.2 Hz, 1H), 8.37 (s, 1H), 8.22 (d, J=2.0 Hz, 1H), 8.16 (s, 1H), 8.00 (d, J=4.8 Hz, 1H), 7.73-7.70 (m, 1H), 7.55 (d, J=2.0 Hz, 1H), 7.36 (d, J=8.4 Hz, 1H), 7.28-7.27 (m, 1H), 3.93-3.91 (m, 4H), 3.55 (s, 1H), 3.30-3.28 (m, 4H), 2.29 (s, 3H). $^{19}$F NMR (376 MHz, Chloroform-d) δ −68.01 (3F).

Example 27: 6-Tert-butyl-N-{4-methyl-3-[5-(morpholin-4-yl)-6-(prop-1-yn-1-yl)pyridin-3-yl]phenyl}pyrimidine-4-carboxamide

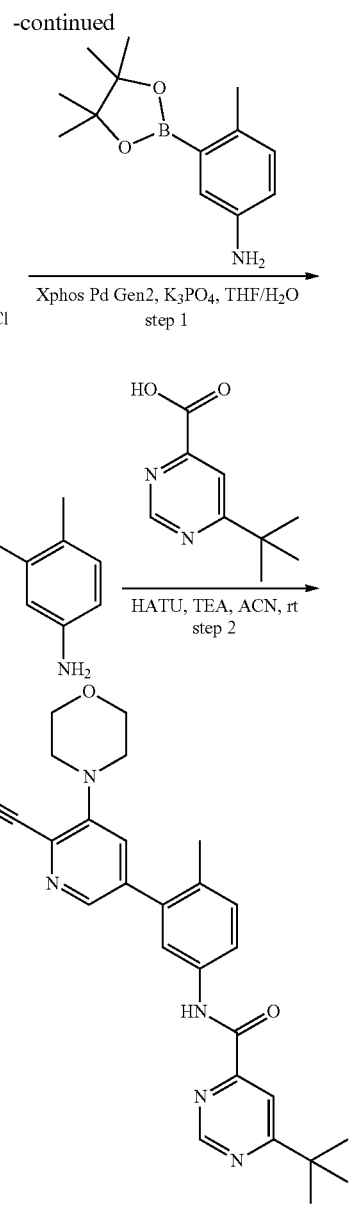

Step 1: 4-Methyl-3-[5-(morpholin-4-yl)-6-(prop-1-yn-1-yl)pyridin-3-yl]aniline

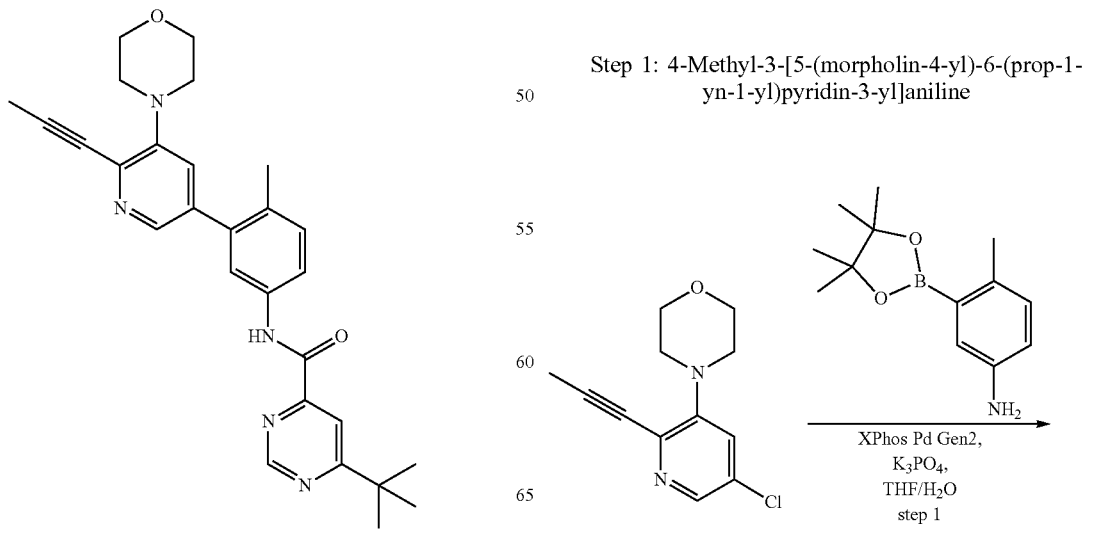

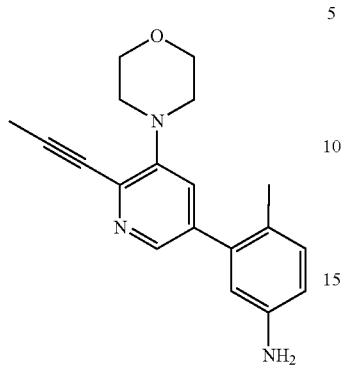

To a stirred mixture of 4-[5-chloro-2-(prop-1-yn-1-yl)pyridin-3-yl]morpholine (1.16 g, 4.901 mmol), 4-methyl-5-(4,4,5,5-tetramethyl-1,3,2-dioxaborolan-2-yl)aniline (1.23 g, 4.901 mmol), $K_3PO_4$ (2.08 g, 9.802 mmol) in THF (10 mL), $H_2O$ (1 mL) was added XPhos palladium(II) biphenyl-2-amine chloride (0.39 g, 0.490 mmol). The reaction mixture was stirred for 2 h at 80° C. under nitrogen atmosphere. The mixture was allowed to cool down to room temperature. The reaction was quenched with water (50 mL). The resulting mixture was extracted with EtOAc (3×50 mL). The combined organic layers were washed with brine (2×80 mL), dried over anhydrous $Na_2SO_4$. After filtration, the filtrate was concentrated under reduced pressure. The residue was purified by silica gel column chromatography, eluted with PE/EA/EtOH (4/3/1). The fractions contained desired product were combined and concentrated to afford 4-methyl-3-[5-(morpholin-4-yl)-6-(prop-1-yn-1-yl)pyridin-3-yl]aniline (1.10 g, 68%) as a light brown solid. MS ESI calculated for $C_{19}H_{21}N_3O$ [M+H]$^+$, 308.17, found 308.17.

Step 2: 6-Tert-butyl-N-{4-methyl-3-[5-(morpholin-4-yl)-6-(prop-1-yn-1-yl)pyridin-3-yl]phenyl}pyrimidine-4-carboxamide

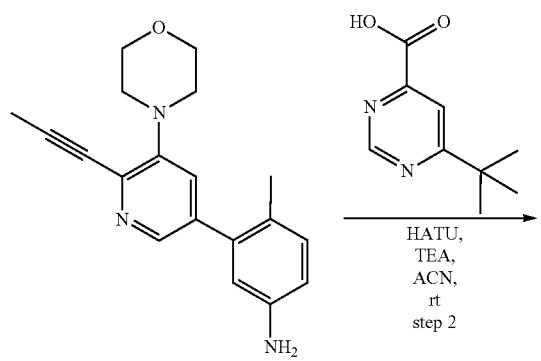

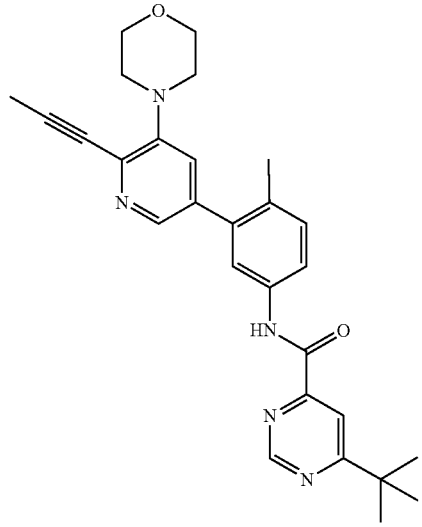 [SMILES: CC#Cc1ncc(-c2cc(NC(=O)c3cc(C(C)(C)C)ncn3)ccc2C)cc1N1CCOCC1]

To a stirred solution of 4-methyl-3-[5-(morpholin-4-yl)-6-(prop-1-yn-1-yl)pyridin-3-yl]aniline (80 mg, 0.260 mmol), 6-tert-butylpyrimidine-4-carboxylic acid (47 mg, 0.260 mmol) and HATU (148 mg, 0.390 mmol) in $CH_3CN$ (1 mL) was added TEA (105 mg, 1.040 mmol) dropwise at room temperature under nitrogen atmosphere. The resulting mixture was stirred for 16 h at room temperature under nitrogen atmosphere. The reaction was quenched by the addition of water (20 mL) at room temperature. The resulting mixture was extracted with EtOAc (3×30 mL). The combined organic layers was washed with brine (2×20 mL), dried over anhydrous $Na_2SO_4$. After filtration, the filtrate was concentrated under reduced pressure. The residue was purified by Prep-TLC (PE/EA/EtOH (8/3/1)) to afford the crude product. The residue was purified by reverse flash chromatography with the following conditions: column, C18 silica gel; mobile phase, $CH_3CN$ in water (10 mmol $NH_4HCO_3$), 35% to 95% gradient in 15 min; detector, UV 254 nm. The fractions contained desired product were combined and concentrated to afford 6-tert-butyl-N-{4-methyl-3-[5-(morpholin-4-yl)-6-(prop-1-yn-1-yl)pyridin-3-yl]phenyl}pyrimidine-4-carboxamide (55 mg, 45%) as an off-white solid. MS ESI calculated for $C_{28}H_{31}N_5O_2$ [M+H]$^+$, 470.25, found 470.20. $^1$H NMR (400 MHz, Chloroform-d) δ 9.96 (s, 1H), 9.22 (s, 1H), 8.26-8.24 (m, 2H), 7.75-7.73 (m, 1H), 7.69 (s, 1H), 7.36-7.34 (d, J=8.2 Hz, 1H), 7.25 (s, 1H), 3.95-3.93 (m, 4H), 3.30-3.28 (m, 4H), 2.29 (s, 3H), 2.22 (s, 3H), 1.44 (s, 9H).

167
Example 28: N-(4-methyl-3-(5-morpholino-6-((tetrahydro-2H-pyran-4-yl)ethynyl)pyridin-3-yl)phenyl)-2-(trifluoromethyl)isonicotinamide
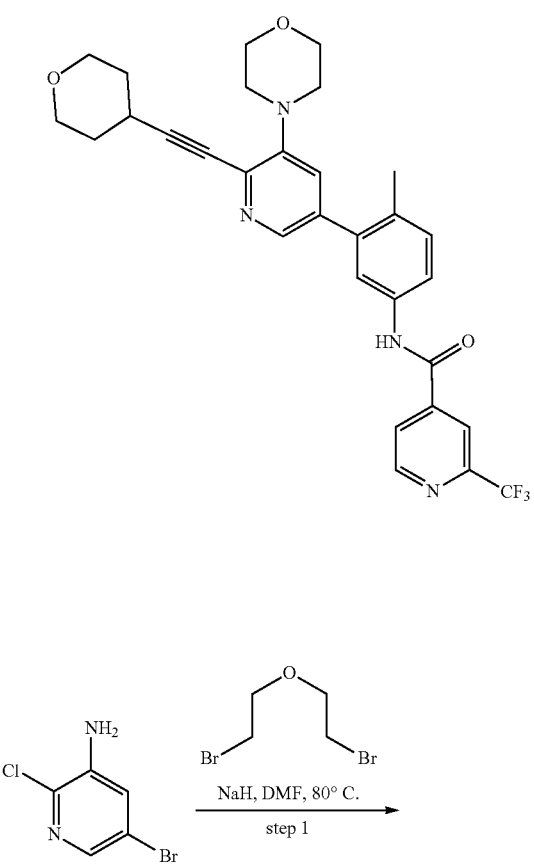
168
-continued
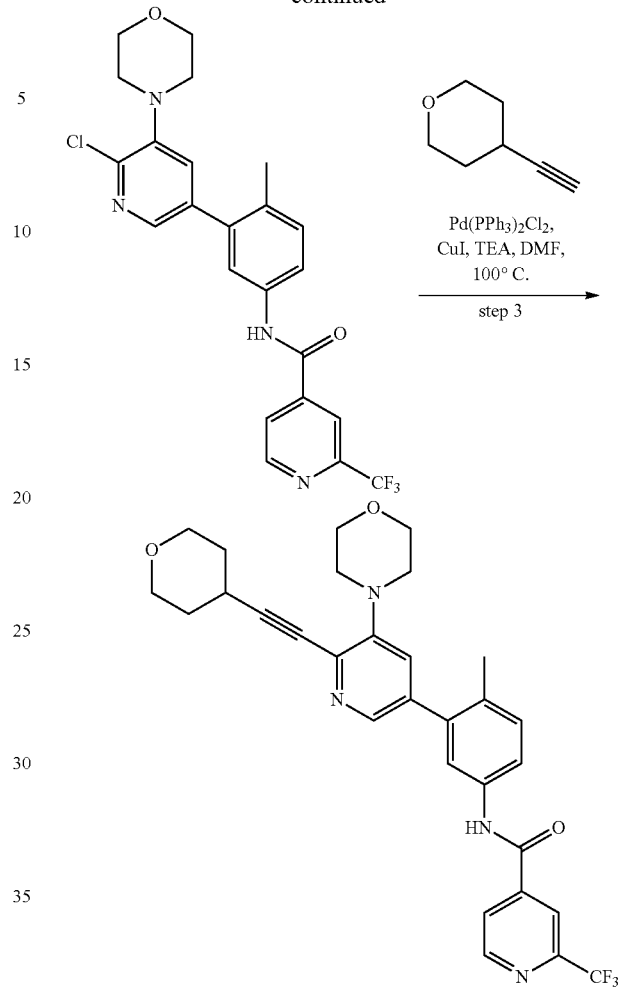
Preparation 28A:
4-(5-bromo-2-chloropyridin-3-yl)morpholine
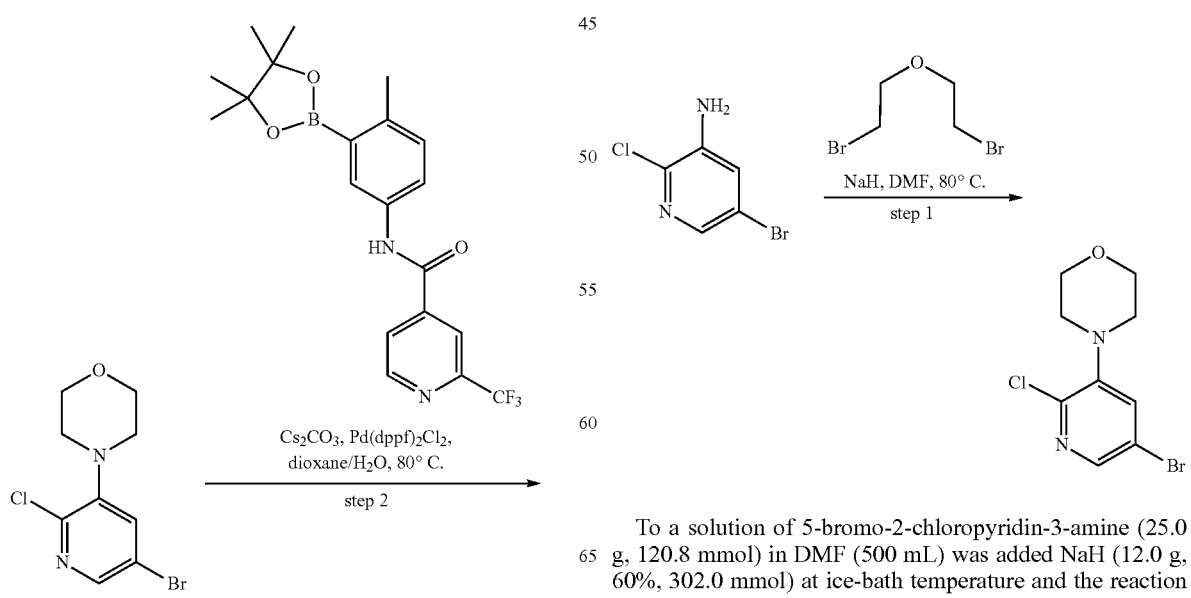
To a solution of 5-bromo-2-chloropyridin-3-amine (25.0 g, 120.8 mmol) in DMF (500 mL) was added NaH (12.0 g, 60%, 302.0 mmol) at ice-bath temperature and the reaction was stirred for 30 min. The reaction was added 1-bromo-2-

(2-bromoethoxy)ethane (30.1 g, 130.0 mmol) at ice-bath temperature and the reaction was stirred at 80° C. for 3 h. The reaction was quenched with water (1000 ml). The mixture was filtered, washed with H$_2$O (200 mL) and PE/EA (30 mL, 3/1) to afford 4-(5-bromo-2-chloropyridin-3-yl)morpholine (26.8 g, 80%) as a yellow solid. MS ESI calculated for C$_9$H$_{10}$BrClN$_2$O [M+H]$^+$, 277.97, found 278.00.

Preparation 28B: N-(3-(6-chloro-5-morpholinopyridin-3-yl)-4-methylphenyl)-2-(trifluoromethyl)isonicotinamide

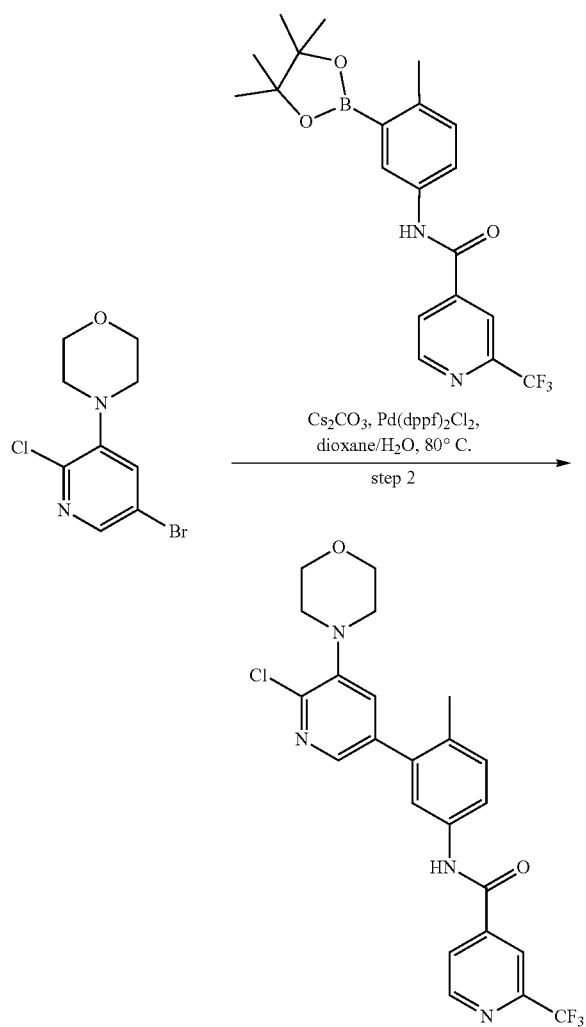

A mixture of 4-(5-bromo-2-chloropyridin-3-yl)morpholine (2.0 g, 7.19 mmol), N-(4-methyl-3-(4,4,5,5-tetramethyl-1,3,2-dioxaborolan-2-yl)phenyl)-2-(trifluoromethyl)isonicotinamide (2.9 g, 7.19 mmol), Pd(dppf)Cl$_2$ (292 mg, 0.40 mmol) and Cs$_2$CO$_3$ (4.7 g, 14.38 mmol) in dioxane (100 mL) and H$_2$O (20 mL) was stirred for 5 h at 80° C. under nitrogen atmosphere. To the resulting mixture was added water (100 mL), extracted with EA (200 mL). The organic layer was dried over Na$_2$SO$_4$, filtered, concentrated under reduced pressure. The residue was purified by FCC with PE/EtOAc (3/1) to afford N-(3-(6-chloro-5-morpholinopyridin-3-yl)-4-methylphenyl)-2-(trifluoromethyl)isonicotinamide (2.5 g, 75%) as a yellow solid. MS ESI calculated for C$_{23}$H$_{30}$ClF$_3$N$_4$O$_2$ [M+H]$^+$, 477.12, found 477.10.

Example 28: N-(4-methyl-3-(5-morpholino-6-((tetrahydro-2H-pyran-4-yl)ethynyl)pyridin-3-yl)phenyl)-2-(trifluoromethyl)isonicotinamide

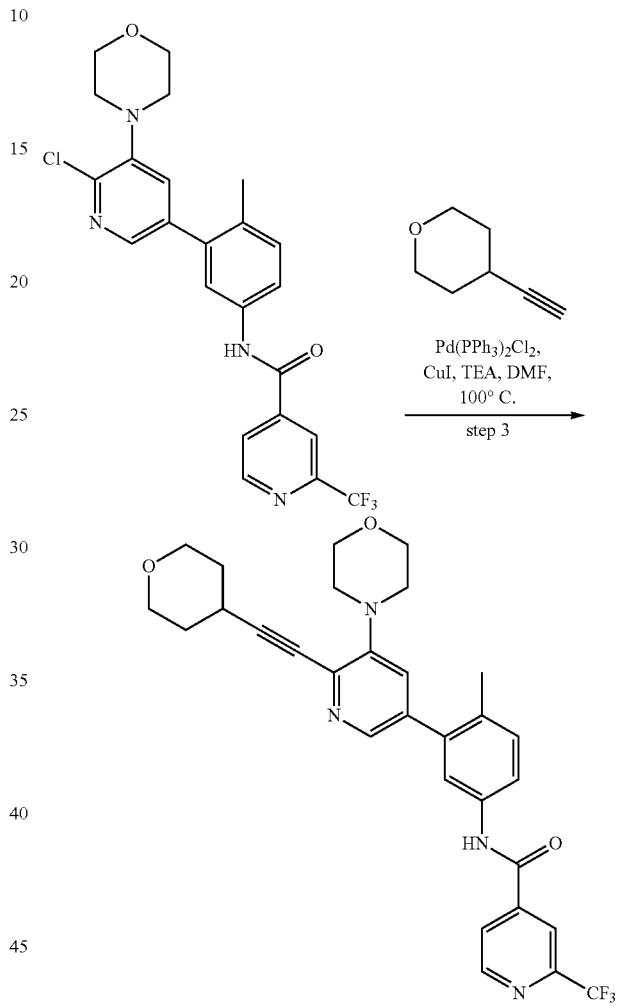

A mixture of N-(3-(6-chloro-5-morpholinopyridin-3-yl)-4-methylphenyl)-2-(trifluoromethyl)isonicotinamide (300 mg, 0.63 mmol), 4-ethynyltetrahydro-2H-pyran (280 mg, 2.52 mmol), Pd(PPh$_3$)$_2$Cl$_2$ (42 mg, 0.06 mmol), CuI (6 mg, 0.03 mmol) and TEA (190 mg, 1.89 mmol) in DMF (10 mL) was stirred at 100° C. for 16 h under nitrogen atmosphere. The resulting mixture was filtered, concentrated under reduced pressure. The residue was purified by prep-HPLC to afford N-(4-methyl-3-(5-morpholino-6-((tetrahydro-2H-pyran-4-yl)ethynyl)pyridin-3-yl)phenyl)-2-(trifluoromethyl)isonicotinamide (150.8 mg, 43%) as a yellow solid. MS ESI calculated for C$_{33}$H$_{34}$F$_3$N$_5$O$_4$ [M+H]$^+$, 551.22, found 551.20. $^1$H NMR (400 MHz, DMSO-d$_6$) δ 10.71 (s, 1H), 8.99 (d, J=5.2 Hz, 1H), 8.37 (s, 1H), 8.20 (dd, J=1.2, 5.2 Hz, 1H), 8.13 (d, J=2.0 Hz, 1H), 7.77 (dd, J=2.4, 8.4 Hz, 1H), 7.65 (d, J=2.4 Hz, 1H), 7.37-7.34 (m, 2H), 3.86-3.76 (m, 6H), 3.50-3.44 (m, 2H), 3.20-3.18 (m, 4H), 3.01-2.99 (m, 1H), 2.24 (s, 3H), 1.91-1.87 (m, 2H), 1.66-1.62 (m, 2H).

Example 29: 5-(5-(2-methyl-5-(2-(trifluoromethyl)isonicotinamido)phenyl)-3-morpholinopyridin-2-yl)pent-4-ynoic Acid
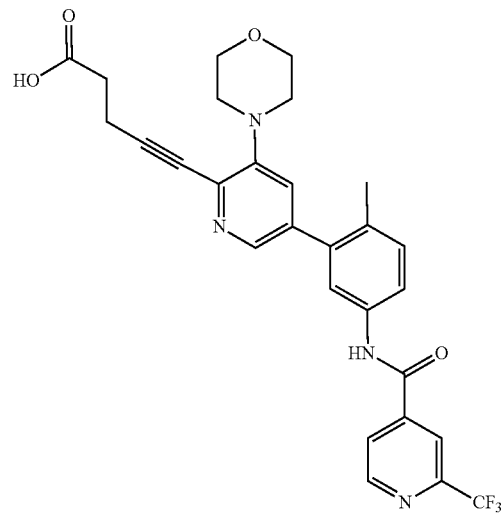 [SMILES: Cc1ccc(NC(=O)c2ccnc(C(F)(F)F)c2)cc1-c1cnc(C#CCCC(=O)O)c(N2CCOCC2)c1]
-continued
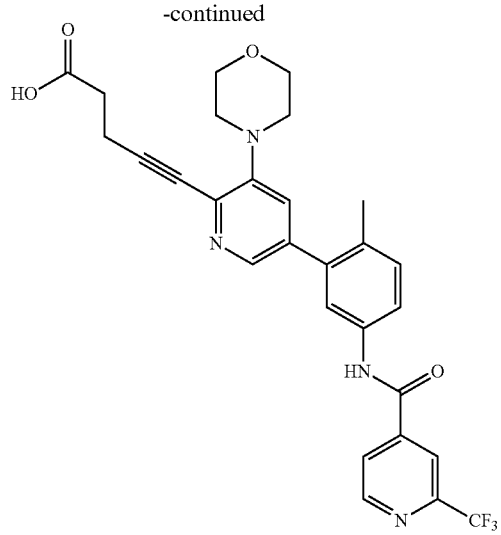
Preparation 29A: methyl 5-(5-(2-methyl-5-(2-(trifluoromethyl)isonicotinamido)phenyl)-3-morpholinopyridin-2-yl)pent-4-ynoate
Synthetic Scheme
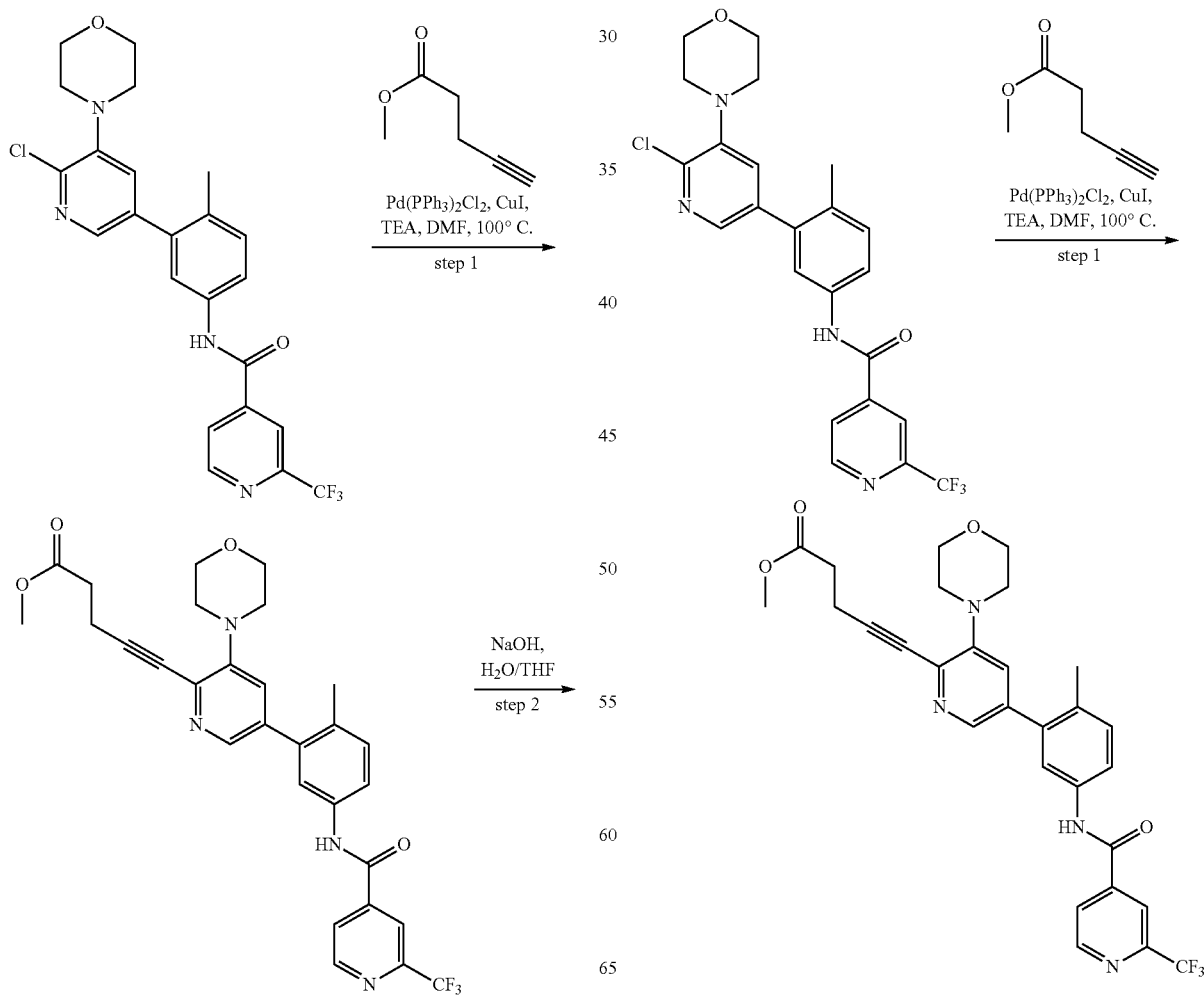

A mixture of N-(3-(6-chloro-5-morpholinopyridin-3-yl)-4-methylphenyl)-2-(trifluoromethyl)isonicotinamide (500 mg, 1.05 mmol), methyl pent-4-ynoate (472 mg, 4.21 mmol), Pd(PPh$_3$)$_2$Cl$_2$ (75 mg, 0.11 mmol), CuI (10 mg, 0.05 mmol) and TEA (0.41 mL, 3.16 mmol) in DMF (20 mL) was stirred at 100° C. for 16 h under nitrogen atmosphere. The resulting mixture was filtered, concentrated under reduced pressure. The residue was purified by prep-HPLC to afford 5-(5-(2-methyl-5-(2-(trifluoromethyl)isonicotinamido)phenyl)-3-morpholinopyridin-2-yl)pent-4-ynoate (350 mg, 60%) as a yellow solid. MS ESI calculated for C$_{29}$H$_{27}$F$_3$N$_4$O$_4$ [M+H]$^+$, 553.20, found 553.20.

Example 29: 5-(5-(2-methyl-5-(2-(trifluoromethyl)isonicotinamido)phenyl)-3-morpholinopyridin-2-yl)pent-4-ynoic acid A solution of -(5-(2-methyl-5-(2-(trifluoromethyl)isonicotinamido)phenyl)-3-morpholinopyridin-2-yl)pent-4-ynoate (200 mg, 0.36 mmol) and NaOH (30 mg, 0.72 mmol) in H$_2$O (5 mL) and THF (5 mL) was stirred at RT for 2 h. The resulting mixture was acidified to pH 5 with 1N HCl, concentrated under reduced pressure. The residue was purified by prep-HPLC to afford 5-(5-(2-methyl-5-(2-(trifluoromethyl)isonicotinamido)phenyl)-3-morpholinopyridin-2-yl)pent-4-ynoic acid (150.3 mg, 77%) as a yellow solid. MS ESI calculated for C$_{28}$H$_{25}$F$_3$N$_4$O$_4$ [M+H]$^+$, 539.18, found 539.20. $^1$H NMR (400 MHz, CD$_3$OD) δ 8.80 (d, J=5.2 Hz, 1H), 8.20 (s, 1H), 8.03-7.97 (m, 2H), 7.61 (dd, J=2.0, 8.0 Hz, 1H), 7.55 (d, J=2.0 Hz, 1H), 7.31 (d, J=2.0 Hz, 1H), 7.25 (d, J=8.0 Hz, 1H), 3.80-3.78 (m, 4H), 3.17-3.14 (m, 4H), 2.73 (t, J=7.2 Hz, 2H), 2.55 (t, J=7.2 Hz, 2H), 2.18 (s, 3H).

Example 30: N-(4-methyl-3-(5-morpholino-6-(pyrrolidin-3-ylethynyl)pyridin-3-yl)phenyl)-2-(trifluoromethyl)isonicotinamide

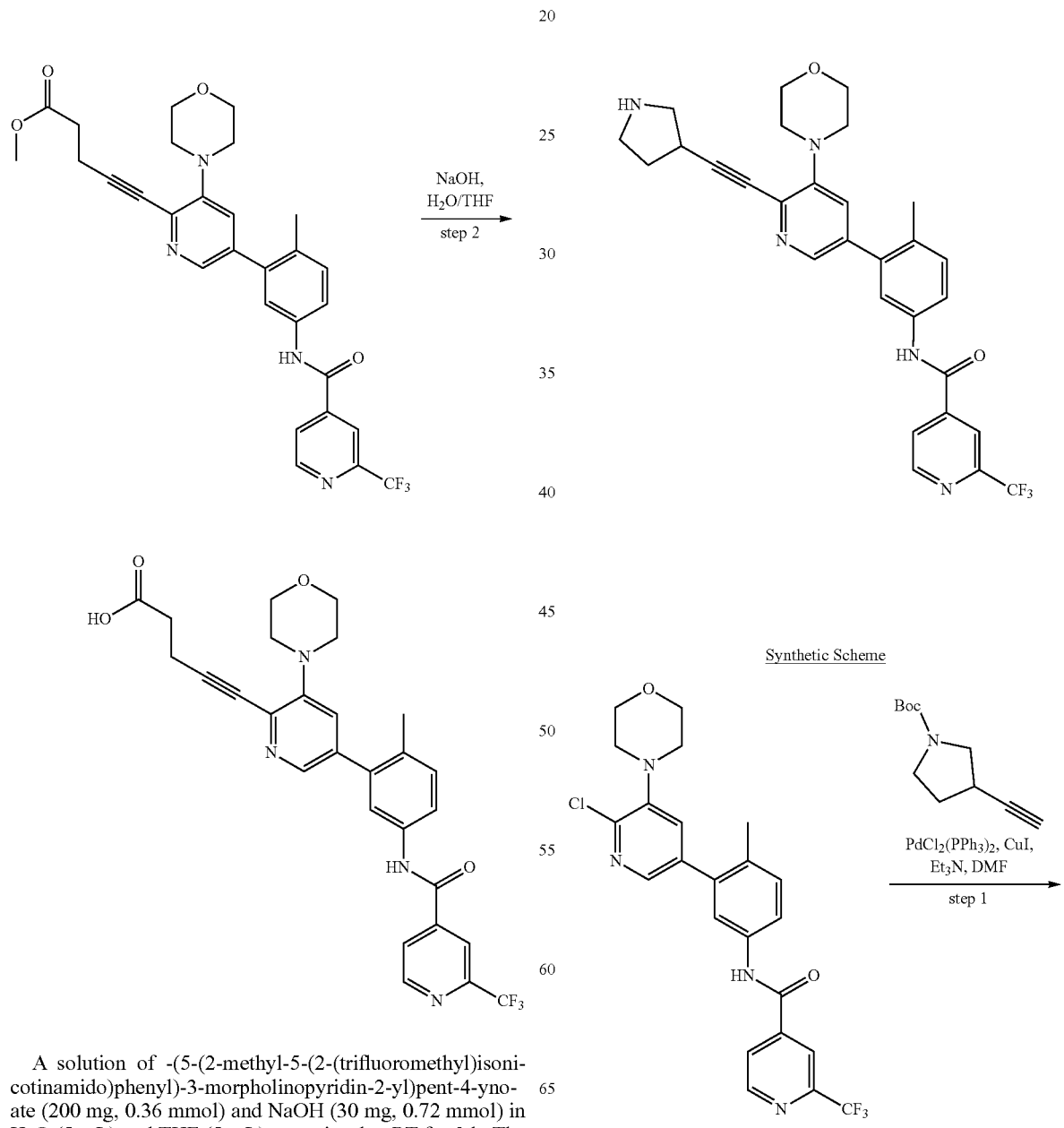

Synthetic Scheme

175

-continued

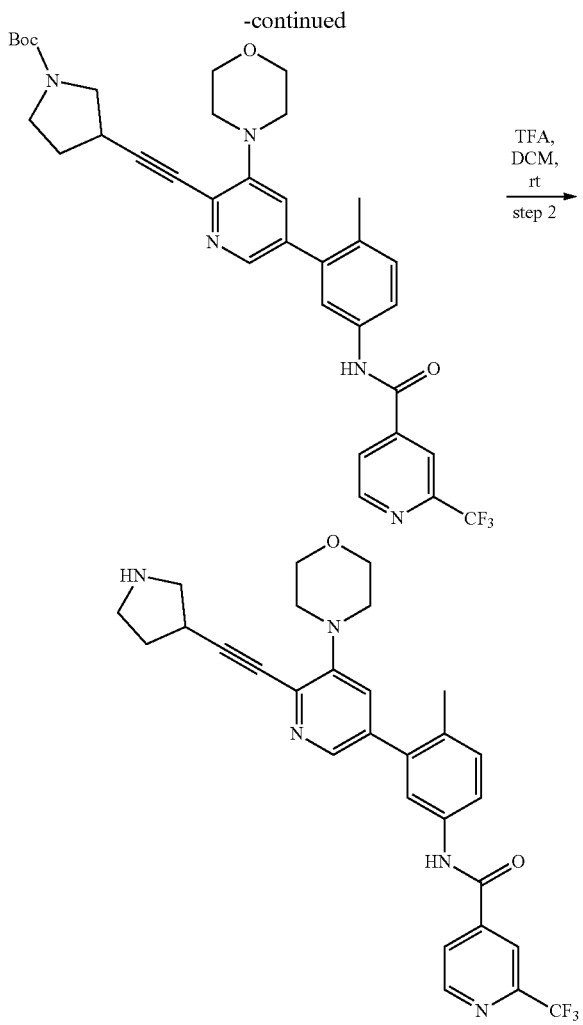

Preparation 30A: tert-butyl 3-((5-(2-methyl-5-(2-(trifluoromethyl)isonicotinamido)phenyl)-3-morpholinopyridin-2-yl)ethynyl)pyrrolidine-1-carboxylate

176

-continued

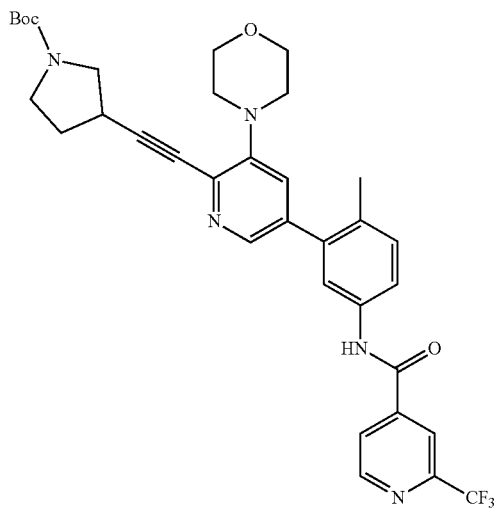

A mixture of N-(3-(6-chloro-5-morpholinopyridin-3-yl)-4-methylphenyl)-2-(trifluoromethyl)isonicotinamide (300 mg, 0.63 mmol), tert-butyl 3-ethynylpyrrolidine-1-carboxylate (490 mg, 2.52 mmol), Pd(PPh$_3$)$_2$Cl$_2$ (60 mg, 0.063 mmol), CuI (24 mg, 0.12 mmol) and TEA (0.41 mL, 3.16 mmol) in DMF (20 mL) was stirred at 100° C. for 16 h under nitrogen atmosphere. The resulting mixture was filtered, concentrated under reduced pressure. The residue was purified by prep-HPLC to afford tert-butyl 3-((5-(2-methyl-5-(2-(trifluoromethyl)isonicotinamido)phenyl)-3-morpholinopyridin-2-yl)ethynyl)pyrrolidine-1-carboxylate (300 mg, 75%) as a yellow oil. MS ESI calculated for C$_{29}$H$_{27}$F$_3$N$_4$O$_4$ [M+H]+, 636.27, found 636.20.

Preparation 30: N-(4-methyl-3-(5-morpholino-6-(pyrrolidin-3-ylethynyl)pyridin-3-yl)phenyl)-2-(trifluoromethyl)isonicotinamide

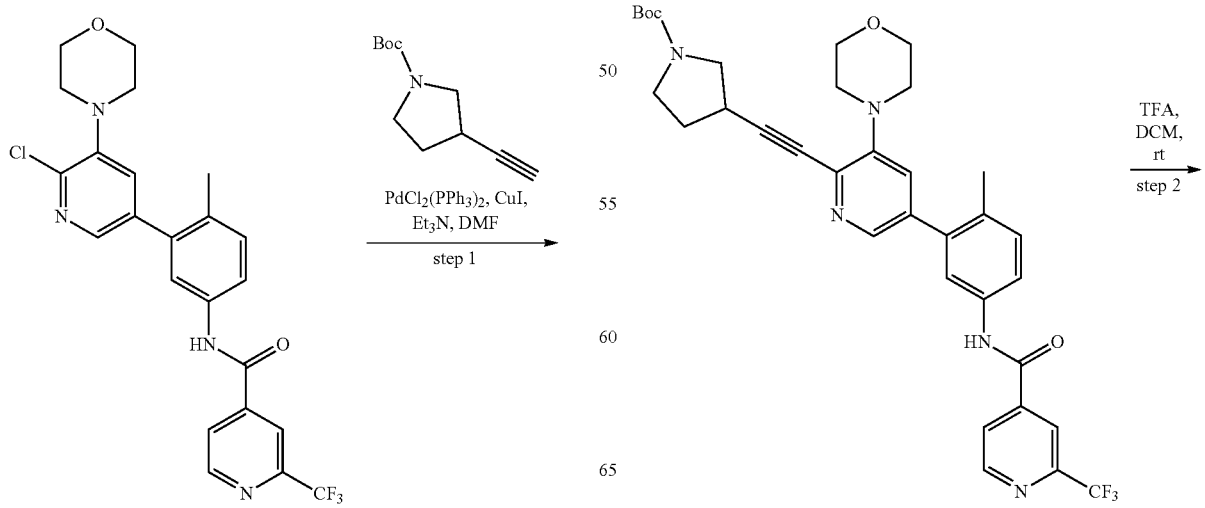

177
-continued

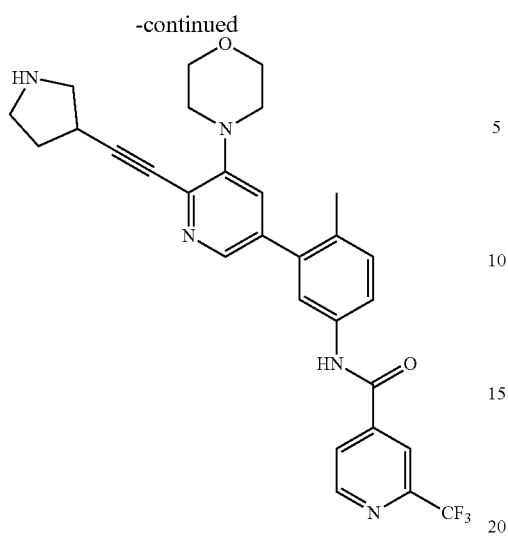

178
-continued

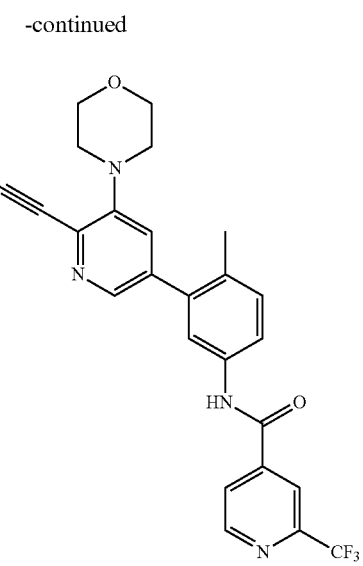

To a solution of tert-butyl 3-((5-(2-methyl-5-(2-(trifluoromethyl)isonicotinamido)phenyl)-3-morpholinopyridin-2-yl)ethynyl)pyrrolidine-1-carboxylate (300 mg, 0.47 mmol) in DCM (5 mL) was added TFA (1 mL) at rt and the reaction mixture was stirred for 3 h. The reaction mixture was then concentrated. The residue was dissolved in water (20 mL) and EA (20 mL), basified to pH 9 with sat. Na$_2$CO$_3$. The organic layer was dried over Na$_2$SO$_4$, filtered, and concentrated. The residue was purified by prep-HPLC to afford HCOOH salt of N-(4-methyl-3-(5-morpholino-6-(pyrrolidin-3-ylethynyl)pyridin-3-yl)phenyl)-2-(trifluoromethyl)isonicotinamide (135 mg, 54%) as a white solid. MS ESI calculated for C$_{29}$H$_{28}$F$_3$N$_5$O$_2$ [M+H]+, 536.22, found 536.20. $^1$H NMR (400 MHz, CD$_3$OD) δ 8.90 (d, J=4.8 Hz, 1H), 8.51 (brs, 1H), 8.29 (s, 1H), 8.15-8.11 (m, 2H), 7.71 (d, J=2.0 Hz, 1H), 7.66-7.63 (m, 1H), 7.46 (d, J=2.0 Hz, 1H), 7.35 (d, J=8.4 Hz, 1H), 3.89-3.86 (m, 4H), 3.60-3.57 (m, 2H), 3.52-3.47 (m, 1H), 3.41-3.37 (m, 2H), 3.29-3.24 (m, 4H), 2.45-2.41 (m, 1H), 2.27 (s, 3H), 2.24-2.19 (m, 1H).

Example 31: N-(3-(6-((1-acetylpyrrolidin-3-yl)ethynyl)-5-morpholinopyridin-3-yl)-4-methylphenyl)-2-(trifluoromethyl)isonicotinamide To a solution of N-(4-methyl-3-(5-morpholino-6-(pyrrolidin-3-ylethynyl)pyridin-3-yl)phenyl)-2-(trifluoromethyl)isonicotinamide (150 mg, 0.23 mmol) and DIEA (149 mg, 1.15 mmol) in DCM (10 mL) was added acetyl chloride (19 mg, 0.23 mmol) and stirred for 30 min at 0° C. The reaction mixture was diluted with water (10 mL) and extracted with DCM (10 mL*2). The combined organic layers were washed with brine (10 mL), dried over anhydrous sodium sulfate, filtered, and concentrated under reduced pressure. The residue was purified by prep-HPLC to give N-(3-(6-((1-acetylpyrrolidin-3-yl)ethynyl)-5-morpholinopyridin-3-yl)-4-methylphenyl)-2-(trifluoromethyl)isonicotinamide (26.3 mg, 23%) as a white solid. MS ESI calculated for C$_{31}$H$_{30}$F$_3$N$_5$O$_3$ [M+H]+, 578.23, found 578.30. $^1$H NMR (400 MHz, CD$_3$OD) δ 8.78 (d, J=5.2 Hz, 1H), 8.18 (s, 1H), 7.99-7.98 (m, 2H), 7.57-7.54 (m, 2H), 7.31 (s, 1H), 7.21 (d, J=8.0 Hz, 1H), 3.82-3.79 (m, 1H), 3.77-3.75 (m, 4H), 3.71-3.62 (m, 1H), 3.55-3.50 (m, 1H), 3.46-3.31 (m, 2H), 3.13-3.12 (m, 4H), 2.30-2.15 (m, 1H), 2.13 (s, 3H), 2.11-2.03 (m, 1H), 2.01 (s, 3H).

Example 32: N-(4-methyl-3-(6-((1-methylpyrrolidin-3-yl)ethynyl)-5-morpholinopyridin-3-yl)phenyl)-2-(trifluoromethyl)isonicotinamide

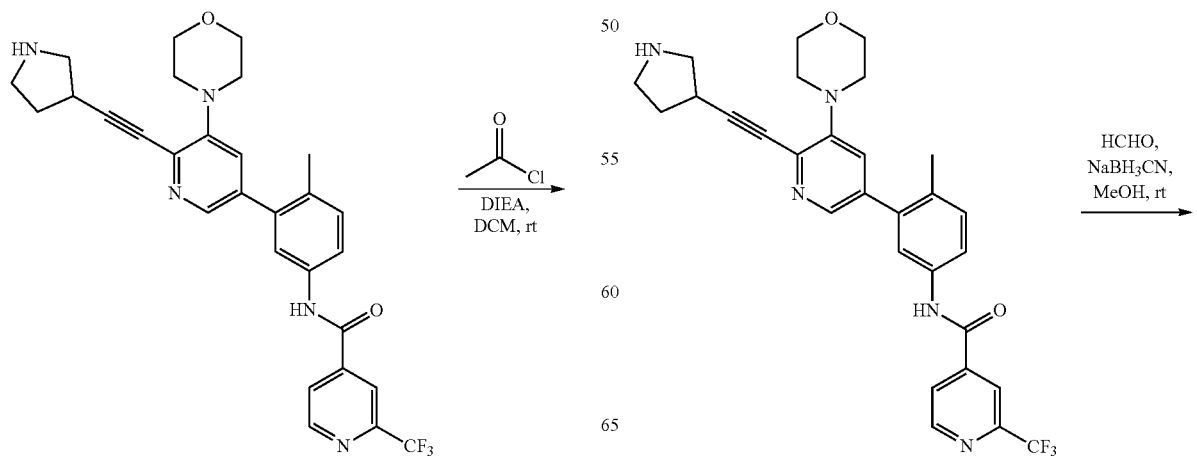

-continued

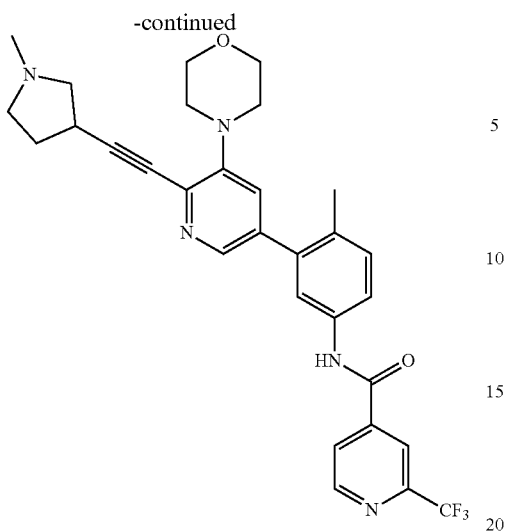

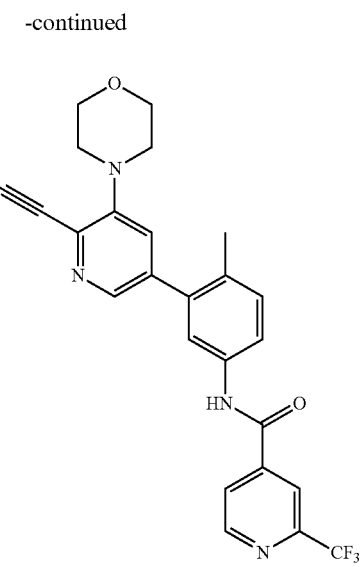

A mixture of N-(4-methyl-3-(5-morpholino-6-(pyrrolidin-3-ylethynyl)pyridin-3-yl)phenyl)-2-(trifluoromethyl)isonicotinamide (100 mg, 0.17 mmol), HCHO (33 mg, 32% in $H_2O$, 0.35 mmol), and $NaBH_3CN$ (44 mg, 0.70 mmol) in MeOH (8 mL) was stirred at 30° C. for 16 h under nitrogen atmosphere. The reaction mixture was diluted with water (10 mL) and extracted with DCM (10 mL*2). The combined organic layers were washed with brine (10 mL), dried over anhydrous sodium sulfate, filtered, and concentrated under reduced pressure. The residue was purified by prep-HPLC to give N-(4-methyl-3-(6-((1-methylpyrrolidin-3-yl)ethynyl)-5-morpholinopyridin-3-yl)phenyl)-2-(trifluoromethyl)isonicotinamide (42.1 mg, 44%) as a white solid. MS ESI calculated for $C_{30}H_{30}F_3N_5O_2$ [M+H]$^+$, 550.24, found 550.20. $^1$H NMR (400 MHz, DMSO-d$_6$) δ 10.72 (s, 1H), 9.01 (d, J=4.8 Hz, 1H), 8.38 (s, 1H), 8.21 (d, J=4.4 Hz, 1H), 8.14 (d, J=1.2 Hz, 1H), 7.80-7.77 (m, 1H), 7.67 (d, J=1.6 Hz, 1H), 7.38-7.34 (m, 2H), 3.80-3.79 (m, 4H), 3.31-3.24 (m, 1H), 3.21-3.20 (m, 4H), 2.89 (t, J=8.4 Hz, 1H), 2.62-2.52 (m, 2H), 2.48-2.44 (m, 1H), 2.30 (s, 3H), 2.28 (s, 3H), 2.25-2.21 (m, 1H), 1.89-1.84 (m, 1H).

Example 33: N-(4-methyl-3-(6-O-(methylsulfonyl)pyrrolidin-3-yl)ethynyl)-5-morpholinopyridin-3-yl)phenyl)-2-(trifluoromethyl)isonicotinamide

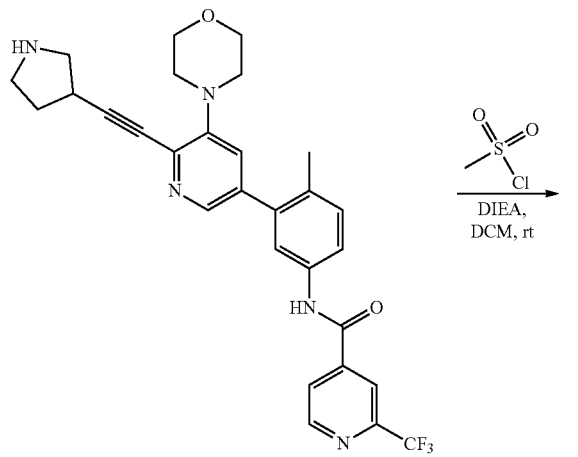

To a solution of N-(4-methyl-3-(5-morpholino-6-(pyrrolidin-3-ylethynyl)pyridin-3-yl)phenyl)-2-(trifluoromethyl)isonicotinamide (300 mg, 0.46 mmol) and DIEA (294 mg, 2.30 mmol) in DCM (10 mL) was added methanesulfonyl chloride (58 mg, 0.51 mmol) and stirred for a hour at 0° C. The reaction mixture was diluted with water (10 mL) and extracted with DCM (15 mL*2). The combined organic layers were washed with brine (10 mL), dried over anhydrous sodium sulfate, filtered, and concentrated under reduced pressure. The residue was purified by prep-HPLC to give N-(4-methyl-3-(6-((1-(methylsulfonyl)pyrrolidin-3-yl)ethynyl)-5-morpholinopyridin-3-yl)phenyl)-2-(trifluoromethyl)isonicotinamide (106.4 mg, 38%) as a white solid. MS ESI calculated for $C_{30}H_{30}F_3N_5O_4S$ [M+H]$^+$, 614.20, found 614.20. $^1$H NMR (400 MHz, DMSO_d6) δ 10.71 (s, 1H), 9.00 (d, J=5.2 Hz, 1H), 8.38 (s, 1H), 8.20 (d, J=4.4 Hz, 1H), 8.14 (d, J=1.6 Hz, 1H), 7.78-7.76 (m, 1H), 7.67 (d, J=2.0 Hz, 1H), 7.38-7.36 (m, 2H), 3.78-3.76 (m, 4H), 3.68-3.64 (m, 1H), 3.48-3.36 (m, 3H), 3.28-3.24 (m, 1H), 3.19-3.17 (m, 4H), 2.97 (s, 3H), 2.34-2.30 (m, 1H), 2.24 (s, 3H), 2.05-2.00 (m, 1H).

Example 34: 5-fluoro-2-isopropyl-N-(4-methyl-3-(5-morpholino-6-(prop-1-yn-1-yl)pyridin-3-yl)phenyl)isonicotinamide

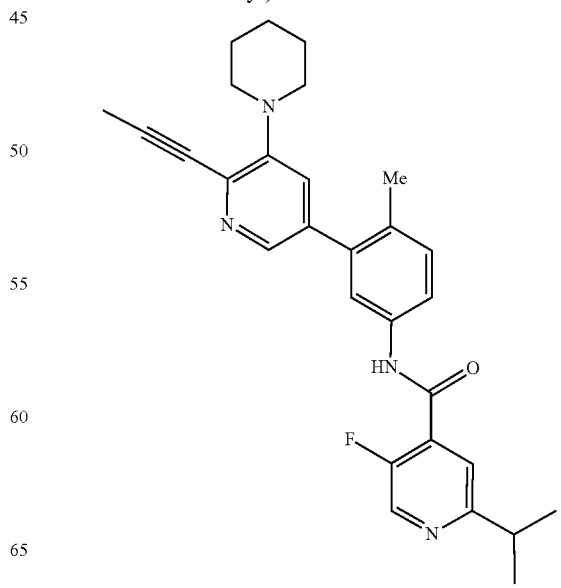

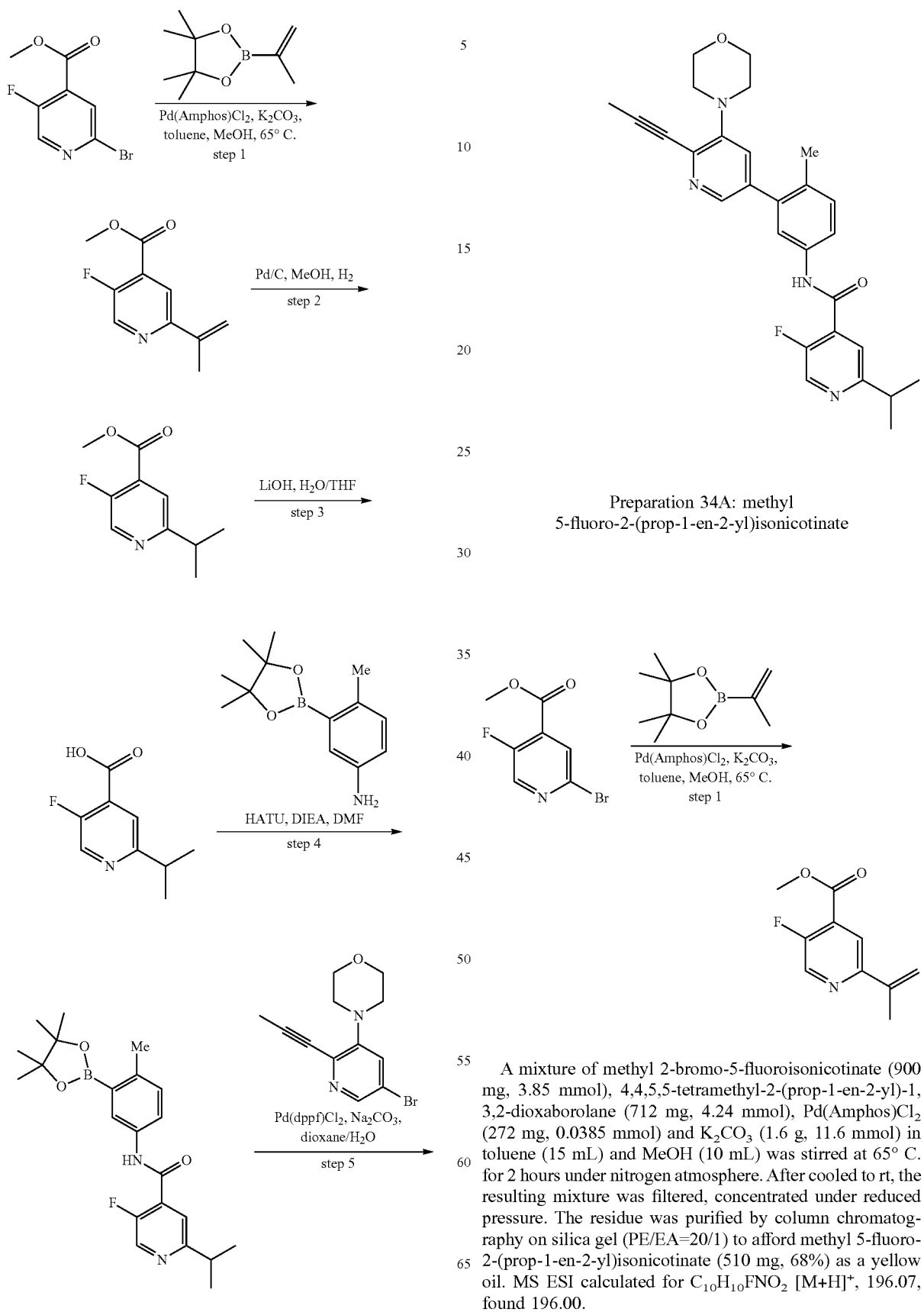

Preparation 34A: methyl 5-fluoro-2-(prop-1-en-2-yl)isonicotinate

A mixture of methyl 2-bromo-5-fluoroisonicotinate (900 mg, 3.85 mmol), 4,4,5,5-tetramethyl-2-(prop-1-en-2-yl)-1,3,2-dioxaborolane (712 mg, 4.24 mmol), Pd(Amphos)Cl$_2$ (272 mg, 0.0385 mmol) and K$_2$CO$_3$ (1.6 g, 11.6 mmol) in toluene (15 mL) and MeOH (10 mL) was stirred at 65° C. for 2 hours under nitrogen atmosphere. After cooled to rt, the resulting mixture was filtered, concentrated under reduced pressure. The residue was purified by column chromatography on silica gel (PE/EA=20/1) to afford methyl 5-fluoro-2-(prop-1-en-2-yl)isonicotinate (510 mg, 68%) as a yellow oil. MS ESI calculated for C$_{10}$H$_{10}$FNO$_2$ [M+H]$^+$, 196.07, found 196.00.

Preparation 34B: methyl 5-fluoro-2-isopropylisonicotinate

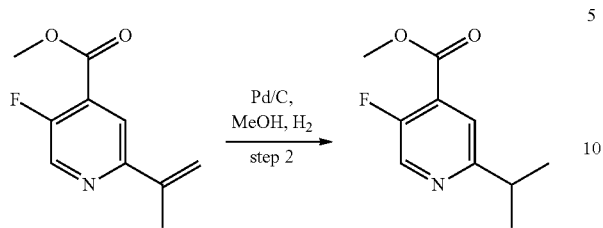

A mixture of methyl 5-fluoro-2-(prop-1-en-2-yl)isonicotinate (500 mg, 2.565 mmol) and Pd/C (100 mg, 5%) in MeOH (20 mL) was stirred at rt under 1 atm H2 for 2 h. The reaction mixture was filtered and concentrated to give methyl 5-fluoro-2-isopropylisonicotinate (400 mg, 44%) as a white solid. MS ESI calculated for C10H12FNO2 [M+H]+, 198.09 found 198.00.

Preparation 34C: 5-fluoro-2-isopropylisonicotinic Acid

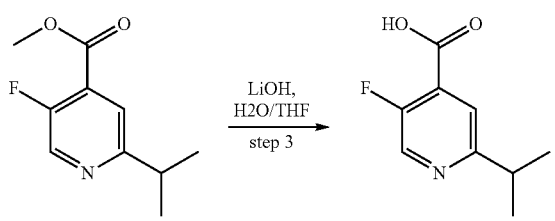

A mixture of methyl 5-fluoro-2-(prop-1-en-2-yl)isonicotinate (200 mg, 1.0 mmol) and LiOH·H2O (126 mg, 3.0 mmol) in THF (5 mL) and H$_2$O (5 mL) was stirred at rt overnight. THF was removed under reduced pressure, the residue was adjusted pH 3 and with 1N HCl, filtered to give 5-fluoro-2-isopropylisonicotinic acid (100 mg, 54%) as a white solid. MS ESI calculated for C$_9$H$_{10}$FNO$_2$ [M+H]$^+$, 184.07 found 184.00.

Preparation 34D: 5-fluoro-2-isopropyl-N-(4-methyl-3-(4,4,5,5-tetramethyl-1,3,2-dioxaborolan-2-yl)phenyl)isonicotinamide

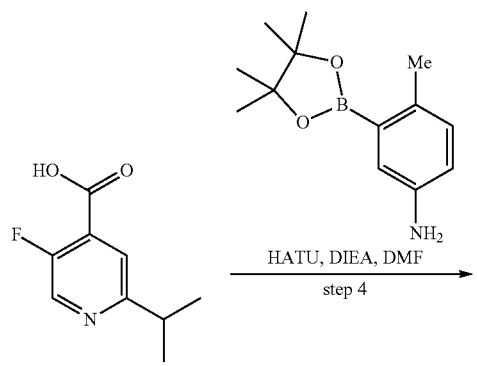

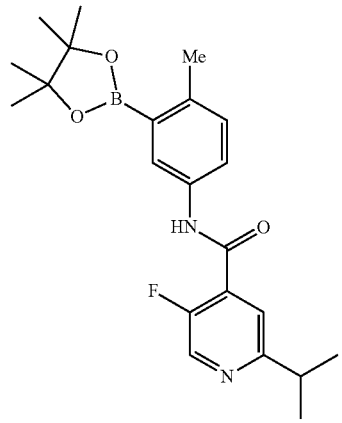

A mixture of 5-fluoro-2-isopropylisonicotinic acid (100 mg, 0.54 mmol) and 4-methyl-3-(4,4,5,5-tetramethyl-1,3,2-dioxaborolan-2-yl)aniline (126 mg, 0.54 mmol), HATU (227 mg, 0.59 mmol), DIEA (210 mg, 1.63 mmol) in DMF (5 mL) was stirred at rt overnight. The reaction mixture was diluted with water (10 mL) and extracted with EA (15 mL*2). The combined organic layers were washed with brine (10 mL), dried over anhydrous sodium sulfate, filtered, and concentrated under reduced pressure. The residue was purified by column chromatography on silica gel (PE/EA=10/1) to afford 5-fluoro-2-isopropyl-N-(4-methyl-3-(4,4,5,5-tetramethyl-1,3,2-dioxaborolan-2-yl)phenyl)isonicotinamide (170 mg, 79%) as a yellow oil. MS ESI calculated for C$_{22}$H$_{28}$BFN$_2$O$_3$ [M+H]$^+$, 399.22, found 399.20.

Preparation 34: 5-fluoro-2-isopropyl-N-(4-methyl-3-(5-morpholino-6-(prop-1-yn-1-yl)pyridin-3-yl)phenyl)isonicotinamide

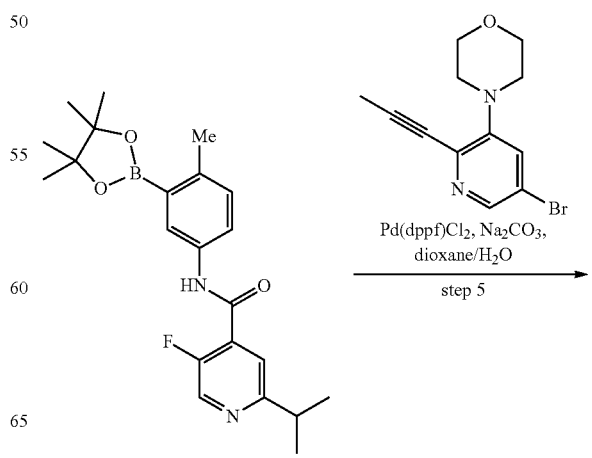

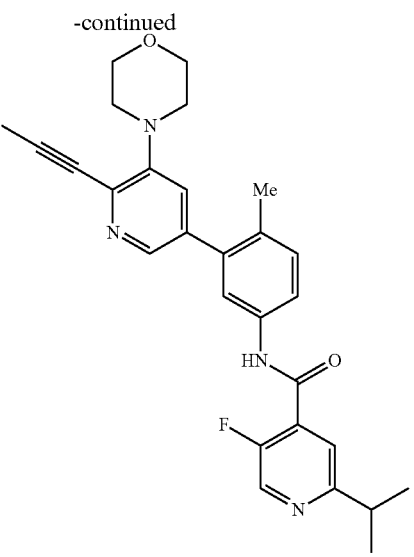

A mixture of 5-fluoro-2-isopropyl-N-(4-methyl-3-(4,4,5,5-tetramethyl-1,3,2-dioxaborolan-2-yl)phenyl)isonicotinamide (170 mg, 0.43 mmol), 4-(5-bromo-2-(prop-1-yn-1-yl)pyridin-3-yl)morpholine (109 mg, 0.39 mmol), Pd(dppf)$_2$Cl$_2$ (29 mg, 0.039 mmol) and K$_2$CO$_3$ (108 mg, 0.78 mmol) in dioxane (10 mL) and H$_2$O (2 mL) was stirred at 85° C. for 5 h under nitrogen atmosphere. The resulting mixture was filtered, concentrated under reduced pressure. The residue was purified by Prep-HPLC to afford 5-fluoro-2-isopropyl-N-(4-methyl-3-(5-morpholino-6-(prop-1-yn-1-yl)pyridin-3-yl)phenyl)isonicotinamide (99.1 mg, 54%) as a white solid. MS ESI calculated for C$_{28}$H$_{29}$FN$_4$O$_2$ [M+H]$^+$, 473.23, found 473.30. $^1$H NMR (400 MHz, CD3OD) δ 8.48 (s, 1H), 8.05 (s, 1H), 7.63-7.55 (m, 3H), 7.38-7.30 (m, 2H), 3.87-3.85 (m, 4H), 3.24-3.23 (m, 4H), 3.14-3.10 (m, 1H), 2.25 (s, 3H), 2.16 (s, 3H), 1.32 (d, J=6.8 Hz, 6H).

The following compounds in Table 5 were prepared using procedures similar to those described in Example 28, 29, 30, 31, 32, 33 and 34 using appropriate starting materials.

TABLE 5

| Entry | Structure | IUPAC Name | Exact Mass [M + H]$^+$ |
|---|---|---|---|
| 35 | 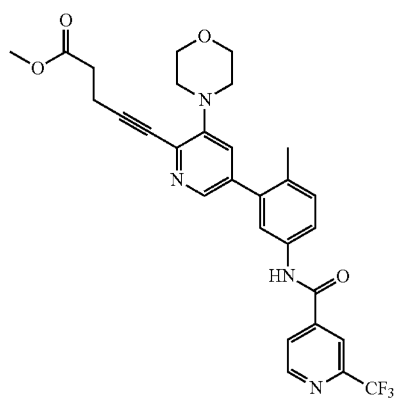 [SMILES: COC(=O)CCC#Cc1ncc(-c2cc(NC(=O)c3ccnc(C(F)(F)F)c3)ccc2C)cc1N1CCOCC1] | methyl 5-(5-(2-methyl-5-(2-(trifluoromethyl)isonicotinamido)phenyl)-3-morpholinopyridin-2-yl)pent-4-ynoate | Calc'd 553.20; found 553.20 |
| 36 | 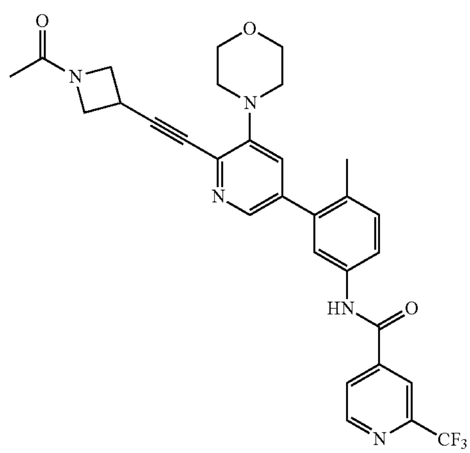 [SMILES: CC(=O)N1CC(C#Cc2ncc(-c3cc(NC(=O)c4ccnc(C(F)(F)F)c4)ccc3C)cc2N2CCOCC2)C1] | N-(3-(6-((1-acetylazetidin-3-yl)ethynyl)-5-morpholinopyridin-3-yl)-4-methylphenyl)-2-(trifluoromethyl)isonicotinamide | Calc'd 564.21; found 564.20 |

TABLE 5-continued

| Entry | Structure | IUPAC Name | Exact Mass [M + H]+ |
|---|---|---|---|
| 37 | 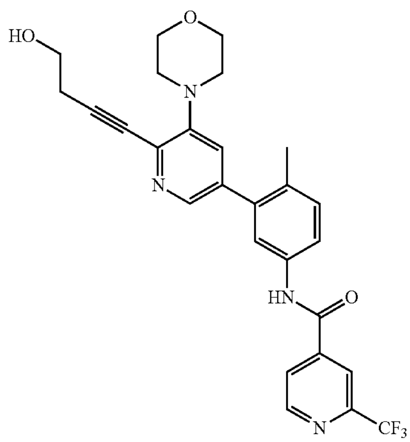 [SMILES: Cc1ccc(NC(=O)c2ccnc(C(F)(F)F)c2)cc1-c1cnc(C#CCCO)c(N2CCOCC2)c1] | N-(3-(6-(4-hydroxybut-1-yn-1-yl)-5-morpholinopyridin-3-yl)-4-methylphenyl)-2-(trifluoromethyl)isonicotinamide | Calc'd 511.19; found 511.20 |
| 38 | 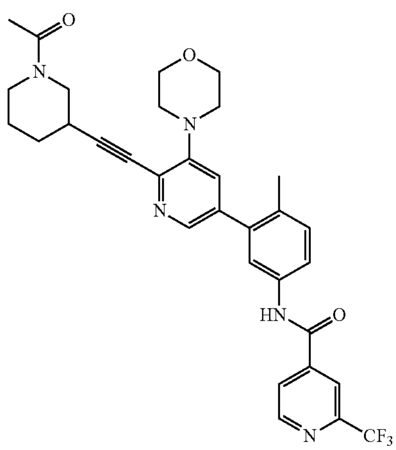 [SMILES: CC(=O)N1CCCC(C#Cc2ncc(-c3cc(NC(=O)c4ccnc(C(F)(F)F)c4)ccc3C)cc2N2CCOCC2)C1] | N-(3-(6-((1-acetylpiperidin-3-yl)ethynyl)-5-morpholinopyridin-3-yl)-4-methylphenyl)-2-(trifluoromethyl)isonicotinamide | Calc'd 592.25; found 592.20 |
| 39 | 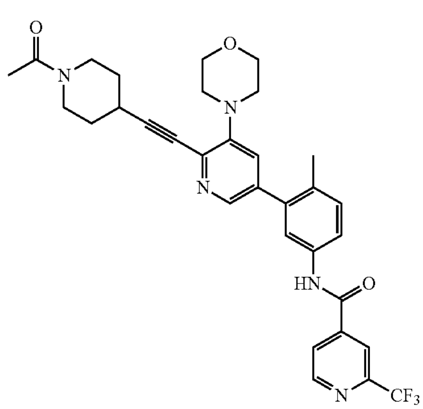 [SMILES: CC(=O)N1CCC(C#Cc2ncc(-c3cc(NC(=O)c4ccnc(C(F)(F)F)c4)ccc3C)cc2N2CCOCC2)CC1] | N-(3-(6-((1-acetylpiperidin-4-yl)ethynyl)-5-morpholinopyridin-3-yl)-4-methylphenyl)-2-(trifluoromethyl)isonicotinamide | Calc'd 592.25; found 592.30 |

TABLE 5-continued

| Entry | Structure | IUPAC Name | Exact Mass [M + H]+ |
|---|---|---|---|
| 40 | 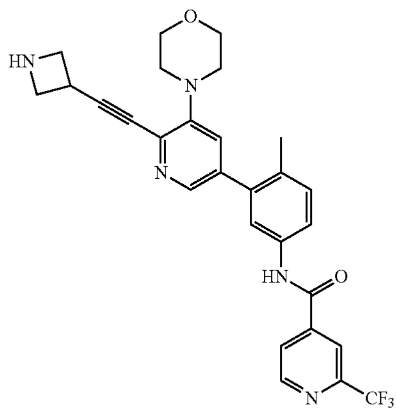 [SMILES: Cc1ccc(NC(=O)c2ccnc(C(F)(F)F)c2)cc1-c1cnc(C#CC2CNC2)c(N2CCOCC2)c1] | N-(3-(6-(azetidin-3-ylethynyl)-5-morpholinopyridin-3-yl)-4-methylphenyl)-2-(trifluoromethyl)isonicotinamide | Calc'd 522.20; found 522.20 |
| 41 | 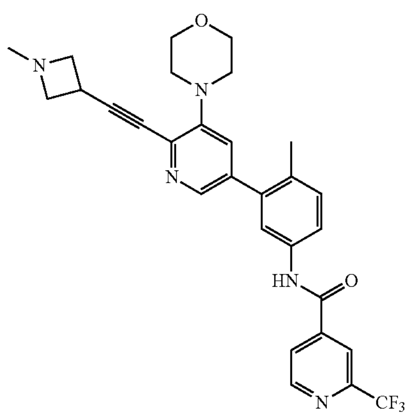 [SMILES: Cc1ccc(NC(=O)c2ccnc(C(F)(F)F)c2)cc1-c1cnc(C#CC2CN(C)C2)c(N2CCOCC2)c1] | N-(4-methyl-3-(6-((1-methylazetidin-3-yl)ethynyl)-5-morpholinopyridin-3-yl)phenyl)-2-(trifluoromethyl)isonicotinamide | Calc'd 536.22; found 536.20 |
| 42 | 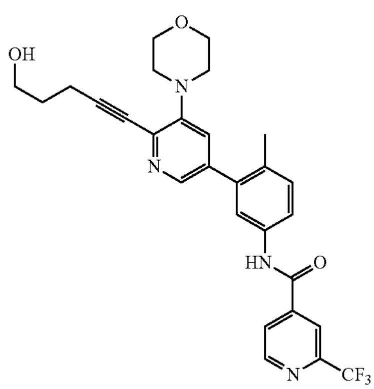 [SMILES: Cc1ccc(NC(=O)c2ccnc(C(F)(F)F)c2)cc1-c1cnc(C#CCCCO)c(N2CCOCC2)c1] | N-(3-(6-(5-hydroxypent-1-yn-1-yl)-5-morpholinopyridin-3-yl)-4-methylphenyl)-2-(trifluoromethyl)isonicotinamide | Calc'd 525.20; found 525.20 |
| 43 | 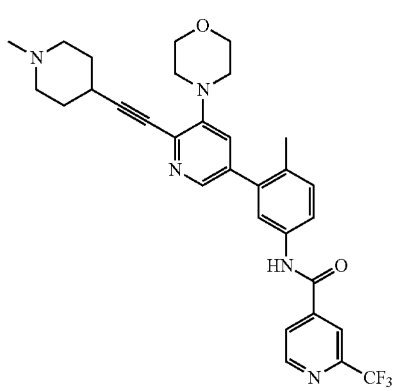 [SMILES: Cc1ccc(NC(=O)c2ccnc(C(F)(F)F)c2)cc1-c1cnc(C#CC2CCN(C)CC2)c(N2CCOCC2)c1] | N-(4-methyl-3-(6-((1-methylpiperidin-4-yl)ethynyl)-5-morpholinopyridin-3-yl)phenyl)-2-(trifluoromethyl)isonicotinamide | Calc'd 564.25; found 564.30 |

TABLE 5-continued

| Entry | Structure | IUPAC Name | Exact Mass [M + H]+ |
|---|---|---|---|
| 44 | 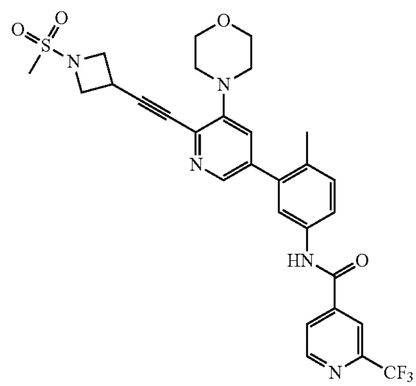 [SMILES: Cc1ccc(NC(=O)c2ccnc(C(F)(F)F)c2)cc1-c1cnc(C#CC2CN(S(C)(=O)=O)C2)c(N2CCOCC2)c1] | N-(4-methyl-3-(6-((1-(methylsulfonyl)azetidin-3-yl)ethynyl)-5-morpholinopyridin-3-yl)phenyl)-2-(trifluoromethyl)isonicotinamide | Calc'd 600.18; found 600.20 |
| 45 | 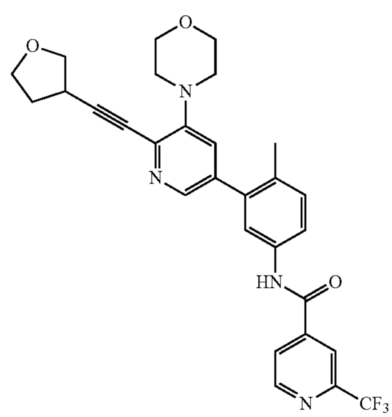 [SMILES: Cc1ccc(NC(=O)c2ccnc(C(F)(F)F)c2)cc1-c1cnc(C#CC2CCOC2)c(N2CCOCC2)c1] | N-(4-methyl-3-(5-morpholino-6-((tetrahydrofuran-3-yl)ethynyl)pyridin-3-yl)phenyl)-2-(trifluoromethyl)isonicotinamide | Calc'd 537.20; found 537.20 |
| 46 | 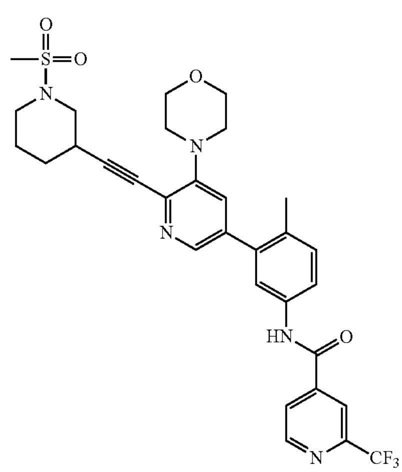 [SMILES: Cc1ccc(NC(=O)c2ccnc(C(F)(F)F)c2)cc1-c1cnc(C#CC2CCCN(S(C)(=O)=O)C2)c(N2CCOCC2)c1] | N-(4-methyl-3-(6-((1-(methylsulfonyl)piperidin-3-yl)ethynyl)-5-morpholinopyridin-3-yl)phenyl)-2-(trifluoromethyl)isonicotinamide | Calc'd 628.21; found 628.20 |

TABLE 5-continued

| Entry | Structure | IUPAC Name | Exact Mass [M + H]+ |
|---|---|---|---|
| 47 | 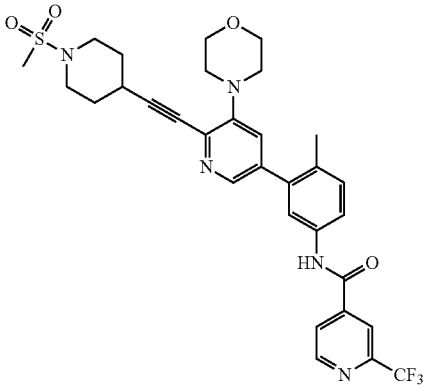 [SMILES: Cc1ccc(NC(=O)c2ccnc(C(F)(F)F)c2)cc1-c1cnc(C#CC2CCN(S(C)(=O)=O)CC2)c(N2CCOCC2)c1] | N-(4-methyl-3-(6-((1-(methylsulfonyl)piperidin-4-yl)ethynyl)-5-morpholinopyridin-3-yl)phenyl)-2-(trifluoromethyl)isonicotinamide | Calc'd 628.21; found 628.20 |
| 48 | 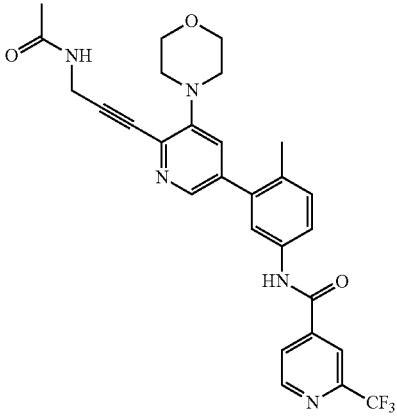 [SMILES: CC(=O)NCC#Cc1ncc(-c2cc(NC(=O)c3ccnc(C(F)(F)F)c3)ccc2C)cc1N1CCOCC1] | N-(3-(6-(3-acetamidoprop-1-yn-1-yl)-5-morpholinopyridin-3-yl)-4-methylphenyl)-2-(trifluoromethyl)isonicotinamide | Calc'd 538.20; found 538.20 |
| 49 | 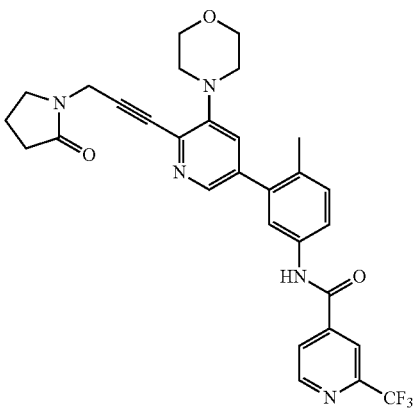 [SMILES: Cc1ccc(NC(=O)c2ccnc(C(F)(F)F)c2)cc1-c1cnc(C#CCN2CCCC2=O)c(N2CCOCC2)c1] | N-(4-methyl-3-(5-morpholino-6-(3-(2-oxopyrrolidin-1-yl)prop-1-yn-1-yl)pyridin-3-yl)phenyl)-2-(trifluoromethyl)isonicotinamide | Calc'd 564.21; found 564.20 |

TABLE 5-continued

| Entry | Structure | IUPAC Name | Exact Mass [M + H]+ |
|---|---|---|---|
| 50 | 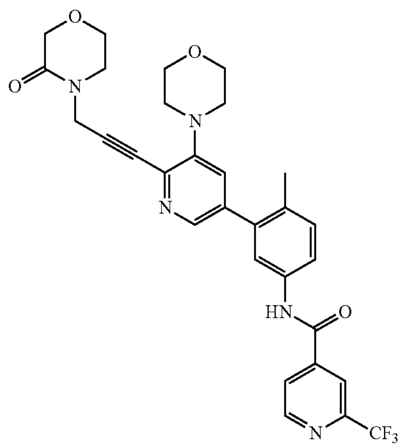 [SMILES: Cc1ccc(NC(=O)c2ccnc(C(F)(F)F)c2)cc1-c1cnc(C#CCN2CCOCC2=O)c(N2CCOCC2)c1] | N-(4-methyl-3-(5-morpholino-6-(3-(3-oxomorpholino)prop-1-yn-1-yl)pyridin-3-yl)phenyl)-2-(trifluoromethyl)isonicotinamide | Calc'd 580.21; found 580.20 |
| 51 | 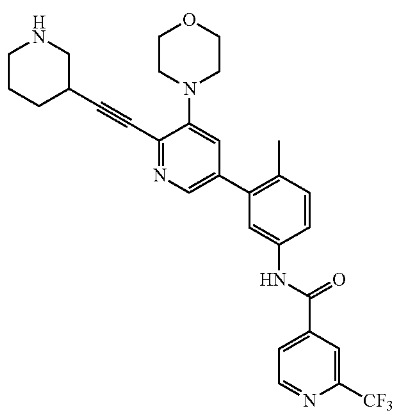 [SMILES: Cc1ccc(NC(=O)c2ccnc(C(F)(F)F)c2)cc1-c1cnc(C#CC2CCCNC2)c(N2CCOCC2)c1] | N-(4-methyl-3-(5-morpholino-6-(piperidin-3-ylethynyl)pyridin-3-yl)phenyl)-2-(trifluoromethyl)isonicotinamide | Calc'd 550.24; found 550.20 |
| 52 | 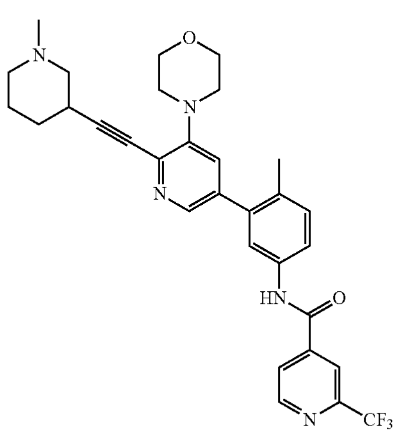 [SMILES: Cc1ccc(NC(=O)c2ccnc(C(F)(F)F)c2)cc1-c1cnc(C#CC2CCCN(C)C2)c(N2CCOCC2)c1] | N-(4-methyl-3-(6-((1-methylpiperidin-3-yl)ethynyl)-5-morpholinopyridin-3-yl)phenyl)-2-(trifluoromethyl)isonicotinamide | Calc'd 564.25; found 564.30 |

TABLE 5-continued

| Entry | Structure | IUPAC Name | Exact Mass [M + H]+ |
|---|---|---|---|
| 53 | 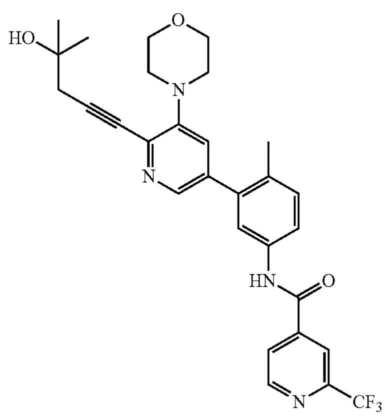 [SMILES: Cc1ccc(NC(=O)c2ccnc(C(F)(F)F)c2)cc1-c1cnc(C#CCC(C)(C)O)c(N2CCOCC2)c1] | N-(3-(6-(4-hydroxy-4-methylpent-1-yn-1-yl)-5-morpholinopyridin-3-yl)-4-methylphenyl)-2-(trifluoromethyl)isonicotinamide | Calc'd 539.22; found 539.20 |
| 54 | 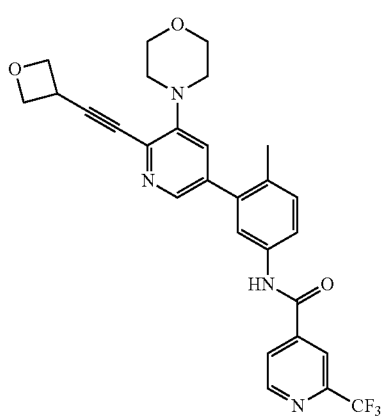 [SMILES: Cc1ccc(NC(=O)c2ccnc(C(F)(F)F)c2)cc1-c1cnc(C#CC2COC2)c(N2CCOCC2)c1] | N-(4-methyl-3-(5-morpholino-6-(oxetan-3-ylethynyl)pyridin-3-yl)phenyl)-2-(trifluoromethyl)isonicotinamide | Calc'd 523.19; found 523.20 |
| 55 | 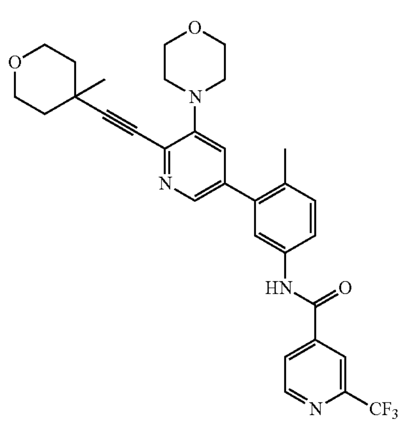 [SMILES: Cc1ccc(NC(=O)c2ccnc(C(F)(F)F)c2)cc1-c1cnc(C#CC2(C)CCOCC2)c(N2CCOCC2)c1] | N-(4-methyl-3-(6-((4-methyltetrahydro-2H-pyran-4-yl)ethynyl)-5-morpholinopyridin-3-yl)phenyl)-2-(trifluoromethyl)isonicotinamide | Calc'd 565.24; found 565.30 |

TABLE 5-continued

| Entry | Structure | IUPAC Name | Exact Mass [M + H]+ |
|---|---|---|---|
| 56 | 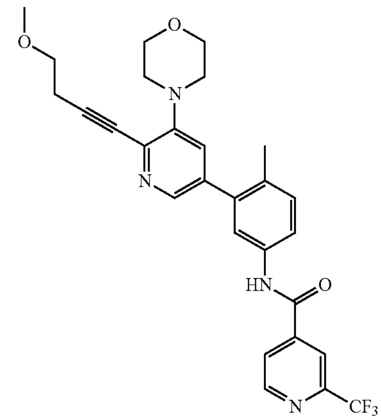 [SMILES: COCCC#Cc1ncc(-c2cc(NC(=O)c3ccnc(C(F)(F)F)c3)ccc2C)cc1N1CCOCC1] | N-(3-(6-(4-methoxybut-1-yn-1-yl)-5-morpholinopyridin-3-yl)-4-methylphenyl)-2-(trifluoromethyl)isonicotinamide | Calc'd 525.20; found 525.20 |
| 57 | 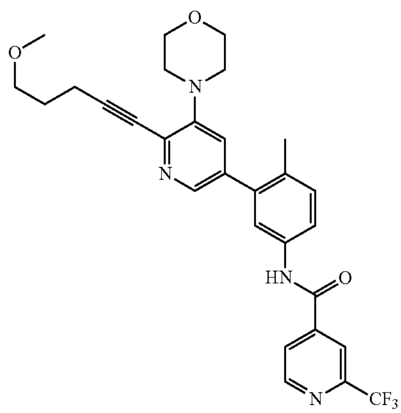 [SMILES: COCCCC#Cc1ncc(-c2cc(NC(=O)c3ccnc(C(F)(F)F)c3)ccc2C)cc1N1CCOCC1] | N-(3-(6-(5-methoxypent-1-yn-1-yl)-5-morpholinopyridin-3-yl)-4-methylphenyl)-2-(trifluoromethyl)isonicotinamide | Calc'd 539.22; found 539.30 |
| 58 | 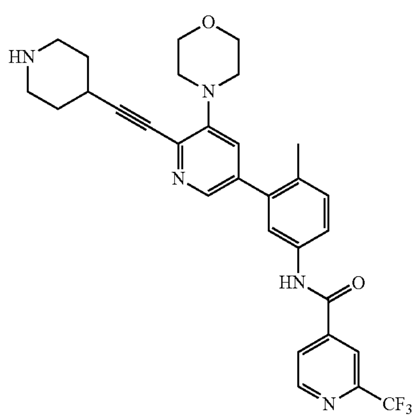 [SMILES: Cc1ccc(NC(=O)c2ccnc(C(F)(F)F)c2)cc1-c1cnc(C#CC2CCNCC2)c(N2CCOCC2)c1] | N-(4-methyl-3-(5-morpholino-6-(piperidin-4-ylethynyl)pyridin-3-yl)phenyl)-2-(trifluoromethyl)isonicotinamide | Calc'd 550.24; found 550.20 |

II. Biological Evaluation

Example 1: Kinase Assay Protocol

Enzymatic BRAF and RAF1 Kinase Activity Determination: Small molecule inhibition of the BRAF and RAF1 kinases was measured using ADP-Glo assay. In the assay, ADP is converted to ATP in the presence of test kinase and substrate, resulting in luciferase reaction and luminescent readout with light generated proportional to the relative kinase activity. Compounds diluted in DMSO were used in 10-point, 3-fold dose curve for both assays. Final concentrations of 6 nM BRAF (CarnaBio, Cat. 09-122) or 3 nM RAF1 (CarnaBio, Cat. 09-125) and 30 nM MEK1 substrate (Millipore, Cat. 14-420) were incubated with 3 μM ATP, 10 mM MgCl2, 0.003% Brij-35, 2 mM DTT, 0.05% BSA, 1 mM EGTA, and 50 mM HEPES for 90 minutes at room temp prior to addition of ADP-Glo reagent (Promega, Cat. V9102) for 40 minutes, and detection reagent for 45 minutes. Luminescence was read on an Envision plate reader (PerkinElmer) and percent remaining activity was used to calculate IC50 using a four-parameter fit model using Dotmatics Knowledge Solutions Studies curve fitting (Dotmatics, Bishops Stortford, UK, CM23).

Representative data for exemplary compounds is presented in Table 6.

TABLE 6

| Synthetic Chemistry Example | RAF-1 IC$_{50}$ |
| --- | --- |
| 1 | B |
| 2 | B |
| 3 | B |
| 4 | B |
| 5 | B |
| 6 | B |
| 7 | B |
| 8 | B |
| 9 | B |
| 10 | B |
| 11 | A |
| 12 | B |
| 13 | B |
| 14 | A |
| 15 | A |
| 16 | A |
| 17 | B |
| 18 | B |
| 19 | B |
| 20 | A |
| 21 | A |
| 22 | A |
| 23 | A |
| 24 | A |
| 25 | A |
| 26 | B |
| 27 | B |
| 28 | A |
| 29 | B |
| 30 | B |
| 31 | B |
| 32 | A |
| 33 | A |
| 34 | A |
| 35 | B |
| 36 | A |
| 37 | A |
| 38 | A |
| 39 | B |
| 40 | A |
| 41 | B |
| 42 | B |
| 43 | A |
| 44 | B |
| 45 | B |
| 46 | B |
| 47 | A |
| 48 | A |
| 49 | A |
| 50 | A |
| 51 | B |
| 52 | B |
| 53 | A |
| 54 | B |
| 55 | B |
| 56 | A |
| 57 | B |
| 58 | A |

Note:
Biochemical assay IC$_{50}$ data are designated within the following ranges:
A: ≤0.001 µM
B: >0.001 µM to ≤0.010 µM
C: >0.010 µM to ≤0.100 µM
D: >0.100 µM to ≤1 µM

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, selected from the group consisting of:

N-(3-[2-[(3R)-3-hydroxybut-1-yn-1-yl]-6-(morpholin-4-yl)pyridin-4-yl]-4-methylphenyl)-2-(trifluoromethyl)pyridine-4-carboxamide;

N-(3-[2-[(3S)-3-hydroxybut-1-yn-1-yl]-6-(morpholin-4-yl)pyridin-4-yl]-4-methylphenyl)-2-(trifluoromethyl)pyridine-4-carboxamide;

N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide;

N-[3-[2-(3-hydroxyprop-1-yn-1-yl)-6-(morpholin-4-yl)pyridin-4-yl]-4-methylphenyl]-2-(trifluoromethyl)pyridine-4-carboxamide;

(3S)—N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide;

N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide;

N-(3-{2-[(3R)-3-aminobut-1-yn-1-yl]-6-(morpholin-4-yl)pyridin-4-yl}-4-methylphenyl)-2-(trifluoromethyl)pyridine-4-carboxamide;

N-(3-{2-[3-(dimethylamino)prop-1-yn-1-yl]-6-(morpholin-4-yl)pyridin-4-yl}-4-methylphenyl)-2-(trifluoromethyl)pyridine-4-carboxamide;

N-{4-methyl-3-[2-(morpholin-4-yl)-6-[3-(pyrrolidin-1-yl)prop-1-yn-1-yl]pyridin-4-yl]phenyl}-2-(trifluoromethyl)pyridine-4-carboxamide;

N-(4-methyl-3-{2-[3-(methylamino)prop-1-yn-1-yl]-6-(morpholin-4-yl)pyridin-4-yl}phenyl)-2-(trifluoromethyl)pyridine-4-carboxamide;

N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide;

N-(4-methyl-3-{2-[(3R)-3-(methylamino)but-1-yn-1-yl]-6-(morpholin-4-yl)pyridin-4-yl}phenyl)-2-(trifluoromethyl)pyridine-4-carboxamide;

N-[3-[2-(3-hydroxyprop-1-yn-1-yl)-6-(morpholin-4-yl)pyridin-4-yl]-4-methylphenyl]-2-(trifluoromethyl)pyridine-4-carboxamide;

N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide;

N-{4-methyl-3-[2-(morpholin-4-yl)-6-[(3S)-4,4,4-trifluoro-3-hydroxybut-1-yn-1-yl)pyridin-4-yl]phenyl}-2-(trifluoromethyl)pyridine-4-carboxamide;

N-{4-methyl-3-[2-(morpholin-4-yl)-6-[(3R)-4,4,4-trifluoro-3-hydroxybut-1-yn-1-yl]pyridin-4-yl]phenyl}-2-(trifluoromethyl)pyridine-4-carboxamide;

N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide; and N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide.

2. The compound, or pharmaceutically acceptable salt or solvate thereof, of claim 1 having the structure of: N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide.

3. The compound, or pharmaceutically acceptable salt or solvate thereof, of claim 1 having the structure of: N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide.

4. The compound, or pharmaceutically acceptable salt or solvate thereof, of claim 1 having the structure of: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide.

5. The compound, or pharmaceutically acceptable salt or solvate thereof, of claim 1 having the structure of: N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide.

6. A pharmaceutical composition comprising a compound, or pharmaceutically acceptable salt or solvate thereof, as described in claim 1 and a pharmaceutically acceptable excipient.

7. The pharmaceutical composition of claim 6, wherein the compound is N-[3-[2-(3-hydroxy-3-methylbut-1-yn-1-yl)-6-(morpholin-4-yl)pyridin-4-yl]-4-methylphenyl]-2-(trifluoromethyl)pyridine-4-carboxamide, or pharmaceutically acceptable salt or solvate thereof.

8. The pharmaceutical composition of claim 6, wherein the compound is N-{3-[2-(3-amino-3-methylbut-1-yn-1-yl)-6-(morpholin-4-yl)pyridin-4-yl]-4-methylphenyl}-2-(trifluoromethyl)pyridine-4-carboxamide, or pharmaceutically acceptable salt or solvate thereof.

9. The pharmaceutical composition of claim 6, wherein the compound is N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide, or pharmaceutically acceptable salt or solvate thereof.

10. The pharmaceutical composition of claim 6, wherein the compound is N-(3-{2-[(3S)-3-aminobut-1-yn-1-yl]-6-(morpholin-4-yl)pyridin-4-yl}-4-methylphenyl)-2-(trifluoromethyl)pyridine-4-carboxamide, or pharmaceutically acceptable salt or solvate thereof.

* * * * *